(12) United States Patent
Dack et al.

(10) Patent No.: US 6,511,993 B1
(45) Date of Patent: *Jan. 28, 2003

(54) METALLOPROTEASE INHIBITORS

(76) Inventors: Kevin Neil Dack, Pfizer Central Research, Ramsgate Road, Sandwich, Kent CT13 9NJ (GB); Michael Jonathan Fray, Pfizer Central Research, Ramsgate Road, Sandwich, Kent, CT13 9NJ (GB); Gavin Alistair Whitlock, Pfizer Central Research, Ramsgate Road, Sandwich, Kent, CT13 9NJ (GB); Mark Llewellyn Lewis, Pfizer Central Research, Ramsgate Road, Sandwich, Kent, CT13 9NJ (GB); Nicholas Murray Thomson, Pfizer Central Research, Ramsgate Road, Sandwich, Kent, CT13 9NJ (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/586,623

(22) Filed: Jun. 2, 2000

Related U.S. Application Data

(60) Provisional application No. 60/169,578, filed on Dec. 8, 1999.

(30) Foreign Application Priority Data

Jun. 3, 1999 (GB) .............................. 9912961

(51) Int. Cl.$^7$ ................... A61K 31/4545; C07D 401/10
(52) U.S. Cl. ................. 514/318; 546/194; 546/186; 546/187; 546/191; 546/209; 546/211; 546/234; 546/268.1; 546/313; 514/316; 514/317; 514/326

(58) Field of Search ................. 514/318, 316, 514/317, 326; 546/194, 186, 187, 191, 209, 211, 234, 268.1, 313

(56) References Cited

FOREIGN PATENT DOCUMENTS

| EP | 0606046 | 7/1994 | |
| EP | 0780386 | 6/1997 | |
| NI | 13622 | 2/1999 | |
| WO | 9837877 | 9/1998 | |
| WO | 9838163 | 9/1998 | |
| WO | 99/29667 | * 6/1999 | ................. 514/318 |
| WO | 0046221 | 8/2000 | |

\* cited by examiner

*Primary Examiner*—Charanjit S. Aulakh

(57) ABSTRACT

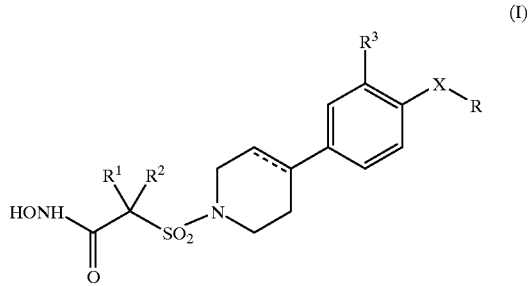

Compounds of formula (I) and pharmaceutically-acceptable derivatives thereof, are matrix metalloprotease inhibitors, useful in treatment of conditions mediated by matrix metalloproteases, such as chronic dermal ulcers.

38 Claims, No Drawings

METALLOPROTEASE INHIBITORS

This application claims priority from Great Britain Application No. GB 9912961.1, filed Jun. 3, 1999, and U.S. Provisional Application Ser. No. 60/169,578, filed Dec. 8, 1999.

This invention relates to a series of substituted α-aminosulphonyl-acetohydroxamic acids which are inhibitors of zinc-dependent metalloprotease enzymes. In particular, the compounds are inhibitors of certain members of the matrix metalloprotease (MMP) family.

Matrix metalloproteases (MMPs) constitute a family of structurally similar zinc-containing metalloproteases, which are involved in the remodelling and degradation of extra-cellular matrix proteins, both as part of normal physiological processes and in pathological conditions. Since they have high destructive potential, MMPs are usually under close regulation and failure to maintain MMP regulation has been implicated as a component of a number of diseases and conditions including pathological conditions, such as atherosclerotic plaque rupture, heart failure, restenosis, periodontal disease, tissue ulceration, cancer metastasis, tumour angiogenesis, age-related macular degeneration, fibrotic disease, rheumatoid arthritis, osteoarthritis and inflammatory diseases dependent on migratory inflammatory cells.

Another important function of certain MMPs is to activate various enzymes, including other MMPs, by cleaving the pro-domains from their protease domains. Thus some MMPs act to regulate the activities of other MMPs, so that over-production of one MMP may lead to excessive proteolysis of extracellular matrix by another. Moreover, MMPs have different substrate preferences (shown in the following Table for selected family members) and different functions within normal and pathological conditions. For recent reviews of MMPs, see Current Pharmaceutical Design, 1996, 2, 624 and Exp. Opin. Ther. Patents, 1996, 6 1305.

TABLE

| Enzyme | Other Names | Preferred Substrates |
|---|---|---|
| MMP-1 | collagenase-1; interstitial collagenase | collagens I, II, III, VII, X; gelatins |
| MMP-2 | gelatinase A; 72kDa gelatinase | gelatins; collagens IV, V, VII, X; elastin; fibronectin; activates pro-MMP-13 |
| MMP-3 | stromelysin-1 | proteoglycans; laminin; fibronectin; gelatins |
| MMP-8 | collagenase-2; neutrophil collagenase | collagens I, II, III |
| MMP-9 | gelatinase B; 92kDa gelatinase | gelatins; collagens IV, V; elastin |
| MMP-13 | collagenase-3 | collagens I, II, III; gelatins |
| MMP-14 | MT-MMP-1 | activates pro-MMP-2 & 13; gelatins |

Excessive production of MMP-3 is thought to be responsible for pathological tissue breakdown which underlies a number of diseases and conditions. For example, MMP-3 has been found in the synovium and cartilage of osteoarthritis and rheumatoid arthritis patients, thus implicating MMP-3 in the joint damage caused by these diseases: see Biochemistry, 1989, 28, 8691 and Biochem. J., 1989, 258, 115. MMP-13 is also thought to play an important role in the pathology of osteoarthritis and rheumatoid arthritis: see Lab. Invest., 1997, 76, 717 and Arthritis Rheum., 1997, 40, 1391.

The over-expression of MMP-3 has also been implicated in the tissue damage and chronicity of chronic wounds, such as venous ulcers, diabetic ulcers and pressure sores: see Brit. J. Dermatology, 1996, 135, 52. Collagenase-3 (MMP-13) has also recently been implicated in the pathology of chronic wounds (*J Invest Dermatol*, 1997, 109, 96–101).

Furthermore, the production of MMP-3 may also cause tissue damage in conditions where there is ulceration of the colon (as in ulcerative colitis and Crohn's disease: see J. Immunol., 1997 158, 1582 and J. Clin. Pathol., 1994, 47, 113) or of the duodenum (see Am. J. Pathol., 1996, 148, 519).

Moreover, MMP-3 is also thought to be involved in skin diseases such as dystrophic epidermolysis bullosa (see Arch. Dermatol. Res., 1995, 287, 428) and dermatitis herpetiformis (see J. Invest. Dermatology, 1995, 105, 184).

Rupture of atherosclerotic plaques by MMP-3 has also been described (see e.g. Circulation, 1997, 96, 396). Thus, MMP-3 inhibitors may find utility in the treatment of conditions caused by or complicated by embolic phenomena such as cardiac or cerebral infarctions.

Studies of human cancers have shown that MMP-2 is activated on the invasive tumour cell surface (see J. Biol. Chem., 1993, 268, 14033) and BB-94, a non-selective peptidic hydroxamate MMP inhibitor, has been reported to decrease the tumour burden and prolong the survival of mice carrying human ovarian carcinoma xenografts (see Cancer Res., 1993, 53, 2087). Various series of MMP inhibitors have appeared in the literature which have a carbonyl moiety (CO) and a sulphone moiety ($SO_2$) with a two atom "spacer" interposed between them. For example, α-arylsulphonamido-substituted acetohydroxamic acids are disclosed in EP-A-0606046, WO-A-9627583 and WO-A-9719068, whilst EP-A-0780386 discloses certain related sulphone-substituted hydroxamic acids.

The compounds of the present invention represent a new class of compounds, and are inhibitors of some of the members of the MMP family. In particular, they are inhibitors of MMP-3 and/or MMP-13, with certain compounds exhibiting varying degrees of selectivity over other MMPs, such as MMP-1, MMP-2, MMP-9 and MMP-14. Thus they may be of utility in treating diseases and conditions mediated by MMPs, in particular MMP-3 and/or MMP-13.

A series of substances related to the instant invention were disclosed in International Patent Application number publication no. WO 99/29667, herein incorporated by reference in its entirety.

According to one aspect of the present invention ("A"), there is provided a compound of formula (I):

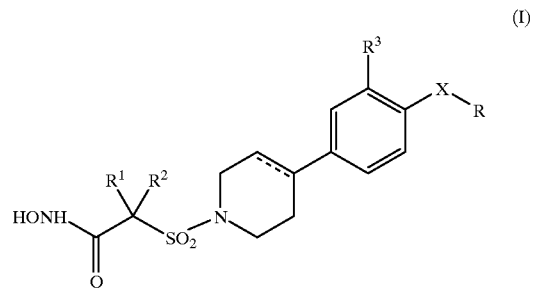

and pharmaceutically-acceptable salts thereof, and solvates thereof, wherein
  the dotted line represents an optional bond,
  X is a monocyclic aromatic linker moiety selected from phenylene, pyridinylene, pyrazolylene, thiazolylene, thienylene, furylene, pyrimidinylene, pyrazinylene, pyridazinylene, pyrrolylene, oxazolylene, isoxazolylene, oxadiazolylene, thiadiazolylene, imidazolylene, triazolylene, or tetrazolylene;

R is H, $C_{1-4}$ alkyl optionally substituted by $C_{1-4}$ alkoxy, $NR^4R^5$ or OH, or R is $C_{1-4}$ alkoxy optionally substituted by 1 or 2 substituents selected from ($C_{1-4}$ alkyl optionally substituted by OH), $C_{1-4}$ alkoxy, OH and $NR^4R^5$;

$R^1$ and $R^2$ are each independently H, $C_{1-6}$ alkyl optionally substituted by OH or $C_{1-4}$ alkoxy, or $C_{2-6}$ alkenyl;

or $R^1$ and $R^2$ are taken together, with the C atom to which they are attached, to form a 3- to 7-membered ring optionally incorporating a hetero-moiety selected from O, S, SO, $SO_2$ and $NR^6$, and which 3- to 7-membered ring is optionally substituted by one or more OH;

$R^3$ is H, halo, methyl, or methoxy;

$R^4$ and $R^5$ are each independently H or $C_1$ to $C_6$ alkyl optionally substituted by OH, $C_1$ to $C_4$ alkoxy or aryl, or $R^4$ and $R^5$ can be taken together with the N atom to which they are attached, to form a 3- to 7-membered ring, optionally incorporating a further hetero-moiety selected from O, S, $SO_2$ and $NR^7$; and $R^6$ and $R^7$ are each independently H or $C_1$ to $C_4$ alkyl.

According to a further aspect of the invention ("B"), there is provided a compound of formula (I):

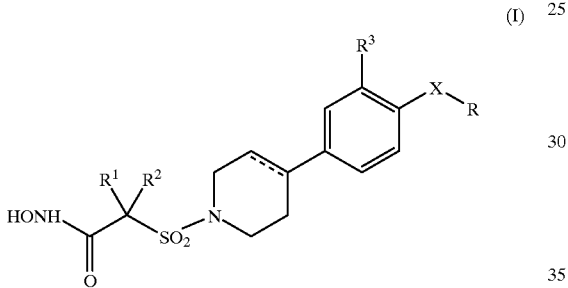

(I)

and pharmaceutically-acceptable salts thereof, and solvates thereof, wherein the dotted line represents an optional bond;

X is a monocyclic aromatic linker moiety selected from pyrazolylene, thiazolylene, pyrazinylene, pyridazinylene, pyrrolylene, oxazolylene, isoxazolylene, oxadiazolylene, thiadiazolylene, imidazolylene, triazolylene, or tetrazolylene;

R is H, $C_{1-4}$ alkyl optionally substituted by $C_{1-4}$ alkoxy or $NR^4R^5$ or OH, or $C_{1-4}$ alkoxy optionally substituted by 1 or 2 substituents selected from ($C_{1-4}$ alkyl optionally substituted by OH), $C_{1-4}$ alkoxy, OH and $NR^4NR^5$;

$R^1$ and $R^2$ are each independently H, $C_{1-6}$ alkyl optionally substituted by OH or $C_{1-4}$ alkoxy, or $C_{2-6}$ alkenyl;

or $R^1$ and $R^2$ are taken, together with the C atom to which they are attached, to form a 3- to 7-membered ring optionally incorporating a hetero-moiety selected from O, S, SO, $SO_2$ and $NR^6$, and which 3- to 7-membered ring is optionally substituted by one or more OH;

$R^3$ is H, halo, methyl, or methoxy;

$R^4$ and $R^5$ are each independently H or $C_1$ to $C_6$ alkyl optionally substituted by OH, $C_1$ to $C_4$ alkoxy or aryl, or $R^4$ and $R^5$ can be taken together with the N atom to which they are attached, to form a 3- to 7-membered ring, optionally incorporating a further hetero-moiety selected from O, S, $SO_2$ and $NR^7$; and $R^6$ and $R^7$ are each independently H or $C_1$ to $C_4$ alkyl.

According to a further aspect of the invention ("C") there is provided a compound of formula (I):

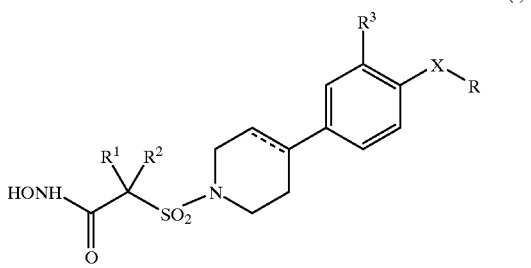

(I)

and pharmaceutically-acceptable salts thereof, and solvates thereof, wherein the dotted line represents an optional bond;

X is a monocyclic aromatic linker moiety selected from phenylene, pyridinylene, pyrazolylene, thiazolylene, thienylene, furylene, pyrimidinylene, pyrazinylene, pyridazinylene, pyrrolylene, oxazolylene, isoxazolylene, oxadiazolylene, thiadiazolylene, imidazolylene, triazolylene, or tetrazolylene;

R is $C_{1-4}$ alkyl substituted by $NR^4R^5$, $C_{1-4}$ alkoxy substituted by $NR^4R^5$, or $C_{1-4}$ alkoxy substituted by 2 substituents selected from ($C_{1-4}$ alkyl optionally substituted by OH), $C_{1-4}$ alkoxy, OH and $NR^4R^5$;

$R^1$ and $R^2$ are each independently H, $C_{1-6}$ alkyl optionally substituted by OH or $C_{1-4}$ alkoxy, or $C_{2-6}$ alkenyl;

or $R^1$ and $R^2$ are taken together, with the C atom to which they are attached, to form a 3- to 7-membered ring optionally incorporating a hetero-moiety selected from O, S, SO, $SO_2$ and $NR^6$, and which 3- to 7-membered ring is optionally substituted by one or more OH;

$R^3$ is H, halo, methyl, or methoxy;

$R^4$ and $R^5$ are each independently H or $C_1$ to $C_6$ alkyl optionally substituted by OH, $C_1$ to $C_4$ alkoxy or aryl, or $R^4$ and $R^5$ can be taken together with the N atom to which they are attached to form a 3- to 7-membered ring, optionally incorporating a further hetero-moiety selected from O, S, $SO_2$ and $NR^7$; and $R^6$ and $R^7$ are each independently H or $C_1$ to $C_4$ alkyl.

According to a further aspect of the invention ("D") there is provided a compound of formula (I):

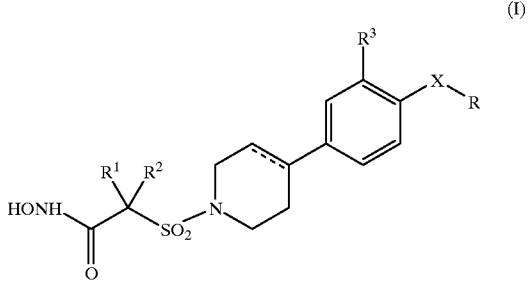

(I)

and pharmaceutically-acceptable salts thereof, and solvates thereof, wherein the dotted line represents an optional bond, X is a monocyclic aromatic linker moiety selected from phenylene, pyridinylene, pyrazolylene, thiazolylene, thienylene, furylene, pyrimidinylene, pyrazinylene, pyridazinylene, pyrrolylene, oxazolylene, isoxazolylene, oxadiazolylene, thiadiazolylene, imidazolylene, triazolylene, or tetrazolylene;

R is H, $C_{1-4}$ alkyl optionally substituted by $C_{1-4}$ alkoxy, $NR^4R^5$ or OH, or $C_{1-4}$ alkoxy optionally substituted by 1 or 2 substituents selected from ($C_{1-4}$ alkyl optionally substituted by OH), $C_{1-4}$ alkoxy, OH and $NR^4R^5$;

$R^1$ and $R^2$ are each independently $C_{1-6}$ alkyl substituted by OH;

or $R^1$ and $R^2$ are taken together, with the C atom to which they are attached, to form a 3- to 7-membered ring optionally incorporating a hetero-moiety selected from O, S, SO, $SO_2$ and $NR^6$, and which 3- to 7-membered ring is substituted by one or more OH;

$R^3$ is H, halo, methyl, or methoxy;

$R^4$ and $R^5$ are each independently H or $C_1$ to $C_6$ alkyl optionally substituted by OH, $C_1$ to $C_4$ alkoxy or aryl, or $R^4$ and $R^5$ can be taken together with the N atom to which they are attached, to form a 3- to 7-membered ring, optionally incorporating a further hetero-moiety selected from O, S, $SO_2$ and $NR^7$; and $R^6$ and $R^7$ are each independently H or $C_1$ to $C_4$ alkyl.

In all the above definitions A, B, C and D, unless otherwise indicated, alkyl, alkenyl, alkoxy, etc. groups having three or more carbon atoms may be straight chain or branched chain.

All the compounds of formula (I) in aspects A, B, C and D above may contain one or more chiral centres and therefore can exist as stereoisomers, i.e. as enantiomers or diastereoisomers, as well as mixtures thereof. The invention includes both the individual stereoisomers of the compounds of formula (I) and any mixture thereof. Separation of diastereoisomers may be achieved by conventional techniques, e.g. by fractional crystallisation or chromatography (including HPLC) of a diastereoisomeric mixture of a compound of formula (I) or a suitable salt or derivative thereof An individual enantiomer of a compound of formula (I) may be prepared from a corresponding optically pure intermediate or by resolution, either by HPLC of the racemate using a suitable chiral support or, where appropriate, by fractional crystallisation of the diastereoisomeric salts formed by reaction of the racemate with a suitable optically active base or acid, as appropriate to the specific compound to be resolved. Furthermore, compound of formula (I) which contain alkenyl groups can exist as cis- or trans-geometric isomers. Again, the invention includes both the separated individual geometric isomers as well as mixtures thereof. Certain of the compounds of formula (I) may be tautomeric and all possible tautomers are included in the scope of this invention. Certain of the compounds of formula (I) may exhibit zwitterionic behaviour and all possible zwitterions are included in the scope of this invention. Also included in the invention are radiolabelled derivatives of compounds of formula (I) which are suitable for biological studies.

The pharmaceutically acceptable salts of all the compounds of the formula (I) include the acid addition and the base salts thereof. The term "pharmaceutically acceptable" means suitable for use in human or non-human animal medicine.

Suitable acid addition salts are formed from acids which form non-toxic salts and examples include the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples include the aluminium, calcium, lithium, magnesium, potassium, sodium, zinc, tris, meglumine, choline, olamine, diolamine, ethylenediamine, benethamine, benzathene, glucosamine, nicotinamide, ornithine, guanidine, guanine, arginine and procaine salts.

For a review on suitable salts see for example Berge et al, J. Pharm. Sci., 66, 1–19 (1977).

Solvates (e.g. hydrates) of the compounds and salts of aspects A, B, C and D of the invention are included in the invention. In some cases, the solvate may be the direct product of a reaction to make a compound or salt of the invention in a solvent, in which case no further transformation step would be necessary. In other cases, solvates may be made by methods known in the art, such as by crystallisation from a solvent.

Prodrugs of the compounds of aspects A, B, C and D of the invention, their pharmaceutically acceptable salts and solvates thereof, are also envisaged by the invention. For reference as to how to prepare prodrugs, see standard texts in this field, for example "Design of Prodrugs" ed. H. Bundgaard (1985, Elsevier, Amsterdam/New York/Oxford).

For aspects C and D of the invention, X is preferably phenylene, pyridinylene, pyrazolylene or thiazolylene.

For aspects C and D of the invention, X is more preferably 1,3-phenylene, 2,6-pyridinylene, 1,3-pyrazolylene or 2,5-thiazolylene.

For aspect B of the invention X is preferably pyrazolylene or thiazolylene. For aspect B of the invention X is more preferably 1,3-pyrazolylene or 2,5-thiazolylene.

For aspects B and D of the invention R is preferably H, methoxy, $O(CH_2)_2OH$, $O(CH_2)_2OCH_3$, $O(CH_2)_2N(CH_3)_2$, $O(CH_2)_2NHCH_3$, $O(CH_2)_2NH_2$, $CH_2NHCH_3$, morpholinomethyl, 2-morpholinoethoxy, 2R-2,3-dihydroxy-1-propyloxy, 2S-2,3-dihydroxy-1-propyloxy or 1,3-dihydroxy-2-propyloxy. For aspects B and D of the invention R is most preferably $O(CH_2)_2OH$ or $O(CH_2)_2NH_2$.

For aspect C of the invention R is preferably $O(CH_2)_2N(CH_3)_2$, $O(CH_2)_2NHCH_3$, $O(CH_2)_2NH_2$, $CH_2NHCH_3$, morpholinomethyl, 2-morpholinoethoxy, 2R-2,3-dihydroxy-1-propyloxy, 2S-2,3-dihydroxy-1-propyloxy or 1,3-dihydroxy-2-propyloxy. For aspect C of the invention R is most preferably $O(CH_2)_2NH_2$.

For aspects B and C of the invention preferably $R^1$ and $R^2$ are each independently $C_{1-6}$ alkyl optionally substituted by OH, or $R^1$ and $R^2$ are taken together, with the C atom to which they are attached, to form a 3- to 7-membered ring optionally incorporating a hetero-moiety selected from O, S, SO, $SO_2$ and $NR^6$, and which 3- to 7-membered ring is optionally substituted by one or more OH. For aspects B and C of the invention more preferably $R^1$ and $R^2$ are each $CH_3$, or $R^1$ and $R^2$ are taken together, with the C atom to which they are attached, to form a tetrahydropyran-4-ylidene, piperidin-4-ylidene, 1-methylpiperidin-4-ylidene, or 3,4-dihydroxycyclopentylidene moiety. For aspects B and C of the invention, yet more preferably $R^1$ and $R^2$ are taken together, with the C atom to which they are attached, to form a tetrahydropyran-4-ylidene, cis-3,4-dihydroxycyclopentylidene, trans-3,4-dihydroxycyclopentylidene or piperidin-4-ylidene moiety. For aspects B and C of the invention, most preferably $R^1$ and $R^2$ are taken together, with the C atom to which they are attached, to form a tetrahydropyran-4-ylidene, piperidin-4-ylidene, or cis-3,4-dihydroxycyclopentylidene where the hydroxy substituents have a cis-relationship to the hydroxamate moiety.

For aspect D of the invention, $R^1$ and $R^2$ are preferably taken together, with the C atom to which they are attached, to form a 3,4-dihydroxycyclopentylidene moiety. For aspect D of the invention, most preferably $R^1$ and $R^2$ are taken together, with the C atom to which they are attached, to form a cis-3,4-dihydroxycyclopentylidene group where the hydroxy substituents have a cis-relationship to the hydroxamate moiety.

For aspects A, B, C and D of the invention $R^3$ is preferably methyl.

A preferred group of substances are those selected from the compounds of the Examples and the pharmaceutically acceptable salts and solvates thereof, especially the compounds of Examples 3, 6 and 14 below, and salts and solvates thereof.

The invention further provides synthetic methods for the production of compounds, salts and solvates of the invention, which are described below and in the Examples. The skilled man will appreciate that the compounds and salts of the invention could be made by methods other than those herein described, by adaptation of the methods herein described and/or adaptation of methods known in the art, for example the art described herein. Specific art which may be mentioned includes WO 99/29667, "Comprehensive Organic Transformations" by R C Larock, VCH Publishers Inc. (1989), "Advanced Organic Chemistry" by J March, Wiley Interscience (1985), "Designing Organic Synthesis" by S Warren, Wiley Interscience (1978), "Organic Synthesis—The Disconnection Approach" by S Warren, Wiley Interscience (1982), "Guidebook to Organic Synthesis" by R K Mackie and D M Smith, Longman (1982), "Protective Groups in Organic Synthesis" by T W Greene and P G M Wuts, John Wiley and Sons Inc. (1999), and P J Kocienski, in "Protecting Groups", Georg Thieme Verlag (1994), references therein, and any updated versions of the aforementioned standard works.

Where desired or necessary, the compound of formula (I) can be converted into a pharmaceutically acceptable salt thereof, conveniently by mixing together solutions of a compound of formula (I) and the desired acid or base, as appropriate. The salt may be precipitated from solution and collected by filtration, or may be collected by other means such as by evaporation of the solvent. In some cases, the salt may be the direct product of a reaction to make a compound or salt of the invention in a solvent, in which case no further transformation step would be necessary.

It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999).

The following methods are illustrative of the general synthetic procedures which may be adopted in order to obtain the compounds of the invention.

In the synthetic methods below, unless otherwise specified, the substituents are as defined above with reference to the compounds of formula (I) as defined above with respect to aspects A, B, C and D.

A compound of formula (I) may be prepared directly from a corresponding acid or acid derivative of formula (II):

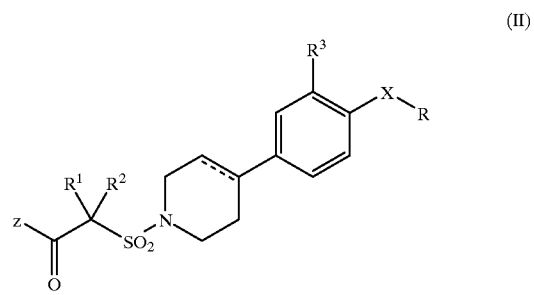

where Z is chloro, bromo, iodo, $C_{1-3}$ alkyloxy or HO.

When prepared directly from the ester of formula (II), where Z is $C_{1-3}$ alkyloxy, the reaction may be carried out by treatment of the ester with hydroxylamine, preferably up to a 3-fold excess of hydroxylamine, in a suitable solvent at from about room temperature to about 85° C. The hydroxylamine is conveniently generated in situ from a suitable salt such as its hydrochloride salt by conducting the reaction in the presence of a suitable base such as an alkali metal carbonate or bicarbonate, e.g. potassium carbonate. Preferably the solvent is a mixture of methanol and tetrahydrofuran and the reaction is temperature is from about 65 to 70° C.

Alternatively, the ester (II, where Z is $C_{1-3}$ alkyloxy) may be converted by conventional hydrolysis to the corresponding carboxylic acid (II, Z is HO) which is then transformed to the required hydroxamic acid of formula (I). [If the R, $R^1$ or $R^2$ moieties contain any free hydroxyl groups, these should be protected with groups inert to this functional group interconversion reaction sequence, and released following it, using standard methodology.]

Preferably the hydrolysis of the ester is effected under basic conditions using about 2- to 6-fold excess of an alkali metal hydroxide in aqueous solution, optionally in the presence of a co-solvent, at from about room temperature to about 85° C. Typically the co-solvent is a mixture of methanol and tetrahydrofuran or a mixture of methanol and 1,4-dioxan and the reaction temperature is from about 40 to about 70° C.

The subsequent coupling step may be achieved using conventional amide-bond forming techniques, e.g. via the acyl halide derivative (II, Z is Cl, I or Br) and hydroxylamine hydrochloride in the presence of an excess of a tertiary amine such as triethylamine or pyridine to act as acid-scavenger, optionally in the presence of a catalyst such as 4-dimethylaminopyridine, in a suitable solvent such as dichloromethane, at from about 0° C. to about room temperature. For convenience, pyridine may also be used as the solvent. Such acyl halide substrates are available from the corresponding acid via conventional methods.

In particular, any one of a host of amino acid coupling variations may be used. For example, the acid of formula (II) wherein Z is HO may be activated using a carbodiimide such as 1,3-dicyclohexylcarbodiimide or 1-(3-dimethylaminopropyl)-3-ethylcarbodiimide hydrochloride (often referred to as "water-soluble carbodiimide" or "WSCDI") optionally in the presence of 1-hydroxybenzotriazole or 1-hydroxy-7-aza-1H-1,2,3-benzotriazole (HOAt) and/or a catalyst such as 4-dimethylaminopyridine, or by using HOAt or a halotrisaminophosphonium salt such as bromotris(pyrrolidino)-phosphonium hexafluorophosphate. Either type of coupling is conducted in a suitable solvent such as dichloromethane, N-methylpyrrolidine (NMP) or dimethylformamide (DMF), optionally in the presence of pyridine or a tertiary amine such as N-methylmorpholine or N-ethyldiisopropylamine (for example when either the hydroxylamine or the activating reagent is presented in the form of an acid addition salt), at from about 0° C. to about room temperature. Typically, from 1.1 to 2.0 molecular equivalents of the activating reagent and from 1.0 to 4.0 molecular equivalents of any tertiary amine present are employed.

Preferred reagents for mediating the coupling reaction are HOAt, WSCDI and O-(7-azabenzotriazol-1-yl)-1,1,3,3-tetramethyluronium hexafluorophosphate (HATU).

Preferably a solution of the acid (II, Z is HO) and N-ethyldiisopropylamine in a suitable solvent such as anhydrous dimethylformamide or anhydrous 1-methylpyrrolidin-2-one, under nitrogen, is treated with up to a 1.5-fold excess of HATU at about room temperature followed, after about 15 to 30 minutes, with up to about a 3-fold excess of hydroxylamine hydrochloride and up to about a 4-fold excess of N-ethyldiisopropylamine, optionally in the same solvent, at the same temperature.

More preferably the acid (II, Z is HO) is reacted with a carbodiimide, HOBt and hydroxylamine hydrochloride in pyridine in a suitable co-solvent such as dichloromethane.

An ester of formula (II, Z is $C_{1-3}$ alkyloxy) may be prepared from an appropriate amine of formula (III) by sulphonylation with an appropriate compound of formula (IV), wherein $R^{10}$ is $C_{1-3}$ alkyloxy and $Z^1$ is a leaving group such as Br, I or Cl.

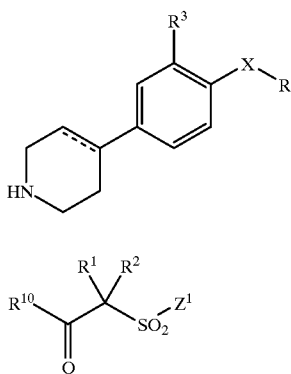

(III)

(VI)

Preferably, $Z^1$ is chloro.

The reaction may be effected in the presence of an appropriate base in a suitable solvent at from about 0° C. to about room temperature. For example, when both $R^1$ and $R^2$ are hydrogen, an appropriate base is 1,8-diazabicyclo[5.4.0] undec-7-ene and a suitable solvent is dichloromethane. Alternatively, the base can be sodium imidazolide. An alternative method is to make a N-trialkylsilyl dervative of (III), and mix with (IV) at room temperature in tetrahydrofuran (THF) in the presence of a catalytic amount of benzenesulphonic acid (BSA).

Certain esters of formula (II, Z is $C_{1-3}$ alkyloxy) wherein at least one of $R^1$ and $R^2$ is other than hydrogen may be conveniently obtained from the α-carbanion of an ester of formula (II) wherein at least one of $R^1$ and $R^2$ is hydrogen by conventional C-alkylation procedures using an alkylating agent of formula (VA) or (VB):

 (VA)

 (VB), where the $(CH_2)_q$ moiety of (VB) optionally incorporates a hetero-moiety selected from O, S, SO, $SO_2$ and $NR^6$, and is optionally substituted by one or more optionally protected OH, and which $NR^6$ group may be optionally protected, wherein $R^1$ and $R^2$ are not hydrogen, $Z^2$ and $Z^3$ may be the same or different and are suitable leaving groups such as chloro, bromo, iodo, $C_1$–$C_4$ alkanesulphonyloxy, trifluoromethanesulphonyloxy or arylsulphonyloxy (e.g. benzenesulphonyloxy or p-toluenesulphonyloxy), and q is 3, 4, 5, 6 or 7. Other conditions are outlined below—sections vii) and x).

Preferably, $Z^2$ and $Z^3$ are selected from bromo, iodo and p-toluenesulphonyloxy.

The carbanion may be generated using an appropriate base in a suitable solvent, optionally in the presence of a phase transfer catalyst (PTC). Typical base-solvent combinations may be selected from lithium, sodium or potassium hydride, lithium, sodium or potassium bis(trimethylsilyl) amide, lithium diisopropylamide and butyllithium, potassium carbonate, sodium or potassium t-butoxide, together with toluene, ether, DMSO, 1,2-dimethoxyethane, tetrahydrofuran, 1,4-dioxan, dimethylformamide, N,N-dimethylacetamide, 1-methylpyrrolidin-2-one and any mixture thereof.

Preferably the base is sodium hydride and the solvent is dimethylformamide, optionally with tetrahydrofuran as co-solvent, or 1-methylpyrrolidin-2-one. For monoalkylation up to about a 10% excess of base is employed whilst, for dialkylation, from about 2 to about 3 molar equivalents are generally appropriate.

Typically, the carbanion is generated at about room temperature, under nitrogen, and subsequently treated with the required alkylating agent at the same temperature. Clearly, when dialkylation is required and $R^1$ and $R^2$ are different, the substituents may be introduced in tandem in a "one-pot reaction" or in separate steps.

An amine of formula (III) may be obtained by standard chemical procedures. Other amines of formula (III), when neither commercially available nor subsequently described, can be obtained either by analogy with the processes described in the Preparations section below or by conventional synthetic procedures, in accordance with standard textbooks on organic chemistry or literature precedent, from readily accessible starting materials using appropriate reagents and reaction conditions.

Another way of making compounds of formula (II) where ZCO is an ester moiety, is via the reaction sequence

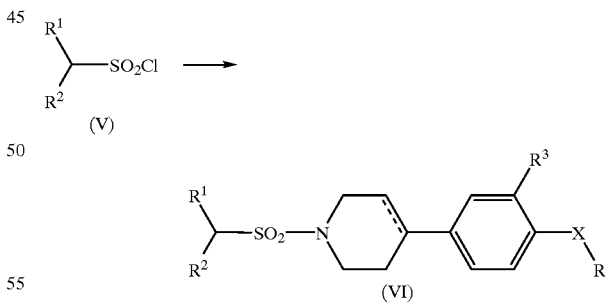

The appropriate sulphonyl chloride (V) is reacted with compound (III—see above) optionally in the presence of a base and in a suitable solvent. The resulting sulphonamide (VI) is reacted with a suitable base such as n-butyllithium, sodium hydride or potassium t-butoxide in a suitable anhydrous non-protic solvent to generate the carbanion α to the sulphonamide moiety, which is then reacted with for example dimethyl carbonate or methyl chloroformate, in suitable conditions, either of which reagent would give the compound (II) where Z is methoxy.

Compounds of formula (I) where R contains a free NH, NH₂ and/or OH group (apart from on the hydroxamic acid moiety) may conveniently be prepared from a corresponding N- or O-protected species (VII below). As such, compounds of formula (VII) where $R^p$ is a O- and/or N-protected version of a corresponding compound of the formula (I), are included in the scope of this invention, with regard to aspects A, B, C and D of the invention and the specific compounds of formula (I) mentioned herein, such as those mentioned in the Preparations, as appropriate, below. Suitable protection/deprotection regimes are well known in the art, such as those mentioned in "Protective Groups in Organic Synthesis" by T W Greene and P G M Wuts, John Wiley & Sons Inc (1999).

Suitable OH-protecting groups and regimes include the ethers such as t-butyloxy, tri($C_{1-4}$)silyloxy, etc., and esters such as carbonates, sulphonates, $C_{1-4}$ acylates, etc. mentioned by Greene and Wuts, ibid. chapter 2. Suitable NH-protecting groups and regimes can be found in Greene and Wuts, ibid. chapter 7, and include amides such as "Boc", amines such as benzyl, etc.

Compounds of formula (VII) may be made by methods described herein and/or by variation of methods described herein which the skilled man will appreciate are routine variations.

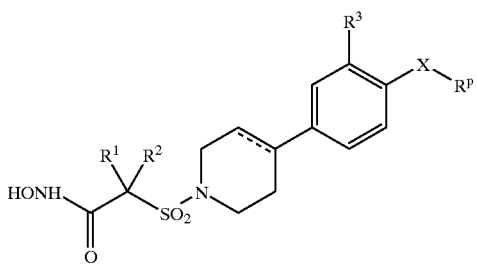

(VII)

An example of a suitable OH-protecting group is the triethylsilyl (TMS) group and the protection, reaction, deprotection sequence can be summarised by steps a) to c) below:
  a) $ClSiMe_3$ (1.1 equiv per OH), WSCDI (1.1 to 1.2 equiv), HOBT or HOAT (1 to 1.1 equiv),
  b) $NH_2OH.HCl$ (3 equiv) in DMF/pyridine or $CH_2Cl_2$/pyridine (3/1 to 1/1) at rt for between 4 and 20 hours.
  c) TMS group removed by acid work-up.

Another example of a suitable OH-protecting group is the t-butyl ($^tBu$) group which can be carried through the synthetic process and removed in the last step of the process. An example of the route is outlined in the scheme below (in relation to the synthesis of the compound of Example 3—via compounds of the Preparations mentioned below).

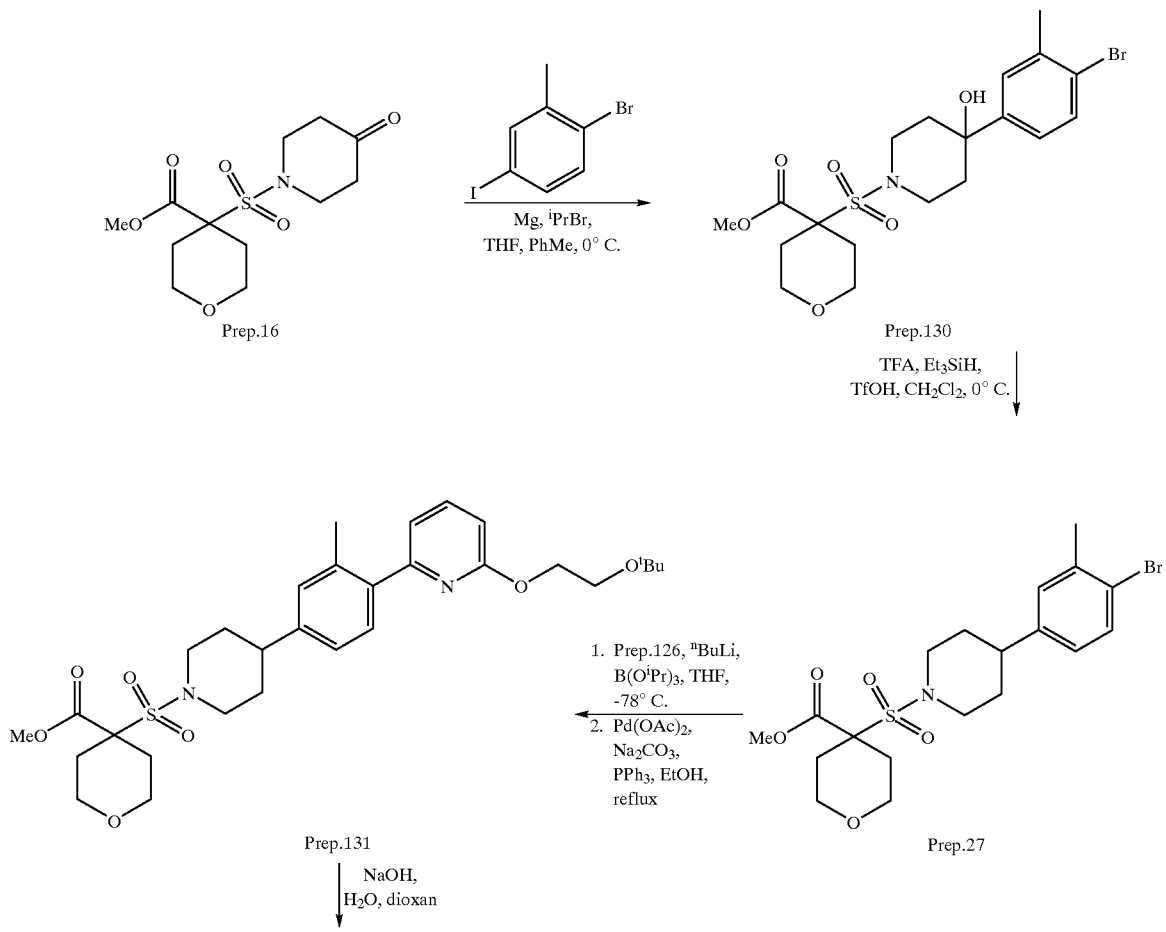

-continued

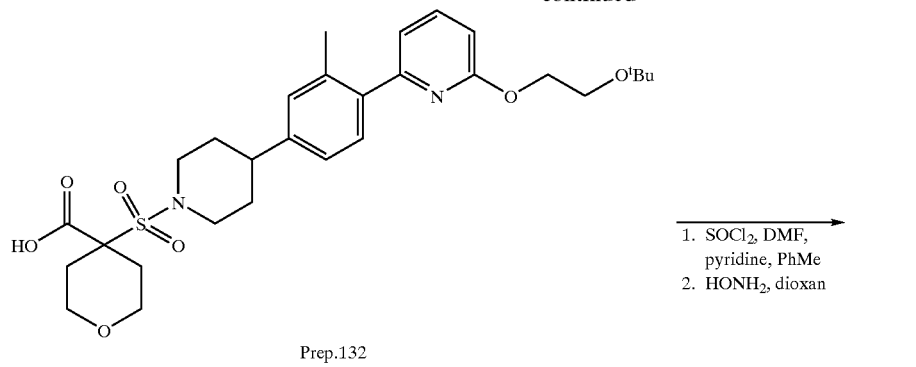

Prep.132

1. SOCl₂, DMF, pyridine, PhMe
2. HONH₂, dioxan

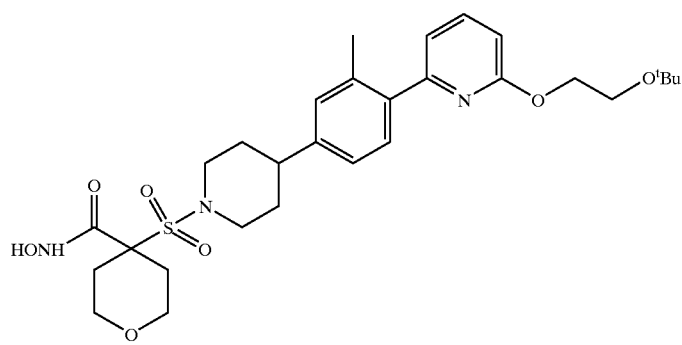

Prep.133

HCl, CH₂Cl₂, r.t.

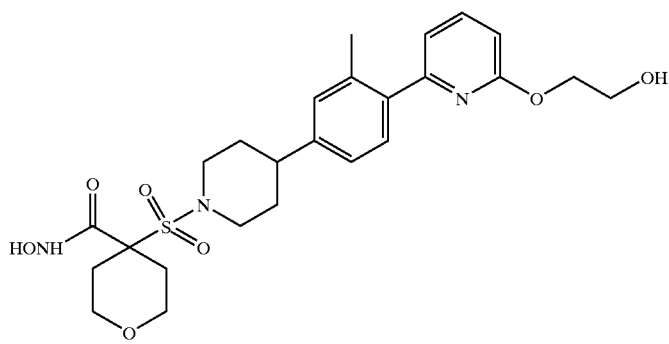

Example 3

An example of a suitable NH-protecting group is the t-butoxycarbonyl (Boc) group. This group can be introduced in standard ways, such as those delineated in the Examples and Preparations section below. After the hydroxamic acid unit has been introduced, the Boc group can be removed for example by treatment of the N-Boc compound in methanol or dichloromethane saturated with HCl gas, at room temperature for 2 to 4 hours.

Compounds of formula (I) where $R^1$ and/or $R^2$, either independently or together, contain a free NH, NH₂ and/or OH group (apart from on the hydroxamic acid moiety) may conveniently be prepared from a corresponding N- and/or O-protected species (XII below). As such, compounds of formula (XII) where $R^{1p}$ and/or $R^{2p}$ is a O- and/or N-protected version of a corresponding compound of the formula (I), are included in the scope of this invention, with regard to aspects A, B, C and D of the invention and the specific compounds of formula (I) mentioned herein, such as those compounds of formula (XII) mentioned in the Preparations, as appropriate, below. Suitable protection/deprotection regimes are well known in the art, such as those mentioned in "Protective Groups in Organic Synthesis" by T W Greene and P G M Wuts, John Wiley & Sons Inc (1999).

Suitable OH-protecting groups and regimes include the ethers such as t-butyloxy, tri($C_{1-4}$)silyloxy, etc., and esters such as carbonates, sulphonates, $C_{1-4}$ acylates, etc. mentioned by Greene and Wuts, ibid. chapter 2. Suitable NH-protecting groups and regimes can be found in Greene and Wuts, ibid. chapter 7, and include amides such as "Boc", amines such as benzyl, etc.

Compounds of formula (XII) may be made by methods described herein and/or by variation of methods described herein which the skilled man will appreciate are routine variations.

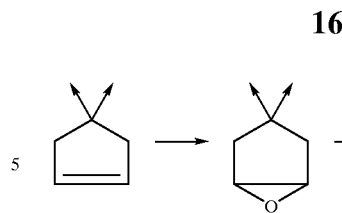

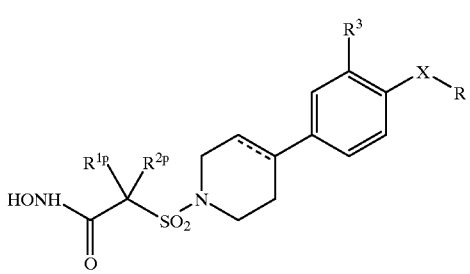
(XII)

An example of a suitable OH-protecting group is the trimethylsilyl (TMS) group and the protection, reaction, deprotection sequence can be summarised by steps a) to c) below:

a) ClSiMe$_3$ (1.1 equiv per OH), WSCDI (1.1 to 1.2 equiv), HOBT or HOAT (1 to 1.1 equiv), b) NH$_2$OH.HCl (3 equiv) in DMF/pyridine or CH$_2$Cl$_2$/pyridine (3/1 to 1/1) at rt for between 4 and 20 hours.

c) TMS group removed by acid work-up.

Another example of a suitable OH-protecting group is the t-butyl ($^t$Bu) group which can be carried through the synthetic process and removed in the last step of the process. An example of the route is outlined in the scheme below (in relation to the synthesis of the compound of Example 3—via compounds of the Preparations mentioned below).

An example of a suitable NH-protecting group is the t-butoxycarbonyl (Boc) group. This group can be introduced in standard ways, such as those delineated in the Examples and Preparations section below. After the hydroxamic acid unit has been introduced, the Boc group can be removed for example by treatment of the N-Boc compound in methanol or dichloromethane saturated with HCl gas, at room temperature for 2 to 4 hours.

An extension of the above is where the compound of formula (I) contains a free, OH, NH and/or NH$_2$ group in R$^1$, R$^2$ and R (e.g. some Examples below). In those case a suitable precursor could be the compound of formula (XIII) below:

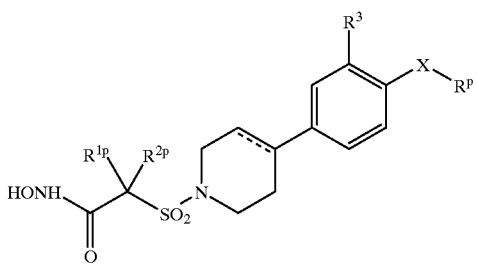
(XIII)

where the substituents are as previously defined

Compounds of formula (I) and appropriate intermediates thereto where R$^1$ and R$^2$ are taken together as 3,4-dihydroxycyclopentylidene can be made via the corresponding intermediary of a corresponding cyclopent-3-enylidene moiety, viz.:

Cyclopentylidene intermediates can be epoxidised to give the corresponding epoxide using standard methods. The epoxide can be reacted in a number of different methods to give the diol product. By suitable choice of reagents, conditions etc., the skilled chemist can make diols with any desired stereochemistry, using well-known methods.

As such, compounds of the formula (VIII) and (IX) below are included in the scope of the invention, with regard to aspects A, B, C and D and also with respect to intermediates to appropriate individual compounds of formula (I) mentioned herein.

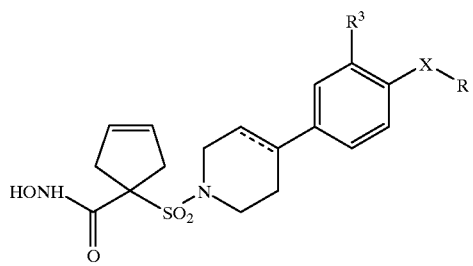
(VIII)

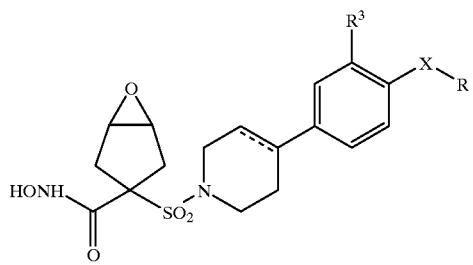
(IX)

Also included in the invention are intermediates of formula (X) and (XI, where R$^p$ is defined as above for compounds of formula (VII) wherein P and P$^1$ represent standard OH and 1,2-diol protecting groups mentioned in Greene and Wuts, ibid., chapter 2. P and P$^1$ are preferably taken together and form an acetonide moiety.

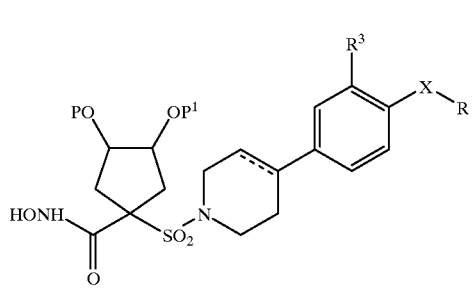
(X)

(XI)

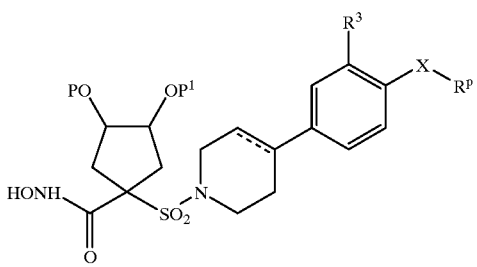

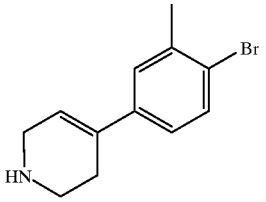

Certain specific compounds of formulae (VIII), (IX), (X) and (XI) are mentioned in the Preparations below.

Moreover, persons skilled in the art will be aware of variations of, and alternatives to, those processes described herein, including in the Examples and Preparations sections, which allow the compounds defined by formula (I) to be obtained, such as carrying out certain bond-forming or functional group interconversion reactions in different sequences.

Examples of the preparation of a number of intermediates and final compounds are outlined in the following synthetic schemes, where the abbreviations used are standard and well-known to the person skilled in the art. Routine variation of these routes can give all the required compounds of the invention.

Route 1 (Pyridyl alcohols)

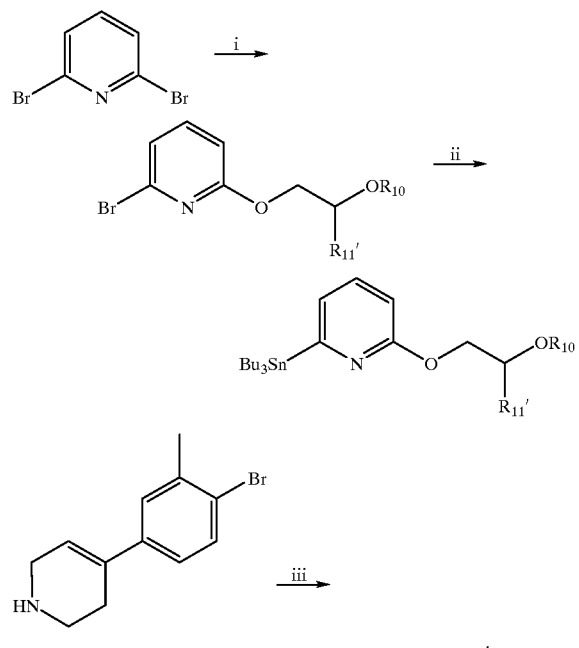

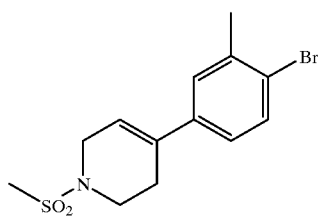

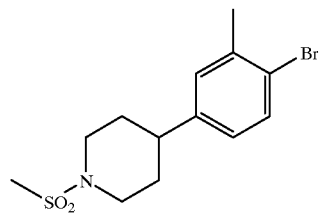

i=NaH (1.1 equiv), HOCH₂CHR11'OR10 (1 equiv) in toluene, reflux for 2 to 5 hours ii=n-BuLi(1.1 equiv), Bu₃SnCl (1.1 equiv), THF, −70° C. to room temperature. Or, Pd(PPh₃)₄ (0.01 to 0.05 equiv), [SnMe₃]₂ (1.1 equiv), dioxan, reflux for 2 to 5 hrs.

iii=BSA (0.5 equiv), MeCO₂CH₂SO₂Cl (1.2 equiv), THF, rt for 18 hours.

iv=MeSO₂Cl (1.2 equiv), Et₃N (1.4 equiv), CH₂Cl₂, rt, for an hour.

v=Et₃SiH (3 equiv), CF₃SO₃H (0.1 equiv), TFA:CH₂Cl₂ (1:1), rt, for 1–24 hrs.

vi=NaH (2 equiv), Me₂CO₃ (4 equiv), toluene, reflux for 2 hours.

R10-alcohol protecting group—e.g. benzyl or dioxalane (for diols)

R11'—H or a protected alcohol

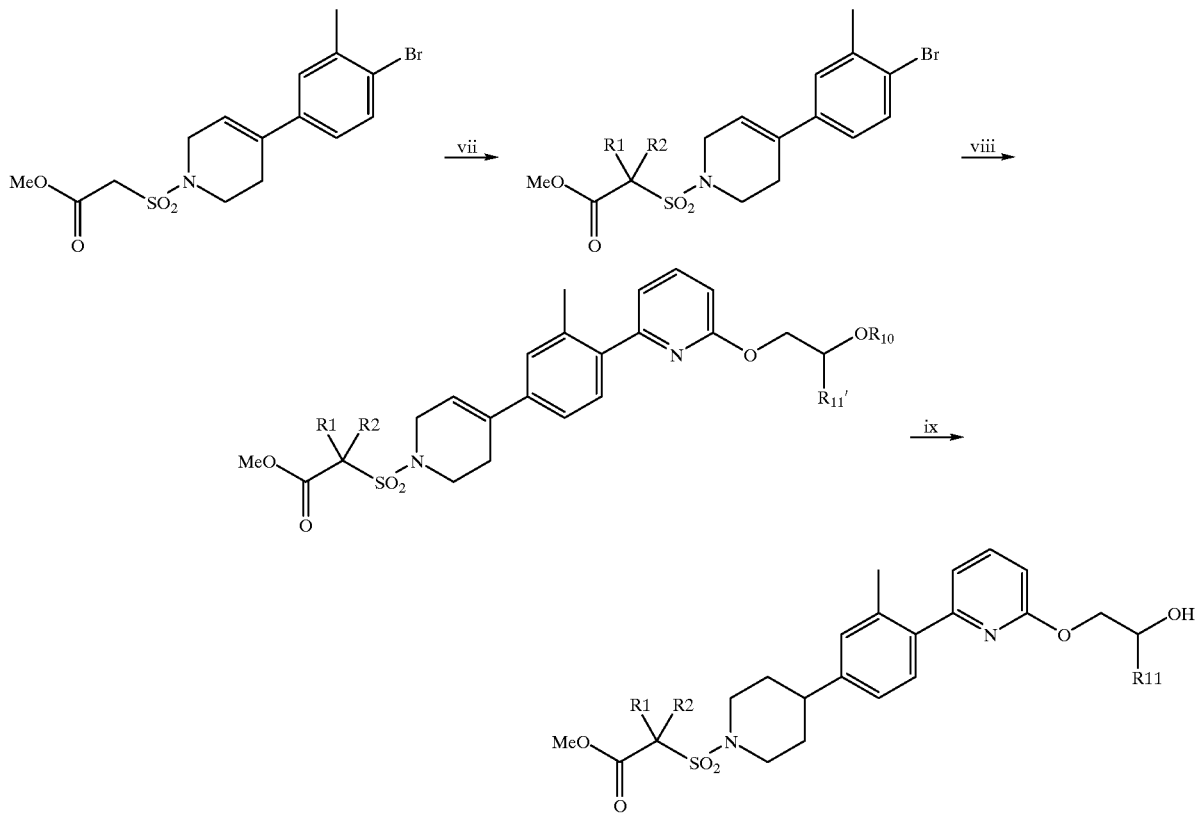

vii=(VB), (1.3 equiv), K$_2$CO$_3$ (3 equiv), DMSO, rt, 18–24 hours, or KOtBu (2.5 equiv), (VA) or (VB) (excess), in THF, rt for 72 hours.

viii=Stille coupling-Pd(PPh$_3$)$_4$ (0.05 equiv), stannane (1.5 equiv), toluene, reflux for 4 to 20 hours OR PdCl$_2$(PPh$_3$)$_2$ (0.05 equiv), stannane(1.1 equiv), THF, reflux for 17 hours.

ix=NH$_4^+$HCO$_3^-$(excess)Pd(OH)$_2$/C, AcOH, MeOH, reflux for 20 hours, OR 10% Pd/C, in MeOH or EtOH, 3.3 atmospheres, room temperature, for 6 to 17 hours,—both methods also deprotect any benzyl group. (2N HCl, dioxan (3:1), rt, 75 mins at rt—deprotects the dioxalane)

OR Pd(OH)$_2$/C, NH$_4^+$HCO$_3^-$(excess), in MeOH:dioxan (2.5:1), 60° C. for 2 hours.

R11=H or deprotected alcohol

Similarly when R1R2 when taken together, are a piperidine group:

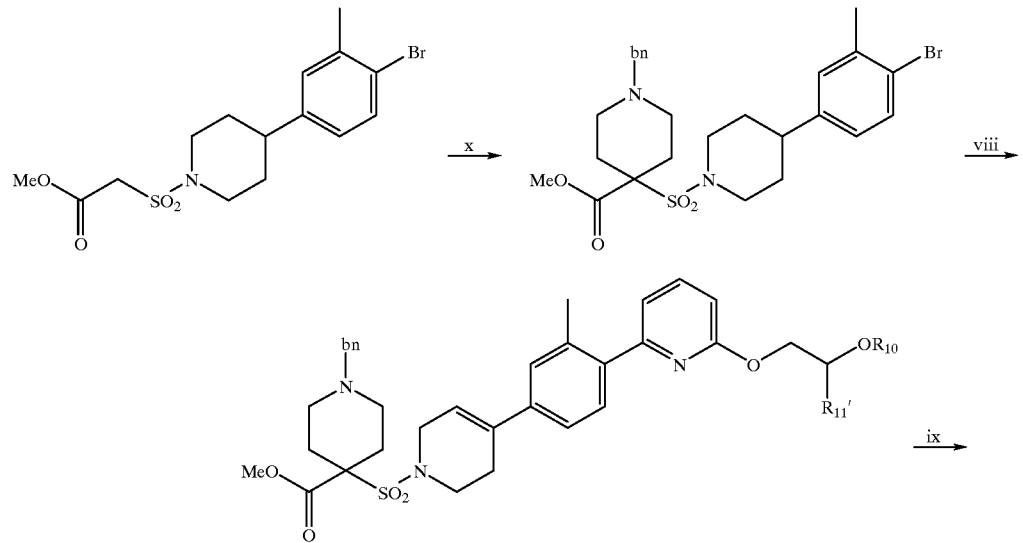

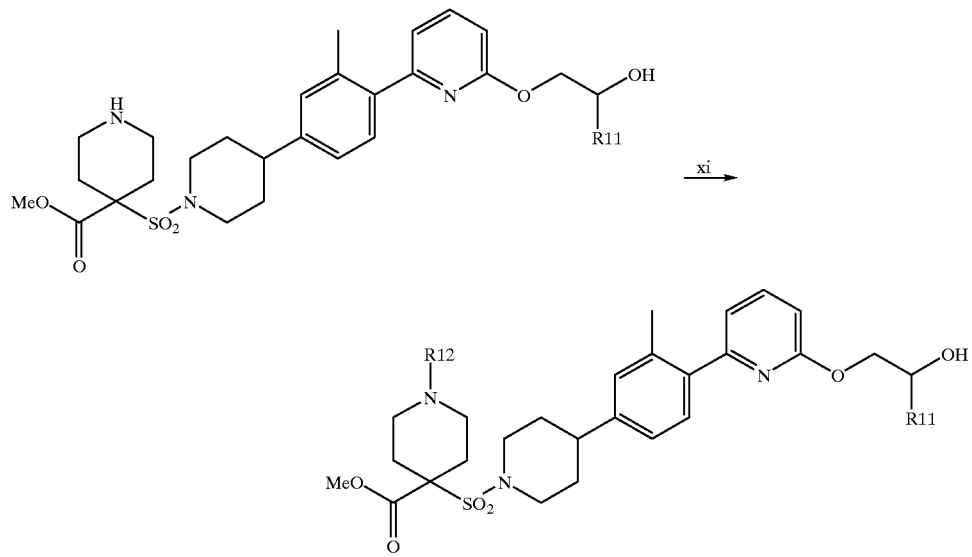
x=NaH (3 equiv), tetra-nBuNH₄Br (1 equiv), BnN(CH₂CH₂Cl)₂ (0.95 equiv), NMP, 60° C. for 6 hours.
xi=When R12 is Me, formaldehyde(4 equiv), Na(OAc)₃BH (2 equiv), CH₂Cl₂, 20 hrs at rt.
When R12 is Boc, (Boc)₂O (1.05 equiv), Et₃N (1.1 equiv), CH₂Cl₂, rt for an hour.
Route 2 (Phenyl alcohols)
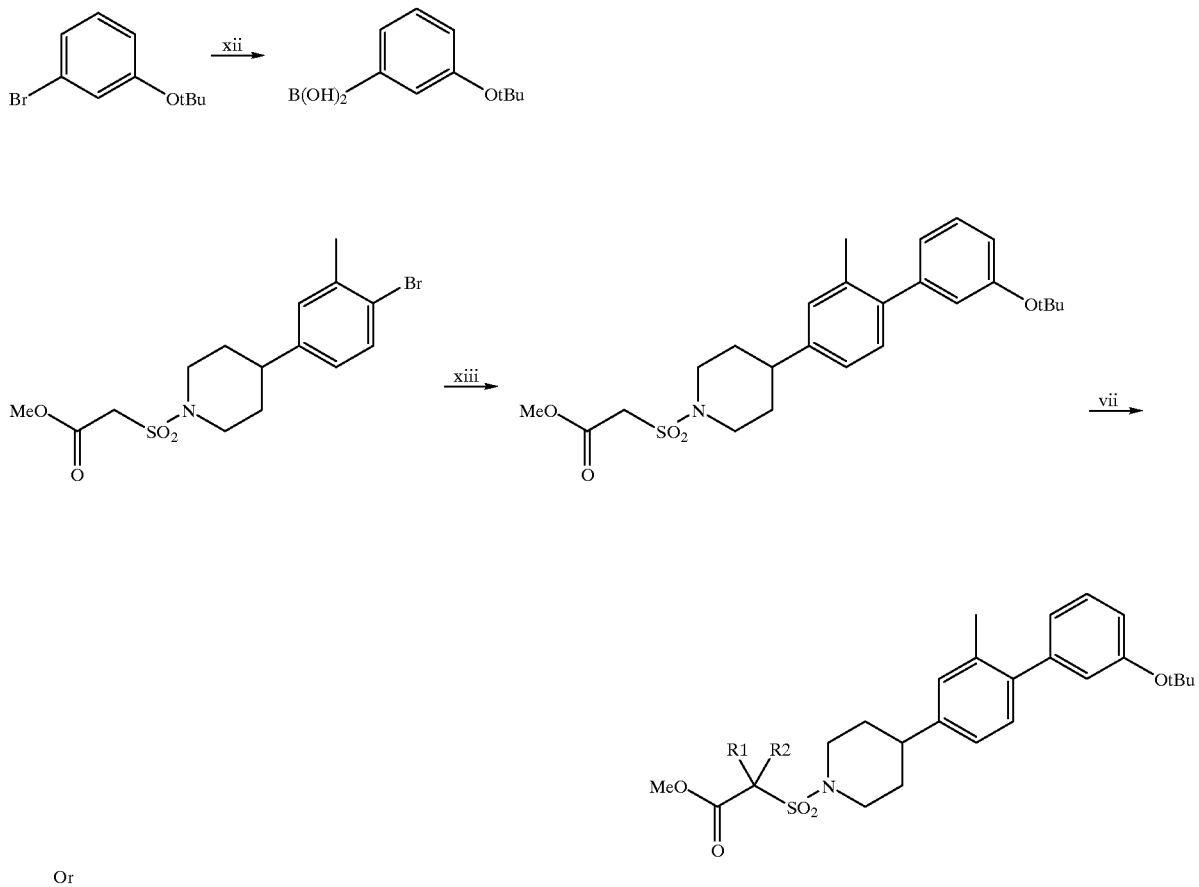
Or

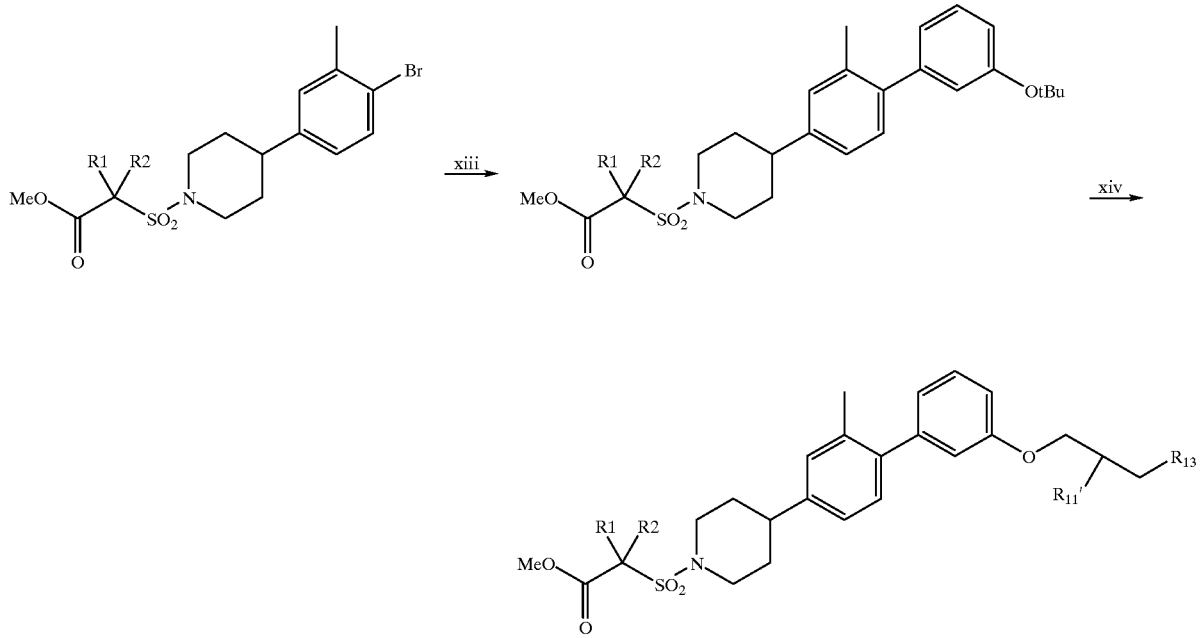

xii=nBuLi (1.1 equiv), B[OCH(CH₃)₂]₃ (1.5 equiv), THF, −70° C. to rt.

xiii=Suzuki coupling-arylboronic acid (1.2 to 1.5 equiv), CsF(2 to 2.6 equiv), P(o-tol)₃ (0.1 equiv), Pd₂(dba)₂ (0.005 equiv), DME, reflux for 6 to 50 hours.

xiv=Et₃SiH (3 equiv), TFA:CH₂Cl₂ (1:1), rt for 2 to 24 hours.

xv=R/S glycidol (1 equiv), Et₃N (catalytic), MeOH, reflux for 20 hours. OR, Mitsunobu reaction -DEAD (1.5 equiv), PPh₃ (1.5 equiv), HOCH(R11')CH₂OR13' (1.5 equiv) in THF, rt for 3 hours.

R11' is H or optionally protected alcohol and R13' is optionally protected alcohol For preparation 50 to 51, requires Bn deprotection using the conditions described in ix.

Alternative route

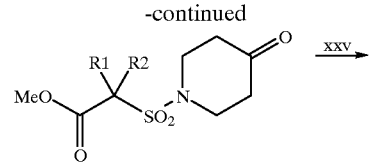

-continued

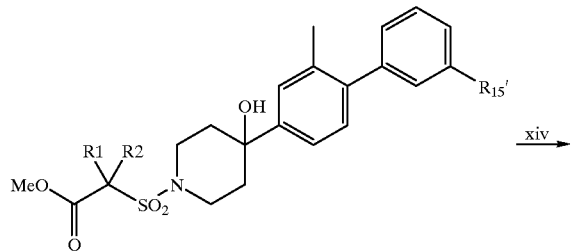

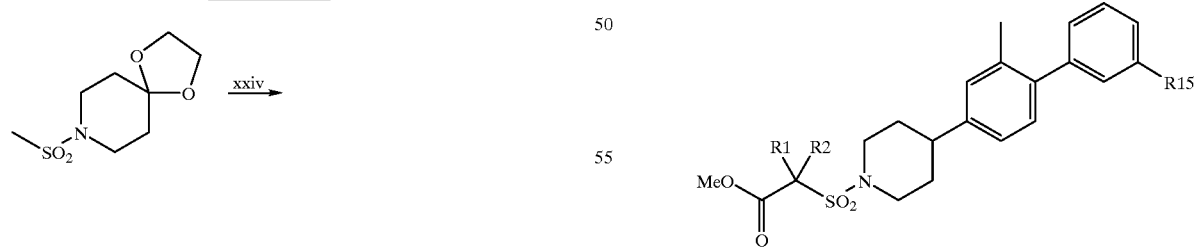

xxiv=i-NaH (2.2 equiv), Me₂CO₃ (5 equiv), toluene, MeOH (catalytic), 90° C., overnight. ii-O(CH₂CH₂Br)₂ (1.3 equiv), NMP, 90° C., 20 hrs.

xxv=Grignard reagant (1.1 equiv), THF, −78° C. to rt over approx hr.

R15'-optionally protected alcohol, in prep 48 this is a t-butyl ether.

R15—OH, for prep 48.

Route 3 (Phenyl aminoalcohols)
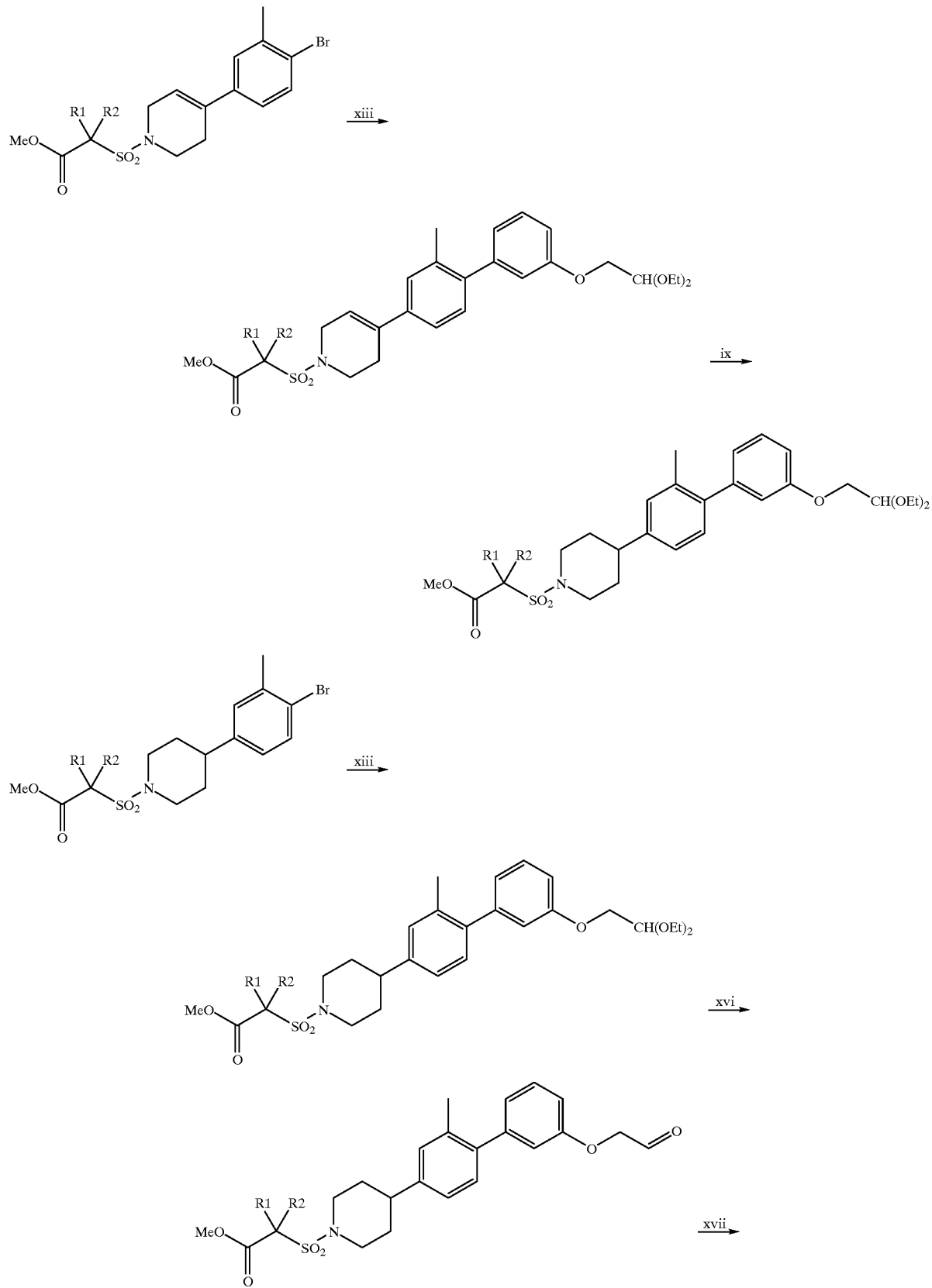

-continued

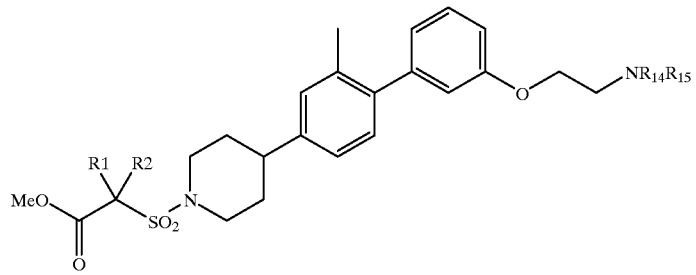

When R15 is a protecting group, eg. benzyl, deprotection, followed by protection using an alternative group eg Boc, can be used as shown below:

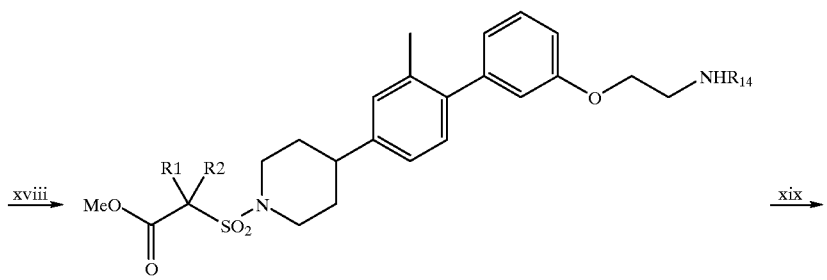

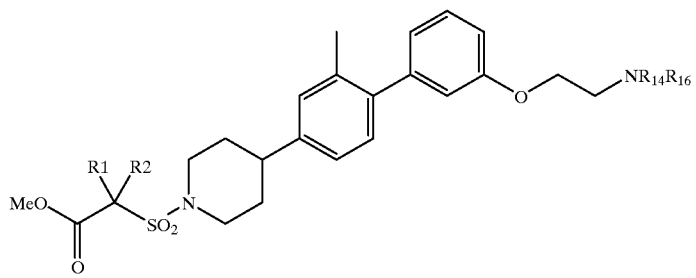

- xvi=1N HCl (1 to 2.3 equiv), acetone:dioxan (1:1), 70° C. for 2 to 6 hours.
- xvii=Reductive amination-amine (5.5 equiv), Na(OAc)$_3$BH (3 to 4 equiv), CH$_2$Cl$_2$, rt, overnight.
- xviii=Pd(OH)$_2$/C, MeOH, 50 psi, rt, 18 hrs.
- xix=When R16 is Boc, (Boc)$_2$O (1 to 1.1 equiv), Et3N (optional, 1 equiv), DMAP (optional, cat), CH$_2$Cl$_2$, rt, 3 hrs.

Roure 4 (aminoalkyl phenyls)

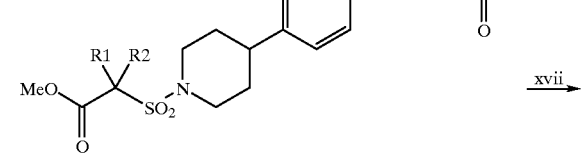

-continued

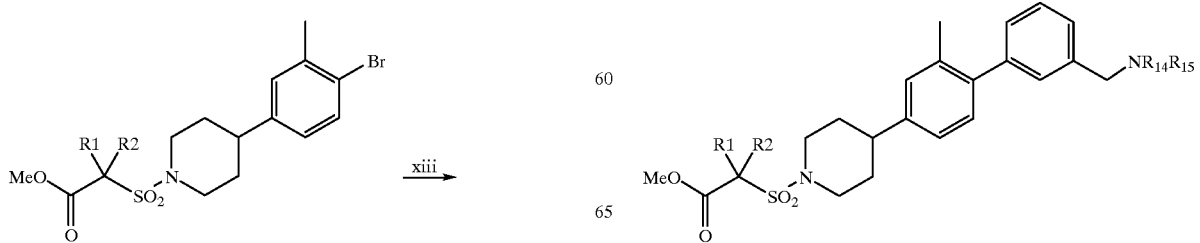

-continued
Route 5 (Heterocyles)
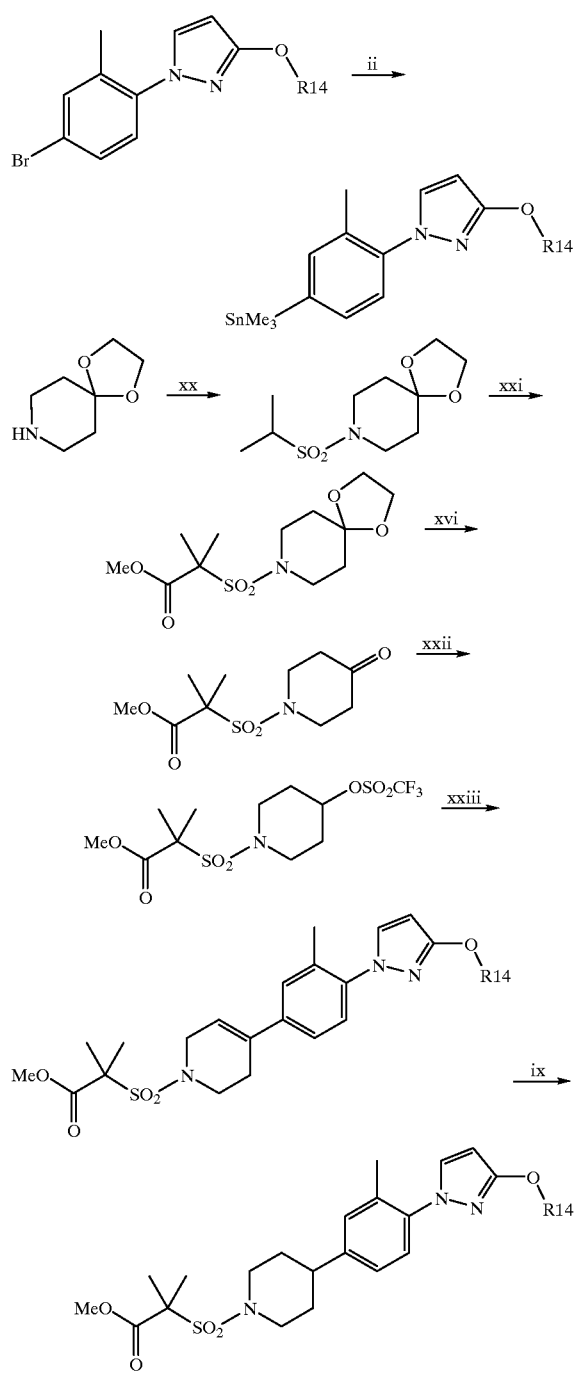
xx=iso-PrSO₂Cl (1 equiv), Et₃N (1.1 equiv), CH₂Cl₂, 3 hours at rt.
xxi=n-BuLi (1.1 equiv), MeOCOCl (1.2 equiv), THF −78° to rt.
xxii=2,6-di-t-Bu-4-Me pyridine (2.5 equiv), (CF₃SO₂)₂O (2.5 equiv), CH₂Cl₂, 4° C. to rt, 5 days.
xxiii=Pd₂(dba)₃ (0.02 equiv), vinyl triflate (1.1 equiv), Ph₃As (0.21 equiv), CuI (0.1 equiv) in NMP, 75° C. for 5 hrs.
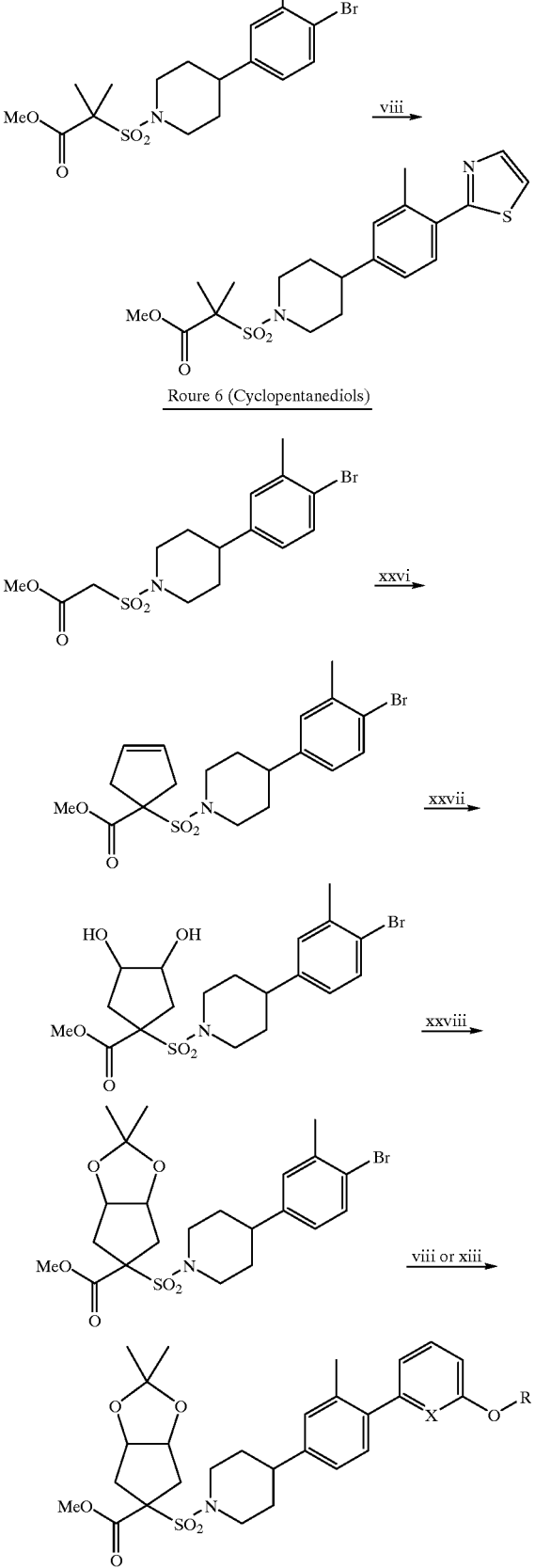
Route 6 (Cyclopentanediols)

xxvi=NaH (1.1 equiv), tetra-nBuNH$_4$Br (1 equiv), ClCH$_2$CHCHCH$_2$Cl (1.1 equiv), NMP, r.t for 3 hours, then NaH (1.1 equiv), 2 days.

xxvii=NMO (1.1 equiv), OsO$_4$ (3 mol%), dioxan/water, r.t. 18 hours OR
  (a) AgOAc (2.3 equiv), AcOH, r.t for 18 hours (b) 1N NaOH, dixoan/water xxviii=2,2-Dimethoxypropane (2 equiv), TsOH (0.1 equiv), DMF, 50° C. for 4.5 hours.

Biological Test Methods

The biological activities of the compounds of the present invention were determined by the following test methods, which are based on the ability of the compounds to inhibit the cleavage of various fluorogenic peptides by MMPs 1, 2, 3, 9, 13 and 14.

The assays for MMPs 2, 3, 9 and 14 are based upon the original protocol described in Fed. Euro. Biochem. Soc., 1992, 296, 263, with the minor modifications described below.

Inhibition of MMP-1

Enzyme Preparation

Catalytic domain MMP-1 was prepared in Pfizer Central Research laboratories in a standard manner from sources known to the skilled person, including some of the references mentioned herein. A stock solution of MMP-1 (1 μM) was activiated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM CaCl$_2$, 20 μM ZnSO$_4$ and 0.05% Brij 35, pH 7.5) to a concentration of 10 nM. The final concentration of enzyme used in the assay was 1 nM.

Substrate

The fluorogenic substrate used in this assay was Dnp-Pro-β-cyclohexyl-Ala-Gly-Cys(Me)-His-Ala-Lys-(N-Me-Ala)-NH$_2$ as originally described in Anal. Biochem., 1993, 212, 58. The final substrate concentration used in the assay was 10 μM.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG LabTechnologies, Aylesbury, UK) at an excitation wavelength of 355 nm and emission wavelength of 440 nm. The potency of inhibition was measured from the amount of substrate cleavage obtained using a range of test compound concentrations and, from the resulting dose-response curve, an IC$_{50}$, value (the concentration of inhibitor required to inhibit 50% of the enzyme activity) was calculated.

Inhibition of MMP-2, MMP-3 and MMP-9

Enzyme Preparation

Catalytic domains MMP-2, MMP-3 and MMP-9 were prepared in Pfizer Central Research laboratories in a standard manner from sources known to the skilled person, including some of the references mentioned herein. A stock solution of MMP-2, MMP-3 or MMP-9 (1 μM) was activated by the addition of APMA. For MMP-2 and MMP-9, a final concentration of 1 mM APMA was added, followed by incubation for 1 hour at 37° C. MMP-3 was activated by the addition of 2 mM APMA, followed by incubation for 3 hours at 37° C. The enzymes were then diluted in Tris-HCl assay buffer (100 mM Tris, 100 mM NaCl, 10 mM CaCl$_2$ and 0.16% Brij 35, pH 7.5) to a concentration of 10 nM. The final concentration of enzyme used in the assays was 1 nM.

Substrate

The fluorogenic substrate used in this screen was Mca-Arg-Pro-Lys-Pro-Tyr-Ala-Nva-Trp-Met-Lys(Dnp)-NH$_2$ (Bachem Ltd., Essex, UK) as originally described in J. Biol. Chem., 1994, 269, 20952. This substrate was selected because it has a balanced hydrolysis rate against MMPs 2, 3 and 9 ($k_{cat}/k_m$ of 54,000, 59,400 and 55,300 s$^{-1}$ M$^{-1}$ respectively). The final substrate concentration used in the assay was 5 μM.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C., prior to determination of fluorescence using a fluorimeter (Fluostar; BMG LabTechnologies, Aylesbury, UK) at an excitation wavelength of 328 nm and emission wavelength of 393 nm. The potency of inhibition was measured from the amount of substrate cleavage obtained using a range of test compound concentrations and, from the resulting dose-response curve, an IC$_{50}$ value (the concentration of inhibitor required to inhibit 50% of the enzyme activity) was calculated.

Inhibition of MMP-13

Enzyme Preparation

Human recombinant MMP-13 was prepared by PanVera Corporation (Madison, Wis.) and characterised at Pfizer Central Research laboratories. A 1.9 mg/ml stock solution was activated with 2 mM APMA for 2 hours at 37° C. MMP-13 was then diluted in assay buffer (50 mM Tris, 200 mM NaCl, 5 mM CaCl$_2$, 20 μM ZnCl$_2$ and 0.02% Brij 35, pH 7.5) to a concentration of 5.3 nM. The final concentration of enzyme used in the assay was 1.3 nM.

Substrate

The fluorogenic substrate used in this screen was Dnp-Pro-Cha-Gly-Cys(Me)-His-Ala-Lys(NMA)-NH$_2$. The final substrate concentration used in the assay was 10 μM.

Determination of Enzyme Inhibition

The test compound was dissolved in dimethyl sulphoxide and diluted with assay buffer so that no more than 1% dimethyl sulphoxide was present. Test compound and enzyme were added to each well of a 96 well plate. The addition of substrate to each well initiated the reaction. Fluorescence intensity was determined using a 96 well plate fluorimeter (Cytofluor II; PerSeptive Biosystems, Inc., Framingham, Mass.) at an excitation wavelength of 360 nm and emission wavelength of 460 nm. The potency of inhibition was measured from the amount of substrate cleavage obtained using a range of test compound concentrations and, from the resulting dose-response curve, an IC$_{50}$ value (the concentration of inhibitor required to inhibit 50% of the enzyme activity) was calculated.

Inhibition of MMP-14

Enzyme Preparation

Catalytic domain MMP-14 was prepared in Pfizer Central Research laboratories in a standard manner from sources known to the skilled person, including some of the references mentioned herein. A 10 μM enzyme stock solution was activated for 20 minutes at 25° C. following the addition of 5 μg/ml of trypsin (Sigma, Dorset, UK). The trypsin activity was then neutralised by the addition of 50 µg/ml of soyabean trypsin inhibitor (Sigma, Dorset, UK), prior to dilution of this enzyme stock solution in Tris-HCl assay buffer (100 mM Tris, 100 mM NaCl, 10 mM $CaCl_2$, 0.16% Brij 35, pH 7.5) to a concentration of 10 nM. The final concentration of enzyme used in the assay was 1 nM.

Substrate

The fluorogenic substrate used in this screen was Mca-Pro-Leu-Gly-Leu-Dpa-Ala-Arg-$NH_2$ (Bachem Ltd., Essex, UK) as described in J. Biol. Chem., 1996, 271, 17119.

Determination of enzyme inhibition

This was performed in the same manner as described for MMPs 2, 3 and 9.

For use in mammals, including humans, the compounds of formula (I) or their salts or solvates of such compounds or salts, can be administered alone, but will generally be administered in admixture with a pharmaceutically or veterinarily acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. The compound or salt could be incorporated into capsules or tablets for targetting the colon or duodenum via delayed dissolution of said capsules or tablets for a particular time following oral administration. Dissolution could be controlled by susceptibility of the formulation to bacteria found in the duodenum or colon, so that no substantial dissolution takes places before reaching the target area of the gastrointestinal tract. The compounds or salts can be injected parenterally, for example, intravenously, intramuscularly or subcutaneously. For parenteral administration, they are best used in the form of a sterile aqueous solution or suspension which may contain other substances, for example, enough salt or glucose to make the solution isotonic with blood. They can be administered topically, in the form of sterile creams, gels, suspensions, lotions, ointments, dusting powders, sprays, drug-incorporated dressings or via a skin patch. For example they can be incorporated into a cream consisting of an aqueous or oily emulsion of polyethylene glycols or liquid paraffin, or they can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly as an eye drop with appropriate buffers, viscosity modifiers (e.g. cellulose derivatives), preservatives (e.g. benzalkonium chloride (BZK)) and agents to adjust tenicity (e.g. sodium chloride). Such formulation techniques are well-known in the art. In some instances the formulations may advantageously also contain an antibiotic. All such formulations may also contain appropriate stabilisers and preservatives.

For veterinary use, a compound of formula (I), or a veterinarily acceptable salt thereof, or a veterinarily acceptable solvate of either entity, is administered as a suitably acceptable formulation in accordance with normal veterinary practice and the veterinary surgeon will determine the dosing regimen and route of administration which will be most appropriate for a particular animal.

Reference to treatment includes prophylaxis as well as alleviation of established conditions, or the symptoms thereof.

For oral and parenteral administration to animal (inc. human) patients, the daily dosage level of the compounds of formula (I) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

For topical administration to animal (inc. human) patients with chronic wounds, the daily dosage level of the compounds, in suspension or other formulation, could be from 0.001 to 30mg/ml, preferably from 0.01 to 10 mg/ml.

The physician or veterinary surgeon in any event will determine the actual dosage which will be most suitable for a an individual patient and it will vary with the age, weight and response of the particular patient. The above dosages are exemplary of the average case; there can of course be individual instances where higher or lower dosage ranges are merited, and such are within the scope of this invention.

Thus the invention provides a pharmaceutical composition comprising a compound of formula (I), or a pharmaceutically acceptable salt thereof, or solvate thereof, together with a pharmaceutically acceptable diluent or carrier.

The invention also provides a compound of formula (I), or a pharmaceutically acceptable salt thereof, or solvate thereof, or a pharmaceutical composition containing any of the foregoing, for use as a human medicament.

In yet another aspect, the invention provides the use of a compound of formula (I), or a pharmaceutically acceptable salt thereof, in the manufacture of a human medicament for the treatment of a condition mediated by one or more MMPs.

Moreover, the invention provides the use of a compound of formula (I), or a pharmaceutically acceptable salt thereof, for the manufacture of a human medicament for the treatment of atherosclerotic plaque rupture, myocardial infarction, heart failure, restenosis, stroke, periodontal disease, tissue ulceration, wounds, skin diseases, cancer metastasis, tumour angiogenesis, age-related macular degeneration, fibrotic disease, rheumatoid arthritis, osteoarthritis and inflammatory diseases dependent on migratory inflammatory cells.

Additionally, the invention provides a method of treating a medical condition for which a MMP inhibitor is indicated, in an animal such as a mammal (including a human being), which comprises administering to said animal a therapeutically effective amount of a compound of formula (I), or a pharmaceutically acceptable salt thereof, or a pharmaceutically acceptable solvate of either entity, or a pharmaceutical composition containing any of the foregoing.

Still further, the invention provides a method of treating atherosclerotic plaque rupture, myocardial infarction, heart failure, restenosis, stroke, periodontal disease, tissue ulceration, wounds, skin diseases, cancer metastasis, tumour angiogenesis, age-related macular degeneration, fibrotic disease, rheumatoid arthritis, osteoarthritis and inflammatory diseases dependent on migratory inflammatory cells, in a animal (including a human being), which comprises administering to said animal a therapeutically effective amount of a compound of formula (I), or a pharmaceutically or veterinarily acceptable salt thereof, or a pharmaceutically acceptable solvate of either entity, or a pharmaceutical composition containing any of the foregoing.

Biological data

The compounds of Examples 3, 4, 5, 6, 7, 10 and 14 gave the following IC$_{50}$ values (in nM concentrations) in tests mentioned above:

| MMP-3 | MMP-2 | MMP-1 | MMP-14 | MMP-9 |
|---|---|---|---|---|
| <10 | >100 | >1000 | >2000 | >70 |

The syntheses of the compounds of the invention and of the intermediates for use therein are illustrated by the following Examples and Preparations.

EXAMPLES AND PREPARATIONS

Room temperature (rt) means 20 to 25° C. Flash chromatography refers to column chromatography on silica gel (Kieselgel 60, 230–400 mesh). Melting points are uncorrected. $^1$H Nuclear magnetic resonance (NMR) spectra were recorded using a Bruker AC300, a Varian Unity Inova-300 or a Varian Unity Inova-400 spectrometer and were in all cases consistent with the proposed structures. Characteristic chemical shifts are given in parts-per-million downfield from tetramethylsilane using conventional abbreviations for designation of major peaks: e.g. s, singlet; d, doublet; t, triplet; q, quartet; m, multiplet; br, broad. Mass spectra were recorded using a Finnigan Mat. TSQ 7000 or a Fisons Intruments Trio 1000 mass spectrometer. LRMS means low resolution mass spectrum and the calculated and observed ions quoted refer to the isotopic composition of lowest mass. Hexane refers to a mixture of hexanes (hplc grade) b.p. 65–70° C. Ether refers to diethyl ether. Acetic acid refers to glacial acetic acid. 1-Hydroxy-7-aza-1H-1,2,3-benzotriazole (HOAt), N-[(dimethylamino)-1H-1,2,3-triazolo[4,5-b]pyridin-1-ylmethylene]-N-methylmethaninium hexafluorophosphate N-oxide (HATU) and 7-azabenzotriazol-1-yloxytris(pyrrolidino)phosphonium hexafluorophosphate (PyAOP) were purchased from PerSeptive Biosystems U.K. Ltd. "Me" is methyl, "Bu" is butyl, "En" is benzyl. Other abbreviations and terms are used in conjunction with standard chemical practice.

Example 1

N-Hydroxy 2-[(4-{4-[6-(2-hydroxyethoxy)pyridin-2-yl]-3-methylphenyl}piperidin-1-yl)sulphonyl]-2-methylpropanamide

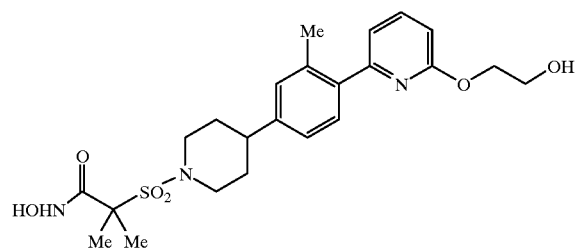

N,N-Dimethylformamide (10 ml) was added to a solution of the acid from preparation 70 (430 mg, 0.93 mmol) in pyridine (5 ml), followed by chlorotrimethylsilane (130 μl, 1.03 mmol) and the solution stirred for 1½ hours. 1-(3-Dimethylaminopropyl)-3-ethylcarbodiimide hydrochloride (215 mg, 1.11 mmol) and 1-hydroxybenzotriazole hydrate (130 mg, 0.93 mmol) were added, and the reaction stirred for a further 2 hours. Hydroxylamine hydrochloride (195 mg, 2.8 mmol) was then added, and the reaction stirred at room temperature overnight. The reaction mixture was acidified to pH 1 using 2N hydrochloric acid, stirred for an hour, and then the pH re-adjusted to pH 4. Water (50 ml) was added, the resulting precipitate filtered, washed with water and dried under vacuum. This solid was purified by column chromatography on silica gel using dichloromethane:methanol:0.88 ammonia (90:10:1) as eluant to afford the title compound as a white solid, (220 mg, 49%).

mp 137–140° C.; $^1$H nmr (DMSO-d$_6$, 300 MHz) δ: 1.50 (s, 6H), 1.61 (m, 2H), 1.80 (m, 2H), 2.36 (s, 3H), 2.68 (m, 1H), 3.05 (m, 2H), 3.72 (m, 4H), 4.25 (t, 2H), 4.79 (t, 1H), 6.76 (d, 1H), 7.05 (d, 1H), 7.17 (m, 2H), 7.35 (d, 1H), 7.76 (dd, 1H), 9.00 (s, 1H), 10.55 (s, 1H).

Example 2

N-Hydroxy 2-{[4-(4-{6-[2-(methoxy)ethoxy]pyridin-2-yl}-3-methylphenyl)piperidin-1-yl]sulphonyl}-2-methylpropanamide

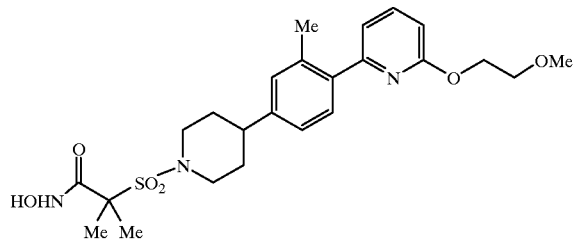

O-(7-Azabenzotriazol-1-yl)-N,N,N'N'-tetramethyluronium hexafluorophosphate (425 mg, 0.95 mmol) and N-ethyldiisopropylamine (150 μl, 0.70 mmol) were added to a solution of the acid from preparation 71 (300 mg, 0.63 mmol) in N,N-dimethylformamide (10 ml), and the solution stirred at room temperature for 30 minutes. Hydroxylamine hydrochloride (158 mg, 1.9 mmol) and additional N-ethyldiisopropylamine (410 μl, 1.9 mmol) were added, and the reaction stirred at room temperature overnight. The reaction mixture was diluted with water (20 ml), and pH 7 buffer solution (20 ml), and then extracted with ethyl acetate (3×30 ml). The combined organic extracts were washed with brine (3×), water (2×), then dried (MgSO$_4$), filtered and evaporated in vacuo. The residue was triturated with di-isopropyl ether to afford the title compound as an off-white solid, (220 mg, 71%).

mp 134–138° C.; $^1$H nmr (DMSO-d$_6$, 300 MHz) δ: 1.48 (s, 6H), 1.61 (m 2H), 1.80 (m, 2H), 2.36 (s, 3H), 2.66 (m, 1H), 3.05 (m, 2H), 3.28 (s, 3H), 3.62 (t, 2H), 3.78 (m, 2H), 4.38 (t, 2H), 6.78 (d, 1H), 7.06 (d, 1H), 7.16 (m, 2H), 7.35 (d, 1H), 7.76 (m, 1H). Anal. Found: C, 59.65; H, 7.12; N, 7.69. C$_{24}$H$_{33}$N$_3$O$_6$S;0.2i-Pr$_2$O requires C, 59.59; H, 7.04; N, 8.04%.

Example 3

N-Hydroxy 4-{[4-(4-{6-[2-hydroxyethoxy]pyridin-2-yl}-3-methylphenyl)piperidin-1-yl]sulphonyl}tetrahydro-2H-pyran-4-carboxamide

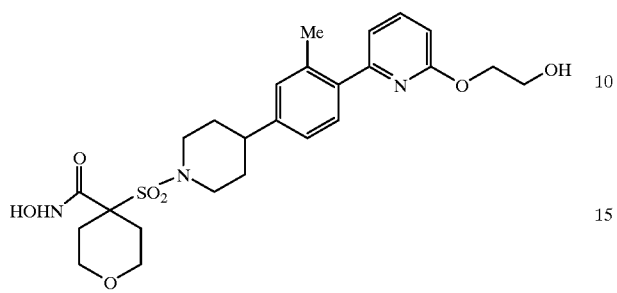

Chlorotrimethylsilane (2.1 ml, 16.46 mmol) was added to a solution of the acid from preparation 72 (7.55 g, 14.96 mmol) in N,N-dimethylformamide (150 ml), and pyridine (150 ml), and the solution stirred at room temperature under a nitrogen atmosphere for 1 hour. 1-(3-Dimethylaminopropyl)-3-ethylcarbodiimide hydrochloride (3.44 g, 17.95 mmol) and 1-hydroxy-7-azabenzotriazole (2.04 g, 14.96 mmol) were added, and stirring was continued for a further 45 minutes. Hydroxylamine hydrochloride (3.12 g, 44.8 mmol) was then added and the reaction stirred at room temperature for 72 hours. The reaction mixture was acidified to pH 2 using hydrochloric acid, stirred for 30 minutes, and the pH then re-adjusted to pH 4 using 1N sodium hydroxide solution. The mixture was extracted with ethyl acetate (3×), the combined organic extracts washed with brine, dried ($MgSO_4$), filtered and evaporated in vacuo. The residue was purified by column chromatography on silica gel using ethyl acetate as eluant, and recrystallised from methanol/ethyl acetate to afford the title compound as a white solid, (3.75 g, 48%).

mp 193–194° C.; $^1$H nmr (DMSO-$d_6$, 400 MHz) δ: 1.61 (m, 2H), 1.79 (m, 2H), 1.92 (m, 2H), 2.36 (m 5H), 2.62 (m, 1H), 3.01 (m, 2H), 3.19 (m, 2H), 3.70 (m, 4H), 3.82 (m, 2H), 4.25 (t, 2H), 4.75 (br, t, 1H), 6.70 (d, 1H), 7.01 (d, 1H), 7.12 (m, 2H), 7.30 (d, 1H), 7.62 (dd, 1H), 9.10 (s, 1H), 10.94 (s, 1H). LRMS: m/z 520 (M+1)$^+$; Anal. Found: C, 57.73; H, 6.39; N, 7.99. $C_{25}H_{33}N_3O_7S$ requires C, 57.79; H, 6.40; N, 8.09%.

Alternative route: Hydrogen chloride gas was bubbled through a solution of the tert-butyl ether from preparation 133 (3.0 g, 5.22 mmol) in anhydrous trifluoroacetic acid (30 ml) and dichloromethane (30 ml) for 10 minutes, then stirred at room temperature overnight. Nitrogen gas was bubbled through the reaction mixture for 1 hour and then 5N NaOH solution until the solution was pH6. The resulting precipitate was cooled to 0° C., filtered and washed with cold water. The resulting solid was dissolved in hot ethyl acetate (500 ml) and the organic layer was washed with water (3×250 ml) and brine (250 ml) and then dried ($Na_2SO_4$), filtered and concentrated in vacuo. On cooling to 0° C. overnight a solid formed and was filtered, washed with cold ethyl acetate and dried. The title compound was obtained as a beige solid (1.6 g, 60%).

Example 4

N-Hydroxy 4-{[4-(4-{6-[(2S)-2,3-dihydroxy-1-propoxy]pyridin-2-yl}-3-methylphenyl)piperidin-1-yl]sulphonyl}tetrahydro-2H-pyran-4-carboxamide

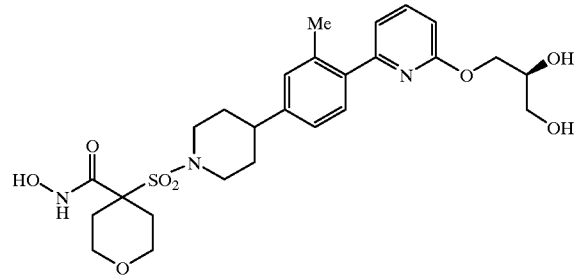

Chlorotrimethylsilane (168 μl, 1.32 mmol) was added to a solution of the acid from preparation 73 (318 mg, 0.60 mmol) in dichloromethane (6 ml), and pyridine (2 ml), and the solution stirred at room temperature under a nitrogen atmosphere for 1 hour. 1-(3-Dimethylaminopropyl)-3-ethylcarbodiimide hydrochloride (138 mg, 0.72 mmol) and 1-hydroxy-7-azabenzotriazole (90 mg, 0.66 mmol) were added, and stirring was continued for a further hour. Hydroxylamine hydrochloride (124 mg, 1.80 mmol) was added and the reaction stirred at room temperature for 2 hours. The reaction mixture was evaporated in vacuo, the residue dissolved in methanol, the solution acidified to pH 1 using hydrochloric acid (2M), then stirred for 10 minutes. The solution was diluted with water, the pH adjusted to 6, and the resulting precipitate filtered and dried. The solid was purified by column chromatography on silica gel using dichloromethane:methanol (90:10) as eluant, and recrystallised from methanol/di-isopropyl ether to give the title compound as a white solid, (200 mg, 60%).

$^1$H nmr (DMSO-$d_6$, 400 MHz) δ: 1.61 (m, 2H), 1.79 (m, 2H), 1.92 (m, 2H), 2.36 (m, 5H), 2.63 (m, 1H), 3.03 (m, 2H), 3.08–3.31 (m, 3H), 3.40 (m, 2H), 3.68–3.89 (m, 4H), 4.15 (m, 1H), 4.25 (m, 1H), 4.56 (br, s, 1H), 4.80 (br, s, 1H), 6.75 (d, 1H), 7.04 (d, 1H), 7.14 (m, 2H), 7.34 (d, 1H), 7.75 (m, 1H), 9.14 (s, 1H), 10.96 (s, 1H). LRMS: m/z 550 (M+1)$^+$; Anal. Found: C, 50.70; H, 6.00; N, 6.93. $C_{26}H_{35}N_3O_8S;0.6H_2O$ requires C, 50.97; H, 6.21; N, 6.86%.

Example 5

N-Hydroxy 4-{[4-(4-{6-[(2R)-2,3-dihydroxy-1-propoxy]pyridin-2-yl}-3-methylphenyl)piperidin-1-yl]sulphonyl}tetrahydro-2H-pyran-4-carboxamide

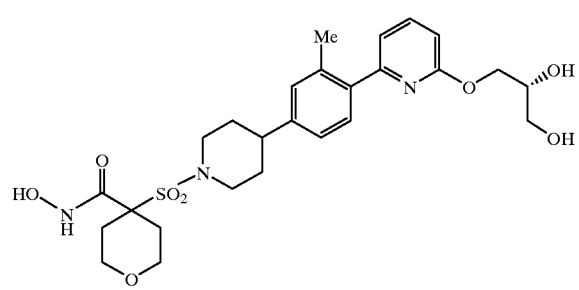

The title compound was prepared from the acid from preparation 74, following the procedure described in example 4. The crude product was purified by crystallisation from ethyl acetate to give an off-white solid (180 mg, 58%).

mp 125–130° C.; $^1$H nmr (DMSO-d$_6$, 400 MHz) δ: 1.60 (m, 2H), 1.78 (m, 2H), 1.90 (m, 2H), 2.36 (m, 5H), 2.64 (m, 1H), 3.02 (m, 2H), 3.20 (m, 2H), 3.40 (m, 2H), 3.72 (m, 2H), 3.78 (m, 1H), 3.83 (m, 2H), 4.14 (m, 1H), 4.24 (m, 1H), 4.55 (dd, 1H), 4.80 (d, 1H), 6.75 (d, 1H), 7.03 (d, 1H), 7.15 (m, 2H), 7.32 (d, 1H), 7.75 (m, 1H), 9.14 (s, 1H), 10.95 (s, 1H). LRMS: m/z 572 (M+23)$^+$; Anal. Found: C, 55.32; H, 6.57; N, 7.28. C$_{26}$H$_{35}$N$_3$O$_8$S;H$_2$O requires C, 55.02; H, 6.57; N, 7.40%.

Example 6

N-Hydroxy 4-{[4-(4-{6-[2-hydroxyethoxy]pyridin-2-yl}-3-methylphenyl)piperidin-1-yl]sulphonyl}-piperidine-4-carboxamide dihydrochloride

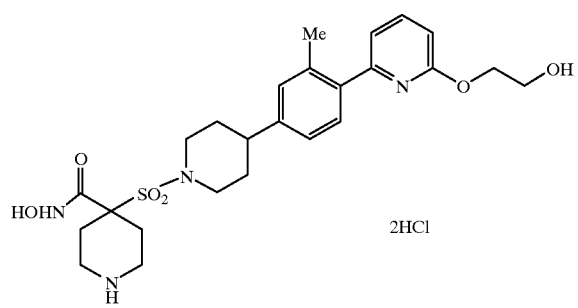

Hydrogen chloride gas was bubbled through an ice-cold solution of the hydroxamic acid from preparation 87 (135 mg, 0.22 mmol) in methanol (20 ml), and the solution was stirred at room temperature. The reaction mixture was evaporated in vacuo, and the residue azeotroped with methanol. The solid was recrystallised from methanol/ether to afford the title compound as a white solid, (88 mg, 64%).

$^1$H nmr (DMSO-d$_6$, 400 MHz) δ: 1.63 (m, 2H), 1.80 (m, 2H), 2.07 (m, 2H), 2.35 (s, 3H), 2.56–2.72 (m, 5H), 2.08 (m, 2H), 2.38 (m, 2H), 3.72 (m, 4H), 4.24 (t, 2H), 4.44–4.67 (br, s, 2H), 6.76 (d, 1H), 7.04 (d, 1H), 7.17 (m, 2H), 7.34 (d, 1H), 7.75 (m, 1H), 8.97 (m, 1H), 9.18 (m, 1H). LRMS: m/z 519 (M+1)$^+$.

Example 7

N-Hydroxy 4-{[4-(4-{6-[2-hydroxyethoxy]pyridin-2-yl}-3-methylphenyl)piperidin-1-yl]sulphonyl}-1-methyl-piperidine-4-carboxamide

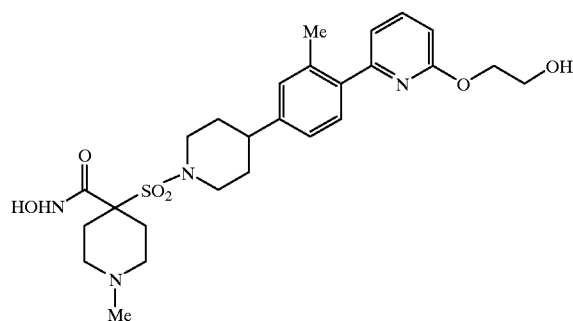

The title compound was prepared from the acid from preparation 75 and hydroxylamine hydrochloride following a similar procedure to that described in example 1. The reaction mixture was acidified to pH 2 using hydrochloric acid, this mixture stirred for 45 minutes, then basified to pH 8 using sodium hydroxide solution (2N). This solution was extracted with ethyl acetate (3x), the combined organic extracts washed with water, then brine, dried (Na$_2$SO$_4$), filtered and evaporated in vacuo. The residue was dried at 60° C., under vacuum to afford the title compound (39 mg, 8%).

$^1$H nmr (DMSO-d$_6$, 400 MHz) δ: 1.60 (m, 2H), 1.78 (m, 4H), 1.86 (m, 2H), 2.8 (s, 3H), 2.35 (s, 3H), 2.40 (m, 2H), 2.59–2.75 (m, 3H), 3.01 (m, 2H), 3.68 (m, 4H), 4.25 (t, 2H), 4.75 (t, 1H), 6.75 (d, 1H), 7.03 (d, 1H) 7.15 (m, 2H), 7.32 (d, 1H), 7.74 (m, 1H), 9.06 (br, s, 1H), 10.88 (br, s, 1H). LRMS: m/z 533 (M+1)$^+$; Anal. Found: C, 57.91; H, 6.82; N, 10.24. C$_{26}$H$_{36}$N$_4$O$_6$S;0.3H$_2$O requires C, 58.04; H, 6.86; N, 10.41%.

Example 8

N-Hydroxy 2-[4-(4-{3-[(2S)-2,3-dihydroxy-1-propoxy]phenyl}-3-methylphenyl)-piperidin-1-ylsulphonyl]-2-methylpropanamide

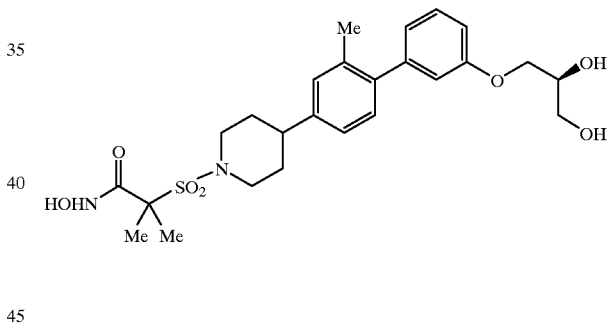

The title compound was prepared from the acid from preparation 77, following a similar procedure to that described in example 3. The crude product was recrystallised from methanol/di-isopropyl ether, to give the desired product (75 mg, 24%) as a white solid. The mother liquors were evaporated in vacuo, and purified by column chromatography on silica gel using an elution gradient of dichloromethane:methanol (98:2 to 95:5) to give an additional (38 mg, 12%) of the desired product.

mp 152–154° C.; $^1$H nmr (DMSO-d$_6$, 400 MHz) δ: 1.44 (s, 6H), 1.60 (m, 2H), 1.78 (m, 2H), 2.18 (s, 3H), 2.61 (m, 1H), 3.02 (m, 2H), 3.39 (m, 2H), 3.71 (m, 3H), 3.82 (m, 1H), 3.98 (m, 1H), 4.56 (m, 1H), 4.82 (m, 1H), 6.82 (m, 3H), 7.08 (m, 2H), 7.12 (s, 1H), 7.26 (m, 1H), 8.94 (s, 1H), 10.69 (s, 1H). LRMS: m/z 529 (M+23)$^+$; Anal. Found: C, 58.10; H, 6.70; N, 5.09. C$_{25}$H$_{34}$N$_2$O$_7$S;0.5MeOH requires C, 58.60; H, 6.94; N, 5.36%.

Example 9

N-Hydroxy 4-{4-[4-(3-[(2R)-2,3-dihydroxy-1-propoxy]phenyl)-3-methylphenyl]-piperidin-1-ylsulphonyl}-tetrahydro-(2H)-pyran-4-carboxamide

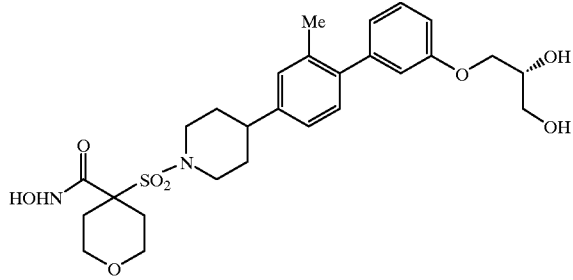

Chlorotrimethylsilane (45 μl, 0.37 mmol) was added to a solution of the acid from preparation 79 (90 mg, 0.17 mmol) in dichloromethane (2 ml), and pyridine (1 ml), and the solution stirred at room temperature under a nitrogen atmosphere for 1 hour. 1-(3-Dimethylaminopropyl)-3-ethylcarbodiimide hydrochloride (40 mg, 0.2 mmol) and 1-hydroxy-7-azabenzotriazole (26 mg, 0.19 mmol) were added, and stirring was continued for a further hour. Hydroxylamine hydrochloride (36 mg, 0.51 mmol) was then added and the reaction stirred at room temperature for a further 2 hours. The reaction mixture was diluted with methanol (5 ml), acidified to pH 1 using hydrochloric acid, and the mixture stirred vigorously for an hour. The mixture was extracted with dichloromethane (3×30 ml), the combined organic extracts dried ($Na_2SO_4$), filtered and evaporated. The residue was purified by column chromatography on silica gel using dichloromethane:methanol (90:10) as eluant to afford the title compound as an off-white solid, (40 mg, 43%).

mp 141–145° C.; $^1$H nmr (DMSO-$d_6$, 400 MHz) δ: 1.60 (m, 2H), 1.78 (m, 2H), 1.90 (m, 2H), 2.20 (s, 3H), 2.38 (m, 2H), 2.62 (m, 1H), 3.03 (m, 2H), 3.20 (m, 2H), 3.42 (m, 2H), 3.66–3.90 (m, 6H), 4.01 (m, 1H), 4.60 (m, 1H), 4.90 (m, 1H), 6.84 (m, 3H), 7.14 (m, 3H), 7.30 (m, 1H), 9.18 (s, 1H), 10.98 (1H, s). LRMS: m/z 571 (M+23)$^+$; Anal. Found: C, 59.22; H, 6.80; N, 5.11. $C_{27}H_{36}N_2O_8S$ requires C, 59.11; H, 6.61; N, 5.11%.

Example 10

N-Hydroxy 4-{4-[4-(3-{(2S)-2-hydroxy-2-hydroxymethyl}ethoxyphenyl)-3-methylphenyl]-piperidin-1-ylsulphonyl}-tetrahydro-2H-pyran-4-carboxamide

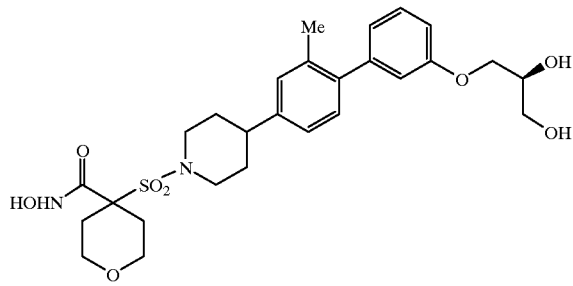

The title compound was prepared, from the acid from preparation 80, following a similar procedure to that described in example 9. The crude product was triturated with methanol/di-isopropyl ether, and the resulting precipitate filtered and dried to afford the title compound as a buff-coloured solid, (158 mg, 45%).

mp 132–134° C.; $^1$H nmr (DMSO-$d_6$, 400 MHz) δ: 1.60 (m, 2H), 1.78 (m, 2H), 1.90 (m, 2H), 2.20 (s, 3H), 2.38 (m, 2H), 2.62 (m, 1H), 3.02 (m, 2H), 3.20 (m, 2H), 3.42 (dd, 2H), 3.68–3.90 (m, 6H), 4.00 (m, 1H), 4.60 (t, 1H), 4.97 (d, 1H), 6.81 (m, 2H), 6.90 (m, 1H), 7.08 (s, 2H), 7.15 (s, 1H), 7.29 (dd, 1H), 9.14 (s, 1H), 10.98 (s, 1H).

Example 11

N-Hydroxy 4-{4-[4-(3-{1,3-dihydroxy-2-propoxyphenyl)-3-methylphenyl]-piperidin-1-ylsulphonyl}-tetrahydro-2H-pyran-4-carboxamide

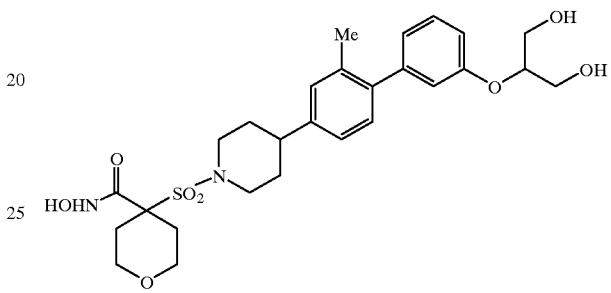

The title compound was obtained (25%) as a white solid, from the acid from preparation 78 and hydroxylamine hydrochloride, using a similar procedure to that described in example 9.

$^1$H nmr (DMSO-$d_6$, 400 MHz) δ: 1.60 (m, 2H), 1.79 (m, 2H), 1.90 (m, 2H), 2.20 (s, 3H), 2.39 (m, 2H), 2.62 (m, 1H), 3.02 (m, 2H), 3.20 (m, 2H), 3.57 (m, 4H), 3.70 (m, 2H), 3.84 (m, 2H), 4.24 (m, 1H), 4.78 (m, 2H), 6.82 (d, 1H), 6.90 (m, 2H), 7.14 (m, 3H), 7.28 (m, 1H), 9.18 (br, s, 1H). LRMS: m/z 570 (M+23)$^+$; Anal. Found: C, 56.98; H, 6.65; N, 5.15. $C_{27}H_{36}N_2O_8S;H_2O$ requires C, 57.22; H, 6.76; N, 4.94%.

Example 12

N-Hydroxy 2-{[4-(4-{3-[2-(methylamino)ethoxy]phenyl}-3-methylphenyl)-piperidin-1-yl]sulphonyl}-2-methylpropanamide hydrochloride

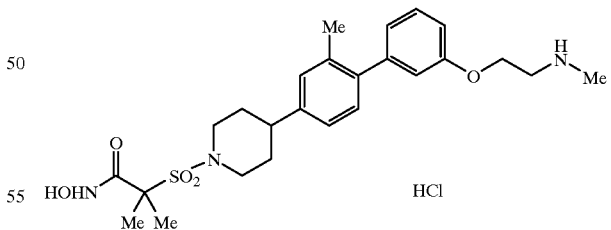

Dichloromethane saturated with hydrogen chloride (12 ml) was added to a solution of the hydroxamic acid from preparation 88 (120 mg, 0.2 mmol) in dichloromethane (1 ml), and the reaction stirred at room temperature for 4 hours. The resulting precipitate was filtered, then washed with, dichloromethane, ether, then dried under vacuum at 60° C., to afford the title compound as a solid, (90 mg, 85%).

mp 180–184° C.; $^1$H nmr (DMSO-$d_6$, 400 MHz) δ: 1.44 (s, 6H), 1.60 (m, 2H), 1.78 (m, 2H), 2.18 (s, 3H), 2.59 (m, 3H), 3.02 (m, 2H), 3.28 (m, 2H), 3.72 (m, 2H), 4.23 (t, 2H), 6.90 (m, 3H), 7.08 (s, 2H), 7.16 (s, 1H), 7.34 (m, 1H), 8.83 (br s, 2H), 10.80 (s, 1H). LRMS: m/z 490 (M+1)$^+$; Anal. Found: C, 54.25; H, 6.93; N, 7.44. $C_{25}H_{35}N_3O_5S;HCl;H_2O;0.1CH_2Cl_2$ requires C, 54.56; H, 6.97; N, 7.60%.

Example 13

N-Hydroxy 2-[4-(4-{3-(2-aminoethoxy)phenyl}-3-methylphenyl)-piperidin-1-ylsulphonyl]-2-methylpropanamide hydrochloride

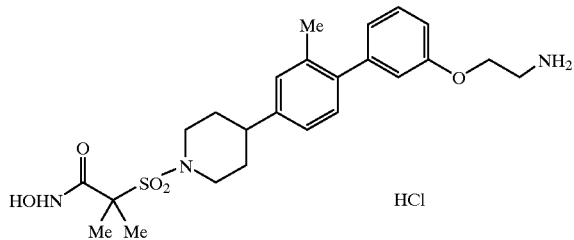

The title compound was obtained as a solid (76%), from the hydroxamic acid from preparation 89, following the procedure described in example 12.

mp 204–206° C.; $^1$H nmr (DMSO-$d_6$, 400 MHz) δ: 1.48 (s, 6H), 1.60 (m, 2H), 1.80 (m, 2H), 2.20 (s, 3H), 2.64 (m, 2H), 3.06 (m, 2H), 3.20 (t, 2H), 3.75 (m, 2H), 4.20 (t, 2H), 6.94 (m, 3H), 7.12 (s, 2H), 7.18 (s, 1H), 7.38 (m, 2H), 8.01 (br s, 1H), 8.99 (s, 1H). LRMS: m/z 476 (M+1)$^+$; Anal. Found: C, 55.21; H, 6.74; N, 7.83. $C_{24}H_{33}N_3O_5S;HCl;0.5H_2O$ requires C, 55.32; H, 6.77; N, 8.06%.

Example 14

N-Hydroxy 4-{[4-(-4-{3-[2-aminoethoxy]phenyl}-3-methylphenyl)piperidin-1-yl]sulphonyl}tetrahydro-2H-pyran-4-carboxamide hydrochloride

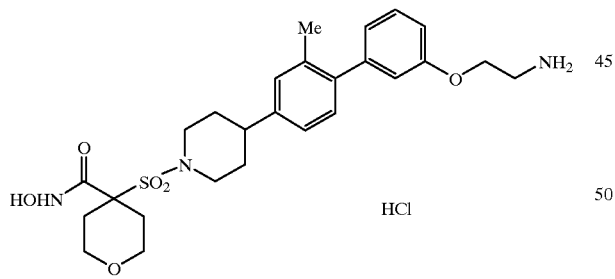

A saturated solution of hydrogen chloride in dichloromethane (250 ml) was added to a solution of the hydroxamic acid from preparation 90 (4.5 g, 7.28 mmol) in dichloromethane (30 ml), and the reaction stirred at room temperature for 3½ hours. The mixture was cooled in an ice-bath, the resulting precipitate filtered off, and washed with dichloromethane, then ether. The solid was then dried under vacuum at 70° C. to afford the title compound (3.1 g, 77%).

mp 208–210° C.; $^1$H nmr (DMSO-$d_6$, 400 MHz) δ: 1.60 (m, 2H), 1.78 (m, 2H), 1.90 (m, 2H), 2.19 (s, 3H), 2.38 (m, 2H), 2.62 (m, 1H), 3.02 (m, 2H), 3.19 (m, 6H), 3.70 (m, 2H), 3.83 (m, 2H), 4.18 (t, 2H), 6.92 (m, 3H), 7.06 (s, 2H), 7.17 (s, 1H), 7.35 (m, 1H), 9.12 (s, 1H). LRMS: m/z 518 (M+1)$^+$;

Example 15

N-Hydroxy 2-[4-(4-{3-(2-N,N-dimethylaminoethoxy)phenyl}-3-methylphenyl)-piperidin-1-ylsulphonyl]-2-methylpropanamide

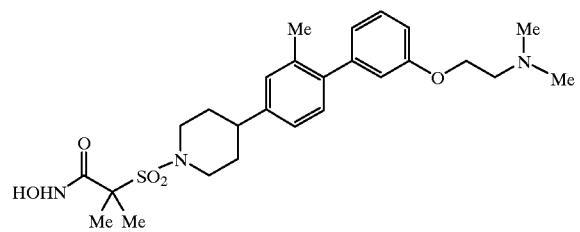

1-(3-Dimethylaminopropyl)-3-ethylcarbodiimide hydrochloride (130 mg, 0.68 mmol) and 1-hydroxy-7-azabenzotriazole (80 mg, 0.59 mmol) were added to a solution of the acid from preparation 83 (270 mg, 0.55 mmol) in pyridine (6 ml) and dichloromethane (6 ml) under a nitrogen atmosphere, and the suspension stirred for 30 minutes. N,N-dimethylformamide (5 ml), was added, and the reaction warmed to 50° C. to obtain a solution. Hydroxylamine hydrochloride (115 mg, 1.65 mmol) was added and the reaction stirred at room temperature for 18 hours. The reaction mixture was partitioned between ethyl acetate (100 ml) and pH 7 buffer solution (30 ml), and the phases separated. The organic layer was washed with water (2×30 ml), brine (30 ml), dried ($Na_2SO_4$), filtered and evaporated in vacuo. The residue was azeotroped with toluene (3×), and ethyl acetate (2×), and dried under vacuum at 60° C., to afford the title compound as a solid, (180 mg, 65%).

$^1$H nmr (DMSO-$d_6$, 400 MHz) δ: 1.48 (s, 6H), 1.60 (m, 2H), 1.78 (m, 2H), 2.19 (s, 9H), 2.60 (m, 3H), 3.03 (m, 2H), 3.76 (m, 2H), 4.05 (t, 2H), 6.80 (m, 2H), 6.86 (m, 1H), 7.06 (m, 2H), 7.12 (s, 1H), 7.28 (m, 1H). LRMS: m/z 504 (M+1)$^+$; Anal. Found: C, 60.43; H, 7.50; N, 8.08. $C_{26}H_{37}N_3O_5S;0.75H_2O$ requires C, 60.38; H, 7.50; N, 8.12%.

Example 16

N-Hydroxy 4-{[4-(4-{3-(N-methylaminomethyl)phenyl}-3-methylphenyl)piperidin-1-yl]sulphonyl}tetrahydro-2H-pyran-4-carboxamide hydrochloride

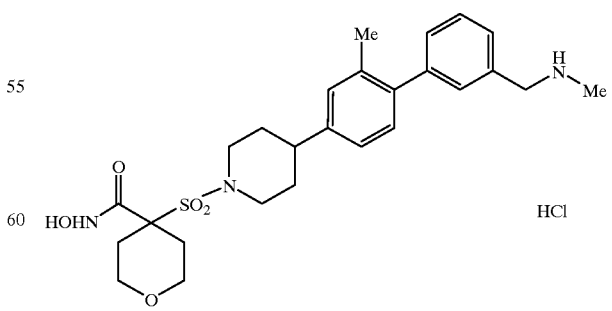

A solution of dichloromethane saturated with hydrogen chloride (20 ml) was add the solution of the hydroxamic acid from preparation 91 (347 mg, 0.58 mmol) in dichloromethane (10 ml), and the solution stirred at room temperature for 4 hours. The reaction mixture was concentrated in vacuo, and the residue triturated with hot methanol/di-isopropyl ether to give the title compound as a white solid, (202 mg, 64%).

mp 213–214° C.; $^1$H nmr (DMSO-d$_6$, 400 MHz) δ: 1.60 (m, 2H), 1.78 (m, 2H), 1.97 (m, 2H), 2.20 (s, 3H), 2.38 (m, 2H), 2.46 (s, 3H), 2.62 (m, 1H), 3.01 (m, 2H), 3.18 (m, 2H), 3.70 (m, 2H), 3.82 (m, 2H), 4.12 (s, 2H), 7.10 (m, 3H), 7.35 (s, 1H), 7.43 (m, 3H), 9.10 (br, s, 1H), 10.92 (s, 1 H). LRMS: m/z 502 (M+1)$^+$; Anal. Found: C, 57.16; H, 6.72; N, 7.64. C$_{26}$H$_{35}$N$_3$O$_5$S;HCl;0.5H$_2$O requires C, 57.08; H, 6.82; N, 7.68%.

Example 17

N-Hydroxy 4-{[4-(3-methyl-4-{3-[4-morpholinylmethyl]}phenyl)piperidin-1-yl]sulphonyl}tetrahydro-2H-pyran-4-carboxamide

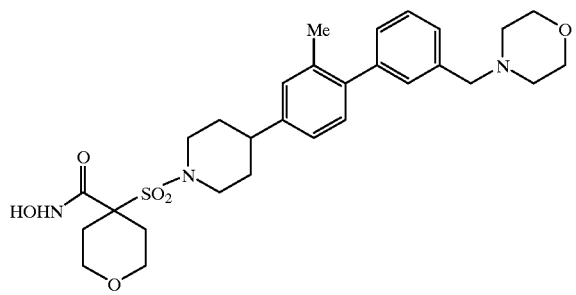

1-(3-Dimethylaminopropyl)-3-ethylcarbodiimide hydrochloride (265 mg, 1.38 mmol) and 1-hydroxy-7-azabenzotriazole (157 mg, 1.15 mmol) were added to a solution of the acid from preparation 86 (625 mg, 1.15 mmol) in pyridine (6 ml) and N,N-dimethylformamide (6 ml) under a nitrogen atmosphere, and the suspension stirred for 1 hour. Hydroxylamine hydrochloride (210 mg, 3.45 mmol) was added and the reaction stirred at room temperature for 18 hours. The reaction mixture was partitioned between ethyl acetate and pH 7 buffer solution, the phases separated, and the aqueous layer extracted with ethyl acetate. The combined organic solutions were washed with water, brine, then dried (MgSO$_4$), filtered and concentrated in vacuo. The crude product was purified by column chromatography on silica gel using dichloromethane:methanol (95:5) as eluant, and recrystallised from ethyl acetate to give the desired product as a white solid, (398 mg, 62%).

mp 177–179° C.; $^1$H nmr (DMSO-d$_6$, 400 MHz) δ: 1.60 (m, 2H), 1.78 (m, 2H), 1.88 (m, 2H), 2.17 (s, 3H), 2.36 (m, 6H), 2.60 (m, 1H), 3.00 (m, 2H), 3.19 (m, 2H), 3.46 (s, 2H), 3.53 (m, 4H), 3.70 (m, 2H), 3.81 (m, 2H), 7.06 (m, 7H), 9.10 (s, 1H), 10.92 (s, 1H). LRMS: m/z 558 (M+1)$^+$; Anal. Found: C, 62.15; H, 7.01; N, 7.40. C$_{29}$H$_{39}$N$_3$O$_6$S requires C, 62.46; H, 7.05; N, 7.53%.

Example 18

N-Hydroxy 2-({4-[4-(3-methoxy-1H-pyrazol-1-yl)-3-methylphenyl]piperidin-1-yl}sulphonyl)-2-methylpropanamide

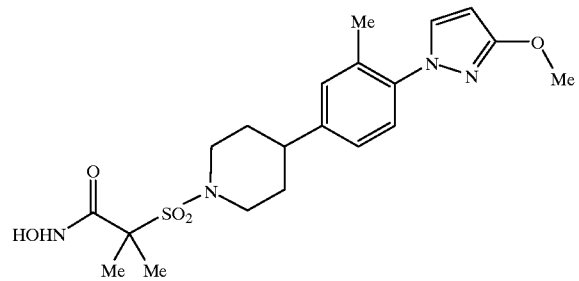

1-(3-Dimethylaminopropyl)-3-ethylcarbodiimide hydrochloride (129 mg, 0.67 mmol) and 1-hydroxy-7-azabenzotriazole (76 mg, 0.56 mmol) were added to a solution of the acid from preparation 103 (235 mg, 0.56 mmol) in pyridine (1.5 ml) and dichloromethane (3 ml) under a nitrogen atmosphere, and the suspension stirred for 30 minutes. Hydroxylamine hydrochloride (78 mg, 1.12 mmol) was added and the reaction stirred at room temperature for 18 hours. The reaction mixture was poured into ethyl acetate (100 ml), washed with pH 7 buffer solution (2×50 ml) then dried (MgSO$_4$), filtered and evaporated in vacuo. The residual white solid was recrystallised from hot ethyl acetate, to afford the title compound as a white solid, (156 mg, 64%).

mp 172–173° C. $^1$H nmr (CD$_3$OD, 400 MHz) δ: 1.58 (s, 6H), 1.74 (m, 2H), 1.82 (m, 2H), 2.20 (s, 3H), 2.70 (m, 1H), 3.09 (m, 2H), 3.87 (m, 5H), 5.84 (s, 1H), 7.16 (m, 1H), 7.20 (m, 2H), 7.48 (s, 1H). Anal. Found: C, 55.04; H, 6.42; N, 12.77. C$_{20}$H$_{28}$N$_4$O$_5$S requires C, 55.03; H, 6.47; N, 12.83%.

Example 19

N-Hydroxy 2-[(4-{4-[3-(2-hydroxyethoxy)-1H-pyrazol-1-yl]-3-methylphenyl}piperidin-1-yl)sulphonyl]-2-methylpropanamide

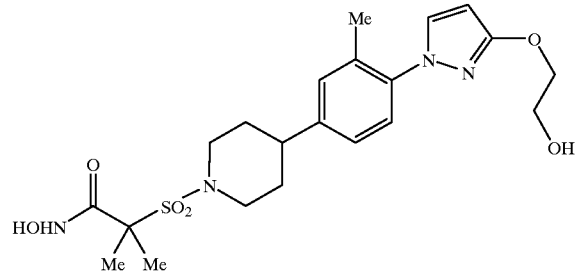

Pyridine (6 ml) was added to a suspension of the acid from preparation 104 (325 mg, 0.72 mmol) in dichloromethane (6 ml), and the solution purged with nitrogen. Chlorotrimethylsilane (858 mg, 0.79 mmol) was added, the solution stirred for an hour, then 1-hydroxy-7-azabenzotriazole (98 mg, 0.72 mmol) was added, followed by 1-(3-dimethylaminopropyl)-3-ethylcarbodiimide hydrochloride (166.8 mg, 0.87 mmol), and the solution was stirred for a further hour. Hydroxylamine hydrochloride (150 mg, 2.16 mmol) was then added and the reaction stirred at room temperature for 17 hours. The reaction was partitioned between ethyl acetate and pH 7 buffer solution, and the pH of the mixture carefully adjusted to 3 using hydrochloric acid (2N). The layers were separated, the organic phase dried (MgSO$_4$), filtered and evaporated in vacuo, and the residue triturated with ether. The resulting white solid was filtered, then dissolved in a solution of acetic acid (10 ml), water (10 ml), and methanol (10 ml), and this mixture stirred at room temperature for 45 minutes. The solution was poured into pH 7 buffer (300 ml), extracted with ethyl acetate (3×100 ml), and the combined organic extracts dried (MgSO$_4$), filtered and concentrated in vacuo. The residue was azeotroped with toluene and ethyl acetate, and triturated several times with ether to give the title compound as a white solid, (141 mg, 42%).

$^1$H nmr (DMSO-d$_6$, 400 MHz) δ: 1.43 (s, 6H), 1.59 (m, 2H), 1.77 (m, 2H), 2.19 (s, 3H), 2.62 (m, 1H), 3.00 (m, 2H), 3.66 (m, 4H), 4.05 (t, 2H), 4.72 (br, t, 1H), 5.84 (s, 1H), 7.15 (m, 1H), 7.19 (m, 2H), 7.72 (s, 1H), 8.90 (s, 1H), 10.66 (s, 1H). Anal. Fond: C, 53.85; H, 6.49; N, 11.86. C$_{21}$H$_{30}$N$_4$O$_6$S requires C, 54.06; H, 6.48; N, 12.01%.

Example 20

N-Hydroxy 2-methyl-2-({4-[3-methyl-4-(1,3-thiazol-2-yl)phenyl]piperidin-1-yl}sulphonyl) propanamide

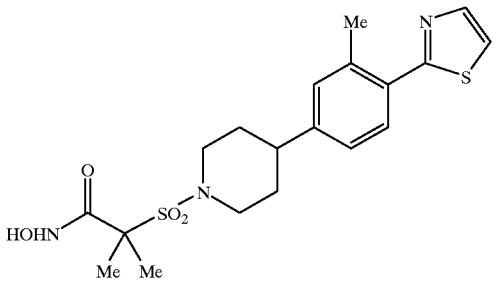

The title compound was prepared from the acid from preparation 105, following the procedure described in example 18. The crude product was crystallised from a minimum volume of methanol to give the desired product as a white solid, (58 mg, 35%).

mp 199–201° C.; $^1$H nmr (DMSO-d$_6$, 400 MHz) δ: 1.45 (s, 6H), 1.60 (m, 2H), 2.44 (s, 3H), 2.65 (m, 1H), 3.01 (m, 2H), 3.14 (s, 2H), 3.72 (m, 2H), 7.18 (d, 1H), 7.20 (s, 1H), 7.61 (d, 1H), 7.75 (s, 1H), 7.90 (s, 1H), 8.82 (br, s, 1H), 10.60 (s, 1H). Anal. Found: C, 53.51; H, 5.92; N, 9.75. C$_{19}$H$_{25}$N$_3$O$_4$S$_2$ requires C, 53.88; H, 5.95; N, 9.92%.

Example 21

(1α,3α,4α)-N,3,4-trihydroxy-1-[(4-{4-[6-(2-hydroxyethoxy)pyridin-2-yl]-3-methylphenyl}piperidin-1-yl)sulfonyl] cyclopentanecarboxamide

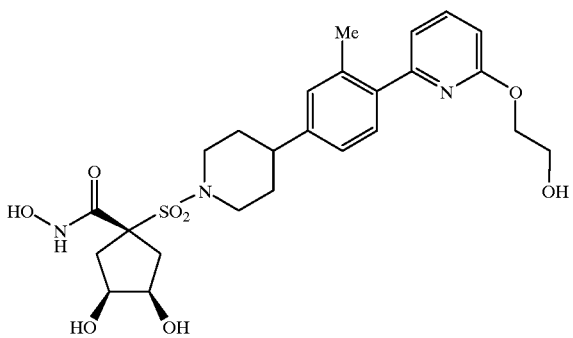

Hydrogen chloride gas was bubbled through a solution of the tert-butyl ether from preparation 121 (260 mg, 0.412 mmol) in trifluoroacetic acid (10 ml) and dichloromethane (10 ml) for 5 minutes, and the reaction was stirred for 5½ hours at ambient temperature. The reaction mixture was evaporated in vacuo and the resulting oil azeotroped with toluene (×2) before partitioning between ethyl acetate (50 ml) and pH7 phosphate buffer solution (40 ml). The organic layer was separated and the aqueous layer was extracted with ethyl acetate (2×50 ml). The combined organic extracts were dried (Na$_2$SO$_4$), filtered and evaporated in vacuo. The resulting solid, which contained some of the starting compound, was resubmitted to the reaction conditions. After 5 hours at ambient temperature nitrogen gas was bubbled through the reaction mixture for 15 minutes. The reaction mixture was then evaporated in vacuo and the resulting oil azeotroped with toluene (×2) before partitioning between ethyl acetate (50 ml) and pH7 phosphate buffer solution (40 ml). The organic layer was separated and the aqueous layer was extracted with ethyl acetate (2×50 ml). The combined organic extracts were dried (Na$_2$SO$_4$), filtered and evaporated in vacuo. The resulting solid was purified by column chromatography on silica gel using dichloromethane/methanol (98:2 to 93:7) as eluant. The title compound was isolated as a white solid (30 mg, 15%).

$^1$H nmr (DMSO-d$_6$, 400 MHz) δ: 1.59 (m, 2H), 1.76 (m, 2H), 2.22 (m, 2H), 2.32 (s, 3H), 2.39 (m, 2H), 2.60 (m, 1H), 2.99 (t, 2H), 3.64 (m, 4H), 3.90 (s, 2H), 4.23 (m, 2H), 4.54 (s, 2H), 4.75 (t, 1H), 6.72 (d, 1H), 7.03 (d, 1H), 7.15 (m, 2H), 7.31 (d, 1H), 7.73 (t, 1H), 8.95 (s, 1H), 10.69 (s, 1H). LRMS: m/z 536 (M+1)$^+$. mp 215–218° C.; Anal. Found: C, 49.73; H, 5.67; N, 6.45. C$_{25}$H$_{33}$N$_3$O$_8$S;TFA, 0.5 MeOH requires C, 49.62; H, 5.45; N, 6.31%.

Example 22

(1α,3α,4α)-1-({4-[4-(6-ethoxypyridin-2-yl)-3-methylphenyl]piperidin-1-yl}sulfonyl)-N,3,4-trihydroxycyclopentanecarboxamide

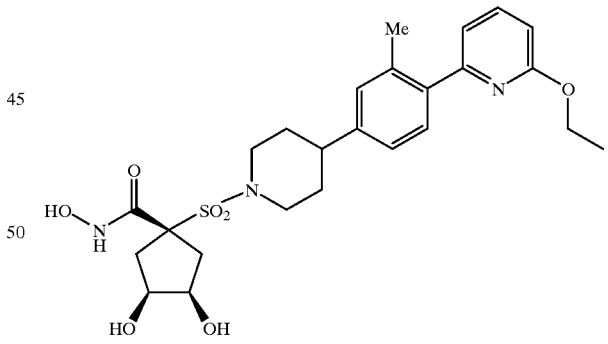

2N Hydrochloric acid (2 ml) was added to a solution of the dioxolane from preparation 122 in dioxan (2 ml) and tetrahydrofuran (2 ml) and the reaction mixture was stirred at ambient temperature for 18 hours. The reaction mixture was evaporated in vacuo and the resulting solid partitioned between pH7 phosphate buffer solution (20 ml) and ethyl acetate (20 ml). The aqueous layer was extracted with ethyl acetate (2×20 ml) and the combined organic extracts were dried (Na$_2$SO$_4$), filtered and concentrated in vacuo. The resulting solid was recrystalised from ethyl acetate to afford the title compound as a white solid (95 mg, 70%).

¹H nmr (DMSO-d₆, 400 MHz) δ: 1.25 (t, 3H), 1.58 (m, 2H), 1.76 (m, 2H), 2.22 (m, 2H), 2.35 (s, 3H), 2.38 (m, 2H), 2.60 (m, 1H), 2.99 (t, 2H), 3.66 (d, 2H), 3.85 (s, 2H), 4.25 (q, 2H), 4.61 (s, 2H), 6.71 (d, 1H), 7.03 (d, 1H), 7.12 (m, 2H), 7.31 (d, 1H), 7.72 (t, 1H), 9.00 (s, 1H), 10.78 (s, 1H). LRMS: m/z 520 (M+1)⁺. mp 204–205° C.; Anal. Found: C, 57.42; H, 6.36; N, 7.98. $C_{25}H_{33}N_3O_7S$;0.25 $H_2O$ requires C, 57.29; H, 6.44; N, 8.02%.

Example 23

(1α,3β,4β)-1-({4-[4-(6-ethoxypyridin-2-yl)-3-methylphenyl]piperidin-1-yl}sulfonyl)-N, 3,4-trihydroxycyclopentanecarboxamide

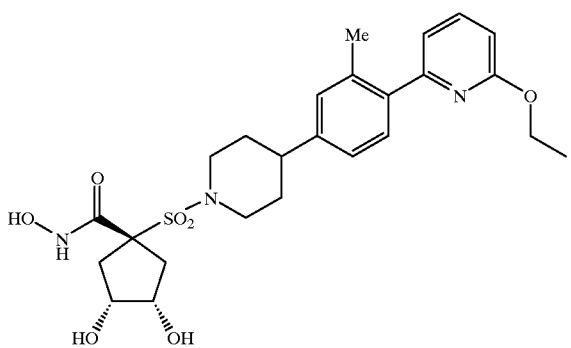

The title compound was prepared from the dioxolane from preparation 123 in a similar procedure to that described in example 22. This afforded the title compound as a white solid (50 mg, 55%).

¹H nmr (DMSO-d₆, 400 MHz) δ: 1.27 (t, 3H), 1.62 (m, 2H), 1.78 (m, 2H), 2.09 (m, 2H), 2.35 (s, 3H), 2.61 (m, 1H), 2.74 (m, 2H), 3.01 (t, 2H), 3.69 (m, 4H), 4.29 (q, 2H), 4.49 (s, 2H), 6.69 (d, 1H), 7.02 (d, 1H), 7.12 (m, 2H), 7.31 (d, 1H), 7.73 (t, 1H), 8.92 (s, 1H), 10.71 (s, 1H). LRMS: m/z 520 (M+1)⁺.

mp 196–197° C.; Anal. Found: C, 56.83; H, 6.32; N, 7.83. $C_{25}H_{33}N_3O_7S$;0.5 $H_2O$ requires C, 56.80; H, 6.48; N, 7.95%.

Example 24

(1α,3α,4α)-N,3,4-trihydroxy-1-{4-[4-(3-methoxyphenyl)-3-methylphenyl]piperidin-1-ylsulfonyl}cyclopentanecarboxamide

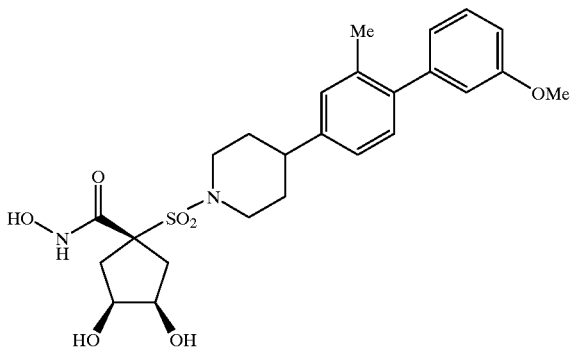

2N Hydrochloric acid (2 ml) was added to a solution of the dioxolane from preparation 124 in dioxan (3 ml) and tetrahydrofuran (2 ml) and the reaction mixture was stirred at ambient temperature for 4 hours. The reaction mixture was evaporated in vacuo and the resulting solid was partitioned between water (20 ml) and ethyl acetate (20 ml). The aqueous layer was extracted with ethyl acetate (2×20 ml) and the combined organic extracts were dried ($Na_2SO_4$) filtered and concentrated in vacuo. The resulting solid was recrystalised from ethyl acetate to afford the title compound as a white solid (60 mg, 46%).

¹H nmr (DMSO-d₆, 400 MHz) δ: 1.58 (m, 2H), 1.76 (m, 2H), 2.19 (s, 3H), 2.24 (m, 2H), 2.38 (m, 2H), 2.60 (m, 1H), 2.99 (t, 2H), 3.71 (m, 5H), 3.79 (s, 2H), 4.54 (s, 2H), 6.82 (m, 3H), 7.11 (m, 3H), 7.32 (t, 1H), 8.97 (s, 1H), 10.70 (s, 1H). LRMS: m/z 527 (M+23)⁺. mp 201–202° C.; Anal. Found: C, 58.85; H, 6.36; N, 5.51. $C_{25}H_{32}N_2O_7S$; 0.25 $H_2O$ requires C, 58.98; H, 6.43; N, 5.50%.

Example 25

(1α,3β,4β)-N,3,4-trihydroxy-1-{4-[4-(3-methoxyphenyl)-3-methylphenyl]piperidin-1-ylsulfonyl}cyclopentanecarboxamide

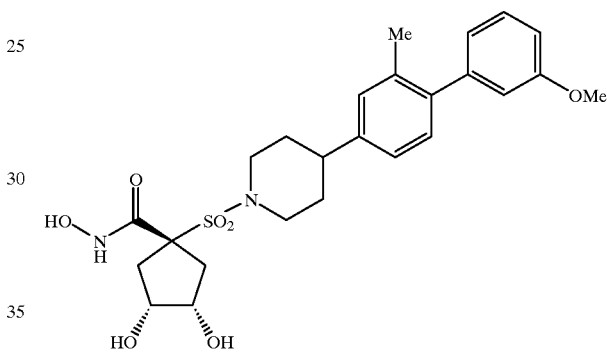

The title compound was prepared from the dioxolane from preparation 125 in a similar procedure to that described in example 24. This afforded the title compound as a white solid (55 mg, 50%).

¹H nmr (DMSO-d₆, 400 MHz) δ: 1.59 (m, 2H), 1.76 (m, 2H), 2.17 (m, 2H), 2.19 (s, 3H), 2.60 (m, 1H), 2.71 (m, 2H), 2.99 (t, 2H), 3.70 (m, 7H), 4.61 (s, 2H), 6.82 (m, 3H), 7.12 (m, 3H), 7.32 (t, 1H), 9.00 (s, 1H), 10.82 (s, 1H). LRMS: m/z 503 (M−1)⁻. mp 188–189° C.; Anal. Found: C, 58.97; H, 6.50; N, 5.49. $C_{25}H_{32}N_2O_7S$; 0.25 $H_2O$ requires C, 58.98; H, 6.43; N, 5.50%.

Preparation 1

2-[2-(Benzyloxy)ethoxy]-6-bromopyridine

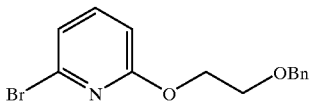

Sodium hydride (900 mg, 60% dispersion in mineral oil, 22.5 mmol) was added portionwise to an ice-cold solution of 2-(benzyloxy)ethanol (3.0 g, 20.0 mmol) in toluene (100 ml), and the solution stirred for 30 minutes. 2,6-Dibromopyridine (4.75 g, 20.0 mmol) was added, and the reaction heated under reflux for 2 hours. The cooled mixture was diluted with water (100 ml), and extracted with ethyl acetate (3×100 ml). The combined organic extracts were dried (MgSO₄), filtered and evaporated in vacuo to give the title compound as a yellow oil, (quantitative).

¹H nmr (CDCl₃, 300 MHz) δ: 3.82 (t, 2H), 4.52 (t, 2H), 4.62 (s, 2H), 6.75 (d, 1H), 7.05 (d, 1H), 7.22–7.46 (m, 6H).

Preparation 2

2-Bromo-6-{[(4R)-2,2-dimethyl-1,3-dioxolan-4-yl]methoxy}pyridine

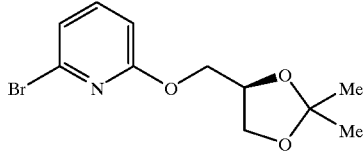

Sodium hydride (1.62 g, 60% dispersion in mineral oil, 40.5 mmol) was added portionwise to an ice-cooled solution of (R)-(−)-1,2-O-isopropylideneglycerol (4.86 g, 36.8 mmol) in toluene (100 ml), and once addition was complete, the solution was allowed to warm to room temperature and stirred for 30 minutes. 2,6-Dibromopyridine (8.72 g, 36.8 mmol) was added, and the reaction heated under reflux for 5 hours. The cooled mixture was diluted with water, the layers separated, and the aqueous phase extracted with ether. The combined organic extracts were dried (MgSO₄), filtered and evaporated in vacuo to afford the title compound as a yellow oil (quantitative).

¹H nmr (CDCl₃, 300 MHz) δ: 1.39 (s, 3H), 1.45 (s, 3H), 3.83 (dd, 1H), 4.16 (dd, 1H), 4.37 (m, 2H), 4.46 (m, 1H), 6.75 (d, 1H), 7.06 (d, 1H), 7.40 (dd, 1H).

Preparation 3

2-Bromo-6-{[(4S)-2,2-dimethyl-1,3-dioxolan-4-yl]methoxy}pyridine

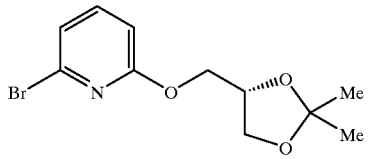

The title compound was obtained as a yellow oil (quantitative), from (S)-(−)-1,2-O-isopropylideneglycerol and 2,6-dibromopyridine, following the procedure described in preparation 2.

¹H nmr (CDCl₃, 300 MHz) δ: 1.40 (s, 3H), 1.45 (s, 3H), 3.83 (dd, 1H), 4.16 (dd, 1H), 4.37 (m, 2H), 4.48 (m, 1H), 6.76 (d, 1H), 7.06 (d, 1H), 7.41 (m/dd, 1H).

Preparation 4

2-[2-(Benzyloxy)ethoxy]-6-(tributylstannyl)pyridine

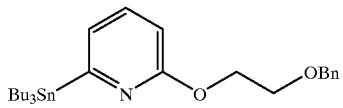

n-Butyllithium (13.8 ml, 1.6M solution in hexanes, 22.0 mmol) was added dropwise to a cooled (−78° C.) solution of the bromide from preparation 1 (20.0 mmol) in anydrous THF (100 ml), so as to maintain the internal temperature <−70° C., and the solution stirred for 20 minutes. Tri-n-butyltin chloride (6.0 ml, 22.0 mmol) was added slowly to maintain the temperature <−70° C., and the reaction then allowed to warm to room temperature over 1 hour. The reaction was diluted with water, the mixture extracted with Et₂O (2×100 ml), and the combined organic extracts dried (MgSO₄), filtered and evaporated in vacuo. The residue was purified by column chromatography on silica gel using pentane:Et₂O (98:2) as eluant, to afford the title compound as a colourless oil, (7.0 g, 67%).

¹H nmr (CDCl₃, 300 MHz) δ: 0.88 (t, 9H), 1.06 (m, 6H), 1.35 (m, 6H), 1.58 (m, 6H), 3.83 (t, 2H), 4.56 (t, 2H), 4.62 (s, 2H), 6.61 (d, 1H), 6.99 (d, 1H), 7.24–7.40 (m, 6H).

Preparation 5

2-{[(4R)-2,2-Dimethyl-1,3-dioxolan-4-yl]methoxy}-6-(tributylstannyl)pyridine

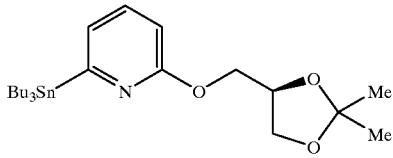

The title compound was prepared as an oil (quantitative) from the bromide of preparation 2, using a similar procedure to that described in preparation 4.

¹H nmr (CDCl₃, 300 MHz) δ: 0.88 (t, 9H), 1.06 (t, 6H), 1.25–1.40 (m, 9H), 1.45 (s, 3H), 1.50–1.70 (m, 6H), 3.83 (dd, 1H), 4.15 (dd, 1H), 4.40 (m, 2H), 4.52 (m, 1H), 6.60 (d, 1H), 7.00 (d, 1H), 7.40 (dd, 1H).

Preparation 6

2-{[(4S)-2,2-Dimethyl-1,3-dioxolan-4-yl]methoxy}-6-(tributylstannyl)pyridine

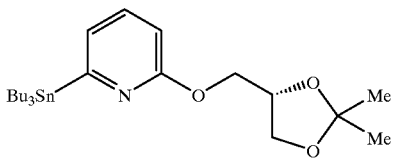

The title compound was obtained as a colourless oil (71%), from the bromide from preparation 3, following a similar procedure to that described in preparation 5.

¹H nmr (CDCl₃, 300 MHz) δ: 0.89 (t, 9H), 1.07 (t, 6H), 1.35 (m, 6H), 1.40 (s, 3H), 1.48 (s, 3H), 1.58 (m, 6H), 3.83 (dd, 1H), 4.16 (dd, 1H), 4.40 (m, 2H), 4.52 (m, 1H), 6.60 (d, 1H), 7.00 (d, 1H), 7.40 (dd, 1H).

Preparation 7

3-Bromo-1-(tert-butoxy)benzene

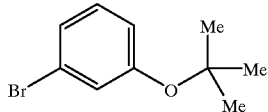

Condensed isobutylene (100 ml) was added via a dry ice/acetone cold finger, to dichloromethane (70 ml) at −30° C., followed by a solution of 3-bromophenol (21.5 g, 125 mmol) in dichloromethane (30 ml). Trifluoromethanesulphonic acid (1.5 g, 10.0 mmol) was added dropwise, the reaction cooled to −75° C., and stirred for 2 hours. Triethylamine (1.4 ml, 10.0 mmol) was then added, the solution allowed to warm to room temperature and then concentrated in vacuo to remove the isobutylene. The remaining solution was washed with water, dried (Na$_2$SO$_4$), filtered and evaporated to give the desired product as a pale yellow oil, (33 g, slightly impure).

$^1$H nmr (CDCl$_3$, 400 MHz) δ: 1.37 (s, 9H), 6.89 (d, 1H), 7.04–7.20 (m, 3H).

Preparation 8

3-(tert-Butoxy)-phenylboronic acid

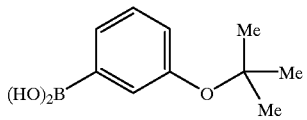

n-Butyllithium (40 ml, 2.5M in hexanes, 100 mmol) was added dropwise to a cooled (−78° C.) solution of the bromide from preparation 7 (23.9 g, 90 mmol) in tetrahydrofuran (300 ml), so as to maintain the temperature below −70° C. The resulting solution was stirred for 1 hour, and triisopropyl borate (30.6 ml, 135 mmol) was added dropwise over 10 minutes. The reaction was allowed to warm to room temperature, diluted with ether (150 mg) then extracted with sodium hydroxide solution (1N). The combined aqueous layers were washed with ether and then re-acidified to pH 2 using hydrochloric acid (2N). This aqueous mixture was extracted with dichloromethane (3×200 ml), the combined organic extracts dried (Na$_2$SO$_4$), filtered and concentrated in vacuo. The resulting white solid was stirred vigorously in pentane, filtered (twice) then dried under vacuum to give the title compound as a white solid, (13.1 g, 75%).

$^1$H nmr (CDCl$_3$, 400 MHz) δ: 1.39 (s, 9H), 7.19 (m, 1H), 7.37 (m, 1H), 7.79 (m, 1H), 7.88 (m, 1H).

Preparation 9

1-Bromo-3-(2,2-diethoxyethoxy)benzene

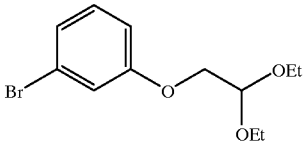

A mixture of potassium carbonate (1.5 g, 10.9 mmol), 3-bromophenol (1.73 g, 10.0 mmol) and bromoacetaldehyde diethyl acetal (1.5 ml, 9.67 mmol) in dimethylsulphoxide (10 ml) was heated at 160° C. for 1½ hours. The cooled reaction was partitioned between water (50 ml) and ethyl acetate (100 ml), and the phases separated. The aqueous layer was extracted with ethyl acetate (50 ml), the combined organic solutions washed consecutively with 1N sodium hydroxide solution, water (2×), brine and then dried (Na$_2$SO$_4$), filtered and evaporated in vacuo. The residue was purified by medium pressure column chromatography on silica gel using an elution gradient of ether:pentane (0:100 to 5:95) to afford the title compound (2.01 g, 72%).

$^1$H nmr (CDCl$_3$, 400 MHz) δ: 1.22 (t, 6H), 3.60 (m, 2H), 3.75 (m, 2H), 3.97 (d, 2H), 4.80 (t, 1H), 6.82 (d, 1H), 7.07 (m, 3H).

Preparation 10

3-(2,2-Diethoxyethoxy)phenylboronic acid

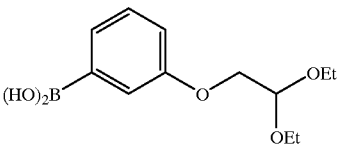

n-Butyllithium (18.5 ml, 2.5M in hexanes, 46.25 mmol) was added dropwise to a cooled (−78° C.) solution of the bromide from preparation 9 (11.4 g, 39.6 mmol) in anhydrous tetrahydrofuran (100 ml), so as to maintain the internal temperature <−70° C. This solution was stirred for 1 hour, then triisopropyl borate (1.13 g, 6.0 mmol) added slowly, and the reaction allowed to warm to room temperature over 3 hours. The mixture was cooled in an ice-bath, acidified to pH 4 using 2N hydrochloric acid, and quickly extracted with ethyl acetate (2×500 ml). The combined organic extracts were washed with water and brine, dried (Na$_2$SO$_4$), filtered and evaporated in vacuo. The residual oil was purified by medium pressure column chromatography on silica gel using an elution gradient of ether:pentane (0:100 to 50:50) to afford the title compound (8.24 g, 82%).

$^1$H nmr (DMSO-d$_6$, 400 MHz) δ: 1.14 (t, 6H), 3.58 (m, 2H), 3.66 (m, 2H), 3.94 (d, 2H), 4.80 (t, 1H), 6.98 (m, 1H), 7.22 (m, 1H), 7.37 (m, 2H), 8.00 (s, 2H).

Preparation 11

1-Methylsulphonyl-piperidin-4-one ethylene ketal

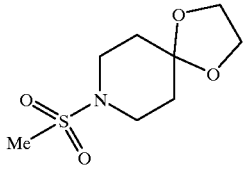

Methanesulphonyl chloride (24.8 g, 0.217mol) was added dropwise to a solution of 4-piperidone ethylene ketal (28.2 g, 0.197 mol) and triethylamine (30.2 ml, 0.217 mol) in ether (280 ml), and the reaction stirred at room temperature for 3 hours. The mixture was washed consecutively with water (2×), hydrochloric acid (1N), and saturated sodium bicarbonate solution, dried (MgSO$_4$), filtered and evaporated in vacuo. The residue was triturated with hexane, filtered and dried to give the desired product as an off-white solid (41.6 g, 95%).

mp 107–109° C.; $^1$H nmr (CDCl$_3$, 400 MHz) δ: 1.78 (m, 4H), 2.75 (s, 3H), 3.32 (m, 4H), 3.92 (s, 4H). Anal. Found: C, 43.23; H, 6.85; N, 6.23. C$_8$H$_{15}$NO$_4$S requires C, 43.42; H, 6.83; N, 6.33%.

Preparation 12

1-Isopropylsulphonyl-piperidin-4-one ethylene ketal

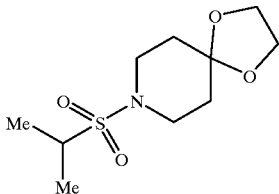

Isopropylsulphonyl chloride (5.6 ml, 50 mmol) was added dropwise to an ice-cooled solution of 4-piperidone ethylene ketal (6.4 ml, 50 mmol) and triethylamine (7.7 ml, 55 mmol) in dichloromethane (100 ml), and the reaction stirred at room temperature for 3 hours. The mixture was washed with water (2×), dried (MgSO$_4$), filtered and evaporated in vacuo. The residue was crystallised from ether/pentane to afford the title compound as a solid, (10.55 g, 85%).

mp 66–67° C.; $^1$H nmr (CDCl$_3$, 400 MHz) δ: 1.34 (d, 6H), 1.77 (m, 4H), 3.18 (m, 1H), 3.43 (m, 4H), 3.92 (s, 4H). Anal. Found: C, 48.19; H, 7.74; N, 5.50. C$_{10}$H$_{19}$NO$_4$S requires C, 48.15; H, 7.75; N, 5.56%.

Preparation 13

Methyl 2-(1,4-dioxa-8-azaspiro[4.5]dec-8-ylsulphonyl)acetate

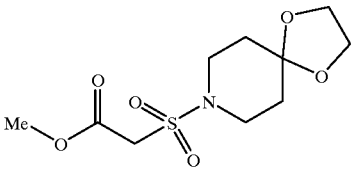

Potassium tert-butoxide (24.6 g, 219 mmol) was added portionwise to a solution of the ethylene ketal from preparation 11 (32.3 g, 146 mmol) and dimethyl carbonate (61 ml, 730 mmol) in tetrahydrofuran (200 ml), and once addition was complete, the reaction was stirred at room temperature overnight under a nitrogen atmosphere. The reaction was poured into a mixture of hydrochloric acid (1N) and ether and the layers separated. The aqueous layer was extracted with ethyl acetate, the combined organic solutions washed with brine, dried (MgSO$_4$), filtered and evaporated in vacuo. The residue was suspended in di-isopropyl ether, the mixture heated to reflux, cooled, and filtered, to afford the title compound as a solid, (26.7 g, 65%).

$^1$H nmr (CDCl$_3$, 400 MHz) δ: 1.77 (m, 4H), 3.42 (m, 4H), 3.78 (s, 3H), 3.92 (s, 2H), 3.95 (s, 4H). Anal. Found: C, 42.69; H, 6.16; N, 4.93. C$_{10}$H$_{17}$NO$_6$S requires C, 43.00; H, 6.14; N, 5.02%.

Preparation 14

Methyl 2-(1,4-dioxa-8-azaspiro[4.5]dec-8-ylsulphonyl)-2-methylpropanoate

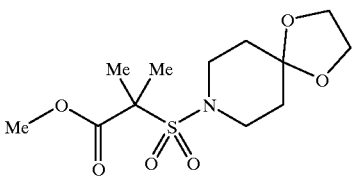

N-Butyl lithium (28 ml, 1.6M in hexanes, 44.1 mmol) was added dropwise to a cooled (−78° C.) solution of the sulphonamide from preparation 12 (10 g, 40.1 mmol) in tetrahydrofuran (100 ml), so as to maintain a temperature below −45° C. Once addition was complete the solution was allowed to warm to 0° C., and then recooled to −78° C. Methyl chloroformate (3.7 ml, 48.1 mmol) was added dropwise so as to maintain the temperature below −45° C., the reaction stirred for 30 minutes, then allowed to warm to room temperature. The reaction mixture was partitioned between ethyl acetate and water, and the layers separated. The organic phase was washed with water, dried (MgSO$_4$), filtered and evaporated in vacuo. The crude product was triturated with ether to give the title compound as a solid, (9.88 g, 80%).

$^1$H nmr (CDCl$_3$, 400 MHz) δ: 1.60 (s, 6H), 1.76 (m, 4H), 3.48 (m, 4H), 3.79 (s, 3H), 3.98 (s, 4H). Anal. Found: C, 46.80; H, 6.87; N, 4.49. C$_{12}$H$_{21}$NO$_6$S requires C, 46.89; H, 6.89; N, 4.56%.

Preparation 15

Methyl 4-(1,4-dioxa-8-azaspiro[4.5]dec-8-ylsulphonyl)tetrahydro-2H-pyran-4-carboxylate

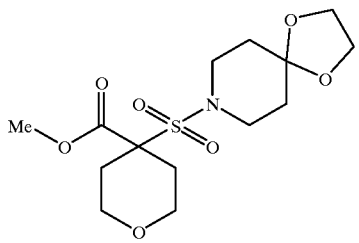

Sodium hydride (880 mg, 60% dispersion in mineral oil, 22 mmol) was added to a solution of the sulphonamide from preparation 11 (2.21 g, 10 mmol) and dimethyl carbonate (4.2 ml, 50 mmol) in dry toluene (40 ml), and the mixture heated at 90° C. for 90 minutes. Tlc analysis showed starting material present, so methanol (20?l) was added, and the reaction stirred at 90° C. overnight. 1-Methyl-2-pyrrolidinone (10 ml) and bis(2-bromoethyl)ether (1.63 ml, 13 mmol) were added, and the reaction stirred for a further 20 hours at 90° C., and at room temperature for 3 days. The reaction mixture was partititoned between 1N citric acid solution and ether, and the layers separated. The organic phase was washed with water, dried (MgSO$_4$), filtered and evaporated in vacuo. The residue was triturated with ether to give the title compound as a white solid, (1.05 g, 30%).

Alternative method

Potassium tert-butoxide (220 ml, 1M in tetrahydrofuran, 220 mmol) was added dropwise to a solution of the acetate from preparation 13 (27.9 g, 100 mmol) and bis(2-bromoethyl)ether (16.3 ml, 130 mmol) in tetrahydrofuran (200 ml) and 1-methyl-2-pyrrolidinone (20 ml), and the reaction stirred at room temperature overnight. Tlc analysis showed starting material remaining, so tetrabutylammonium iodide (3.7 g, 10 mmol) and sodium hydride (2.0 g, 60% dispersion in mineral oil, 50 mmol) were added, and the reaction stirred for a further 72 hours. Additional 1-methyl-2-pyrrolidinone (100 ml), sodium hydride (4.0 g, 60% dispersion in mineral oil, 100 mmol) and bis(2-bromoethyl)ether (12.6 ml, 100 mmol) were added, and the reaction continued for a further 24 hours. The reaction was poured into a mixture of ether and 10% citric acid solution, and the layers separated. The aqueous phase was extracted with ether, the combined organic solutions washed with water, dried (MgSO$_4$), filtered and evaporated in vacuo. The residue was suspended in ether, the mixture heated to reflux, cooled and the resulting precipitate filtered, washed with ether and dried to give the title compound, (7.2 g, 21%).

$^1$H nmr (CDCl$_3$, 400 MHz) δ: 1.70 (m, 4H), 2.16 (m, 2H), 2.35 (m, 2H), 3.24 (m, 2H), 3.41 (m, 4H), 3.80 (s, 3H), 3.94 (m, 6H). LRMS: m/z 372 (M+23)$^+$.

Preparation 16

Methyl 4-(4-oxo-piperidin-1-ylsulphonyl)tetrahydro-2H-pyran-4-carboxylate

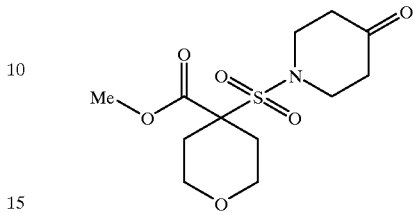

Hydrochloric acid (20 ml, 1N) was added to a solution of the ethylene ketal from preparation 15 (7.1 g, 20.3 mmol) in acetone (20 ml) and 1,4-dioxan (20 ml), and the reaction stirred at 60° C. for 6 hours, and then left at room temperature overnight. The reaction was neutralised by adding sodium bicarbonate portionwise, and this mixture concentrated in vacuo. The residue was diluted with water, then extracted with ethyl acetate (3×). The combined organic extracts were dried (MgSO$_4$), filtered and evaporated in vacuo. The crude product was triturated with ether/diisopropyl ether, to give the desired product as a solid (4.1 g, 66%).

mp 158–160° C.; $^1$H nmr (CDCl$_3$, 400 MHz) δ: 2.18 (m, 2H), 2.38 (m, 2H), 2.48 (m, 4H), 3.26 (m, 2H), 3.60 (br, m, 4H), 3.82 (s, 3H), 3.98 (m, 2H). Anal. Found: C, 47.14; H, 6.28; N, 4.54. C$_{12}$H$_{19}$NO$_6$S requires C, 47.20; H, 6.27; N, 4.59%.

Preparation 17

Methyl 2-methyl-2-(4-oxo-piperidin-1-ylsulphonyl)propanoate

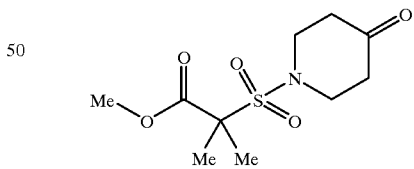

The title compound was obtained as a solid (98%) after trituration with pentane from the ethylene ketal from preparation 14, following a similar method to that described in preparation 16.

$^1$H nmr (CDCl$_3$, 400 MHz) δ: 1.67 (s, 6H), 2.57 (m, 4H), 3.68 (m, 4H), 3.80 (s, 3H). Anal. Found: C, 45.51; H, 6.52; N, 5.14. C$_{10}$H$_{17}$NO$_5$S requires C, 45.61; H, 6.51; N, 5.32%.

Preparation 18 tert-Butyl 4-[4-(4-bromo-3-methylphenyl)-4-hydroxypiperidine-1-carboxylate

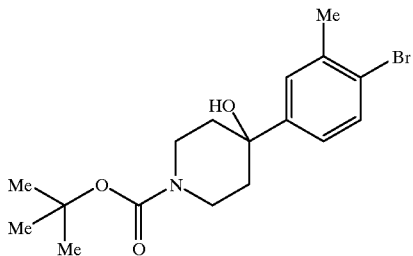

A 2.5M solution of n-butyl lithium in hexane (38 ml, 94 mmol) was added over about 10 minutes to a stirred mixture of 2-bromo-5-iodo-toluene (28 g, 94 mmol) in anhydrous ether (500 ml) under nitrogen, at about −75° C. After a further 15 minutes, a solution of t-butyl 4-oxopiperidine-1-carboxylate (17 g, 85 mmol) in anhydrous tetrahydrofuran (50 ml) was added at such a rate that the reaction temperature was maintained below −60° C. The reaction mixture was stirred at about −75° C. for 1 hour, and allowed to warm to 0° C. and quenched with aqueous ammonium chloride solution. The organic phase was separated, washed with water, dried (MgSO$_4$), filtered and evaporated in vacuo. The residue was dissolved in pentane and cooled to 0° C. to crystallise the title compound, which was collected by filtration as a colourless solid (20.1 g, 64%).

m.p. 102–103° C.; $^1$H nmr (CDCl$_3$) δ: 1.48 (s, 9H), 1.51 (s, 1H), 1.70 (d, 2H), 1.96 (m, 2H), 2.40 (s, 3H), 3.22 (t, 2H), 4.02 (m, 2H), 7.15 (dd, 1H), 7.36 (d, 1H), 7.50 (d, 1H). LRMS: m/z 369/371 (M+1)$^+$; Anal. Found: C, 55.14; H, 6.58; N, 3.76. C$_{17}$H$_{24}$BrNO$_3$ requires C, 55.14; H, 6.53; N, 3.78%.

Preparation 19

4-(4-Bromo-3-methylphenyl)-1,2,3,6-tetrahydropyridine

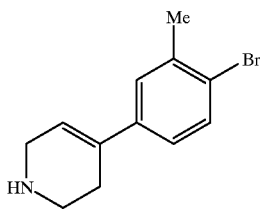

Trifluoroacetic acid (100 ml) was added to a stirred solution of the bromide from preparation 18 (20 g, 54 mmol) in dichloromethane (100 ml) at room temperature. After a further 18 hours, the reaction mixture was evaporated in vacuo and the residue basified with 2M aqueous sodium hydroxide solution to pH>12. The resulting mixture was extracted with ether, the combined extracts washed with water, dried (MgSO$_4$), filtered and evaporated under reduced pressure to yield the title compound as a low melting solid, (13.6 g, 100%).

$^1$H nmr (CDCl$_3$) δ: 1.60 (br, s, 1H), 2.40 (m, 5H), 3.10 (t, 2H), 3.52 (m, 2H), 6.10 (br, s, 1H), 7.05 (dd, 1H), 7.22 (d, 1H), 7.46 (d, 1H). LRMS: m/z 251/253 (M+1)$^+$.

Alternative Method

Para-toluenesulphonic acid (10.27 g, 54 mmol) was added to a stirred solution of the bromide from preparation 18 (10 g, 27 mmol) in toluene (130 ml) at room temperature. The gelatinous mixture was heated to reflux in a Dean-Stark apparatus for 90 minutes, and then cooled to room temperature which resulted in a thick white precipitate. The mixture was basified with 2M sodium hydroxide solution, and extracted with ethyl acetate (3×), then the combined extracts were washed with water, dried (MgSO$_4$) and evaporated under reduced pressure to yield the title as a low melting solid, (6.8 g, 100%).

Preparation 20

4-(4-Bromo-3-methylphenyl)-1-methylsulphonyl-1,2,3,6-tetrahydropyridine

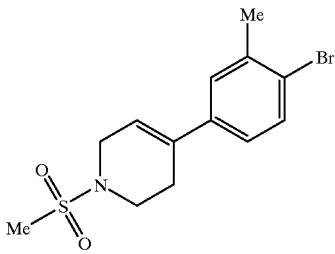

Methanesulphonyl chloride (17.5 ml, 227 mmol) was added dropwise to an ice-cooled solution of triethylamine (34.4 ml, 247 mmol) and the amine from preparation 19 (51.8 g, 206 mmol) in dichloromethane (400 ml), and the reaction then stirred at room temperature for 1 hour. Tlc analysis showed starting material remaining, so additional methanesulphonyl chloride (1.75 ml, 22.7 mmol) and triethylamine (5 ml, 35.9 mmol) were added, and stirring continued for a further hour. The reaction was diluted with hydrochloric acid (200 ml, 2N) and water (300 ml), and the phases separated. The aqueous layer was extracted with dichloromethane (2×250 ml) the combined organic extracts washed with brine (200 ml), dried (MgSO$_4$), filtered and concentrated in vacuo. The residual solid was triturated with iso-propyl ether, filtered and dried to afford the title compound as a pale yellow solid, (65.1 g, 96%).

$^1$H nmr (CDCl$_3$, 300 MHz) δ: 2.40 (s, 3H), 2.62 (m, 2H), 2.85 (s, 3H), 3.54 (m, 2H), 3.95 (m, 2H), 6.04 (m, 1H), 7.04 (dd, 1H), 7.21 (m, 1H), 7.50 (d, 1H). LRMS m/z 347, 349 (M+18)$^+$.

Preparation 21

Methyl 2-[4-(4-bromo-3-methylphenyl)-1,2,3,6-tetrahydropyridin-1-ylsulphonyl]acetate

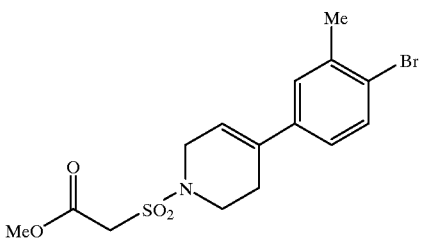

N,O-Bis(trimethylsilyl)acetamide (0.9 ml, 4.0 mmol) was added to a stirred solution of the amine from preparation 19

(2.0 g, 7.9 mmol) in anhydrous tetrahydrofuran (40 ml), under nitrogen, at room temperature. A solution of methyl chlorosulphonylacetate (1.64 g, 9.5 mmol) in anhydrous tetrahydrofuran (15 ml) was added and the reaction mixture stirred at room temperature for 18 hours. The resulting mixture was evaporated in vacuo, and partitioned between ethyl acetate and aqueous sodium bicarbonate solution. The organic layer was separated and washed with water, dried (MgSO$_4$), filtered and evaporated in vacuo. The residue was purified by column chromatography on silica gel, using dichloromethane as eluant, followed by crystallisation from diisopropyl ether, to give the title compound as a colourless solid, (1.65 g, 55%).

m.p. 110–112° C.; $^1$H nmr (CDCl$_3$) δ: 2.40 (s, 3H), 2.60 (m, 2H), 3.60 (t, 2H), 3.80 (s, 3H), 4.01 (s, 2H), 4.07 (m, 2H), 6.02 (br, s,1H), 7.02 (dd, 1H), 7.21 (d, 1H), 7.50 (d, 1H). LRMS: m/z 404/406 (M+18)$^+$; Anal. Found: C, 46.32; H, 4.62; N, 3.55. C$_{15}$H$_{18}$BrNO$_4$S requires C, 46.40; H, 4.67; N, 3.61%.

Preparation 22

Methyl 2-[4-(4-bromo-3-methylphenyl)-1,2,3,6-tetrahydropyridin-1-ylsulphonyl]-2-methyl-propanoate

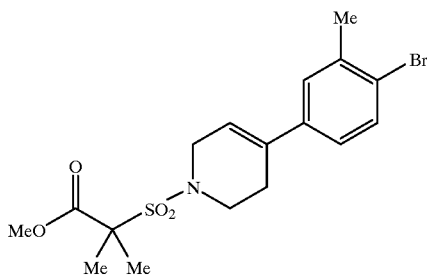

Iodomethane (2 ml, 32.1 mmol) was added to a stirred mixture of the acetate from preparation 21 (5 g, 12.9 mmol) and potassium carbonate (5.4 g, 39.1 mmol), in anhydrous dimethylsulfoxide (50 ml), under nitrogen, at room temperature. After 24 hours the reaction mixture was partitioned between ether and water, separated, and the organic layer was washed with water, dried (MgSO$_4$), filtered and evaporated in vacuo. The residue was purified by flash chromatography, using diethyl ether:pentane (40:60 to 100:0) as eluant, followed by crystallisation from diisopropyl ether, to give the title compound as a colourless solid, (4.7 g, 87%).

m.p. 100–101° C.; $^1$H nmr (CDCl$_3$) δ: 1.67 (s, 6H), 2.40 (s, 3H), 2.58 (m, 2H), 3.60 (t, 2H), 3.80 (s, 3H), 4.08 (m, 2H), 6.00 (br, s, 1H), 7.03 (dd, 1H), 7.21 (d, 1H), 7.49 (d, 1H). Anal. Found: C, 49.00; H, 5.33; N, 3.28. C$_{17}$H$_{22}$BrNO$_4$S requires C, 49.04; H, 5.33; N, 3.36%.

Preparation 23

Methyl 4-[4-(4-bromo-3-methylphenyl)-1,2,3,6-tetrahydropyridin-1-ylsulphonyl]tetrahydro-2H-pyran-4-carboxylate

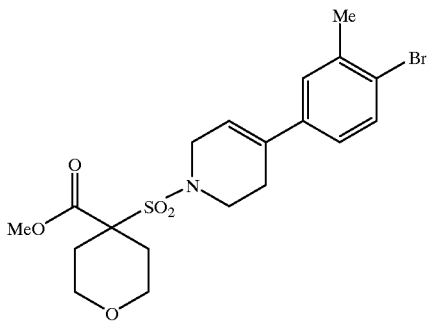

Bis-2-iodoethyl ether (3.9 g, 12.0 mmol) was added to a stirred mixture of the acetate from preparation 21 (3.6 g, 9.3 mmol) and potassium carbonate (3.8 g, 27.8 mmol), in anhydrous dimethylsulfoxide (50 ml), under nitrogen, at room temperature. After 18 hours the reaction mixture was partitioned between diethyl ether and water, separated, and the organic layer was washed with water, dried (MgSO$_4$), filtered and evaporated in vacuo. The residue was purified by flash chromatography, using a mixture of dichloromethane and methanol (99:1) as eluant, followed by crystallisation from diisopropyl ether, to give the title compound as a colourless solid, (3.43 g, 80%).

m.p. 128–130° C. $^1$H nmr (CDCl$_3$) δ: 2.23 (m, 2H), 2.40 (s, 3H), 2.42 (m, 2H), 2.58 (m, 2H), 3.30 (m, 2H), 3.58 (m, 2H), 3.87 (s, 3H), 4.00–4.10 (m, 4H), 6.00 (br, s, 1H), 7.02 (dd, 1H), 7.21 (d, 1H), 7.49 (d, 1H). LRMS: m/z 477 (M+18)$^+$; Anal. Found: C, 49.92; H, 5.40; N, 2.90. C$_{19}$H$_{24}$BrNO$_5$S requires C, 49.78; H, 5.28; N, 3.06%.

Preparation 24

4-(4-Bromo-3-methylphenyl)-1-(methylsulphonyl) piperidine

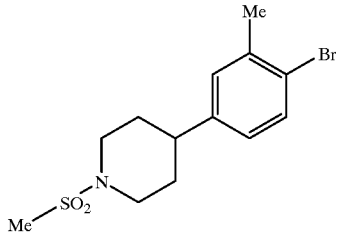

Triethylsilane (47.2 ml, 296 mmol), followed by trifluoromethanesulphonic acid (1.73 ml, 19.7 mmol) were added to a solution of the sulphonamide from preparation 20 (65.0 g, 197 mmol) in dichloromethane (300 ml) and trifluoroacetic acid (300 ml), and the reaction stirred at room temperature for an hour. Tlc analysis showed starting material remaining, so additional triethylsilane (75.2 ml, 471 mmol) and trifluoromethanesulphonic acid (0.86 ml, 9.8 mmol) were added and the reaction stirred for a further 20 hours at room temperature. The reaction was concentrated in vacuo, the residue poured into saturated aqueous potassium carbonate solution, and the mixture extracted with dichloromethane (3×650 ml). The combined organic extracts were washed with brine (500 ml), dried (MgSO$_4$), filtered and concentrated in vacuo. The crude product was triturated with hot methanol/hexane, filtered and dried to give the title compound (52.43 g, 80%) as a buff-coloured solid.

$^1$H nmr (CDCl$_3$, 400 MHz) δ: 1.78 (m, 2H), 1.90 (m, 2H), 2.37 (s, 3H), 2.52 (m, 1H), 2.77 (m, 5H), 3.94 (m, 2H), 6.83 (m, 1H), 7.02 (s, 1H), 7.42 (m, 1H). LRMS: m/z 354, 356 (M+23)$^+$.

Preparation 25

Methyl 2-[4-(4-bromo-3-methylphenyl)piperidin-1-ylsulphonyl]acetate

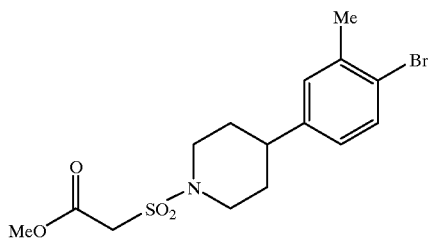

Sodium hydride (12.2 g, 60% dispersion in mineral oil, 305 mmol) was added to a solution of the sulphonamide from preparation 24 (50.61 g, 152 mmol) and dimethylcarbonate (63.8 ml, 760 mmol) in toluene (600 ml), and the reaction heated under reflux for 1½ hours. The reaction was partitioned between ethyl acetate (1000 ml), and cooled hydrochloric acid (600 ml, 1N), and the layers separated. The aqueous layer was extracted with ethyl acetate (500 ml), the combined organic extracts washed with brine (3×300 ml), dried (MgSO$_4$), filtered and concentrated in vacuo. The residue was triturated with hexane, and the solid filtered. This was re-crystallised from di-isopropyl ether and dried in vacuo to give the title compound as buff-coloured crystals, (40.9 g, 69%).

$^1$H nmr (CDCl$_3$, 400 MHz) δ: 1.77 (m, 2H), 1.84 (m, 2H), 2.37 (s, 3H), 2.58 (m, 1H), 2.97 (m, 2H), 3.80 (s, 3H), 3.96 (m, 4H), 6.84 (m, 1H), 7.02 (s, 1H), 7.42 (d, 1H). LRMS m/z 412, 414 (M+23)$^+$.

Preparation 26

Methyl 2-[4-(4-bromo-3-methylphenyl)piperidin-1-ylsulphonyl]-2-methyl-propanoate

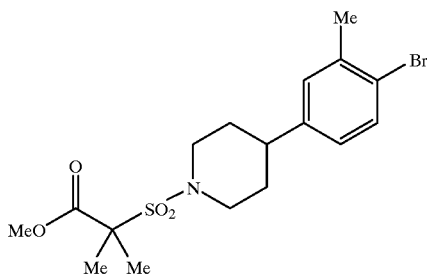

Triethylsilane (1.43 ml, 9.0 mmol) followed by trifluoromethanesulphonic acid (0.02 ml, 0.3 mmol) were added to a solution of the 1,2,3,6-tetrahydropyridine from preparation 22 (1.25 g, 3.0 mmol) and trifluoroacetic acid (15 ml) in dichloromethane (15 ml), and the reaction was stirred for an hour at room temperature. The reaction mixture was concentrated in vacuo, the residue diluted with dichloromethane (25 ml), then partitioned between ethyl acetate (150 ml) and saturated sodium bicarbonate solution (150 ml), and the layers separated. The aqueous phase was extracted with ethyl acetate (2×35 ml), the combined organic solutions dried (MgSO$_4$), filtered and evaporated in vacuo. The residual solid was triturated with di-isopropyl ether to give the title compound as a white solid, (963 mg, 77%).

mp 103–106° C.; $^1$H nmr (DMSO-d$_6$, 400 MHz) δ: 1.52 (m, 8H), 1.77 (m, 2H), 2.28 (s, 3H), 2.63 (m, 1H), 3.00 (m, 2H), 3.70 (m, 5H), 6.98 (dd, 1H), 7.20 (s, 1H), 7.42 (dd, 1H). Anal. Found: C, 48.42; H, 5.74; N, 3.27. C$_{17}$H$_{24}$BrNSO$_4$ requires C, 48.81; H, 5.78 N, 3.35%.

Preparation 27

Methyl 4-[4-(4-bromo-3-methylphenyl)piperidin-1-ylsulphonyl]tetrahydro-2H-pyran-4-carboxylate

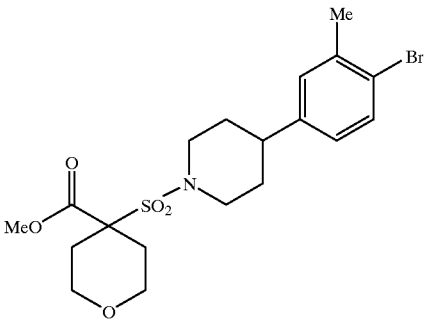

Sodium hydride (60% dispersion in mineral oil, 1.16 g, 29.0 mmol) was added to a stirred solution of the acetate from preparation 25 (10.14 g, 26.0 mmol) in N-methyl pyrrolidinone (60 ml) at ambient temperature under nitrogen. After 45 minutes, bis-2-bromoethyl ether (4.26 ml, 33.8 mmol) was added to the stirred mixture, and after a further 150 minutes an additional portion of sodium hydride (60% dispersion in mineral oil; 1.16 g, 29 mmol) was added, and the mixture left stirring for 18 hours. The solvent was removed under reduced pressure, and the residues was partitioned between ethyl acetate and water. The organic layer was collected, washed with brine, dried (MgSO$_4$), and evaporated under reduced pressure. The residue was crystallised from ethyl acetate and diisopropyl ether to give the title compound as a colourless solid (7.34 g, 61%). The filtrate was evaporated and purified by flash chromatography eluting with dichloromethane, and crystallisation from ethyl acetate and diisopropyl ether to give an additional batch of the title compound as a colourless solid (1.86 g, 15%). A small sample was recrystallised from ethyl acetate for further characterisation.

m.p. 162–163° C.; $^1$H nmr (CDCl$_3$) δ: 1.65–1.83 (m, 4H), 2.20 (m, 2H), 2.38 (s, 3H), 2.40 (m, 2H), 2.57 (m, 1H), 3.00 (m, 2H), 3.29 (m, 2H), 3.85 (s, 3H), 3.87–4.00 (m, 4H), 6.83 (d, 1H), 7.02 (s, 1H), 7.41 (d, 1H). LRMS: m/z 460/462 (M+1)$^+$. Anal. Found: C,49.49; H,5.68; N,2.93. C$_{19}$H$_{26}$BrNO$_5$S requires C,49.57; H,5.69; N,3.04%

Alternative Route: Triethylsilane (50 ml, 0.30 mol) was added dropwise over 2 min to a solution of the carbinol from preparation 130 (60 g, 0.12 mol) in dichloromethane (150 ml) and trifluoroacetic acid (150 ml), at 0° C., under nitrogen. Triflic acid (0.53 ml, 6.0 mmol) was added dropwise over 10 min and the resulting mixture was stirred at 0° C. for 4 h. Dichloromethane (300 ml) and demineralised water (300 ml) were added and the aqueous phase was separated. The organic phase was washed with water (200 ml), saturated sodium bicarbonate solution (2×200 ml) and demineralised water (200 ml) and then concentrated in vacuo to a colourless solid. The solid was slurried in hot ethyl acetate (300 ml) for 20 min and the mixture was cooled to 0° C. and then filtered. The residue was dried in vacuo to leave the title compound as a colourless solid (53 g, 92%).

Preparation 28

Methyl 1-benzyl-4-[4-(4-bromo-3-methylphenyl) piperidin-1-ylsulphonyl]4-piperidinecarboxylate

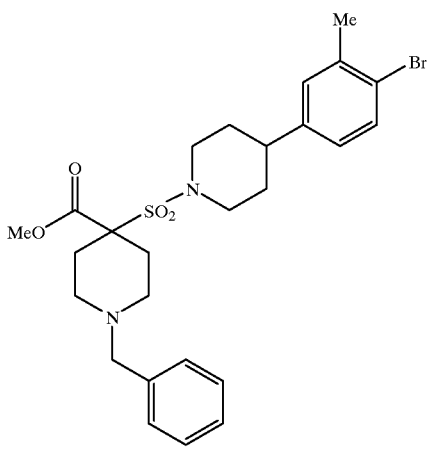

The acetate from preparation 25 (4.17 g, 10.7 mmol) was added portionwise to a suspension of sodium hydride (994 mg, 60% dispersion in mineral oil, 33.1 mmol) in 1-methyl-2-pyrrolidinone (40 ml), and the resulting solution stirred for an hour. Tetra-butyl ammonium bromide (3.44 g, 10.7 mmol) and N-benzyl-bis-(2-chloroethyl)amine (2.73 g, 10.1 mmol) were added portionwise, and once addition was complete, the reaction was stirred at 60° C. for 6 hours. The cooled reaction was partitioned between water and ethyl acetate, the layers separated, and the aqueous phase extracted with ethyl acetate. The combined organic extracts were washed with water, dried ($Na_2SO_4$), filtered and concentrated in vacuo. The crude product was purified by column chromatography on silica gel twice, using an elution gradient of dichloromethane:ether (100:0 to 90:10) to afford the title compound (3.04 g, 52%).

$^1$H nmr (CDCl$_3$, 400 MHz) δ: 1.63–1.81 (m, 4H), 1.88 (m, 2H), 2.16 (m, 2H), 2.36 (s, 3H), 2.42 (m, 2H), 2.55 (m, 1H), 2.88 (m, 2H), 2.98 (m, 2H), 3.40 (s, 2H), 3.82 (m, 5H), 6.83 (d, 1H), 7.00 (s, 1H), 7.22 (m, 5H), 7.40 (d, 1H). LRMS m/z 549, 551 (M+1)$^+$.

Preparation 29

Methyl 2-methyl-2-{4-[trifluoromethanesulphonyloxy]-1,2,3,6-tetrahydropyridin-1-ylsulphonyl}propanoate

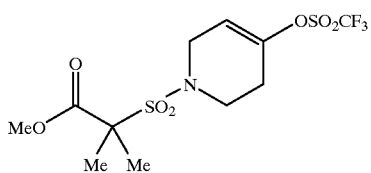

2,6-Di-tert-butyl-4-methylpyridine (3.7 g, 18 mmol) was added to a solution of the ketone from preparation 17 (3.8 g, 14.5 mmol) in dichloromethane (50 ml), and the solution then cooled to 4° C. Trifluoromethane sulphonic anhydride (2.95 ml, 17.5 mmol) was added dropwise, and the reaction then stirred at room temperature for 17 hours. Tlc analysis showed starting material remaining, so additional 2,6-di-tert-butyl-4-methylpyridine (3.7 g, 18 mmol) and trifluoromethane sulphonic anhydride (2.7 ml, 16 mmol) were added portionwise to the stirred reaction over the following 4 days. The mixture was then filtered, the filtrate concentrated in vacuo, and the residue triturated with ether. The resulting solid was filtered off, and the filtrate evaporated in vacuo. This crude product was purified by column chromatography on silica gel using an elution gradient of hexane-:ethyl acetate (91:9 to 50:50) to afford the title compound (4.25 g, 74%) as a white solid.

$^1$H nmr (CDCl$_3$, 400 MHz) δ: 1.64 (s, 6H), 2.56 (m, 2H), 3.60 (m, 2H), 3.79 (s, 3H), 4.06 (m, 2H), 5.80 (m, 1H).

Anal. Found: C, 33.62; H, 4.03; N, 3.43. $C_{11}H_{16}F_3NO_7S_2$ requires C, 33.42; H, 4.08;N, 3.54%.

Preparation 30

Methyl 2-[4-(4-{3-formylphenyl}-3-methylphenyl)-piperidin-1-ylsulphonyl]tetrahydro-2H-pyran-4-carboxylate

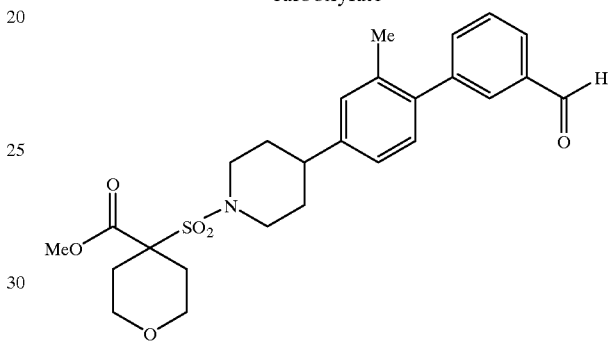

A mixture of the bromide from preparation 27 (4.02 g, 8.73 mmol), 3-formylphenylboronic acid (1.83 g, 11.56 mmol), cesium fluoride (3.46 g, 22.8 mmol), tris (dibenzylideneacetone)palladium (0) (430 mg, 0.47 mmol) and tri(o-tolyl)phosphine (284 mg, 0.93 mmol) in 1,2-dimethoxyethane (70 ml) was heated under reflux for 6 hours. The cooled reaction was diluted with water and the mixture extracted with ethyl acetate (3×). The combined organic extracts were washed with brine, dried (MgSO$_4$), filtered and concentrated under reduced pressure. The residue was purified by column chromatography on silica gel using an elution gradient of ethyl acetate:hexane (25:75 to 40:60), and triturated with di-isopropyl ether to give the title compound as a solid, (2.69 g, 63%).

$^1$H nmr (CDCl$_3$, 400 MHz) δ: 1.75–1.95 (m, 4H), 2.20 (m, 5H), 2.40 (m, 2H), 2.62 (m, 1H), 3.03 (m, 2H), 3.30 (m, 2H), 3.82–4.02 (m, 7H), 7.07 (m, 2H), 7.16 (m, 1H), 7.56 (m, 2H), 7.81 (m, 2H), 10.02 (s, 1H). LRMS: m/z 508 (M+23)$^+$.

Preparation 31

Methyl 2-[4-(4-{6-[2-benzyloxy]ethoxypyridin-2-yl}-3-methylphenyl)-1,2,3,6-tetrahydropyridin-1-ylsulphonyl]-2-methyl-propanoate

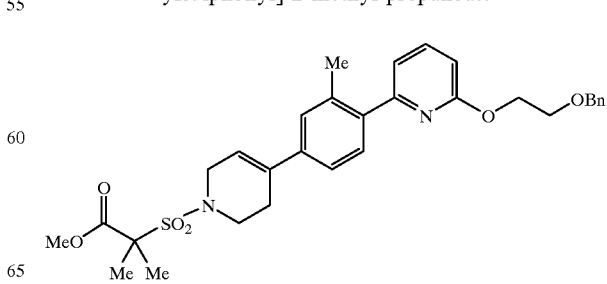

A mixture of the stannane from preparation 4 (2.8 g, 5.4 mmol) and the bromide from preparation 22 (1.5 g, 3.62 mmol), and tetrakis(triphenylphosphine)palladium (0) (205 mg, 0.18 mmol) in toluene (35 ml) was heated under reflux overnight. The cooled mixture was evaporated in vacuo and the residue purified by column chromatography on silica gel using pentane:ethyl acetate (75:25) as eluant, to afford the title compound as a colourless oil, (1.7 g, 83%).

$^1$H nmr (CDCl$_3$, 300 MHz) δ: 1.69 (s, 6H), 2.42 (s, 3H), 2.64 (m, 2H), 3.62 (t, 2H), 3.82 (m, 5H), 4.14 (m, 2H), 4.56 (t, 2H), 4.62 (s, 2H), 6.06 (s, 1H), 6.77 (d, 1H), 7.0 (d, 1H), 7.22–7.42 (m, 8H),7.62 (m, 1H). LRMS: m/z 565 (M+1)$^+$.

Preparation 32

Methyl 4-[4-(4-{6-[2-benzyloxy]ethoxypyridin-2-yl}-3-methylphenyl)-1,2,3,6-tetrahydropyridin-1-ylsulphonyl]tetrahydro-2H-pyran-4-carboxylate

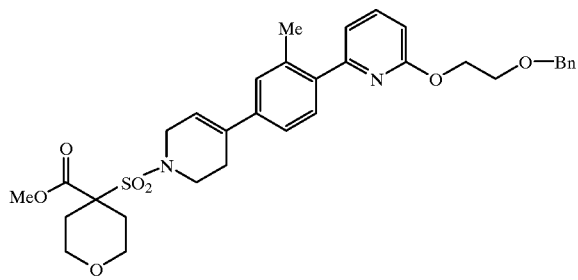

A mixture of the stannane from preparation 4 (1.74 g, 3.36 mmol) and the bromide from preparation 23 (1.1 g, 2.4 mmol) and tetrakis(triphenylphosphine)palladium (0) (138 mg, 0.14 mmol) in toluene (16 ml) was heated under reflux for 4 hours. The cooled reaction was diluted with water, and the mixture extracted with ether (3×). The combined organic extracts were washed with brine, dried (MgSO$_4$), filtered through Arbocel® and evaporated in vacuo. The residual yellow oil was purified by column chromatography on silica gel using an elution gradient of pentane:ether (50:50 to 25:75) to afford the title compound as a pale yellow oil, (1.18 g, 81%).

$^1$H nmr (CDCl$_3$, 400 MHz) δ: 2.22 (m, 2H), 2.42 (m, 5H), 2.62 (m, 2H), 3.34 (m, 2H), 3.60 (m, 2H), 3.82 (t, 2H), 3.88 (s, 3H), 4.01 (m, 2H), 4.09 (m, 2H), 4.55 (t, 2H), 4.61 (s, 2H), 6.05 (m, 1H), 6.76 (d, 1H), 6.99 (d, 1H), 7.21–7.41 (m, 78H), 7.61 (m, 1H). LRMS: m/z 607 (M+1)$^+$.

Preparation 33

Methyl 1-benzyl-4-{[4-(4-{6-[2-benzyloxyethoxy]pyridin-2-yl}-3-methylphenyl)piperidin-1-yl]sulphonyl}-piperidin-4-carboxylate

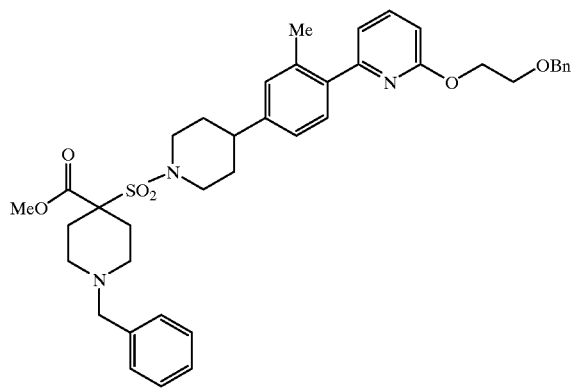

The stannane from preparation 4 (4.05 g, 7.8 mmol), followed by tris(triphenylphosphine) palladium (0) (410 mg, 0.35 mmol) were added to a solution of the bromide from preparation 28 (3.91 g, 7.1 mmol) in toluene (50 ml), and the reaction de-gassed, then heated under a nitrogen atmosphere reflux for 7 hours. Aqueous potassium fluoride solution (20 ml, 25%) was added to the cooled reaction, the mixture stirred at room temperature for 20 minutes, then filtered through Arbocel®. The filtrate was diluted with ethyl acetate, washed with brine, dried (Na$_2$SO$_4$), filtered and evaporated in vacuo. The residue was purified by column chromatography on silica gel twice, using an elution gradient of ethyl acetate:hexane (40:60 to 60:40) to give the desired product as a yellow crystalline solid, (2.77 g, 56%).

$^1$H nmr (CDCl$_3$, 400 MHz) δ: 1.74–1.95 (m, 6H), 2.17 (m, 2H), 2.37 (s, 3H), 2.44 (m, 2H), 2.60 (m, 1H), 2.88 (m, 2H), 3.00 (m, 2H), 3.40 (s, 2H), 3.80 (m, 5H), 3.88 (m, 2H), 4.52 (t, 2H), 4.59 (s, 2H), 6.70 (d, 1H), 6.95 (d, 1H), 7.03 (m, 2H), 7.18–7.37 (m, 11H), 7.58 (m, 1H). LRMS: m/z 699 (M+1)$^+$.

Preparation 34

Methyl 2-[4-(4-{3-[2,2-diethoxyethoxy]phenyl}-3-methylphenyl)-1,2,3,6-tetrahydropyridin-1-ylsulphonyl]-2-methyl-propanoate

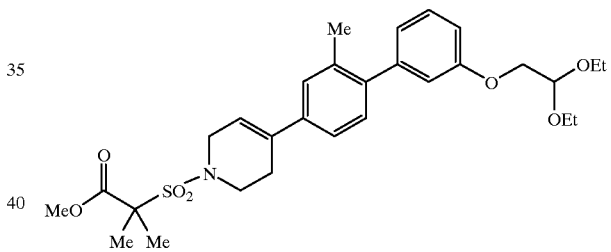

A mixture of cesium fluoride (1.81 g, 11.92 mmol), tri-o-tolyl phosphine (180 mg, 0.59 mmol), tris(dibenzylideneacetone)dipalladium (0) (280 mg, 0.31 mmol) and the boronic acid from preparation 10 (1.83 g, 7.2 mmol) and the bromide from preparation 22 (2.5 g, 6.0 mmol) in anhydrous 1,2-dimethoxyethane (60 ml), was heated under reflux for 5½ h. The cooled reaction mixture was partitioned between water and ethyl acetate, and this mixture filtered through Arbocel®. The filtrate was separated, the organic phase washed with water, then brine, dried (Na$_2$SO$_4$), filtered and evaporated in vacuo. The residual green oil was purified by medium pressure column chromatography on silica gel using an elution gradient of pentane:ethyl acetate (100:0 to 85:15) to afford the title compound, (3.04 g, 93%).

$^1$H nmr (CDCl$_3$, 300 MHz) δ: 1.24 (t, 6H), 1.69 (s, 6H), 2.28 (s, 3H), 2.64 (m, 2H), 3.62 (m, 4H), 3.80 (m, 5H), 4.04 (d, 2H), 4.12 (m, 2H), 4.84 (t, 1H), 6.06 (m, 1H), 6.92 (m, 3H), 7.14–7.38 (m, 4H). LRMS: m/z 563 (M+18)$^+$.

Preparation 35

Methyl 2-[(4-{4-[6-(2-hydroxyethoxy)pyridin-2-yl]-3-methylphenyl}-piperidin-1-yl)sulphonyl]-2-methyl-propanoate

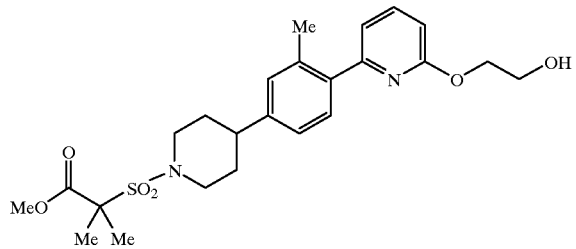

A mixture of the benzyl ether from preparation 31 (1.7 g, 3.0 mmol), ammonium formate (3.0 g, 50.0 mmol), palladium hydroxide on carbon (500 mg) and acetic acid (10 ml) in methanol (30 ml) was heated under reflux overnight. Additional ammonium formate (1.5 g, 25.0 mmol) and palladium hydroxide on carbon (1.5 g) were added and the reaction heated under reflux for a further 72 hours. The cooled mixture was filtered through Arbocel®, and the filter pad washed well with ethyl acetate. The combined filtrates were neutralised using saturated sodium bicarbonate solution, the phases separated, and the aqueous layer extracted with ethyl acetate (2×100 ml). The combined organic extracts were dried (MgSO$_4$), filtered and evaporated in vacuo to give the title compound as a colourless solid, (1.2 g, 84%).

mp 108–111° C.; $^1$H nmr (CDCl$_3$, 300 MHz) δ: 1.64 (s, 6H), 1.78–1.94 (m, 4H), 2.40 (s, 3H), 2.65 (m, 1H), 3.07 (m, 2H), 3.82 (s, 3H), 3.97 (m, 4H), 4.50 (t, 2H), 6.7 (d, 1H), 7.00 (d, 1H), 7.10 (m, 2H), 7.38 (d, 1H), 7.65 (m, 1H). LRMS: m/z 477 (M+1)$^+$.

Preparation 36

Methyl 4-{[4-(4-{6-[2-hydroxyethoxy]pyridin-2-yl}-3-methylphenyl)piperidin-1-yl]sulphonyl}tetrahydro-2H-pyran-4-carboxylate

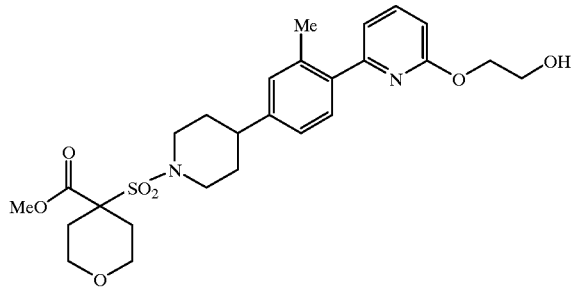

The title compound was prepared from the benzyl ether from preparation 32 in 93% yield, following a similar procedure to that described in preparation 35.

$^1$H nmr (CDCl$_3$, 300 MHz) δ: 1.70–1.95 (m, 4H), 2.22 (m, 2H), 2.40 (m, 5H), 2.64 (m, 1H), 3.06 (m, 2H), 3.34 (m, 2H), 3.92 (m, 7H), 4.00 (m, 2H), 4.50 (t, 2H), 6.78 (d, 1H), 7.00 (d, 1H), 7.10 (m, 2H), 7.38 (d, 1H), 7.65 (m, 1H). LRMS: m/z 519 (M+1)$^+$.

Preparation 37

Methyl 4-({4-[4-(6-{[(4R)-2,2-dimethyl-1,3-dioxolan-4-yl]methoxy}pyridin-2-yl)-3-methylphenyl]piperidin-1-yl}sulphonyl)tetrahydro-2H-pyran-4-carboxylate

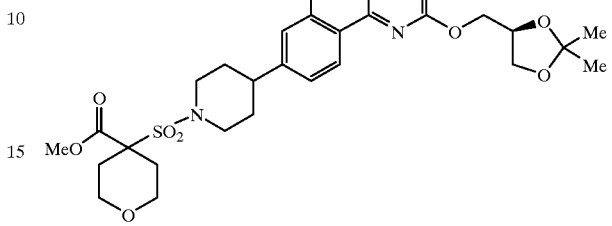

A mixture of the stannane from preparation 5 (2.0 g, 4.97 mmol) and the bromide from preparation 27 (1.76 g, 3.82 mmol) and tetrakis(triphenylphosphine)palladium (0) (242 mg, 0.21 mmol) in toluene (50 ml) was heated under reflux for 7 hours. The cooled mixture was concentrated under reduced pressure and the residue purified by column chromatography on silica gel twice, using an elution gradient of ether:pentane (66:34 to 34:66) to give the title compound as a white solid, (1.29 g, 57%).

$^1$H nmr (CDCl$_3$, 300 MHz) δ: 1.40 (s, 3H), 1.46 (s, 3H), 1.77–1.95 (m, 4H), 2.21 (m, 2H), 2.40 (m, 5H), 2.64 (m, 1H), 3.04 (m, 2H), 3.34 (m, 2H), 3.81–4.04 (m, 8H), 4.15 (dd, 1H), 4.40 (m, 2H), 4.50 (m, 1H), 6.75 (d, 1H), 7.00 (d, 1H), 7.09 (m, 2H), 7.38 (d, 1H), 7.62 (m, 1H). LRMS: m/z 611 (M+23)$^+$.

Preparation 38

Methyl 4-({4-[4-(6-{[(4S)-2,2-dimethyl-1,3-dioxolan-4-yl]methoxy}pyridin-2-yl)-3-methylphenyl]piperidin-1-yl}sulphonyl)tetrahydro-2H-pyran-4-carboxylate

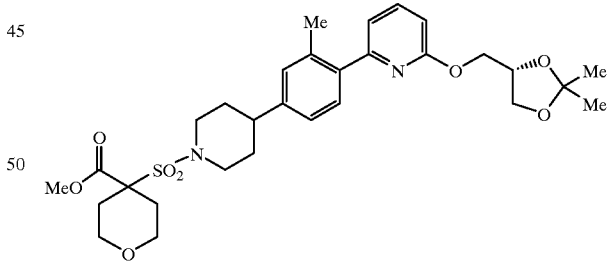

The title compound was obtained as a white solid (65%), after recrystallisation from methanol, from the stannane from preparation 6 and the bromide from preparation 27, following a similar procedure to that described in preparation 37.

$^1$H nmr (CDCl$_3$, 300 MHz) δ: 1.40 (s, 3H), 1.46 (s, 3H), 1.78–1.95 (m, 4H), 2.21 (m, 2H), 2.42 (m, 5H), 2.65 (m, 1H), 3.08 (m, 2H), 3.35 (m, 2H), 3.81–4.05 (m, 8H), 4.14 (dd, 1H), 4.40 (m, 2H), 4.50 (m, 1H), 6.76 (d, 1H), 6.99 (d, 1H), 7.08 (m, 2H), 7.38 (d, 1H), 7.62 (m, 1H). LRMS: m/z 589 (M+1)$^+$.

Preparation 39

Methyl 4-{[4-(4-{6-[(2S)-2,3-dihydroxy-1-propoxy]pyridin-2-yl)-3-methylphenyl)piperidin-1-yl]sulphonyl}tetrahydro-2H-pyran-4-carboxylate

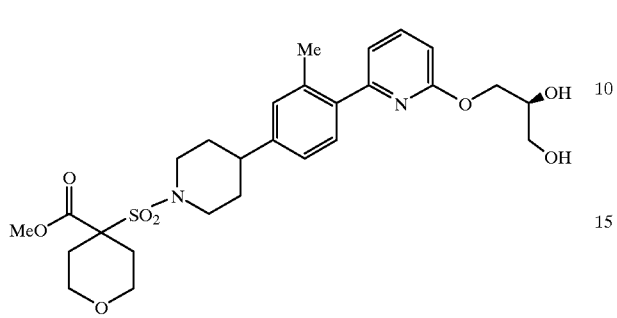

A solution of the dioxolane from preparation 37 (799 mg, 1.36 mmol) in 1,4-dioxan (10 ml) was added to an ice-cooled solution of hydrochloric acid (30 ml, 2N), and the reaction stirred for 75 minutes. The solution was poured into saturated sodium bicarbonate solution (200 ml), and the resulting precipitate filtered and dried. The solid was recrystallised from ethy acetate/di-isopropyl ether, to afford the desired product as a white powder, (642 mg, 86%).

$^1$H nmr (CDCl$_3$, 300 MHz) δ: 1.70–2.42 (m, 12H), 2.64 (m, 1H), 3.04 (m, 2H), 3.34 (m, 2H), 3.63 (m, 6H), 3.84–4.19 (m, 5H), 4.50 (m, 2H), 6.77 (d, 1H), 7.00 (d, 1H), 7.09 (m, 2H), 7.35 (d, 1H), 7.68 (m, 1H).

Preparation 40

Methyl 4-{[4-(-4-{6-[(2R)-2,3-dihydroxy-1-propoxy]pyridin-2-yl}-3-methylphenyl)piperidin-1-yl]sulphonyl}tetrahydro-2H-pyran-4-carboxylate

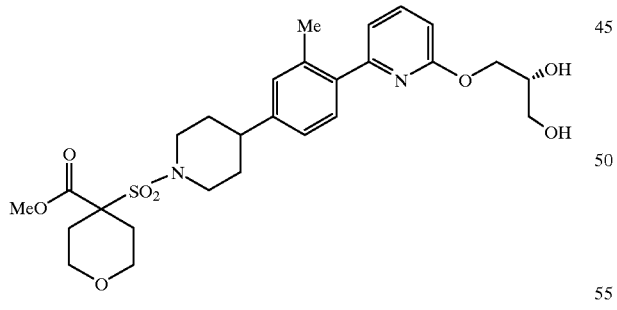

The title compound was obtained as a white crystalline solid (86%), from the dioxolane from preparation 38, following the procedure described in preparation 39.

$^1$H nmr (CDCl$_3$, 400 MHz) δ: 1.76–1.92 (m, 4H), 2.21 (m, 2H), 2.40 (m, 5H), 2.50 (t, 1H), 2.64 (m, 1H), 3.06 (m, 2H), 3.34 (m, 2H), 3.64 (m, 2H), 3.72 (m, 5H), 4.00 (m, 3H), 4.12 (d, 1H), 4.50 (m, 2H), 6.78 (d, 1H), 7.01 (d, 1H), 7.10 (m, 2H), 7.36 (d, 1H), 7.68 (m, 1H). LRMS: m/z 571 (M+23)$^+$.

Preparation 41

Methyl 4-{[4-(4-{6-[2-hydroxyethoxy]pyridin-2-yl}-3-methylphenyl)piperidin-1-yl]sulphonyl}-piperidine-4-carboxylate

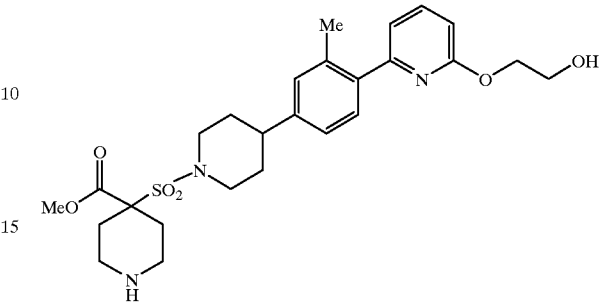

A mixture of the benzyl piperidine from preparation 33 (3.32 g, 4.76 mmol), ammonium formate (3.0 g, 47.6 mmol) and palladium hydroxide on carbon (3.32 g) in a solution of acetic acid:methanol:tetrahydrofuran (2:2:1, 30 ml) was heated under reflux for 2 hours. The cooled reaction was filtered through Arbocel®, washing through with tetrahydrofuran, and the filtrate concentrated in vacuo. The residue was partitoned between water and ethyl acetate, and the layers separated. The organic phase was dried (Na$_2$SO$_4$), filtered and evaporated in vacuo. The crude product was purified by column chromatography on silica gel using an elution gradient of dichloromethane:methanol (90:10 to 85:15) to afford the title compound, (1.28 g, 52%).

$^1$H nmr (CDCl$_3$, 400 MHz) δ: 1.73–1.88 (m, 4H), 2.00 (m, 2H), 2.38 (s, 3H), 2.42–2.64 (m, 5H), 3.02 (m, 2H), 3.16 (m, 2H), 3.85 (m, 7H), 4.46 (t, 2H), 6.73 (d, 1H), 6.98 (d, 1H), 7.05 (m, 2H), 7.34 (d, 1H), 7.60 (m, 1H). LRMS: m/z 518 (M+1)$^+$.

Preparation 42

Methyl 4-{[4-(4-{6-[2-hydroxyethoxy]pyridin-2-yl}-3-methylphenyl)piperidin-1-yl]sulphonyl}-1-methylpiperidine-4-carboxylate

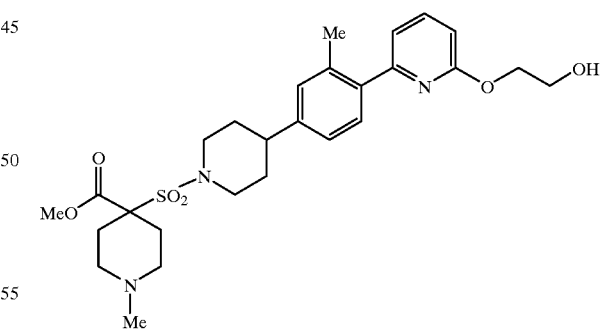

Formaldehyde (0.49 ml, 37 wt. % in water, 4.9 mmol) was added to a solution of the piperidine from preparation 41 (634 mg, 1.22 mmol) in dichloromethane (30 ml), and the solution was stirred vigorously at room temperature for 30 minutes. Sodium triacetoxyborohydride (519 mg, 2.45 mmol) was added and the reaction was stirred at room temperature for 20 hours. The reaction was washed with water, dried (Na$_2$SO$_4$), filtered and evaporated in vacuo. The crude product was purified by column chromatography on silica gel using dichloromethane:methanol (95:5) as eluant to give the title compound (559 mg, 86%).

¹H nmr (CDCl₃, 400 MHz) δ: 1.76–1.95 (m, 6H), 2.20 (m, 5H), 2.38 (s, 3H), 2.50 (m, 2H), 2.62 (m, 1H), 2.90 (m, 2H), 3.03 (m, 2H), 3.84 (s, 3H), 3.94 (m, 4H), 4.48 (m, 2H), 6.76 (d, 1H), 6.99 (d, 1H), 7.06 (m, 2H), 7.35 (d, 1H), 7.63 (m, 1H). LRMS: m/z 554 (M+23)⁺.

Preparation 43

Methyl 1-(tert-butoxycarbonyl)-4-{[4-(4-{6-[2-hydroxyethoxy]pyridin-2-yl}-3-methylphenyl)piperidin-1-yl]sulphonyl}-4-piperidinecarboxylate

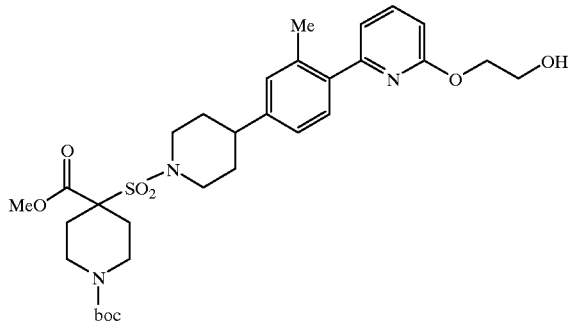

Triethylamine (175μl, 1.26 mmol) was added to a solution of the amine from preparation 41 (594 mg, 1.15 mmol) in dichloromethane (100 ml), followed by portionwise addition of di-tert-butyl dicarbonate (262 mg, 1.20 mmol). The reaction mixture was stirred at room temperature for an hour, then concentrated in vacuo to a volume of 20 ml. The solution was diluted with ether (150 ml), washed with hydrochloric acid (0.5N), brine, then dried (MgSO₄), filtered and evaporated in vacuo. The residue was purified by column chromatography on silica gel using dichloromethane:methanol (95:5) as eluant to give the title compound (653 mg, 92%) as a white foam.

¹H nmr (CDCl₃, 400 MHz) δ: 1.42 (s, 9H), 1.75–1.90 (m, 4H), 2.01 (m, 2H), 2.38 (s, 3H), 2.45 (m, 2H), 2.63 (m, 3H), 3.02 (m, 2H), 3.50 (m, 1H), 3.87 (m, 7H), 4.17 (m, 2H), 4.46 (m, 2H), 6.75 (m, 1H), 6.98 (m, 1H), 7.05 (m, 2H), 7.35 (m, 1H), 7.62 (m, 1H). LRMS: m/z 640 (M+23)⁺.

Preparation 44

Methyl 2-[4-(4-{3-tert-butoxyphenyl})-3-methylphenyl)-piperidin-1-ylsulphonyl]acetate

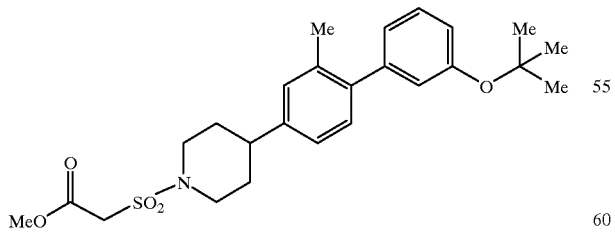

Nitrogen was bubbled through a mixture of cesium fluoride (3.71 g, 24.44 mmol), tri-o-tolyl phosphine (34 mg, 0.11 mmol), tris(dibenzylideneacetone)dipalladium (0) (50 mg, 0.05 mmol) the bromide from preparation 25 (4.27 g, 11.0 mmol) and the boronic acid from preparation 8 (3.2 g, 16.5 mmol) in anhydrous 1,2-dimethoxyethane (40 ml). The reaction was then heated at 90° C. under a nitrogen atmosphere for 50 hours. The cooled reaction mixture was diluted with ethyl acetate, the mixture washed with water (3×), dried (MgSO₄), filtered and concentrated in vacuo. The residue was purified by column chromatography on silica gel using an elution gradient of hexane:ethyl acetate (95:5 to 50:50) to give the title compound as an oil, that crystallised on standing, (3.15 g, 62%).

¹H nmr (CDCl₃, 400 MHz) δ: 1.36 (s, 9H), 1.83 (m, 2H), 1.97 (m, 2H), 2.22 (s, 3H), 2.62 (m, 1H), 2.98 (m, 2H), 3.80 (s, 3H), 3.98 (m, 4H), 6.94 (m, 3H), 7.04 (m, 2H), 7.17 (d, 1H), 7.23 (m, 1H). LRMS: m/z 582 (M+23)⁺.

Preparation 45

Methyl 2-[4-(4-{3-tert-butoxyphenyl-3-methylphenyl)-piperidin-1-ylsulphonyl]-2-methyl-propanoate

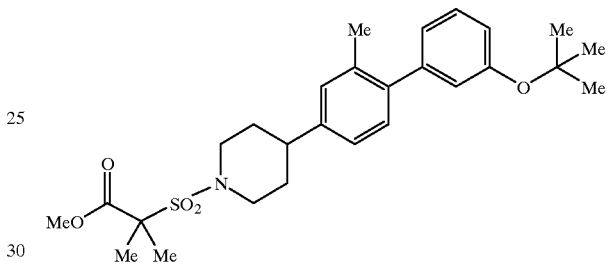

Potassium tert-butoxide (13.63 ml, 1M in tetrahydrofuran, 13.63 mmol) was added dropwise to a solution of the acetate from preparation 44 (2.5 g, 5.45 mmol) and methyl iodide (3.4 ml, 54.5 mmol) in tetrahydrofuran, and once addition was complete, the reaction was stirred at room temperature for 72 hours. The mixture was partitioned between ethyl acetate and water and the layers separated. The organic phase was dried (MgSO₄), filtered and evaporated in vacuo, to give the crude title compound, which was used without further purification (3.1 g).

¹H nmr (CDCl₃, 400 MHz) δ: 1.36 (s, 9H), 1.63 (s, 6H), 1.77–1.94 (m, 4H), 2.22 (s, 3H), 2.63 (m, 1H), 3.05 (m, 2H), 3.80 (s, 3H), 3.95 (m, 2H), 6.90–7.10 (m, 5H), 7.18 (m, 1H), 7.24 (m, 1H). LRMS: m/z 488 (M+1)⁺.

Preparation 46

Methyl 4-[4-(4-{3-tert-butoxyphenyl}-3-methylphenyl)-piperidin-1-ylsulphonyl]-tetrahydro-2H-pyran-4-carboxylate

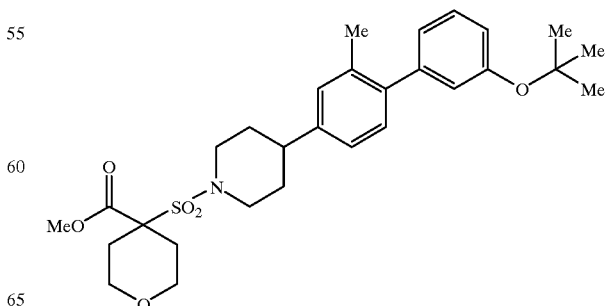

Nitrogen was bubbled through a mixture of cesium fluoride (2.19 g, 14.43 mmol), tri-o-tolyl phosphine (20 mg, 0.065 mmol), tris(dibenzylideneacetone)dipalladium (0) (30 mg, 0.032 mmol) and the bromide from preparation 27 (2.9 g, 6.5 mmol) and the boronic acid from preparation 8 (1.78 g, 9.75 mmol) in anhydrous 1,2-dimethoxyethane (40 ml). The reaction was then heated under reflux under a nitrogen atmosphere for 24 hours. The cooled reaction was partitioned between ethyl acetate and water, the organic phase dried (MgSO$_4$), filtered and concentrated in vacuo. The residue was triturated with di-isopropyl ether, the solid filtered and dried under vacuum, to give the desired product as a cream-coloured solid, (2.0 g, 58%). The filtrate was concentrated in vacuo and the residual oil purified by column chromatography on silica gel using an elution gradient of hexane:dichloromethane:methanol (50:50:0 to 0:100:0 to 0:99:1) to provide an additional (630 mg, 18%) of the title compound.

$^1$H nmr (CDCl$_3$, 400 MHz) δ: 1.37 (s, 9H), 1.76–1.92 (m, 4H), 2.20 (m, 5H), 2.40 (m, 2H), 2.60 (m, 1H), 3.02 (m, 2H), 3.29 (m, 2H), 3.86 (m, 5H), 3.98 (m, 2H), 6.94 (m, 3H), 7.02 (m, 2H), 7.14 (m, 1H), 7.22 (m, 1H). LRMS: m/z 552 (M+23)$^+$.

Preparation 47

Methyl 2-[4-(4-{3-hydroxyphenyl}-3-methylphenyl)-piperidin-1-ylsulphonyl]-2-methyl-propanoate

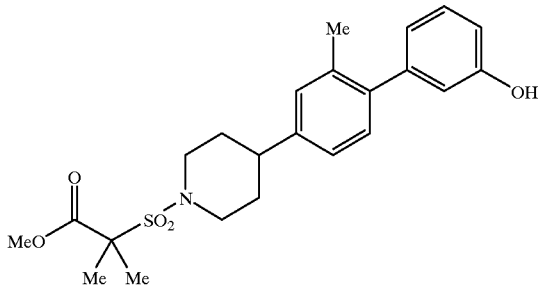

Trifluoroacetic acid (25 ml) was added to a solution of the tert-butoxy ether from preparation 45 (4.8 g, 9.80 mmol) in dichloromethane (50 ml), and the solution stirred for 4 hours. The reaction mixture was concentrated in vacuo, and the residue purified by column chromatography on silica gel, twice using an elution gradient of dichloromethane:methanol (10:0 to 95:5) to give the desired product (536 mg, 13%).

$^1$H nmr (CDCl$_3$, 400 MHz) δ: 1.62 (s, 6H), 1.76–1.92 (m, 4H), 2.22 (s, 3H), 2.62 (m, 1H), 3.04 (m, 2H), 3.78 (s, 3H), 3.95 (m, 2H), 6.78 (m, 2H), 6.83 (m, 1H), 7.03 (m, 2H), 7.15 (m, 1H), 7.21 (m, 1H). LRMS: m/z 454 (M+23)$^+$; Anal. Found: C, 63.70; H, 6.70; N, 3.20. C$_{23}$H$_{29}$NO$_5$S requires C, 64.01; H, 6.77; N, 3.25%.

Preparation 48

Methyl 4-[4-(4-{3-hydroxyphenyl}-3-methylphenyl)-piperidin-1-ylsulphonyl]-tetrahydro-2H-pyran-4-carboxylate

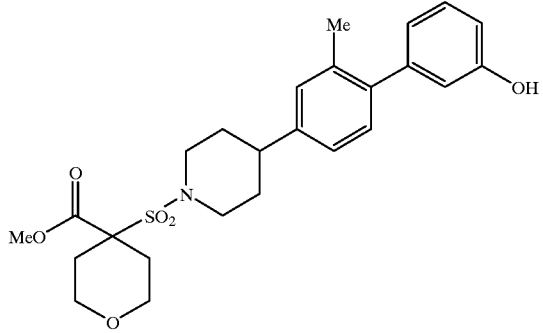

Triethylsilane (2 ml, 13.05 mmol), followed by trifluoroacetic acid (5 ml) were added to an ice-cooled solution of the tert-butyl ether from preparation 46 (2.3 g, 4.35 mmol) in dichloromethane (5 ml) and the reaction stirred for 2 hours. The mixture was concentrated in vacuo, and the residue azeotroped with toluene. The resulting foam was triturated with di-isopropyl ether, filtered and dried to afford the title compound as a solid, (1.94 g, 94%).
Alternative method
Palladium (II) acetate (300 mg, 1.34 mmol) and triphenylphosphine (708 mg, 2.70 mmol) were suspended in acetone (90 ml), and sonicated for 2 minutes. The suspension was then added to a mixture of 5-bromo-2-iodotoluene (7.9 g, 27 mmol), and the boronic acid from preparation 8 (5.7 g, 29.4 mmol) in aqueous sodium carbonate (42 ml, 2N). The reaction mixture was heated under reflux for 2 hours, then cooled and diluted with water (300 ml). This mixture was extracted with ether (2×250 ml), the combined organic extracts dried (MgSO$_4$), filtered and evaporated in vacuo. The residue was purified by column chromatography on silica gel using hexane:ether (99:1) as eluant to give 3-(4-bromo-2-methylphenyl)phenyl tert-butyl ether, 7.9 g. A solution of this intermediate ether (480 mg, 1.5 mmol) in tetrahydrofuran (2 ml), followed by a crystal of iodine, were added to magnesium (45 mg, 1.8 mmol), and the mixture was heated under reflux for 2 hours. The solution was diluted with tetrahydrofuran (3 ml), cooled to −78° C., and a solution of the ketone from preparation 16 (425 mg, 1.4 mmol) in tetrahydrofuran (15 ml) added dropwise. The reacton mixture was stirred at −78° C. for 30 minutes, then allowed to warm to room temperature. Aqueous ammonium chloride was added, the mixture extracted with ethyl acetate (2×50 ml) and the combined organic extracts were dried (MgSO$_4$), filtered and evaporated in vacuo. The residue was purified by column chromatography on silica gel using pentane:ethyl acetate (50:50) to afford methyl 4-[4-(4-{3-tert-butoxyphenyl}-3-methylphenyl)-4-hydroxypiperidin-1-ylsulphonyl]-tetrahydro-2H-pyran-4-carboxylate as a clear oil, 280 mg.
Triethylsilane (0.5 ml, 3.14 mmol), followed by trifluoroacetic acid (5 ml) were added to a solution of this intermediate (350 mg, 0.64 mmol) in dichloromethane (5 ml), and the reaction stirred at room temperature overnight. The reaction mixture was concentrated in vacuo, the residue azeotroped with toluene and the resulting solid dried under vacuum to afford the title compound, (300 mg).

$^1$H nmr (CDCl$_3$, 400 MHz) δ: 1.74–1.90 (m, 4H), 2.20 (m, 5H), 2.40 (m, 2H), 2.62 (m, 1H), 3.02 (m, 2H), 3.29 (m, 2H), 3.87 (m, 5H), 3.98 (m, 2I), 6.77 (m, 2H), 6.83 (d, 1H), 7.02 (m, 2H), 7.15 (d, 1H), 7.21 (m, 1H).

Preparation 49

Methyl 2-[4-(4-{3-[(2S)-2,3-dihydroxypropoxy]phenyl}-3-methylphenyl)-piperidin-1-ylsulphonyl]-2-methyl-propanoate

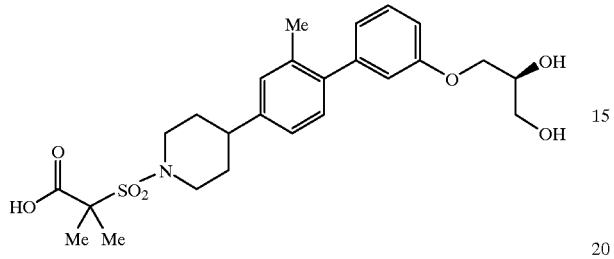

A mixture of the alcohol from preparation 47 (800 mg, 1.86 mmol), S-glycidol (0.12 ml, 1.86 mmol), and triethylamine (10 μl, 0.09 mmol) in methanol (10 ml) was heated under reflux overnight. tlc analysis showed starting material remaining, so the mixture was concentrated to low volume, and heated under reflux for a further 4 hours. The cooled reaction was evaporated in vacuo and the residue purified by column chromatography on silica gel using an elution gradient of hexane:ethyl acetate (91:9 to 50:50). The desired product was obtained as an oil, that gave a white foam on drying under vacuum, (391 mg, 42%).

¹H nmr (DMSO-d₆, 400 MHz) δ: 1.50 (s, 6H), 1.58 (m, 2H), 1.80 (m, 2H), 2.18 (s, 3H), 2.67 (m, 1H), 3.02 (m, 2H), 3.40 (m, 2H), 3.74 (m, 6H), 3.83 (m, 1H), 3.98 (m, 1H), 4.55 (m, 1H), 4.80 (m, 1H), 6.80 (m, 2H), 6.84 (m, 1H), 7.05 (m, 3H), 7.26 (m, 1H). LRMS: m/z 528 (M+23)⁺.

Preparation 50

Methyl 4-[4-(4-{3-[1,3-dibenzyloxy-2-propoxy]phenyl}-3-methylphenyl)-piperidin-1-ylsulphonyl]-tetrahydro-2H-pyran-4-carboxylate

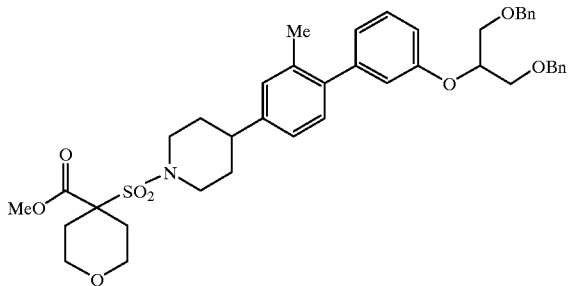

A mixture of the alcohol from preparation 48 (300 mg, 0.63 mmol), diethyl azodicarboxylate (150 μl, 0.95 mmol), triphenylphosphine (250 mg, 0.95 mmol), and 1,3-dibenzyloxy-2-propanol (260 mg, 0.95 mmol) in tetrahydrofuran (6 ml), was stirred at room temperature for 3 hours. Tlc analysis showed some starting material remaining, so additional 1,3-dibenzyloxy-2-propanol (80 mg, 0.3 mmol), triphenyl phosphine (80 mg, 0.3 mmol) and diethyl azodicarboxylate (50 μl, 0.32 mmol) were added, and stirring was continued for an hour. The mixture was evaporated in vacuo, and the residue purified by column chromatography on silica gel using pentane:ethyl acetate (66:34) as eluant to give the title compound as a colourless oil, (400 mg, 87%).

¹H nmr (CDCl₃, 400 MHz) δ: 1.75–1.94 (m, 4H), 2.20 (m, 5H), 2.40 (m, 2H), 2.62 (m, 1H), 3.04 (m, 2H), 3.30 (m, 2H), 3.75 (m, 4H), 3.89 (m, 5H), 3.99 (m, 2H), 4.57 (m, 5H), 6.89 (m, 3H), 7.02 (m, 2H), 7.14 (d, 1H), 7.24 (m, 11H).

Preparation 51

Methyl 4-[4-(4-{3-[1,3-dihydroxy-2-propoxy]phenyl}-3-methylphenyl)-piperidin-1-ylsulphonyl]-tetrahydro-2H-pyran-4-carboxylate

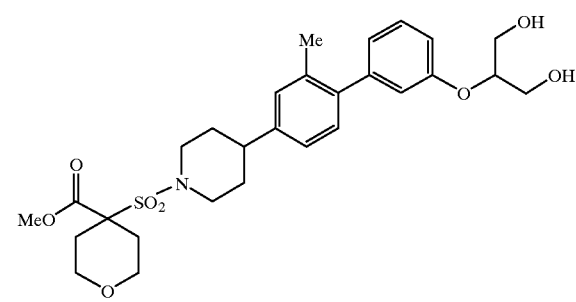

A mixture of the dibenzyl ether from preparation 50 (770 mg, 1.06 mmol), ammonium formate (1.4 g, 11.0 mmol) and palladium hydroxide on carbon (400 mg) in methanol (40 ml) was heated under reflux for 2 hours. Tlc analysis showed some starting material remaining, so additional palladium hydroxide (300 mg) was added, and the reaction was heated under reflux overnight. The cooled mixture was filtered through Arbocel®, and the filtrate evaporated in vacuo. The crude product was purified by column chromatography on silica gel using ethyl acetate:pentane (84:16) as eluant to afford the title compound as a white foam, (375 mg, 65%).

¹H nmr (CDCl₃, 400 MHz) δ: 1.76–1.94 (m, 6H), 2.20 (m, 5H), 2.40 (m, 2H), 2.62 (m, 1H), 3.04 (m, 2H), 3.29 (m, 2H), 3.90 (m, 10H), 3.99 (m, 2H), 6.94 (m, 3H), 7.03 (m, 2H), 7.16 (d, 1H), 7.30 (m, 1H).

Preparation 52

Methyl 4-[4-(4-{3-[(2R)-2,3-dihydroxypropoxy]phenyl-3-methylphenyl)-piperidin-1-ylsulphonyl]-tetrahydro-2H-pyran-4-carboxylate

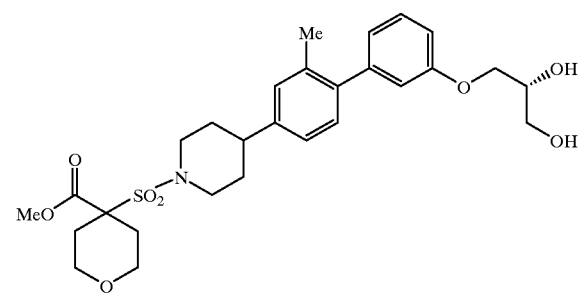

The title compound was obtained (17%) from the compound from preparation 48 and R-glycidol, following a similar procedure to that described in preparation 49.

¹H nmr (CDCl₃, 400 MHz) δ: 1.75–1.97 (m, 4H), 2.20 (m, 5H), 2.40 (m, 2H), 2.61 (m, 1H), 3.02 (m, 2H), 3.28 (m, 2H), 3.58–4.14 (m, 12H), 6.84 (m, 3H), 7.02 (m, 2H), 7.15 (m, 1H), 7.26 (m, 1H). LRMS: m/z 570 (M+23)⁺.

Preparation 53

Methyl 4-[4(4-{3-[(2S)-2,3-dihydroxypropoxy]phenyl)-3-methylphenyl)-piperidin-1-ylsulphonyl]-tetrahydro-2H-pyran-4-carboxylate

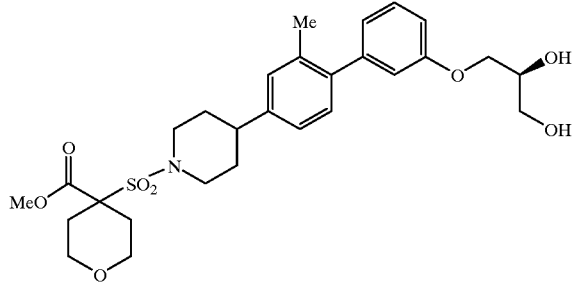

The title compound was obtained as a white solid (52%) after recrystallisation from di-isopropylether, from the alcohol of preparation 48 and S-glycidol, following a similar procedure to that described in preparation 49.

¹H nmr (DMSO-d₆, 300 MHz) δ: 1.50–1.66 (m, 2H), 1.81 (m, 2H), 1.99 (m, 2H), 2.19–2.34 (m, 5H), 2.70 (m, 1H), 3.06 (m, 2H), 3.20 (m, 2H), 3.43 (m, 2H), 3.70–3.98 (m, 9H), 4.00 (dd, 1H), 4.60 (t, 1H), 4.90 (d, 1H), 6.80–6.95 (m, 3H), 7.15 (m, 3H), 7.31 (m, 1H). LRMS: m/z 570 (M+23)⁺.

Preparation 54

Methyl 2-[4-(4-{3-(2,2-diethoxyethoxy)phenyl}-3-methylphenyl)-piperidin-1-ylsulphonyl]-2-methylpropanoate

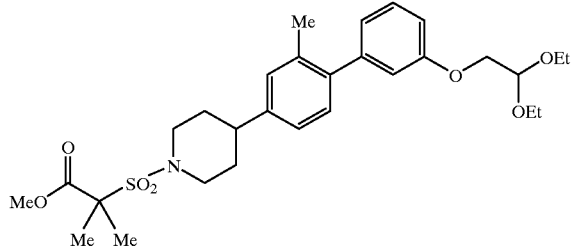

20% Palladium hydroxide on carbon (250 mg) was added to a solution of the 1,2,3,6-tetrahydropyridine from preparation 34 (3.0 g, 5.5 mmol) and ammonium formate (1.04 g, 16.5 mmol) in methanol (70 ml) and 1,4-dioxan (28 ml), and the reaction was stirred at 60° C. for 2 hours. Additional ammonium formate (1.0 g, 15.8 mmol) and palladium hydroxide on carbon (250 mg) were added and stirring was continued for a further 2 hours. The mixture was cooled, filtered through Arbocel®, and the filter pad washed well with methanol. The combined filtrates were evaporated in vacuo and the residue partitioned between water and ether. The layers were separated, the organic phase washed with water, brine, dried (MgSO₄), filtered and evaporated in vacuo to give the title compound as a colourless oil (2.8 g, 93%).

¹H nmr (CDCl₃, 300 MHz) δ: 1.22 (t, 6H), 1.68 (s, 6H), 1.78–1.96 (m, 4H), 2.25 (s, 3H), 2.64 (m, 1H), 3.08 (m, 2H), 3.60–3.82 (m, 7H), 3.94–4.05 (m, 4H), 4.84 (t, 1H), 6.90 (m, 3H), 7.09 (m, 2H), 7.18 (d, 1H), 7.29 (d, 1H). Anal. Found: C, 63.43; H, 7.75; N, 2.46. C₂₉H₄₁NO₇S requires C, 63.60; H, 7.55; N, 2.56%.

Preparation 55

Methyl 4-[4-(4-{3-(2,2-diethoxyethoxy)phenyl}-3-methylphenyl)-piperidin-1-ylsulphonyl]-tetrahydro-2H-pyran-4-carboxylate

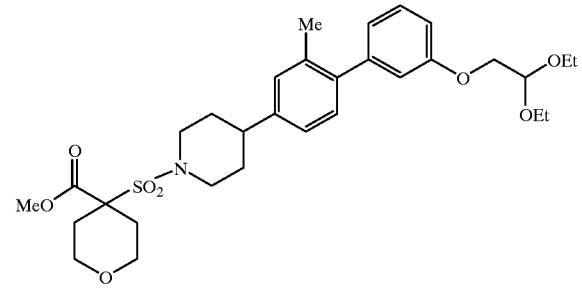

A mixture of cesium fluoride (4.3 g, 28.3 mmol), tri-o-tolyl phosphine (352 mg, 1.15 mmol), tris(dibenzylideneacetone)dipalladium (0) (535 mg, 0.59 mmol) and the boronic acid from preparation 10 (3.89 g, 14.95 mmol) and bromide from preparation 27 (5.0 g, 10.86 mmol) in anhydrous 1,2-dimethoxyethane (70 ml), was heated under reflux for 4½ h. The cooled reaction mixture was concentrated in vacuo to half its volume, then partitioned between water and ethyl acetate. The layers were separated, the aqueous phase extracted with ethyl acetate (3×), and the combined organic solutions filtered through Arbocel®. The filtrate was washed with brine, dried (Na₂SO₄), filtered and evaporated in vacuo. The residual green oil was purified twice, by column chromatography on silica gel using an elution gradient of dichloromethane:methanol (100:0 to 97:3), then triturated with di-isopropyl ether, to afford the title compound as a white solid, (2.38 g, 37%).

¹H nmr (CDCl₃, 400 MHz) δ: 1.20 (t, 6H), 1.76–1.94 (m, 4H), 2.20 (m, 5H), 2.40 (m, 2H), 2.61 (m, 1H), 3.02 (m, 2H), 3.31 (m, 2H), 3.61 (m, 2H), 3.74 (m, 2H), 3.90 (m, 5H), 4.00 (m, 3H), 4.80 (m, 1H), 6.85 (m, 3H), 7.03 (m, 2H), 7.16 (d, 1H), 7.24 (m, 2H). LRMS: m/z 612 (M+23)⁺.

Preparation 56

Methyl 2-methyl-2-[4-(4-{3-(2-oxoethoxy)phenyl}-3-methylphenyl)-piperidin-1-ylsulphonyl]propanoate

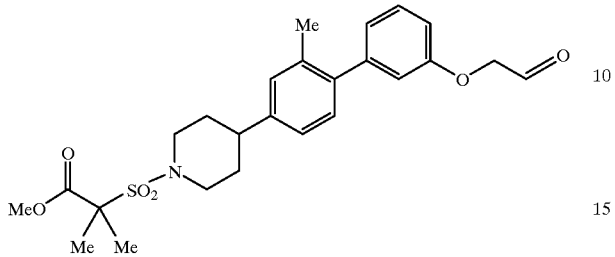

Hydrochloric acid (19 ml, 1N, 19 mmol) was added to a solution of the diethyl ketal from preparation 54 (4.43 g, 8.1 mmol) in acetone (19 ml) and 1,4-dioxan (22 ml), and the reaction stirred at 70° C. for 2 hours. The cooled mixture was neutralised using sodium bicarbonate, concentrated in vacuo, and the residue partitioned between ether and water. The layers were separated, and the organic phase was washed with water, brine, then dried ($Na_2SO_4$), filtered and evaporated in vacuo. The residue was azeotroped with ethyl acetate, to afford the title compound (quantitative).

$^1$H nmr (CDCl$_3$, 300 MHz) δ: 1.67 (s, 6H), 1.78–1.96 (m, 4H), 2.26 (s, 3H), 2.66 (m, 1H), 3.09 (m, 2H), 3.82 (s, 3H), 3.98 (m, 2H), 4.60 (s, 2H), 6.86 (m, 2H), 6.98 (d, 1H), 7.09 (m, 2H), 7.17 (d, 1H), 7.35 (m, 1H), 9.90 (s, 1H). LRMS: m/z 491 (M+18)$^+$.

Preparation 57

Methyl 4-[4-(4-{3-(2-oxoethoxy)phenyl}-3-methylphenyl)-piperidin-1-ylsulphonyl]-tetrahydro-2H-pyran-4-carboxylate

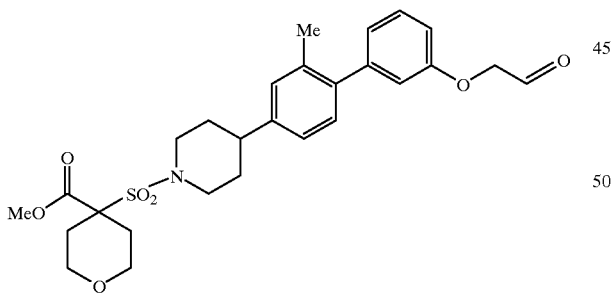

The title compound was obtained as a white foam (quantitative), from the diethyl ketal from preparation 55, following the procedure described in preparation 56.

$^1$H nmr (CDCl$_3$, 400 MHz) δ: 1.77–1.93 (m, 4H), 2.21 (m, 5H), 2.40 (d, 2H), 2.62 (m, 1H), 3.02 (m, 2H), 3.30 (m, 2H), 3.88 (m, 5H), 3.99 (m, 2H), 4.57 (s, 2H), 6.83 (m, 2H), 6.94 (d, 1H), 7.03 (m, 2H), 7.15 (d, 1H), 7.30 (m, 1H), 9.83 (s, 1H). Anal. Found: C, 61.79; H, 6.66; N, 2.46. $C_{27}H_{33}NO_7S$;0.25CH$_3$CO$_2$C$_2$H$_5$;0.4H$_2$O requires C, 61.72; H, 6.62; N, 2.57%.

Preparation 58

Methyl 2-methyl-2-[4-(4-{3-(2-methylaminoethoxy)phenyl}-3-methylphenyl)-piperidin-1-ylsulphonyl]propanoate

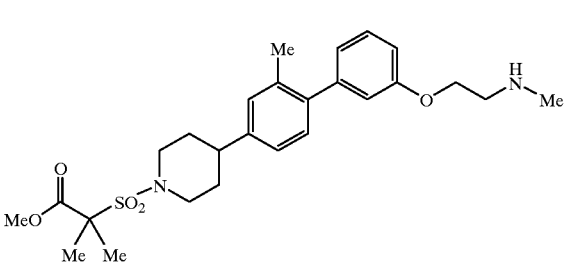

Sodium triacetoxyborohydride (1.5 g, 7.08 mmol) was added portionwise over 1 hour to a solution of the aldehyde from preparation 56 (1.0 g, 2.1 mmol) and methylamine (5.8 ml, 2N in tetrahydrofuran, 11.6 mmol) in dichloromethane (50 ml), and once addition was complete, the reaction was stirred at room temperature overnight. The reaction was partitioned between ethyl acetate and saturated sodium bicarbonate solution, and the layers separated, The organic phase was washed with water, brine, dried ($Na_2SO_4$), filtered and evaporated in vacuo to give a colourless oil. This was purified by medium pressure column chromatography on silica gel using an elution gradient of dichloromethane:methanol (100:0 to 90:10) to afford the title compound as a foam, (650 mg, 63%).

$^1$H nmr (CDCl$_3$, 400 MHz) δ: 1.62 (s, 6H), 1.76–1.90 (m, 4H), 2.22 (s, 3H), 2.56 (s, 3H), 2.61 (m, 1H), 3.04 (m, 4H), 3.78 (s, 3H), 3.95 (m, 2H), 4.12 (t, 2H), 6.83 (m, 3H), 7.03 (m, 2H), 7.14 (d, 1H), 7.24 (m, 1H). Anal. Found: C, 58.39; H, 6.90; N, 4.97. $C_{26}H_{36}N_2O_5S$;0.75CH$_2$Cl$_2$ requires C, 58.17; H, 6.84; N, 5.70%.

Preparations 59 to 63

The compounds of the general formula:

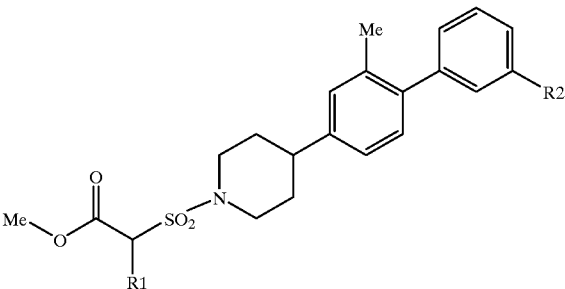

were prepared from the corresponding aldehydes and amines, following similar procedures to those described in preparation 58.

| Prep No. | Aldehyde | R1 | R2 | Data |
|---|---|---|---|---|
| 59 | 56 | (Me)$_2$ | *–O–CH$_2$CH$_2$–N(Me)$_2$ | mp 83–85° C.<br>$^1$H nmr (CDCl$_3$, 400 MHz) δ: 1.62 (s, 6H), 1.78–1.94 (m, 4H), 2.22 (s, 3H), 2.30 (s, 6H), 2.60 (m, 1H), 2.70 t, 2H), 3.02 (m, 2H), 3.79 (s, 3H), 3.96 (m, 2H), 4.06 (t, 2H), 6.83 (m, 3H), 7.02 (m, 2H), 7.15 (d, 1H), 7.22 (m, 1H).<br>LRMS: m/z 503 (M + 1)$^+$<br>Anal. Found: C, 63.82; H, 7.52; N, 5.45. C$_{27}$H$_{38}$N$_2$O$_5$S;0.1CH$_2$Cl$_2$ requires C, 63.68; H, 7.53; N, 5.48%. |
| 60 | 56 | (Me)$_2$ | *–O–CH$_2$CH$_2$–NHBn | $^1$Hmnr(CDCl$_3$,400 MHz) δ: 1.66 (s,6H), 1.59–1.95 (m, 4H), 2.24 (s, 3H), 2.65 (m, 1H), 3.05 (m, 4H), 3.80 (s, 3H), 3.96 (m, 2H), 4.12 (t, 2H), 4.42 (d, 2H), 5.70 (br, s, 1H), 6.85 (m, 3H), 7.07 (m, 2H), 7.17 (d, 1H), 7.24–7.38 (m, 6H).<br>LRMS : m/z 565 (M + 1)$^+$ |
| 61 | 57 | tetrahydropyran | *–O–CH$_2$CH$_2$–NHBn | $^1$H nmr (CDCl$_3$, 400 MHz)?: 1.75–1.92 (m, 4H), 2.20 (m, 5H), 2.40 (d, 2H), 2.62 (m, 1H), 3.00 (m, 4H), 3.28 (m, 2H), 3.88 (m, 5H), 3.99 (m, 2H), 4.09 (m, 2H), 4.40 (m, 2H), 5.60 (br s, 1H), 6.82 (m, 3H), 7.02 (m, 2H), 7.16 (d, 1H), 7.19–7.35 (m, 6H).<br>LRMS: m/z 607 (M + 1)$^+$ |
| 62[1] | 30 | tetrahydropyran | *–CH$_2$–NHMe | mp 119–120° C.<br>$^1$H nmr (CDCl$_3$, 400 MHz) δ: 1.50 (s, br, 1H), 1.75–1.92 (m, 4H), 2.20 (m, 5H), 2.40 (m, 5H), 2.61 (m, 1H), 3.02 (m, 2H), 3.30 (m, 2H), 3.75–4.01 (m, 9H), 7.01 (m, 2H), 7.16 (m, 2H), 7.24 (m, 3H).<br>LRMS: m/z 501 (M + 1)$^+$ |
| 63[2] | 30 | tetrahydropyran | *–CH$_2$–morpholine | $^1$H nmr (CDCl$_3$, 400 MHz) δ: 1.75–1.94 (m, 4H), 2.20 (m, 5H), 2.40 (m, 6H), 2.61 (m, 1H), 3.02 (t, 2H), 3.30 (t, 2H), 3.50 (s, 2H), 3.66 (m, 4H), 3.87 (m, 7H), 7.02 (m, 2H), 7.16 (m, 2H), 7.26 (m, 3H).<br>LRMS: m/z 557 (M + 1)$^+$ |

[1] = purified by crystallisation from ethyl acetate/dichloromethane/di-isopropyl ether.
[2] = purified by column chromatography on silica gel using ethyl acetate:pentane (75:25) as eluant, and recrystallised from ethyl acetate.

Preparation 64

Methyl 2-[4-(4-{3-(2-[(N-tert-butoxycarbonyl)(N-methyl)amino]ethoxy)phenyl}-3-methylphenyl)-piperidin-1-ylsulphonyl]-2-methyl-propanoate

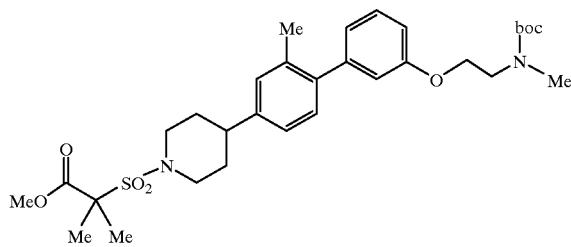

A mixture of the compound from preparation 58 (640 mg, 1.31 mmol), triethylamine (180 μl, 1.30 mol), di-tert-butyl dicarbonate (290 mg, 1.33 mmol) and 4-dimethylaminopyridine (catalytic) in dichloromethane (10 ml) was stirred at room temperature for 3 hours. The reaction mixture was diluted with dichloromethane (50 ml), and washed with water, brine, dried (Na$_2$SO$_4$), filtered and evaporated in vacuo.

The residual oil was purified by medium pressure column chromatography on silica gel using an elution gradient of pentane:dichloromethane:methanol (100:0:0 to 0:99.5:0.5) to afford the title compound as a gum, (590 mg, 77%).

$^1$H nmr (CDCl$_3$, 400 MHz) δ: 1.42 (s, 9H), 1.62 (s, 6H), 1.77–1.90 (m, 4H), 2.22 (s, 3H), 2.63 (m, 1H), 2.97 (s, 3H), 3.03 (m, 2H), 3.58 (m, 2H), 3.78 (s, 3H), 3.95 (m, 2H), 4.08 (m, 2H), 6.82 (m, 3H), 7.04 (m, 2H), 7.16 (d, 1H), 7.25 (m, 1H). LRMS: m/z 611 (M+23)$^+$; Anal. Found: C, 60.51; H, 7.19; N, 4.47. C$_{31}$H$_{44}$N$_2$O$_7$S;0.4CH$_2$Cl$_2$ requires C, 60.56; H, 7.25; N, 4.50%.

Preparation 65

Methyl 2-[4-(4-{3-(2-aminoethoxy)phenyl}-3-methylphenyl)-piperidin-1-ylsulphonyl]-2-methyl-propanoate

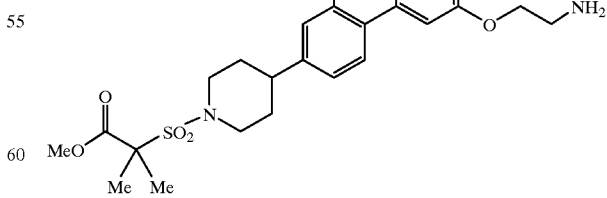

A mixture of the amine from preparation 60 (1.2 g, 2.12 mmol) and 20% palladium hydroxide on carbon (250 mg) in methanol (75 ml), was hydrogenated at 50 psi and room temperature for 18 hours. The reaction mixture was filtered

Preparation 66

Methyl 4-[4-(4-{3-(2-aminoethoxy)phenyl}-3-methylphenyl)-piperidin-1-ylsulphonyl]-tetrahydro-2H-pyran-4-carboxylate

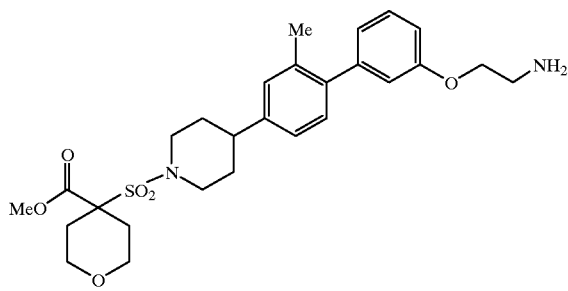

The title compound was obtained as a solid (65%) from the compound from preparation 61, following the procedure described in preparation 65.

$^1$H nmr (CDCl$_3$, 400 MHz) δ: 1.76–1.92 (m, 4H), 2.20 (m, 5H), 2.40 (m, 2H), 2.62 (m, 1H), 3.04 (m, 4H), 3.30 (m, 2H), 3.88 (m, 5H), 3.98 (m, 4H), 6.82 (m, 3H), 7.03 (m, 2H), 7.16 (d, 1H), 7.22 (m, 1H). LRMS: m/z 517 (M+1)$^+$; Anal. Found: C, 62.30; H, 6.98; N, 5.40. C$_{27}$H$_{36}$N$_2$O$_6$S;0.05CH$_2$Cl$_2$ requires C, 62.37; H, 6.99; N, 5.38%.

Preparation 67

Methyl 2-[4-(4-{3-(2-[(tert-butoxycarbonyl)amino]ethoxy)phenyl}-3-methylphenyl)-piperidin-1-ylsulphonyl]-2-methyl-propanoate

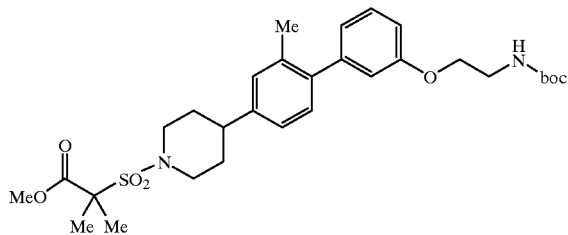

The title compound was obtained as a white foam (69%) from the amine from preparation 65, following a similar procedure to that described in preparation 64.

$^1$H nmr (CDCl$_3$, 300 MHz) δ: 1.44 (s, 9H), 1.65 (s, 6H), 1.78–1.95 (m, 4H), 2.25 (s, 3H), 2.64 (m, 1H), 3.08 (m, 2H), 3.55 (m, 2H), 3.81 (s, 3H), 3.97 (m, 2H), 4.04 (t, 2H), 4.99 (br, s, 1H), 6.80–6.94 (m, 3H), 7.08 (m, 2H), 7.18 (d, 1H), 7.32 (m, 1H). LRMS: m/z 597 (M+23)$^+$; Anal. Found: C, 62.49; H, 7.46; N, 4.78. C$_{30}$H$_{42}$N$_2$O$_7$S requires C, 62.69; H, 7.37; N, 4.87%.

Preparation 68

Methyl 4-[4-(4-{3-(2-[(tert-butoxycarbonyl)amino]ethoxy)phenyl}-3-methylphenyl)-piperidin-1-ylsulphonyl]-tetrahydro-2H-pyran-4-carboxylate

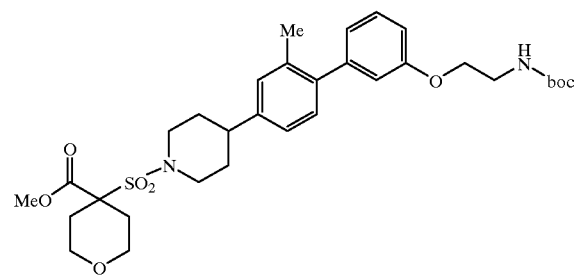

Di-tert-butyl dicarbonate (300 mg, 1.37 mmol) was added to a solution of the amine from preparation 66 (650 mg, 1.26 mmol) in dichloromethane (10 ml), and the reaction stirred at room temperature for 18 hours. The reaction was diluted with dichloromethane (50 ml), then washed with water (2×), brine, then dried (Na$_2$SO$_4$), filtered and evaporated in vacuo. The residue was purified by medium pressure column chromatography on silica gel using an elution gradient of dichloromethane:methanol (99.5:0.5 to 99:1) to afford the title compound as a white foam, (710 mg, 91%).

$^1$H nmr (CDCl$_3$, 400 MHz) δ: 1.40 (s, 9H), 1.78–1.92 (m, 4H), 2.20 (m, 5H), 2.40 (d, 2H), 2.61 (m, 1H), 3.02 (m, 2H), 3.30 (m, 2H), 3.50 (m, 2H), 3.88 (m, 5H), 4.00 (m, 4H), 4.86 (br, s, 1H), 6.82 (m, 3H), 7.02 (m, 2H), 7.15 (d, 1H), 7.05 (m, 1H). LRMS: m/z 639 (M+23)$^+$; Anal. Found: C, 62.15; H, 7.20; N, 4.47. C$_{32}$H$_{44}$N$_2$O$_8$S requires C, 62.32; H, 7.19; N, 4.54%.

Preparation 69

Methyl 4-[4-(4-{3-([N-tert-butoxycarbonyl-N-methylamino]methyl)phenyl)-3-methylphenyl)-piperidin-1-ylsulphonyl]-tetrahydro-2H-pyran-4-carboxylate

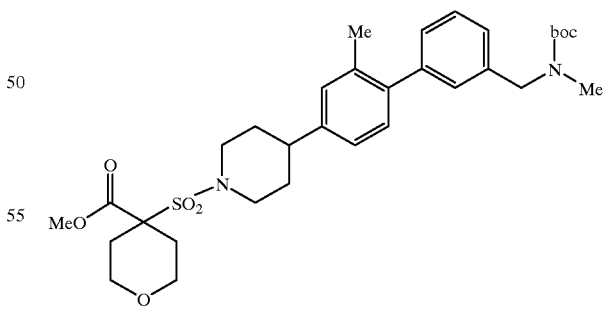

The title compound was prepared from the amine from preparation 62, using a similar procedure to that described in preparation 64. The crude product was purified by column chromatography on silica gel using an elution gradient of ethyl acetate:pentane (25:75 to 50:50) and triturated with di-isopropyl ether to give the title compound as a white solid, (714 mg, 65%).

mp 122–123° C.; ¹H nmr (CDCl₃, 400 MHz) δ: 1.42 (s, 9H), 1.75–1.92 (m, 4H), 2.20 (m, 5H), 2.40 (m, 2H), 2.61 (m, 1H), 2.82 (s, 3H), 3.03 (m, 2H), 3.30 (m, 2H), 3.85 (m, 5H), 3.99 (m, 2H), 4.42 (s, 2H), 7.03 (m, 2H), 7.17 (m, 4H), 7.35 (m, 1H). LRMS: m/z 623 (M+23)⁺; Anal. Found: C, 63.92; H, 7.36; N, 4.57. $C_{32}H_{44}N_2O_7S$ requires C, 63.98; H, 7.38; N, 4.66%.

Preparation 70

2-[4-{4-[6-(2-Hydroxyethoxy)pyridin-2-yl]-3-methylphenyl-piperidin-1-ylsulphonyl]-2-methylpropanoic acid

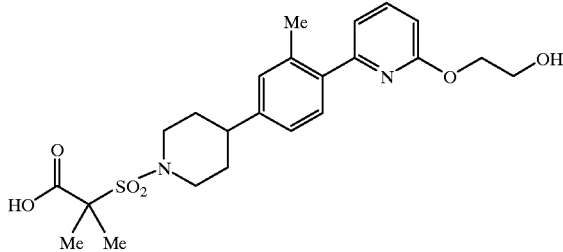

A mixture of the methyl ester from preparation 35 (4.1 g, 8.6 mmol) and aqueous sodium hydroxide (17 ml, 1N, 17.0 mmol) in methanol (50 ml), was heated under reflux for 30 minutes, then cooled. The reaction was concentrated in vacuo, the residue dissolved in water (200 ml), and the solution acidified to pH 4. The resulting precipitate was filtered off, washed with water, dried under vacuum, and recrystallised from ethyl acetate, to afford the title compound as a white solid, (3.15 g, 79%).

¹H nmr (DMSO-d₆, 300 MHz) δ: 1.42–1.70 (m, 8H), 1.80 (m, 2H), 2.37 (s, 3H), 2.70 (t, 1H), 3.06 (m, 2H), 3.68 (m, 2H), 3.80 (m, 2H), 4.25 (t, 2H), 4.80 (br, s, 1H), 6.77 (d, 1H), 7.06 (d, 1H), 7.17 (m, 2H), 7.35 (d, 1H), 7.77 (m, 1H), 13.38 (br, s, 1H). Anal. Found: C, 58.35; H, 6.38; N, 5.83. $C_{23}H_{30}N_2O_6S;0.5H_2O$ requires C, 58.85; H, 6.62; N, 5.94%.

Preparation 71

2-(4-{4-[6-(2-Methoxyethoxy)pyridin-2-yl]-3-methylphenyl}-piperidin-1-ylsulphonyl)-2-methylpropanoic acid

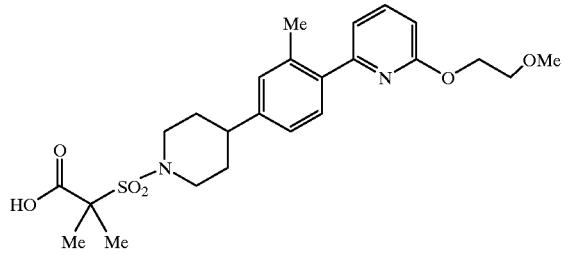

Sodium hydride (60 mg, 60% dispersion in mineral oil, 1.5 mmol) was added to a solution of the methyl ester from preparation 35 (300 mg, 0.63 mmol) in tetrahydrofuran (10 ml), and the solution stirred for 15 minutes. Methyl iodide (200 µl, 3.3 mmol) was added and the reaction heated under reflux for 45 minutes. Aqueous sodium hydroxide solution (2 ml, 1N, 2.0 mmol) and methanol (5 ml) were then added, and the mixture heated under reflux for a further 30 minutes. The reaction mixture was cooled to room temperature, diluted with water (20 ml), and acidified to pH 4. This solution was extracted with dichloromethane (3×30 ml), the combined organic extracts dried (Na₂SO₄), filtered and evaporated in vacuo to afford the title compound as a pale yellow foam, (quantitative).

mp 142–146° C. ¹H nmr (CDCl₃, 300 MHz) δ: 1.68 (s, 6H), 1.78–1.96 (m, 4H), 2.41 (s, 3H), 2.66 (m, 1H), 3.09 (m, 2H), 3.43 (s, 3H), 3.78 (t, 2H), 4.00 (m, 2H), 4.52 (t, 2H), 6.78 (d, 1H), 6.98 (d, 1H), 7.08 (m, 2H), 7.38 (d, 1H), 7.61 (d, 1H). LRMS: m/z 433 (M−CO₂)⁺.

Preparation 72

4-[4-(4-{6-[2-Hydroxyethoxypyridin-2-yl}-3-methylphenyl)piperidin-1-ylsulphonyl]tetrahydro-2H-pyran-4-carboxylic acid

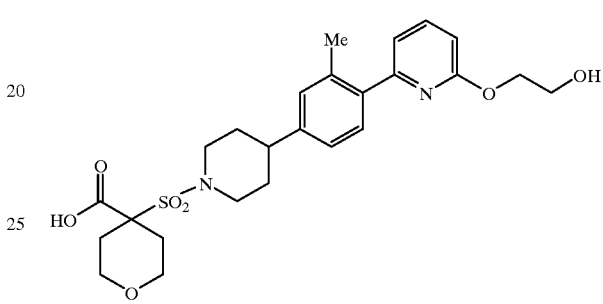

Aqueous sodium hydroxide (5.56 ml, 1N, 5.56 mmol) was added to a solution of the methyl ester from preparation 36 (720 mg, 1.39 mmol) in methanol (20 ml), and the reaction heated under reflux for 3 hours, and stirred for a further 18 hours, at room temperature. The mixture was concentrated in vacuo to remove the methanol, and the solution acidified to pH 4 using acetic acid solution. This was extracted with ethyl acetate (3×), the combined organic extracts washed with brine, dried (MgSO₄), filtered and evaporated in vacuo. The residual solid was recrystallised from ethyl acetate/di-isopropyl ether to afford the title compound as a solid, (517 mg, 74%).

¹H nmr (DMSO-d₆, 300 MHz) δ: 1.62 (m, 2H), 1.82 (m, 2H), 1.98 (m, 2H), 2.24 (m, 2H), 2.36 (s, 3H), 2.74 (m, 1H), 3.09 (t, 2H), 3.22 (m, 2H), 3.64–3.82 (m, 4H), 3.94 (dd, 2H), 4.28 (t, 2H), 4.80 (br s, 1H), 6.78 (d, 1H), 7.06 (d, 1H), 7.16 (m, 2H), 7.36 (d, 1H), 7.78 (m, 1H), 13.82 (br s, 1H). LRMS: m/z 527 (M+18)⁺.

Preparation 73

4-[4-(4-{6-[(2S)-2,3-dihydroxy-1-propoxy]pyridin-2-yl}-3-methylphenyl)piperidin-1-ylsulphonyl]-tetrahydro-2H-pyran-4-carboxylic acid

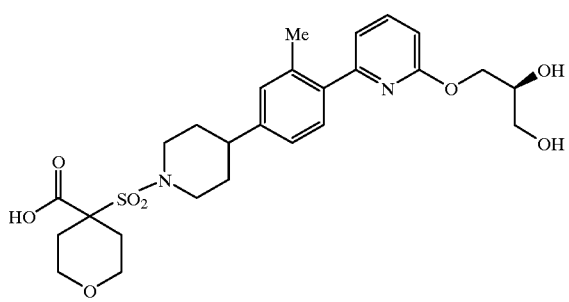

89

Aqueous sodium hydroxide (3.5 ml, 1M, 3.5 mmol) was added to a solution of the methyl ester from preparation 39 (640 mg, 1.17 mmol) in methanol (15 ml) and 1,4-dioxan (15 ml), and the reaction heated under reflux for 2 hours. Tlc analysis showed starting material remaining, so additonal sodium hydroxide (2 ml, 1M, 2 mmol) was added and the reaction heated under reflux for a further 3 hours. The cooled reaction mixture was concentrated under reduced pressure, the residue dissolved in water, and the pH adjusted to 4 using hydrochloric acid (2N). The resulting precipitate was filtered and dried, and the filtrate extracted with dichloromethane (2×). The combined organic extracts were dried (MgSO$_4$), filtered and evaporated in vacuo, and the product combined with the filtered solid. This was recrystallised from dichloromethane/ethyl acetate twice, to yield the title compound as a white solid, (579 mg, 92%).

$^1$H nmr (DMSO-d$_6$, 400 MHz) δ: 1.60 (m, 2H), 1.80 (m, 2H), 1.92 (m, 2H), 2.23 (d, 2H), 2.34 (s, 3H), 2.66 (m, 1H), 3.08 (m, 2H), 3.17–3.42 (m, 3H), 3.78 (m, 3H), 3.88 (m, 2H), 4.14 (dd, 1H), 4.26 (dd, 1H), 4.60 (br, s, 1H), 4.85 (br, s, 1H), 6.76 (d, 1H), 7.04 (d, 1H), 7.15 (m, 2H), 7.34 (m, 2H), 7.74 (dd, 1H). LRMS: m/z 557 (M+23)$^+$.

Preparation 74

4-[4-(4-{6-[(2R)-2,3-dihydroxy-1-propoxy]pyridin-2-yl}-3-methylphenyl)piperidin-1-ylsulphonyl]-tetrahydro-2H-pyran-4-carboxylic acid

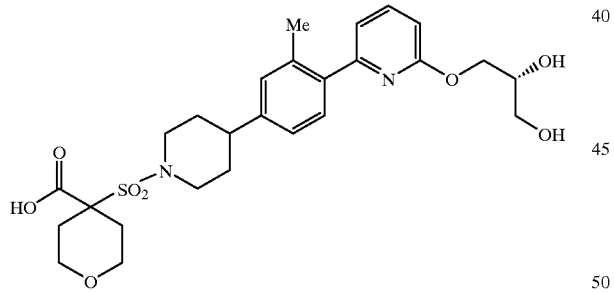

The title compound was obtained as a white solid (87%) from the methyl ester of preparation 40, following a similar procedure to that described in preparation 73.

$^1$H nmr (DMSO-d$_6$, 300 MHz) δ: 1.61 (m, 2H), 1.80 (m, 2H), 1.96 (m, 2H), 2.24 (m, 2H), 2.36 (s, 3H), 2.70 (m, 1H), 3.06 (m, 2H), 3.14–3.44 (m, 4H), 3.78 (m, 3H), 3.93 (m, 2H), 4.14 (m, 1H), 4.26 (m, 1H), 4.59 (m, 1H), 4.84 (m, 1H), 6.76 (d, 1H), 7.06 (d, 1H), 7.15 (m, 2H), 7.35 (d, 1H), 7.76 (m, 1H), 13.80 (br, s, 1H). LRMS: m/z 557 (M+23)$^+$.

90

Preparation 75

4-[4-(4-{6-[2-Hydroxyethoxy]pyridin-2-yl}-3-methylphenyl)piperidin-1-ylsulphonyl]-1-methylpiperidine-4-carboxylic acid

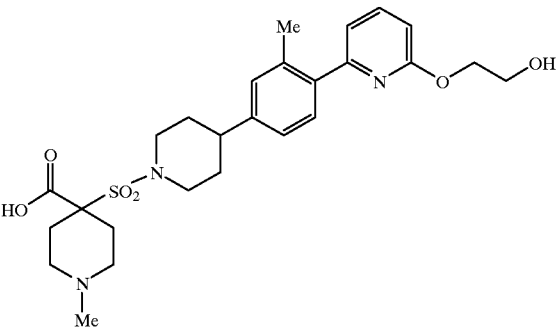

A mixture of the methyl ester from preparation 42 (200 mg, 0.38 mmol) and aqueous sodium hydroxide (1.5 ml, 1N, 1.5 mmol) in methanol (8 ml) and 1,4-dioxan (8 ml) was heated under reflux overnight. The cooled reaction was concentrated in vacuo, the residue acidified to pH 4 using acetic acid, and extraction with ethyl acetate attempted. A precipitate formed in the organic layer, that was filtered off, and combined with the residual solid in the separating funnel, to provide the desired compound as a white powder, (quantitative). LRMS: m/z 518 (M+1)$^+$.

Preparation 76

1-(tert-Butoxycarbonyl)-4-[4-(4-{6-[2-hydroxyethoxy]pyridin-2-yl}-3-methylphenyl)piperidin-1-ylsulphonyl]-piperidine-4-carboxylic acid

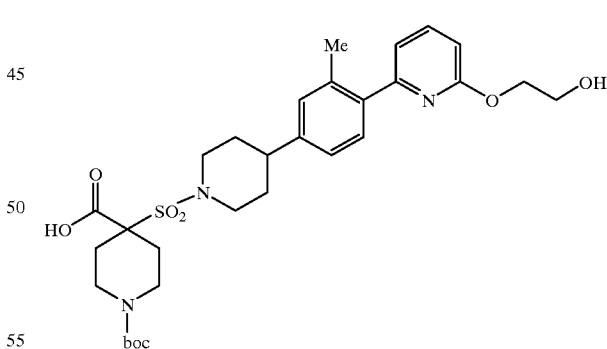

The title compound was obtained as a white solid (87%), from the methyl ester from preparation 43, following a similar procedure to that described in preparation 75.

mp 148–149° C.; $^1$H nmr (CDCl$_3$, 300 MHz) δ: 1.42 (s, 9H), 1.80 (m, 4H), 2.00 (m, 2H), 2.36 (s, 3H), 2.41 (m, 2H), 2.58–2.79 (m, 4H), 3.02 (m, 4H), 3.92 (m, 5H), 4.44 (m, 2H), 6.76 (m, 1H), 6.99 (m, 1H), 7.07 (m, 2H), 7.34 (m, 1H), 7.65 (m, 1H).

Preparation 77

2-[4-(4-{3-[(2S)-2,3-Dihydroxy-1-propoxy]phenyl}-3-methylphenyl)-piperidin-1-ylsulphonyl]-2-methyl-propanoic acid

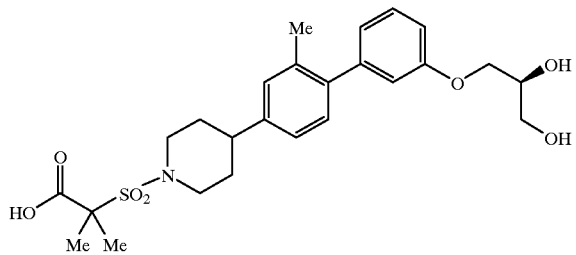

Aqueous sodium hydroxide (1.55 ml, 1M, 1.55 mmol) was added to a solution of the methyl ester from preparation 49 (391 mg, 0.77 mmol) in methanol (5 ml), and the reaction stirred at room temperature overnight. The mixture was partitioned between ethyl acetate and hydrochloric acid (2N), and the phases separated. The organic layer was dried (MgSO$_4$), filtered and concentrated in vacuo. The residual solid was triturated with di-isopropyl ether, filtered and dried under vacuum, to give the title compound as a white solid, (320 mg, 85%).

$^1$H nmr (DMSO-d$_6$, 400 MHz) δ: 1.48 (s, 6H), 1.59 (m, 2H), 1.79 (m, 2H), 2.18 (s, 3H), 2.64 (m, 1H), 3.04 (m, 2H), 3.40 (m, 2H), 3.78 (m, 3H), 3.82 (m, 1H), 3.98 (m, 1H), 4.57 (br, s, 1H), 4.82 (br, s, 1H), 6.80 (m, 2H), 6.85 (m, 1H), 7.05 (m, 2H), 7.12 (m, 1H), 7.27 (m, 1H), 13.25 (br, s, 1H). Anal. Found: C, 60.77; H, 6.89; N, 2.78. C$_{25}$H$_{33}$NO$_7$S requires C, 61.08; H, 6.77; N, 2.85%.

Preparation 78

4-[4-(4-{3-[2,3-dihydroxy-2-propoxy]phenyl}-3-methylphenyl)-piperidin-1-ylsulphonyl]-tetrahydro-2H-pyran-4-carboxylic acid

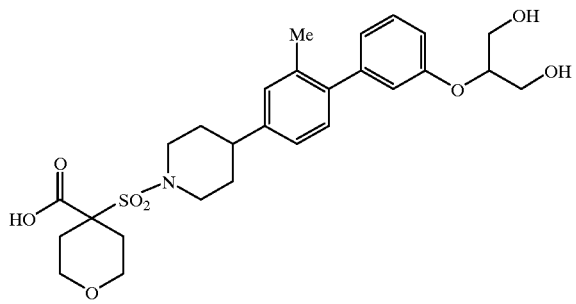

A mixture of the methyl ester from preparation 51 (370 mg, 0.68 mmol), aqueous sodium hydroxide (3 ml, 1M, 3 mmol) in methanol (5 ml) and 1,4-dioxan (5 ml), was heated under reflux for 6 hours. The cooled reaction was concentrated in vacuo, and then diluted with water. This aqueous solution was acidified to pH 2 using hydrochloric acid (2N), and the resulting precipitate filtered, washed with water and dried under vacuum, to give the desired product (270 mg, 74%).

$^1$H nmr (DMSO-d$_6$, 400 MHz) δ: 1.60 (m, 2H), 1.79 (m, 2H), 1.95 (m, 2H), 2.19 (m, 5H), 2.63 (m, 1H), 3.02 (m, 4H), 3.56 (m, 4H), 3.76 (m, 2H), 3.88 (m, 2H), 4.22 (m, 1H), 4.68 (m, 2H), 6.78–6.95 (m, 3H), 7.08 (m, 3H), 7.25 (m, 1H).

Preparation 79

4-[4-(4-{3-[(2R)-2,3-Dihydroxy-1-propoxy]phenyl}-3-methylphenyl)-piperdin-1-ylsulphonyl]-tetrahydro-(2H)-pyran-4-carboxylic acid

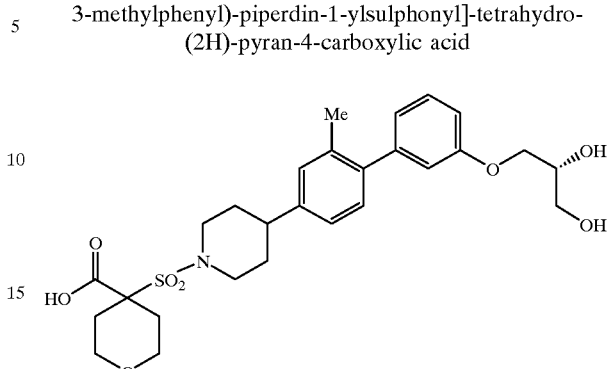

A mixture of the methyl ester from preparation 52 (110 mg, 0.20 mmol), aqueous sodium hydroxide (1 ml, 1M, 1 mmol) in methanol (5 ml) and 1,4-dioxan (5 ml) was heated under reflux for 2 hours. The cooled reaction was evaporated in vacuo, the residue dissolved in water and acidified to pH 1 using hydrochloric acid (1N). The resulting precipitate was filtered, the solid washed with water, and dried under vacuum to give the title compound (91 mg, 85%) as a white solid.

$^1$H nmr (DMSO-d$_6$, 400 MHz) δ: 1.60 (m, 2H), 1.80 (m, 2H), 1.94 (m, 2H), 2.20 (m, 5H), 2.65 (m, 1H), 3.05 (m, 2H), 3.18–3.48 (m, 4H), 3.77 (m, 3H), 3.88 (m, 3H), 4.00 (m, 1H), 6.81 (m, 2H), 6.89 (m, 1H), 7.10 (m, 3H), 7.30 (m, 1H). LRMS: m/z 556 (M+23)$^+$.

Preparation 80

4-[4-(4-{3-[(2S)-2,3-Dihydroxy-1-propoxy]phenyl}-3-methylphenyl)-piperidin-1-ylsulphonyl]-tetrahydro-(2H)-pyran-4-carboxylic acid

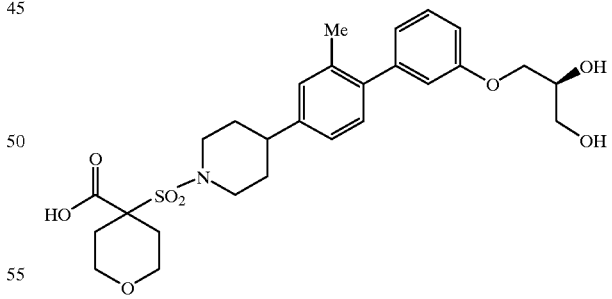

The title compound was obtained as a solid (66%) from the methyl ester from preparation 53, following the procedure described in preparation 79.

$^1$H nmr (DMSO-d$_6$, 400 MHz) δ: 1.60 (m, 2H), 1.80 (m, 2H), 1.96 (m, 2H), 2.22 (m, 5H), 2.68 (m, 1H), 3.06 (m, 2H), 3.21 (m, 2H), 3.42 (d, 2H), 3.78 (m, 3H), 3.90 (m, 3H), 4.00 (m, 1H), 6.81 (m, 2H), 6.90 (d, 1H), 7.12 (m, 3H), 7.31 (dd, 1H).

Preparation 81

2-[4-(4-{3-(2-[N-tert-Butoxycarbonyl-N-methylamino]ethoxy)phenyl}-3-methylphenyl)-piperidin-1-ylsulphonyl]-2-methylpropanoic acid

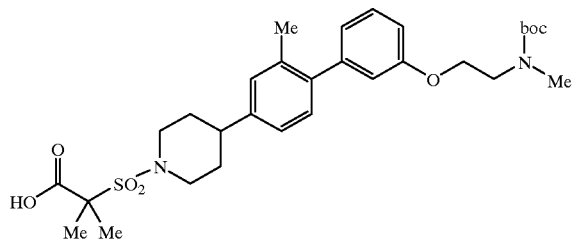

A mixture of the methyl ester from preparation 64 (540 mg, 0.92 mmol), and aqueous sodium hydroxide (6 ml, 1N, 6.0 mmol) in 1,4-dioxan (2.3 ml) and methanol (6 ml) was heated under reflux for 3½ h. The cooled mixture was concentrated in vacuo to remove the organic solvents, and the residual aqueous solution was acidified to pH 4 using acetic acid. This was extracted with ethyl acetate (2×), the combined organic extracts washed with water, brine, dried ($Na_2SO_4$), filtered and evaporated in vacuo. The residue was azeotroped with toluene, then ethyl acetate, and finally dichloromethane to afford the title compound as a white foam, (520 mg, 98%).

$^1$H nmr ($CDCl_3$, 400 MHz) δ: 1.41 (s, 9H), 1.64 (s, 6H), 1.78–1.94 (m, 4H), 2.22 (s, 3H), 2.63 (m, 1H), 2.97 (s, 3H), 3.06 (m, 2H), 3.59 (m, 2H), 3.98 (m, 2H), 4.08 (t, 2H), 6.83 (m, 3H), 7.04 (m, 2H), 7.16 (d, 1H), 7.26 (m, 1H). LRMS: m/z 597 (M+23)$^+$; Anal. Found: C, 61.17; H, 7.27; N, 4.65. $C_{30}H_{42}N_2O_7S;0.2CH_2Cl_2$ requires C, 61.30; H, 7.22; N, 4.73%.

Preparations 82 to 86

The compounds of the general formula:

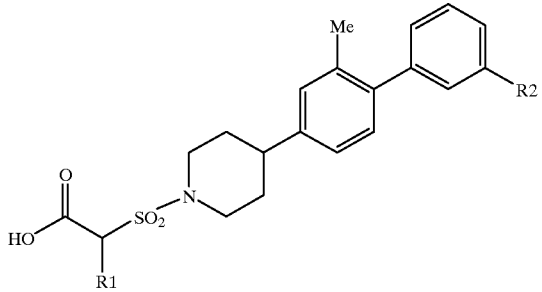

were prepared from the corresponding methyl esters, following similar procedures to those described in preparation 81.

| Prep No. | Starting ester | R1 | R2 | Data |
|---|---|---|---|---|
| 82 | 67 | (Me)$_2$ | *∼O∼∼NHBoc | $^1$H nmr (DMSO-d$_6$, 300 MHz) δ: 1.36 (s, 9H), 1.50 (s, 6H), 1.62 (m, 2H), 1.81 (m, 2H), 2.20 (s, 3H), 2.68 (m, 1H), 3.06 (m, 2H), 3.28 (m, 4H), 3.80 (m, 2H), 3.98 (t, 2H), 6.80–6.99 (m, 3H), 7.14 (m, 2H), 7.30 (m, 1H). LRMS: m/z 583 (M + 23)$^+$ Anal. Found: C 58.94; H, 7.02; N, 4.64. $C_{29}H_{40}N_2O_7S;0.4CH_2Cl_2$ requires C,59.02; H,6.94; N, 4.68%. |
| 83[1] | 59 | (Me)$_2$ | *∼O∼∼N(Me)$_2$ | mp 230–232° C. $^1$H nmr (DMSO-d$_6$, 400 MHz) δ: 1.46 (s, 6H), 1.60 (m, 2H), 1.80 (m, 2H), 2.18 (s, 3H), 2.25 (s, 6H), 2.64 (m, 3H), 3.02 (m, 2H), 3.78 (m, 2H), 4.06 (t, 2H), 6.80 (m, 2H), 6.86 (d, 1H), 7.08 (m, 2H), 7.28 (dd, 1H). Anal. Found: C, 62.70; H, 7.37; N, 5.53. $C_{26}H_{36}N_2O_5S;0.5H_2O$ requires C, 62.75; H, 7.49; N,5.63%. |
| 84 | 68 | tetrahydropyran | *∼O∼∼NHBoc | mp 194–196° C. $^1$H nmr (CDCl$_3$, 400 MHz) δ: 1.42 (s, 9H), 1.75–1.92 (m, 4H), 2.22 (m, 5H), 2.38 (d, 2H), 2.61 (m, 1H), 3.06 (m, 2H), 3.40 (m, 2H), 3.50 (m, 2H), 3.98 (m, 6H), 6.82 (m, 3H), 7.02 (m, 2H), 7.14 (d, 1H), 7.23 (m, 1H). Anal. Found: C, 61.20; H, 7.05; N, 4.60. $C_{31}H_{42}N_2O_8S;0.25H_2O$ requires C, 61.32; H, 7.05; N, 4.61%. |
| 85[2] | 69 | tetrahydropyran | *∼NBoc,Me | mp 196–197° C. $^1$H nmr (DMSO-d$_6$, 400 MHz) δ: 1.38 (s, 9H), 1.60 (m, 2H), 1.80 (m, 2H), 1.95 (m, 2H), 2.19 (s, 3H), 2.20 (m, 2H), 2.64 (m, 1H), 2.76 (s, 3H), 3.02 (t, 2H), 3.18 (m/t, 2H), 3.77 (m, 2H), 3.86 (m, 2H), 4.38 (s, 2H), 7.12 (m, 6H), 7.37 (m, 1H). LRMS : m/z 609 (M + 23)$^+$ |
| 86[3] | 63 | tetrahydropyran | *∼N-morpholine | $^1$H nmr (DMSO-d$_6$, 400 MHz) δ: 1.59 (m, 2H), 1.80 (m, 2H), 1.90 (m, 2H), 2.20 (m, 6H), 2.62–2.79 (m, 4H), 3.00–3.22 (m, 6H), 3.65 (m, 4H), 3.76 (m, 2H), 3.88 (m, 2H), 7.12 (m, 4H), 7.25 (m, 1H), 7.39 (m, 2H). LRMS: m/z 543 (M + 1)$^+$ |

[1] = isolated by filtration from aqueous acetic acid solution.
[2] = recrystallised from ethyl acetate/methanol
[3] = triturated with di-isopropyl ether

Preparation 87

N-Hydroxy 1-(tert-butoxycarbonyl)4-{[4-(4-{6-[2-hydroxyethoxy]pyridin-2-yl}-3-methylphenyl)piperidin-1-yl]sulphonyl}-piperidine-4-carboxamide

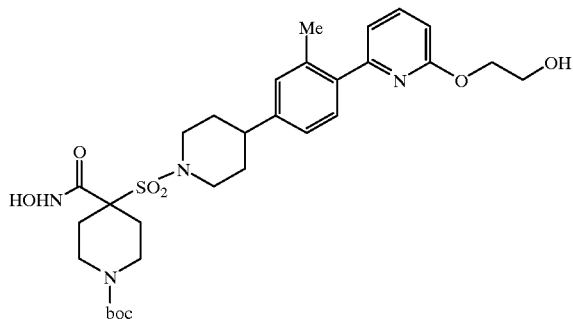

Chlorotrimethylsilane (70 μl, 0.55 mmol) was added to a solution of the acid from preparation 76 (300 mg, 0.50 mmol) in dichloromethane (4 ml), and pyridine (2 ml), and the solution stirred at room temperature under a nitrogen atmosphere for 1 hour. 1-(3-Dimethylaminopropyl)-3-ethylcarbodiimide hydrochloride (115 mg, 0.60 mmol) and 1-hydroxy-7-azabenzotriazole (75 mg, 0.55 mmol) were added, and stirring was continued for a further hour. Hydroxylamine hydrochloride (104 mg, 1.50 mmol) was added and the reaction stirred at room temperature overnight. The reaction mixture was diluted with water, the solution acidified to pH 1 using hydrochloric acid (2M), then extracted with ethyl acetate. The combined organic solutions were washed with brine, dried (MgSO$_4$), filtered and evaporated in vacuo. The residue was triturated with ethyl acetate, the resulting precipitate filtered and the filtrate evaporated in vacuo. The residue was recrystallised from ethyl acetate to afford the title compound (148 mg, 48%) as a white solid.

mp 180–181° C.; $^1$H nmr (DMSO-d$_6$, 400 MHz) δ: 1.39 (s, 9H), 1.55–1.81 (m, 6H), 2.36 (s, 3H), 2.42 (m, 2H), 2.62 (m, 3H), 3.03 (m, 2H), 3.70 (m, 4H), 3.95 (m, 2H), 4.24 (t, 2H), 4.78 (br, t, 1H), 6.75 (d, 1H), 7.04 (d, 1H), 7.15 (m, 2H), 7.34 (d, 1H), 7.75 (m, 1H), 9.16 (s, 1H), 11.00 (s, 1H). LRMS: m/z 617 (M−1)$^+$.

Preparation 88

N-Hydroxy 2-[4-(4-{3-(2-[(N-tert-butoxycarbony-N-methyl)amino]ethoxy)phenyl}-3-methylphenyl)-piperidin-1-ylsulphonyl]-2-methylpropanamide

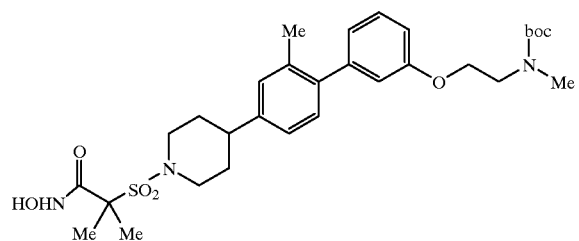

O-(7-Azabenzotriazol-1-yl)-N,N,N'N'-tetramethyluronium hexafluorophosphate (540 mg, 1.42 mmol) was added to a solution of the acid from preparation 81 (520 mg, 0.90 mmol) and N-ethyldiisopropylamine (193 μl, 1.12 mmol) in N-methylpyrrolidinone (10 ml), and the reaction stirred at room temperature under a nitrogen atmosphere for 40 minutes. Hydroxylamine hydrochloride (210 mg, 3.02 mmol) and additional N-ethyldiisopropylamine (730 μl, 4.23 mmol) were added, and the reaction stirred at room temperature overnight. The mixture was partitioned between ethyl acetate and pH 7 buffer solution, and the layers separated. The organic phase was washed consecutively with water, brine, then dried (NaSO$_4$), filtered and evaporated in vacuo. The crude product was purified by medium pressure column chromatography on silica gel using an elution gradient of dichloromethane:methanol (99.5:0.5 to 98:2 to 80:20) to afford the title compound, (180 mg, 34%).

$^1$H nmr (CDCl$_3$, 400 MHz) δ: 1.40 (s, 9H), 1.63 (s, 6H), 1.78 (m, 2H), 1.86 (m, 2H), 2.22 (s, 3H), 2.61 (m, 1H), 2.97 (s, 3H), 3.03 (m, 2H), 3.58 (m, 2H), 3.94 (m, 2H), 4.08 (m, 2H), 6.60 (s, 1H), 6.64 (m, 2H), 7.02 (m, 2H), 7.17 (d, 1H), 7.26 (dd, 1H), 8.99 (s, 1H), 10.75 (s, 1H). Anal. Found: C, 60.96; H., 7.33; N, 7.11. C$_{30}$H$_{43}$N$_3$O$_7$S requires C, 61.10; H, 7.35; N, 7.12%.

Preparation 89

N-Hydroxy 2-[4-(4-{3-(2-[(tert-butoxycarbonyl)amino]ethoxy)phenyl}-3-methylphenyl)-piperidin-1-ylsulphonyl]-2-methylpropionamide

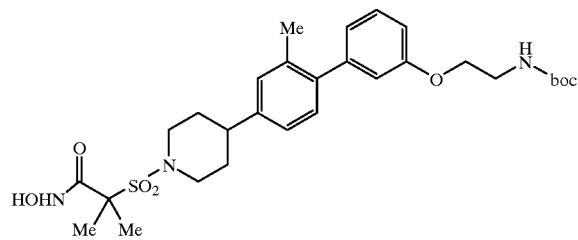

The title compound was obtained (49%) from the acid from preparation 82, following a similar procedure to that described in preparation 88.

$^1$H nmr (DMSO-d$_6$, 400 MHz) δ: 1.37 (s, 9H), 1.48 (s, 6H), 1.60 (m, 2H), 1.79 (m, 2H), 2.20 (s, 3H), 2.64 (m, 1H), 3.04 (m, 2H), 3.28 (m, 2H), 3.75 (m, 2H), 3.98 (t, 2H), 6.80–6.98 (m, 4H), 7.10 (s, 2H), 7.15 (s, 1H), 7.30 (dd, 1H), 8.99 (s, 1H), 10.55 (s, 1H). LRMS: m/z 598 (M+23)$^+$; Anal. Found: C, 59.25; H, 7.09; N, 7.38. C$_{29}$H$_{41}$N$_3$O$_7$S;0.1CH$_2$Cl$_2$ requires C, 59.83; H, 7.11; N, 7.19%.

Preparation 90

N-Hydroxy 4-[4-(4-{3-(2-[(N-tert-butoxycarbonyl)amino]ethoxy)phenyl}-3-methylphenyl)-piperidin-1-ylsulphonyl]-tetrahydro-2H-pyran-4-carboxamide

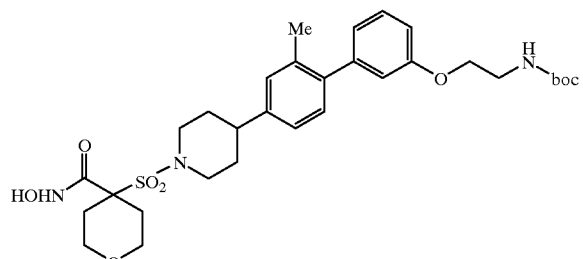

1-(3-Dimethylaminopropyl)-3-ethylcarbodiimide hydrochloride (260 mg, 1.36 mmol) and 1-hydroxy-7-azabenzotriazole (150 mg, 1.1 mmol) were added to a solution of the acid from preparation 84 (620 mg, 1.03 mmol) in pyridine (2 ml) and dichloromethane (6 ml), and the mixture stirred at room temperature for 30 minutes. Hydroxylamine hydrochloride (155 mg, 2.25 mmol) was added and the reaction stirred at room temperature for 18 h. The reaction mixture was partitioned between ethyl acetate and pH 7 buffer solution, and the layers separated. The aqueous phase was extracted with ethyl acetate, the combined organic solutions washed again with pH 7 buffer solution, then brine, dried ($Na_2SO_4$), filtered and evaporated in vacuo. The residue was azeotroped with toluene, and then purified by medium pressure column chromatography on silica gel using an elution gradient of dichloromethane:methanol (100:0 to 90:10). The product was recrystallised from ethyl acetate/pentane to afford the title compound as a solid, (340 mg, 53%).

mp 181–182° C.; $^1H$ nmr (DMSO-$d_6$, 400 MHz) δ: 1.35 (s, 9H), 1.60 (m, 2H), 1.78 (m, 2H), 1.90 (m, 2H), 2.19 (s, 3H), 2.28 (m, 2H), 2.61 (m, 1H), 3.02 (m, 2H), 3.20 (m, 2H), 3.22 (m, 2H), 3.70 (m, 2H), 3.84 (m, 2H), 3.98 (t, 2H), 6.79–6.95 (m, 4H), 7.08 (s, 2H), 7.15 (s, 1H), 7.28 (m, 1H), 9.10 (s, 1H), 10.93 (s, 1H). LRMS: m/z 640 (M+23)$^+$; Anal. Found: C, 60.27; H, 7.04; N, 6.63. $C_{31}H_{43}N_3O_8S$ requires C, 60.27; H, 7.02; N, 6.88%.

Preparation 91

N-Hydroxy 4-[4-(4-{3-(N-tert-butoxycarbonyl-N-methyl)aminomethyl)phenyl}-3-methylphenyl)-piperidin-1-ylsulphonyl]-tetrahydro-2H-pyran-4-carboxamide

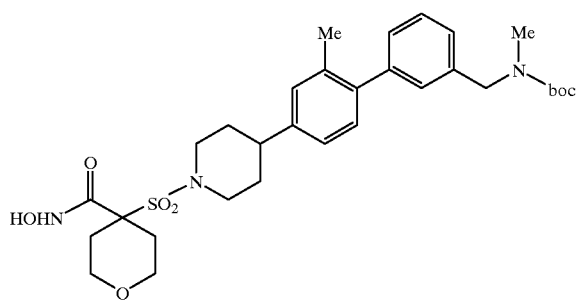

1-(3-Dimethylaminopropyl)-3-ethylcarbodiimide hydrochloride (216 mg, 1.12 mmol) and 1-hydroxy-7-azabenzotriazole (128 mg, 0.94 mmol) were added to a solution of the acid from preparation 85 (550 mg, 0.94 mmol) in pyridine (2 ml) and N,N dimethylformamide (6 ml), and the mixture stirred at room temperature for 1 hour. Hydroxylamine hydrochloride (195 mg, 2.82 mmol) was added and the reaction stirred at room temperature overnight. The reaction mixture was partitioned between ethyl acetate and pH 7 buffer solution, and the layers separated. The aqueous phase was extracted with ethyl acetate (×2), the combined organic solutions washed with 2N hydrochloric acid, dried (MgSO$_4$), filtered and evaporated in vacuo. The residue was crystallised from methanol/ethyl acetate to afford the title compound as a solid, (393 mg, 70%).

$^1H$ nmr (DMSO-$d_6$, 400 MHz) δ: 1.36 (s, 9H), 1.59 (m, 2H), 1.78 (m, 2H), 1.88 (m, 2H), 2.18 (s, 3H), 2.27 (m, 2H), 2.61 (m, 1H), 2.76 (s, 3H), 3.00 (m, 2H), 3.18 (m, 2H), 3.68 (m, 2H), 3.82 (m, 2H), 4.38 (s, 2H), 7.09 (m, 3H), 7.18 (m, 3H), 7.38 (m, 1H), 9.10 (s, 1H), 10.92 (s, 1H). LRMS: m/z 624 (M+1)$^+$.

Preparation 92

1-(4-Bromo-2-methylphenyl)-1H-pyrazol-3-ol

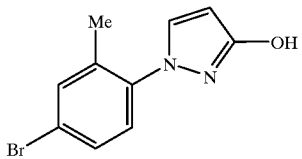

Potassium tert-butoxide (20 ml, 1M in tert-butanol, 20.0 mmol) was added to 1-(4-bromo-2-methylphenyl)hydrazine (J. Chem. Soc. 109; 1916; 582)(2.01 g, 10.0 mmol) to give a dark brown suspension. Ethyl propiolate (1.02 ml, 10 mmol) was then added dropwise over 10 minutes, with cooling, and once addition was complete, the reaction was heated under reflux for 4 hours. The reaction was diluted with water (200 ml) and this mixture washed with dichloromethane (2×50 ml). The aqueous phase was acidified using hydrochloric acid (2N), extracted with dichloromethane (5×100 ml), these combined organic extracts dried (MgSO$_4$), filtered and evaporated in vacuo. The crude product was purified by column chromatography on silica gel using dichloromethane:methanol (98:2) as eluant, and triturated with ether/di-isopropyl ether to give the title compound (615 mg, 24%) as a solid.

mp 208–210° C.; $^1H$ nmr (DMSO-$d_6$, 400 MHz) δ: 2.26 (s, 3H), 5.75 (s, 1H), 7.22 (d, 1H), 7.44 (d, 1H), 7.57 (s, 1H), 7.74 (s, 1H), 10.00 (s, 1H). LRMS: m/z 253, 255 (M+1)$^+$; Anal. Found: C, 47.31; H, 3.52; N, 10.99. $C_{10}H_9BrN_2O$ requires C, 47.46; H, 3.58; N, 11.07%.

Preparation 93

1-(4-Bromo-2-methylphenyl)-3-methoxy-1H-pyrazole

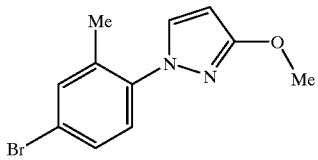

A mixture of the pyrazole from preparation 92 (1.52 g, 6.0 mmol), potassium carbonate (828 mg, 6.0 mmol), and dimethylsulphate (624 ml, 6.6 mmol) in 1-methyl-2-pyrrolidinone (15 ml) was heated at 90° C. for 5 hours. Tlc analysis showed starting material remaining, so additional potassium carbonate (828 mg, 6.0 mmol) and dimethylsulphoxide (624?l, 6.6 mmol) were added, and stirring continued at 90° C. for a further 18 hours. The cooled reaction was poured into water (200 ml), and the mixture extracted with ethyl acetate (3×100 ml). The combined organic extracts were washed with brine (3×100 ml), dried (MgSO$_4$), filtered and concentrated in vacuo. The residue was purified by column chromatography on silica gel using dichloromethane as the eluant, to give the desired product as a pale yellow oil, (970 mg, 61%).

$^1H$ nmr (CDCl$_3$, 400 MHz) δ: 2.30 (s, 3H), 3.95 (s, 3H), 5.30 (s, 1H), 5.85 (s, 1H), 7.19 (d, 1H), 7.38 (m, 1H), 7.43 (s, 1H). LRMS: m/z 267, 269 (M+1)$^+$.

Preparation 94

1-(4-Bromo-2-methylphenyl)-3-(2-hydroxyethoxy)-1H-pyrazole

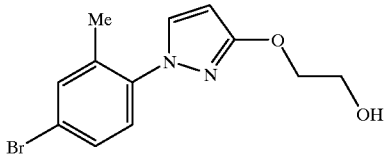

2-Bromoethanol (1.55 ml, 21.8 mmol) was added to a mixture of the alcohol from preparation 92 (2.76 g, 10.9 mmol) and potassium carbonate (3.01 g, 21.8 mmol) in N,N-dimethylformamide (50 ml), and the reaction stirred at 80° C. for 5 hours. The cooled mixture was concentrated in vacuo, the residue suspended in ethyl acetate (250 ml), and the mixture washed with water (5×50 ml). The organic phase was dried (MgSO$_4$), filtered and evaporated in vacuo. The crude product was purified by column chromatography on silica gel using dichloromethane:ether (80:20) as eluant, and crystallised from di-isopropyl ether to give the desired product as buff-coloured crystals, (1.61 g, 50%).

mp 104–105° C.; $^1$H nmr (CDCl$_3$, 400 MHz) δ: 2.24 (s, 3H), 2.58 (br, s, 1H), 3.92 (m, 2H), 4.36 (t, 2H), 5.84 (d, 1H), 7.15 (d, 1H), 7.35 (m, 2H), 7.40 (s, 1H). Anal. Found: C, 48.38; H, 4.30; N, 9.34. C$_{12}$H$_{13}$BrN$_2$O$_2$ requires C, 48.50; H, 4.41; N, 9.43%.

Preparation 95

3-(2-Benzyloxyethoxy)-1-(4-bromo-2-methylphenyl)-1H-pyrazole

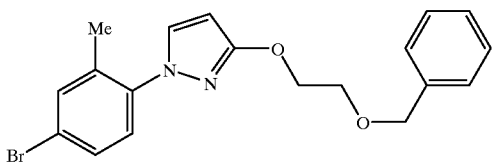

A solution of the alcohol from preparation 94 (1.55 g, 5.2mmol) in tetrahydrofuran (122 ml) was added to a suspension of sodium hydride (229 mg, 60% dispersion in mineral oil, 5.73 mmol) in tetrahydrofuran (10 ml), and the resulting mixture stirred for 2 minutes under a nitrogen atmosphere. Benzyl bromide (681 μl, 5.73 mmol) was then added and the reaction heated under reflux for 16 hours. The cooled reaction mixture was poured into brine (70 ml) and extracted with ethyl acetate (3×50 ml). The combined organic solutions were dried (MgSO$_4$), filtered and concentrated in vacuo to give a yellow oil. The crude product was purified by column chromatography on silica gel using an elution gradient of hexane:ethyl acetate (90:10 to 80:20) to give the title compound as a colourless oil, (1.93 g, 96%).

$^1$H nmr (CDCl$_3$, 400 MHz) δ: 2.24 (s, 3H), 3.80 (t, 2H), 4.38 (t, 2H), 4.60 (s, 2H), 5.66 (s, 1H), 7.12 (d, 1H), 7.21 (m, 2H), 7.32 (m, 5H), 7.40 (s, 1H). LRMS: m/z 409, 411 (M+23)$^+$.

Preparation 96

3-Methoxy-1-[(2-methyl-4-trimethylstannyl)phenyl]-1H-pyrazole

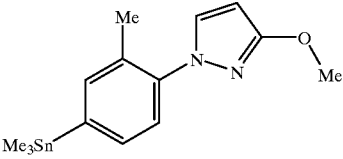

Tetrakis(triphenylphosphine)palladium (0) (30 mg, 0.026 mmol) was added to a solution of the bromide from preparation 93 (659 mg, 2.47 mmol), and hexamethylditin (889 mg, 2.71 mmol) in 1,4-dioxan (8 ml), and nitrogen bubbled through the resulting mixture. The reaction was heated under reflux for 4½ hours, then tlc analysis showed starting material remaining. Additional tetrakis(triphenylphosphine) palladium (0) (48 mg) was added and the reaction heated under reflux for a further 16 hours. 50% Aqueous potassium fluoride solution (5 ml) was added to the cooled reaction, the mixture stirred for 15 minutes, then filtered through Arbocel®, washing through with ether. The filtrate was washed with brine (30 ml), dried (MgSO$_4$), filtered and evaporated in vacuo. The crude product was purified by column chromatography on silica gel using pentane:ether (90:10) as eluant to give the title compound as a pale yellow oil, (598 mg, 69%).

$^1$H nmr (CDCl$_3$, 400 MHz) δ: 0.27 (s, 9H), 2.26 (s 3H), 3.92 (s, 3H), 5.80 (s, 1H), 7.21 (m, 2H), 7.35 (m, 2H).

Preparation 97

3-(2-Benzyloxyethoxy)-1-[2-methyl-4-(trimethylstannyl)phenyl]-1H-pyrazole

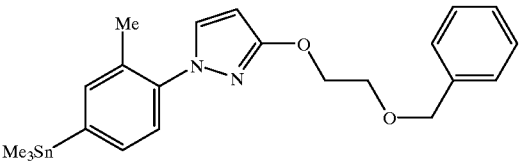

Tetrakis(triphenylphosphine)palladium (0) (286 mg, 0.25 mmol) was added to a solution of the bromide from preparation 95 (1.92 g, 4.96 mmol), and hexamethylditin (1.78 g, 5.45 mmol) in 1,4-dioxan (18 ml), and nitrogen bubbled through the resulting mixture. The reaction was heated under reflux for 2 hours, then cooled. Potassium fluoride solution (5 ml, 50%) was added, the mixture stirred for 30 minutes, and filtered though Arbocel®, washing through well with ethyl acetate (150 ml). The filtrate was washed with brine (2×30 ml), dried (MgSO$_4$), filtered and evaporated in vacuo. The residue was purified by column chromatography on silica gel using hexane:ether (84:16) to afford the desired product as a crystalline solid, (1.87 g, 80%).

mp 50–52° C.; $^1$H nmr (CDCl$_3$, 400 MHz) δ: 0.28 (s, 9H), 2.24 (s, 3H), 3.80 (t, 2H), 4.40 (t, 2H), 4.60 (s, 2H), 5.82 (s, 1H), 7.22 (m, 3H), 7.33 (m, 6H). Anal. Found: C, 56.21; H, 5.97; N, 5.95. C$_{22}$H$_{28}$N$_2$O$_2$Sn requires C, 56.08; H, 5.99; N, 5.95%.

Preparation 98

Methyl 2-{4-[4-(3-methoxy-1H-pyrazol-1-yl}-3-methylphenyl]-1,2,3,6-tetrahydropyridin-1-ylsulphonyl}-2-methyl-propanoate

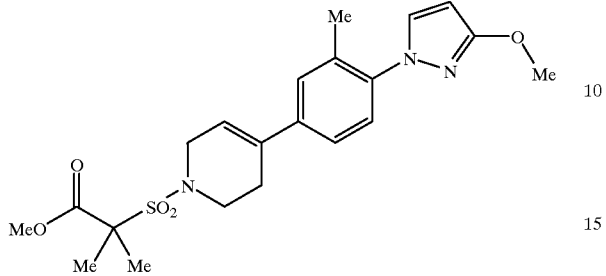

Tris(dibenzylideneacetone)dipalladium(0) (30.7 mg, 0.034 mmol) was added to a solution of the vinyl triflate from preparation 29 (727 mg, 1.84 mmol), the stannane from preparation 96 (590 mg, 1.68 mmol), and triphenylarsine (104 mg, 0.36 mmol) in 1-methyl-2-pyrrolidinone (4 ml), and the solution stirred under a nitrogen atmosphere. Copper (I) iodide (16 mg, 0.17 mmol) was added, the solution de-gassed, and the reaction then stirred at 60° C. for 30 minutes, and at 75° C. for a further 4½ hours. Potassium fluoride solution (3 ml, 50%) was added to the cooled reaction, stirring continued for 15 minutes, and the mixture filtered through Arbocel®, washing through with ethyl acetate (150 ml). The filtrate was washed with water (30 ml), brine (30 ml), dried (MgSO$_4$), filtered and evaporated in vacuo. The residual orange foam was purified by column chromatography on silica gel using pentane:ether (50:50) to afford the title compound as a pale yellow gum, (588 mg, 81%).

$^1$H nmr (CDCl$_3$, 400 MHz) δ: 1.63 (s, 6H), 2.30 (s, 3H), 2.59 (m, 2H), 3.60 (t, 2H), 3.79 (s, 3H), 3.94 (s, 3H), 4.08 (m, 2H), 5.81 (d, 1H), 6.00 (m, 1H), 7.21 (m, 3H), 7.36 (s, 1H). LRMS: m/z 434 (M+1)$^+$.

Preparation 99

Methyl 2-{4-[4-(3-{2-benzyloxyethoxy}-1H-pyrazol-1-yl}-3-methylphenyl]-1,2,3,6-tetrahydropyridin-1-ylsulphonyl}-2-methyl-propanoate

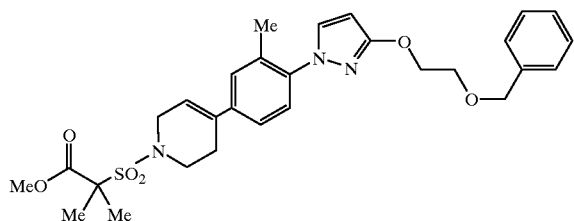

The title compound was obtained as a yellow oil (75%) from the triflate from preparation 29 and the stannane of preparation 97, using a similar method to that described in preparation 98.

$^1$H nmr (CDCl$_3$, 400 MHz) δ: 1.64 (s, 6H), 2.27 (s, 3H), 2.58 (m, 2H), 3.59 (m, 2H), 3.78 (s, 3H), 3.80 (t, 2H), 4.09 (m, 2H), 4.39 (t, 2H), 4.60 (s, 2H), 5.85 (s, 1H), 6.00 (m, 1H), 7.21 (m, 4H), 7.34 (m, 5H). LRMS: m/z 576 (M+23)$^+$.

Preparation 100

Methyl 2-{4-[4-(3-methoxy-1H-pyrazol-1-yl}-3-methylphenyl]piperidin-1-ylsulphonyl}-2-methylpropanoate

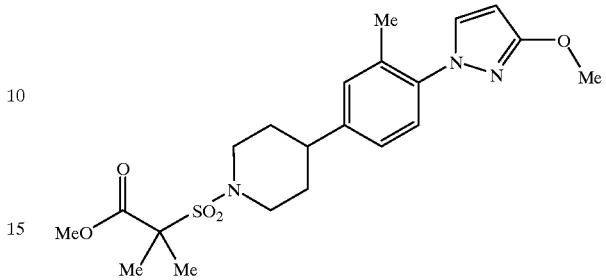

10% Palladium on charcoal (60 mg) was added to a solution of the 1,2,3,6-tetrahydropyridine from preparation 98 (580 mg, 1.38 mmol) in methanol (20 ml), and the mixture hydrogenated at 50 psi and room temperature for 6 hours. Tlc analysis showed starting material remaining, so additional 10% palladium on charcoal (50 mg) was added, and the mixture hydrogenated for a further 18 hours. The reaction mixture was filtered through Arbocel®, the filtrate suspended in dichloromethane (50 ml), re-filtered through Arbocel®, and the filtrate evaporated in vacuo, to give the desired product as a colourless solid, (365 mg, 61%).

mp 109–110° C.; $^1$H nmr (CDCl$_3$, 400 MHz) δ: 1.61 (s, 6H), 1.75–1.86 (m, 4H), 2.25 (s, 3H), 2.62 (m, 1H), 3.02 (m, 2H), 3.79 (s, 3H), 3.94 (m, 5H), 5.80 (d, 1H), 7.06 (m, 2H), 7.21 (m, 2H). LRMS: m/z 458 (M+23)$^+$.

Preparation 101

Methyl 2-{4-[4-(3-{2-hydroxyethoxy}-1H-pyrazol-1-yl}-3-methylphenyl]piperidin-1-ylsulphonyl}-2-methylpropanoate

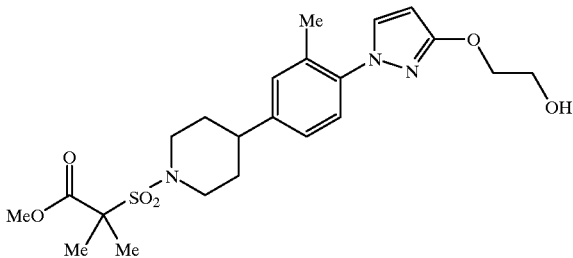

A mixture of the benzyl ether from preparation 99 (790 mg, 1.42 mmol) and 10% palladium on charcoal (160 mg) in ethanol (35 ml) was hydrogenated at 50 psi and room temperature for 17 hours. Tlc analysis showed starting material remaining, so acetic acid (2 ml), and additional 10% palladium on charcoal (80 mg) were added, and the reaction continued for a further 48 hours, with additional 10% palladium on charcoal (160 mg) added portionwise. The reaction mixture was filtered through Arbocel®, washing through with ethanol, and the filtrate concentrated in vacuo. The residue was partitioned between ethyl acetate (100 ml) and saturated sodium bicarbonate solution (100 ml), the layers separated and the organic phase dried (MgSO$_4$), filtered and evaporated in vacuo to give the title compound as a colourless oil, (630 mg, 95%).

¹H nmr (DMSO-d₆, 400 MHz) δ: 1.46–1.62 (m, 8H), 1.80 (m, 2H), 2.19 (s, 3H), 2.71 (m, 1H), 3.02 (m, 2H), 3.10 (m, 2H), 3.62–3.79 (m, 5H), 4.10 (m, 2H), 4.60 (m, 1H), 5.84 (s, 1H), 7.12 (m, 1H), 7.19 (m, 2H), 7.69 (s, 1H). LRMS: m/z 488 (M+23)⁺.

Preparation 102

Methyl 2-methyl-2-{4-[3-methyl4-(1,3-thiazol-2-yl)phenyl]piperidin-1-ylsulphonyl}-propanoate

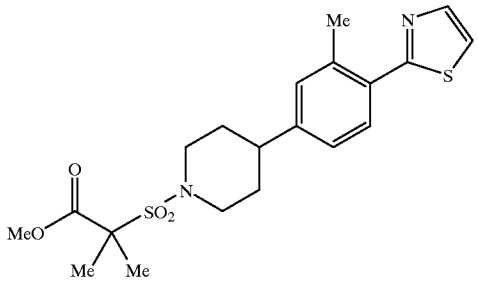

Bis(triphenylphosphine)palladium (II) chloride (49 mg, 0.07 mmol) was added to a solution of the bromide from preparation 26 (577 mg, 1.38 mmol) and 2-(trimethylstannyl)-1,3-thiazole (Synthesis, 1986, 757) (372 mg, 1.5 mmol) in tetrahydrofuran (3.5 ml), and the resulting mixture was de-gassed, and placed under an argon atmosphere. The reaction was heated under reflux for 17 hours. Tlc analysis showed starting material remaining, so additional 2-(trimethylstannyl)-1,3-thiazole (173 mg, 0.8 mmol) and bis(triphenylphosphine)palladium (II) chloride (49 mg, 0.07 mmol) were added, the mixture was de-gassed, and then heated under reflux for a further 17 hours. The cooled mixture was concentrated in vacuo, and the residue purified by column chromatography on silica gel using an elution gradient of hexane:ethyl acetate (91:9 to 66:34). The product was re-purified by column chromatography on silica gel using ether as eluant to give the title compound as a buff-coloured solid, (240 mg, 40%).

mp 111–114° C.; ¹H nmr (DMSO-d₆, 400 MHz) δ: 1.52 (s, 6H), 1.58 (m, 2H), 1.81 (m, 2H), 2.45 (s, 3H), 2.74 (m, 1H), 3.04 (m, 2H), 3.74 (m, 5H), 7.18 (d, 1H), 7.21 (s, 1H), 7.62 (d, 1H), 7.78 (d, 1H), 7.92 (d, 1H). LRMS: m/z 445 (M+23)⁺; Anal. Found: C, 56.64; H, 6.19; N, 6.55. C₂₀H₂₆N₂S₂O₄ requires C, 56.85; H, 6.20; N, 6.63%.

Preparation 103

2-{4-[4-(3-Methoxy-1H-pyrazol-1-yl}-3-methylphenyl]piperidin-1-ylsulphonyl}-2-methylpropanoic acid

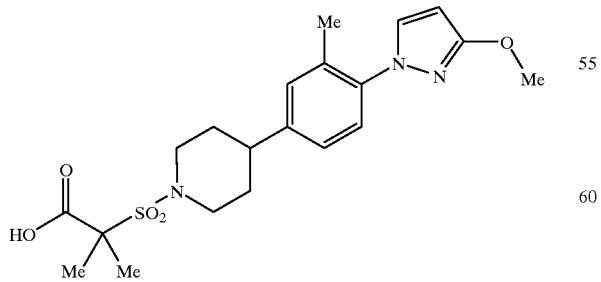

A mixture of the methyl ester from preparation 100 (355 mg, 0.82 mmol), and aqueous sodium hydroxide (5.9 ml, 1M, 5.9 mmol) in methanol (5 ml) and 1,4-dioxan (5 ml) was heated under reflux for 2 hours. The cooled reaction was diluted with water and acidified to pH 3 using hydrochloric acid (2N). The resulting precipitate was filtered off, washed with water, and dried under vacuum at 75° C. to give the title compound as a white powder, (281 mg, 82%).

¹H nmr (CDCl₃, 400 MHz) δ: 1.63 (s, 6H), 1.70–1.90 (m, 4H), 2.24 (s, 3H), 2.62 (m, 1H), 3.04 (m, 2H), 3.90 (s, 3H), 3.98 (m, 2H), 5.80 (s, 1H), 7.04 (m, 3H), 7.32 (m, 1H). Anal. Found: C, 56.78; H, 6.40; N, 9.71. C₂₀H₂₇N₃O₅S requires C, 56.99; H, 6.46; N, 9.97%.

Preparation 104

2-{4-[4-(3-{2-Hydroxyethoxy}-1H-pyrazol-1-yl}-3-methylphenyl]piperidin-1-ylsulphonyl}-2-methylpropanoic acid

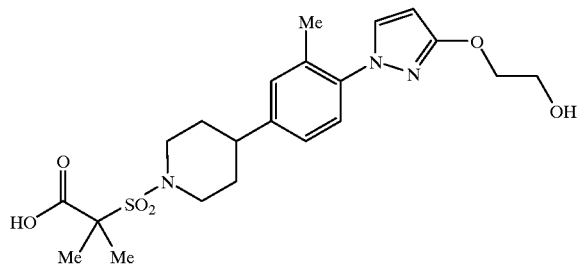

A mixture of the methyl ester from preparation 101 (520 mg, 1.2 mmol), and aqueous sodium hydroxide (3.6 ml, 1M, 3.6 mmol) in 1,4-dioxan (5 ml) was heated under reflux for 2½ hours. The cooled reaction was partitioned between water (100 ml) and ethyl acetate (100 ml), acidified to pH 2 using hydrochloric acid (2N), and the phases separated. The aqueous layer was extracted with ethyl acetate (2×35 ml), the combined organic solutions dried (MgSO₄), filtered and concentrated in vacuo. The residue was triturated with ether twice, to afford the title compound as a white solid, (338 mg, 62%).

¹H nmr (DMSO-d₆, 300 MHz) δ: 1.47 (s, 6H), 1.59 (m, 2H), 1.79 (m, 2H), 2.19 (s, 3H), 2.70 (m, 1H), 3.02 (m, 2H), 3.64 (m, 2H), 3.79 (m, 2H), 4.09 (t, 2H), 4.62 (m, 1H), 5.84 (s, 1H), 7.12 (m, 1H), 7.18 (m, 2H), 7.69 (s, 1H), 13.1 (br, s, 1H). LRMS: m/z 474 (M+23)⁺.

Preparation 105

2-Methyl-2-{4-[3-methyl-4-(1,3-thiazol-2-yl)phenyl]piperidin-1-ylsulphonyl}-propanoic acid

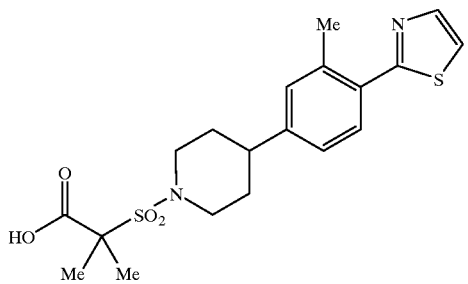

The title compound was obtained as a white solid (92%) from the methyl ester of preparation 102, following a similar procedure to that described in preparation 104.

¹H nmr (DMSO-d₆, 400 MHz) δ: 1.47 (s, 6H), 1.60 (m, 2H), 1.80 (m, 2H), 2.45 (s, 3H), 2.70 (m, 1H), 3.03 (m, 2H), 3.78 (m, 2H), 7.18 (d, 1H), 7.21 (s, 1H), 7.63 (d, 1H), 7.78 (s, 1H), 7.92 (s, 1H), 13.37 (br, s, 1H). Anal. Found: C, 55.28; H, 5.90; N, 6.70. $C_{19}H_{24}N_2O_4S_2$ requires C, 55.86; H, 5.92; N, 6.86%.

Preparation 106

Methyl 1-{[4-(4-bromo-3-methylphenyl)piperidin-1-yl]sulfonyl}-3-cyclopentene-1-carboxylate

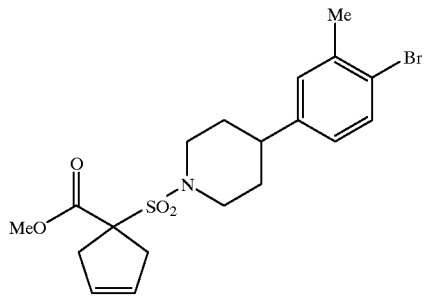

A suspension of sodium hydride (1.1 g, 60% dispersion in mineral oil, 28 mmol) was cooled to 0° C. in anhydrous N-methyl pyrrolidinone (30 ml) under nitrogen. A solution of the ester from preparation 25 (10 g, 26 mmol) in N-methyl pyrrolidinone (70 ml) was added dropwise with stirring and the reaction mixture allowed to warm to ambient temperature over 50 minutes. 1,4-dichlorobut-2-ene (3.0 ml, 28 mmol) and tetrabutylammonium bromide (8.3 g, 26 mmol) were added to the reaction mixture and after a further 3 hours an additional portion of sodium hydride (1.1 g, 60% dispersion in mineral oil, 28 mmol) was added. The mixture was stirred for a further 2 days. The reaction mixture was partitioned between ethyl acetate (300 ml) and water (300 ml) and the layers separated. The aqueous layer was extracted with ethyl acetate (300 ml) and the combined organic extracts were dried (Na₂SO₄), filtered and concentrated in vacuo. The residue was purified by flash chromatography eluting with dichloromethane to give the title compound as a white solid (7.4 g, 65%).

¹H nmr (DMSO-d₆, 400 MHz) δ: 1.45 (m, 2H), 1.75 (m, 2H), 2.28 (s, 3H), 2.64 (m, 1H), 2.95 (m, 4H), 3.14 (d, 2H), 3.75 (s, 3H), 3.78 (s, 2H), 5.63 (s, 2H), 6.98 (d, 1H), 7.21 (s, 1H), 7.43 (m, 1H). LRMS:m/z 464/466 (M+23)⁺.

Preparation 107

Methyl (1α,3α,4α)-1-{[4-(4-bromo-3-methylphenyl)piperidin-1-yl]sulfonyl}-3,4-dihydroxycyclopentanecarboxylate

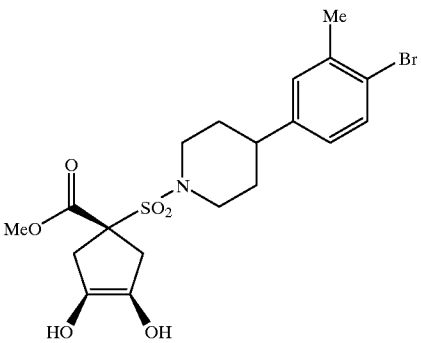

N-methylmorpholine N-oxide (580 mg, 4.97 mmol) and osmium tetroxide (2.5 weight % in tert-butanol, 1.1 ml, 0.136 mmol) were added to a solution of the cyclopentene from preparation 106 (2.0 g, 4.52 mmol) in dioxan (20 ml), water (0.1 ml), and the solution stirred at room temperature for 18 hours. The reaction mixture was partitioned between ethyl acetate (200 ml) and water (300 ml) and the layers separated. The aqueous layer was extracted with ethyl acetate (2×200 ml), and the combined organic extracts were dried (Na₂SO₄), filtered and concentrated in vacuo. The residue was purified by column chromatography on silica gel using dichloromethane/methanol (100:0 to 97:3) as eluant to afford the title compound as a white solid (1.2 g, 56%).

¹H nmr (DMSO-d₆, 400 MHz) δ: 1.47 (m, 2H), 1.77 (m, 2H), 2.28 (m, 5H), 2.42 (s, 2H), 2.63 (m, 1H), 2.91 (m, 2H), 3.75 (m, 5H), 3.85 (s, 2H), 4.62 (s, 2H), 6.98 (d, 1H), 7.21 (s, 1H), 7.43 (d, 1H). LRMS: m/z 498/500 (M+23)⁺.

Preparation 108

Methyl (1α,3β,4β)-1-{[4-(4-bromo-3-methylphenyl)piperidin-1-yl]sulfonyl}-3,4-dihydroxycyclopentanecarboxylate

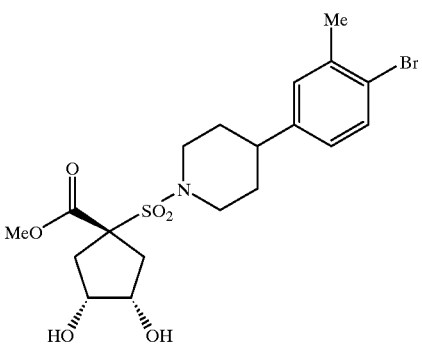

Silver acetate (2.1 g, 12.46 mmol) and iodine (1.5 g, 5.81 mmol) were added to a solution of the cyclopentene from preparation 106 (2.45 g, 5.54 mmol) in glacial acetic acid (125 ml) and the mixture was stirred at ambient temperature for 1 hour. Wet acetic acid (2.5 ml of a 1:25 water/glacial acetic acid mixture) was then added and the reaction was heated to 95° C. for 3 hours and then stirred at ambient temperature for 18 hours. Sodium chloride was added to the mixture and the resulting precipitate was filtered through arbocel® and then washed with toluene. The resulting filtrate was concentrated in vacuo, azeotroped with toluene to give a solid which was triturated with diisopropyl ether. This solid was further purified by flash chromatography eluting with dichloromethane to give the intermediate monoacetate compound as a beige solid (1.35 g, 50%). 1N sodium hydroxide (4 ml) was added to a solution of the monoacetate intermediate in dioxan/methanol (12 ml/8 ml) and the reaction was stirred at ambient temperature for 1 hour. The solvent was removed under reduced pressure, and the residue was partitioned between ethyl acetate (50 ml) and water (75 ml), and the layers separated. The aqueous layer was extracted with ethyl acetate (2×50 ml), and the combined organic extracts were dried ($Na_2SO_4$), filtered and concentrated in vacuo to give the title compound as a white solid (875 mg, 70%).

$^1$H nmr (DMSO-$d_6$, 400 MHz) δ: 1.55 (m, 2H), 1.87 (m, 2H), 2.18 (m, 2H), 2.30 (s, 3H), 2.63 (m, 3H), 2.98 (t, 2H), 3.72 (m, 7H), 4.68 (s, 2H), 6.98 (d, 1H), 7.22 (s, 1H), 7.43 (d, 1H). LRMS: m/z 498/500(M+23)$^+$.

Preparation 109

Methyl (3aα,5α,6aα)-5-{[4-(4-bromo-3-methylphenyl)piperidin-1-yl]sulfonyl}-2,2-dimethyltetrahydro-3aH-cyclopenta[d][1,3]dioxole-5-carboxylate

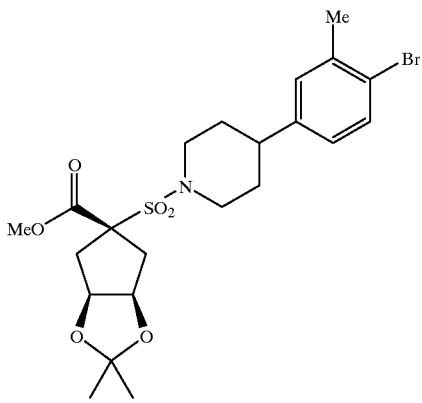

2,2-Dimethoxypropane (0.74 ml, 6 mmol) and p-toluenesulfonic acid (60 mg, 0.3 mmol) were added to a solution of the diol from preparation 107 (1.43 g, 3 mmol) in anhydrous dimethylformamide (10 ml) under nitrogen. The reaction was warmed to 50° C. for 4.5hours. The mixture was diluted with ethyl acetate (50 ml) and water (40 ml) and the layers separated. The aqueous layer was extracted with ethyl acetate (2×50 ml), and the combined organic extracts were dried ($Na_2SO_4$), filtered and concentrated in vacuo. The resulting solid was recrystalised from ethyl acetate/di-isopropyl ether to give the title compound as a white solid (1.05 g, 70%).

$^1$H nmr (DMSO-$d_6$, 400 MHz) δ: 1.17 (s, 3H), 1.20 (s, 3H), 1.47 (m, 2H), 1.77 (m, 2H), 2.23 (m, 2H), 2.32 (s, 3H), 2.65 (m, 3H), 2.95 (t, 2H), 3.72 (m, 5H), 4.64 (s, 2H), 6.98 (d, 1H), 7.21 (s, 1H), 7.43 (d, 1H). LRMS: m/z 538/540 (M+23)$^+$.

Preparation 110

Methyl (3aβ,5α,6aβ)-5-{[4-(4-bromo-3-methylphenyl)piperidin-1-yl]sulfonyl}-2,2-dimethyltetrahydro-3aH-cyclopenta[d][1,3]dioxole-5-carboxylate

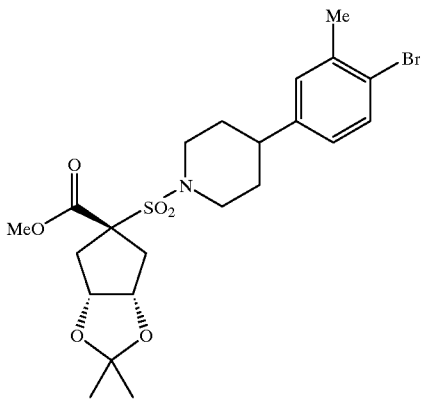

The title compound was prepared from the diol from preparation 108 in a similar procedure to that described in preparation 109. The title compound was isolated as a pale yellow solid (1.3 g, 75%).

$^1$H nmr (DMSO-$d_6$, 400 MHz) δ: 1.11 (s, 3H), 1.42 (s, 3H), 1.57 (m, 2H), 1.78 (m, 2H), 2.18 (m, 2H), 2.30 (s, 3H), 2.62 (m, 1H), 2.78 (m, 2H), 2.98 (t, 2H), 3.72 (m, 5H), 4.58 (m, 2H), 6.98 (d, 1H), 7.22 (s, 1H), 7.43 (d, 1H). LRMS: m/z 538/540(M+23)$^+$.

Preparation 111

Methyl (3aα,5α,6aα)-5-{[4-(4-{6-[2-(tert-butoxy)ethoxy]pyridin-2-yl}-3-methylphenyl)piperidin-1-yl]sulfonyl}-2,2-dimethyltetrahydro-3aH-cyclopenta[d][1,3]dioxole-5-carboxylate

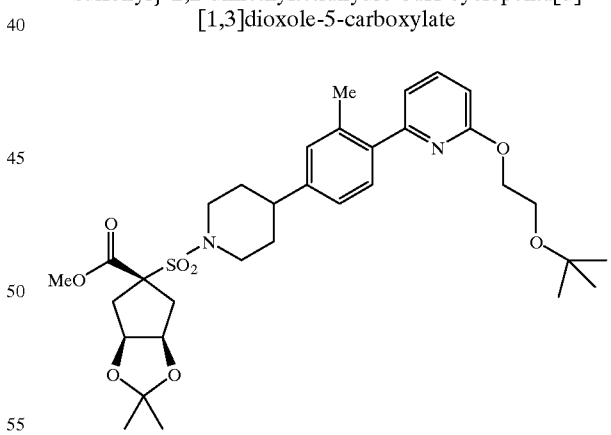

A mixture of the stannane from preparation 127 (2.3 g, 4.78 mmol) and the aryl bromide from preparation 109 (1.9 g, 3.68 mmol), and tetrakis(triphenylphosphine)palladium (0) (213 mg, 0.18 mmol) in toluene (25 ml) was refluxed under nitrogen for 10 hours, then stirred at ambient temperature for 7 hours. The mixture was evaporated in vacuo and to the resulting oil was added ethyl acetate (30 ml) and aqueous potassium fluoride solution (20 ml) and stirred rapidly for 10 minutes. The resulting precipitate was filtered off on arbocel® washing with ethyl acetate. The filtrate was allowed to separate, and the aqueous layer extracted with ethyl acetate (30 ml). The combined organic extracts were dried (Na$_2$SO$_4$), filtered and concentrated in vacuo. The residue was purified by column chromatography on silica gel using pentane:ethyl acetate (98:2 to 60:40) as eluant. The resulting solid was recrystalised from ethyl acetate to afford the title compound as a white solid, (1.4 g, 60%).

$^1$H nmr (DMSO-d$_6$, 400 MHz) δ: 1.13 (s, 9H), 1.17 (s, 3H), 1.20 (s, 3H), 1.57 (m, 2H), 1.80 (m, 2H), 2.23 (m, 2H), 2.32 (s, 3H), 2.69 (m, 3H), 2.95 (t, 2H), 3.60 (m, 2H), 3.72 (m, 5H), 4.29 (m, 2H), 4.68 (s, 2H), 6.73 (d, 1H), 7.03 (d, 1H) 7.15 (m, 2H), 7.31 (d, 1H), 7.75 (t, 1H). LRMS: m/z 654 (M+23)$^+$.

Preparation 112
Methyl (3aα,5α,6aα)-5-({4-[4-(6-ethoxypyridin-2-yl)-3-methylphenyl]piperidin-1-yl}sulfonyl)-2,2-dimethyltetrahydro-3aH-cyclopenta[d][1,3]dioxole-5-carboxylate

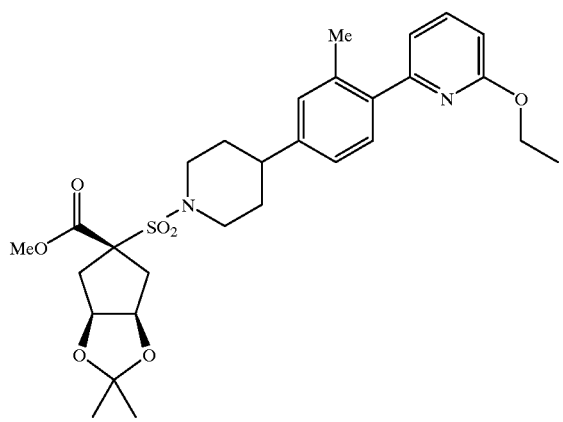

The title compound was prepared from the aryl bromide from preparation 109 and the stannane from preparation 129 in a similar procedure to that described in preparation 111. The title compound was isolated as a white solid (1.1 g, 50%).

$^1$H nmr (DMSO-d$_6$, 400 MHz) δ: 1.15 (s, 3H), 1.19 (s, 3H), 1.25 (t, 3H), 1.57 (m, 2H), 1.80 (m, 2H), 2.23 (m, 2H), 2.35 (s, 3H), 2.65 (m, 3H), 2.95 (t, 2H), 3.65 (m, 2H), 3.72 (m, 3H), 4.28 (q, 2H), 4.66 (d, 2H), 6.68 (d, 1H), 7.03 (d, 1H), 7.15 (m, 2H), 7.33 (d, 1H), 7.72 (t, 1H). LRMS: m/z 581 (M+23)$^+$.

Preparation 113
Methyl (3aβ,5α,6aβ)-5-({4-[4-(6-ethoxypyridin-2-yl)-3-methylphenyl]piperidin-1-yl}sulfonyl)-2,2-dimethyltetrahydro-3aH-cyclopenta[d][1,3]dioxole-5-carboxylate

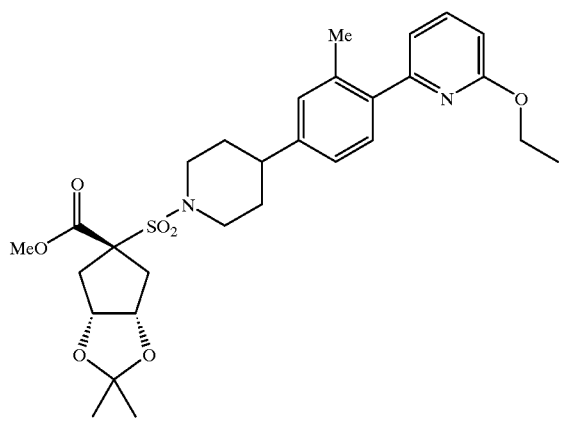

The title compound was prepared from the aryl bromide from preparation 110 and the stannane from preparation 129 in a similar procedure to that described in preparation 111. The title compound was isolated as a white foam (413 mg, 60%).

$^1$H nmr (DMSO-d$_6$, 400 MHz) δ: 1.21 (s, 3H), 1.28 (t, 3H), 1.42 (s, 3H), 1.57 (m, 2H), 1.80 (m, 2H), 2.18 (m, 2H), 2.35 (s, 3H), 2.65 (m, 1H), 2.80 (m, 2H), 3.00 (t, 2H), 3.75 (m, 2H), 3.77 (s, 3H), 4.28 (q, 2H), 4.56 (m, 2H), 6.68 (d, 1H), 7.03 (d, 1H), 7.15 (m, 2H), 7.35 (d, 1H), 7.72 (t, 1H). LRMS: m/z 559 (M+1)$^+$.

Preparation 114

Methyl (3aα,5α,6aα)-5-{4-[4-(3-methoxyphenyl)-3-methylphenyl]piperidin-1-ylsulfonyl}-2,2-dimethyltetrahydro-3aH-cyclopenta[d][1,3]dioxole-5-carboxylate

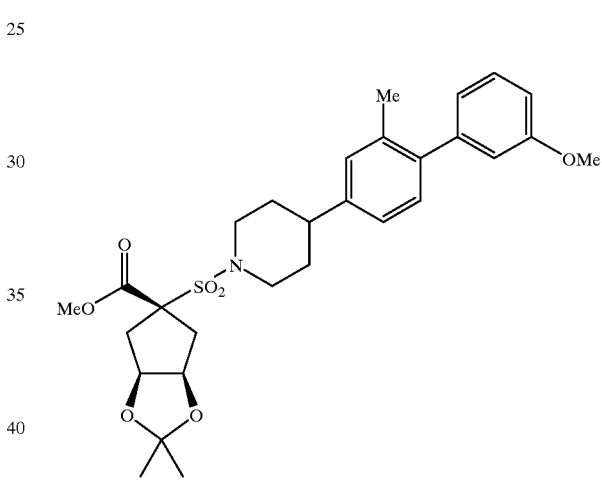

A mixture of the aryl bromide from preparation 109 (1.03, 1.99 mmol), 3-methoxyphenylboronic acid (364 mg, 2.40 mmol), cesium fluoride (606 mg, 4.00 mmol), tris(dibenzylideneacetone)dipalladium (0) (91 mg, 0.1 mmol) and tri(o-tolyl)phosphine (61 mg, 0.2 mmol) in 1,2-dimethoxyethane (25 ml) was heated under reflux under nitrogen for 9 hours. The cooled reaction was diluted with water and ethyl acetate, filtered through arbocel®, which was washed with water and ethyl acetate. The organic layer was separated, and washed with brine, dried (Na$_2$SO$_4$), filtered and concentrated in vacuo. The residue was purified by column chromatography on silica gel using pentane:ethyl acetate (95:5 to 60:40) as eluant. The title compound was obtained as a white solid (630 mg, 60%).

$^1$H nmr (DMSO-d$_6$, 400 MHz) δ: 1.15 (s, 3H), 1.18 (s, 3H), 1.57 (m, 2H), 1.79 (m, 2H), 2.18 (m, 5H), 2.65 (m, 3H), 2.95 (t, 2H), 3.65 (m, 8H), 4.64 (m, 2H), 6.82 (m, 3H), 7.10 (m, 3H), 7.29 (m, 1H). LRMS: m/z 566 (M+23)$^+$.

Preparation 115

Methyl (3aβ,5α,6aβ)-5-{4-[4-(3-methoxyphenyl)-3-methylphenyl]piperidin-1-ylsulfonyl}-2,2-dimethyltetrahydro-3aH-cyclopenta[d][1,3]dioxole-5-carboxylate

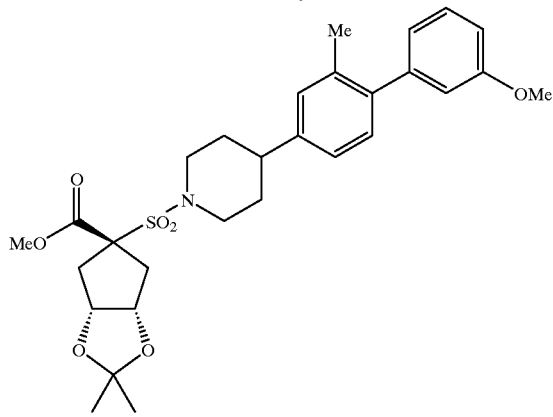

The title compound was prepared from the aryl bromide from preparation 110 in a similar procedure to that described in preparation 114 and was isolated as a white foam (310 mg, 45%).

$^1$H nmr (DMSO-d$_6$, 400 MHz) δ: 1.20 (s, 3H), 1.40 (s, 3H), 1.57 (m, 2H), 1.80 (m, 2H), 2.18 (m, 5H), 2.67 (m, 1H), 2.81 (m, 2H), 2.95 (t, 2H), 3.75 (m, 8H), 4.57 (m, 2H), 6.82 (m, 3H), 7.10 (m, 3H), 7.29 (m, 1H). LRMS: m/z 566 (M+23)$^+$.

Preparation 116

(3aα,5α,6aα)-5-{[4-(4-{6-[2-(tert-butoxy)ethoxy]pyridin-2-yl}-3-methylphenyl)piperidin-1-yl]sulfonyl}-2,2-dimethyltetrahydro-3aH-cyclopenta[d][1,3]dioxole-5-carboxylic acid

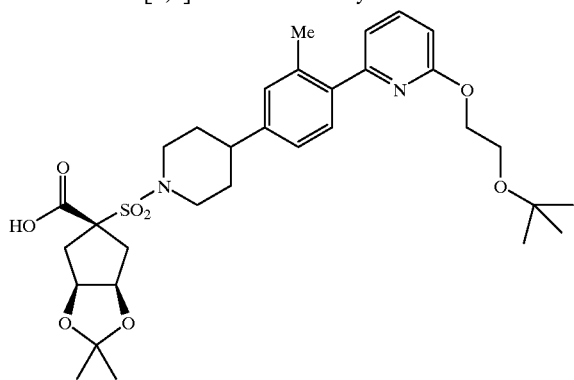

A mixture of the methyl ester from preparation 111 (1.4 g, 2.22 mmol) and aqueous sodium hydroxide (5.5 ml, 2N, 11.1 mmol) in methanol (7 ml) and dioxan (7 ml) was heated under reflux for 1 hour, then allowed to cool. The reaction was concentrated in vacuo, the residue dissolved in water (20 ml), and the solution acidified to pH 4 with glacial acetic acid. The aqueous was extracted with ethyl acetate (2×50 ml) and the collected organic layers dried (Na$_2$SO$_4$), filtered and concentrated in vacuo. The resulting oily solid was azeotroped with toluene then triturated with cold ethyl acetate to afford the title compound as a white solid (1.0 g, 75%).

$^1$H nmr (DMSO-d$_6$, 400 MHz) δ: 1.13 (s, 9H), 1.16 (s, 3H), 1.28 (s, 3H), 1.57 (m, 2H), 1.75 (m, 2H), 2.26 (m, 5H), 2.59 (m, 3H), 3.05 (t, 2H), 3.60 (m, 2H), 3.72 (d, 2H), 4.28 (m, 2H), 4.58 (m, 2H), 6.73 (d, 1H), 7.03 (d, 1H), 7.15 (m, 2H), 7.31 (d, 1H), 7.75 (t, 1H) 12.9 (s, 1H). LRMS: m/z 617 (M+1)$^+$.

Preparation 117

(3aα,5α,6aα)-5-({4-[4-(6-ethoxypyridin-2-yl)-3-methylphenyl]piperidin-1-yl}sulfonyl)-2,2-dimethyltetrahydro-3aH-cyclopenta[d][1,3]dioxole-5-carboxylic acid

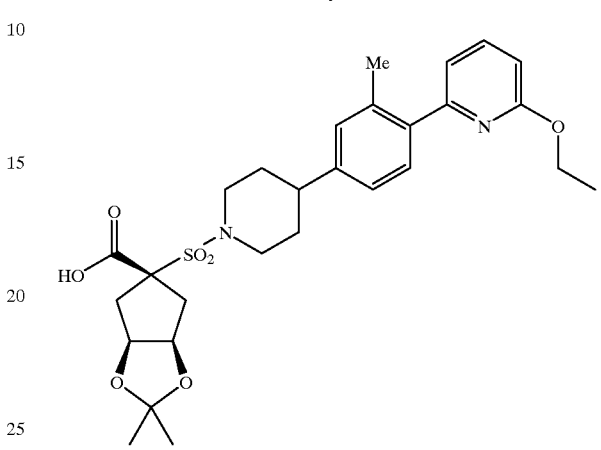

A mixture of the methyl ester from preparation 112 (780 mg, 1.40 mmol) and aqueous sodium hydroxide (3.5 ml, 2N, 6.98 mmol) were dissolved in methanol (5 ml) and dioxan (5 ml) and were heated under reflux for 1.5 hour, then allowed to cool. The reaction was concentrated in vacuo, the residue dissolved in water (20 ml), and the solution acidified to pH 4 with glacial acetic acid. The resulting mixture was extracted with ethyl acetate (2×50 ml) and the collected organic layers dried (Na$_2$SO$_4$), filtered and concentrated in vacuo. This afforded the title compound as a white solid (240 mg, 85%).

$^1$H nmr (DMSO-d$_6$, 400 MHz) δ: 0.93 (s, 3H), 1.14 (m, 6H), 1.41 (m, 2H), 1.58 (m, 2H), 2.01 (m, 2H), 2.13 (s, 3H), 2.43 (m, 3H), 2.78 (m, 2H), 3.50 (m, 2H), 4.08 (m, 2H), 4.43 (m, 2H), 6.48 (m, 1H), 6.80 (d, 1H), 6.91 (m, 2H), 7.10 (m, 1H), 7.51 (m, 1H) 13.10 (s, 1H). LRMS: m/z 545 (M+1)$^+$.

Preparation 118

(3aβ,5α,6aβ)-5-({4-[4-(6-ethoxypyridin-2-yl)-3-methylphenyl]piperidin-1-yl}sulfonyl)-2,2-dimethyltetrahydro-3aH-cyclopenta[d][1,3]dioxole-5-carboxylic acid

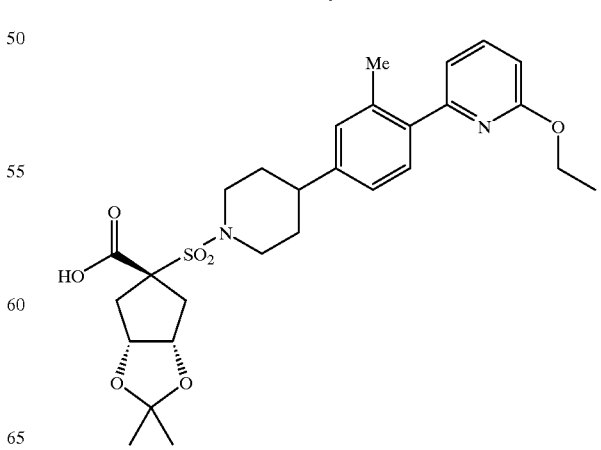

The title compound was prepared from the methyl ester from preparation 113 in a similar procedure to that described in preparation 117 and was isolated as a white foam (250 mg, 65%).

¹H nmr (DMSO-d₆, 400 MHz) δ: 1.21 (s, 3H), 1.28 (t, 3H), 1.42 (s, 3H), 1.61 (m, 2H), 1.80 (d, 2H), 2.18 (m, 2H), 2.35 (s, 3H), 2.65 (m, 1H), 2.80 (m, 2H), 3.00 (t, 2H), 3.78 (d, 2H), 4.28 (q, 2H), 4.56 (m, 2H), 6.68 (d, 1H), 7.01 (d, 1H), 7.15 (m, 2H), 7.35 (d, 1H), 7.72 (t, 1H), 13.65 (s, 1H). LRMS: m/z 545 (M+1)⁺.

Preparation 119
(3aα,5α,6aα)-5-{4-[4-(3-methoxyphenyl)-3-methylphenyl]piperidin-1-ylsulfonyl}-2,2-dimethyltetrahydro-3aH-cyclopenta[d][1,3]dioxole-5-carboxylic acid

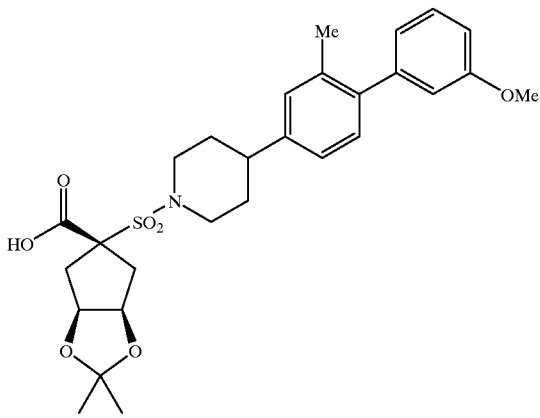

A mixture of the methyl ester from preparation 114 (630 mg, 1.16 mmol) and aqueous sodium hydroxide (3.0 ml, 2N, 5.80 mmol) were dissolved in methanol (5 ml) and dioxan (5 ml) and heated under reflux for 1 hour, then allowed to cool. The reaction was concentrated in vacuo, the residue dissolved in water (20 ml), and the solution acidified to pH 1 with 2N hydrochloric acid. The resulting mixture was extracted with ethyl acetate (2×50 ml) and the collected organic layers dried (Na₂SO₄), filtered and concentrated in vacuo. This afforded the title compound as a white solid (500 mg, 83%).

¹H nmr (DMSO-d₆, 400 MHz) δ: 1.13 (s, 3H), 1.22 (s, 3H), 1.58 (m, 2H), 1.79 (m, 2H), 2.18 (m, 5H), 2.62 (m, 3H), 2.97 (t, 2H), 3.71 (m, 5H), 4.64 (m, 2H), 6.82 (m, 3H), 7.06 (m, 2H), 7.14 (s, 1H), 7.29 (t, 1H). LRMS: m/z 528 (M−1)⁻.

Preparation 120
(3aβ,5α,6aβ)-5-{4-[4-(3-methoxyphenyl)-3-methylphenyl]piperidin-1-ylsulfonyl}-2,2-dimethyltetrahydro-3aH-cyclopenta[d][1,3]dioxole-5-carboxylic acid

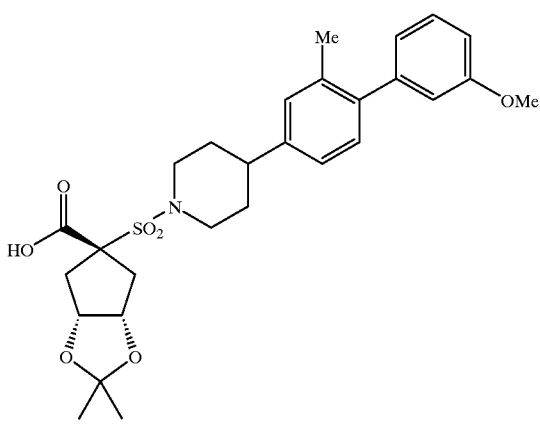

The title compound was prepared from the methyl ester from preparation 115 in a similar procedure to that described in preparation 119 and was isolated as a white foam (250 mg, 85%).

¹H nmr (DMSO-d₆, 400 MHz) δ: 1.20 (s, 3H), 1.40 (s, 3H), 1.58 (m, 2H), 1.80 (m, 2H), 2.15 (m, 2H), 2.18 (s, 3H), 2.65 (m, 1H), 2.78 (m, 2H), 2.99 (t, 2H), 3.77 (m, 5H), 4.56 (m, 2H), 6.82 (m, 3H), 7.10 (m, 3H), 7.29 (t, 1H), 13.78 (s, 1H). LRMS: m/z 528 (M−1)⁻.

Preparation 121

(3aα,5α,6aα)-N-hydroxy-5-{[4-(4-{6-[2-(tert-butoxy)ethoxy]pyridin-2-yl}-3-methylphenyl)piperidin-1-yl]sulfonyl}-2,2-dimethyltetrahydro-3aH-cyclopenta[d][1,3]dioxole-5-carboxamide

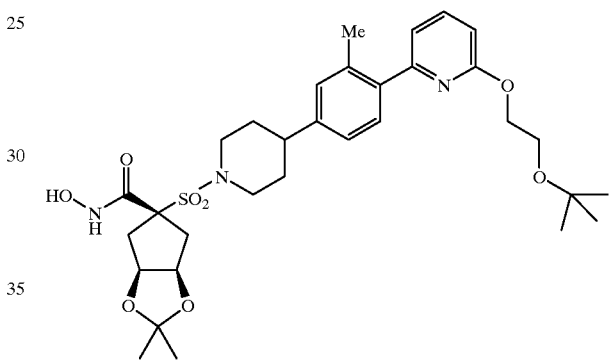

1-(3-Dimethylaminopropyl)-3-ethylcarbodiimide hydrochloride (190 mg, 0.973 mmol) and 1-hydroxy-7-azabenzotriazole (121 mg, 0.892 mmol) were added to a solution of the acid from preparation 116 (500 mg, 0.81 1 mmol) in N,N-dimethylformamide (6 ml) and pyridine (3 ml) and the reaction was stirred under nitrogen for 50 minutes. Hydroxylamine hydrochloride (170 mg, 2.43 mmol) was then added, and the reaction stirred at room temperature overnight. The reaction was diluted with ethyl acetate (50 ml) and washed with pH 7 phosphate buffer solution (30 ml). The aqueous layer was extracted with ethyl acetate (2×50 ml) and the combined organic extracts were washed with brine, then water, dried (Na₂SO₄), filtered and concentrated in vacuo. The resulting solid was recrystallised from ethyl acetate to afford the title compound as a white solid (260 mg, 50%).

¹H nmr (DMSO-d₆, 400 MHz) δ: 1.15 (s, 9H), 1.16 (s, 3H), 1.20 (s, 3H), 1.59 (m, 2H), 1.75 (m, 2H), 2.17 (m, 2H), 2.31 (s, 3H), 2.59 (m, 1H), 2.66 (d, 2H), 2.99 (t, 2H), 3.59 (m, 2H), 3.64 (d, 2H), 4.28 (m, 2H), 4.62 (m, 2H), 6.72 (d, 1H), 7.03 (d, 1H), 7.15 (m, 2H), 7.29 (d, 1H), 7.70 (t, 1H), 8.85 (s, 1H), 10.82 (s, 1H). LRMS: m/z 632 (M+1)⁺.

Preparation 122

(3aα,5α,6aα)-N-hydroxy-5-({4-[4-(6-ethoxypyridin-2-yl)-3-methylphenyl]piperidin-1-yl}sulfonyl-2,2-dimethyltetrahydro-3aH-cyclopenta[d][1,3]dioxole-5-carboxamide

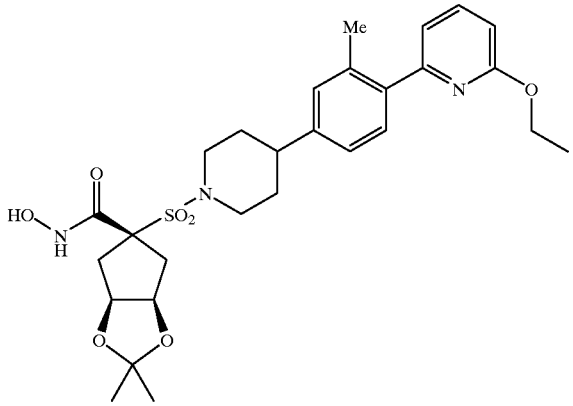

The title compound was prepared from the acid from preparation 117 in a similar procedure to that described in preparation 121, and was isolated as a white solid (50 mg, 60%).

$^1$H nmr (DMSO-d$_6$, 400 MHz) δ: 1.13 (s, 3H), 1.21 (s, 3H), 1.25 (t, 3H), 1.61 (m, 2H), 1.76 (m, 2H), 2.18 (m, 2H), 2.32 (s, 3H), 2.60 (m, 1H), 2.77 (d, 2H), 2.99 (t, 2H), 3.63 (d, 2H), 4.25 (q, 2H), 4.63 (m, 2H), 6.68 (d, 1H), 7.02 (d, 1H), 7.14 (m, 2H), 7.30 (d, 1H), 7.71 (t, 1H), 8.86 (s, 1H), 10.82 (s, 1H). LRMS: m/z 560 (M+1)$^+$.

Preparation 123

(3aβ,5α,6aβ)-N-hydroxy-5-({4-[4-(6-ethoxy-pyridin-2-yl)-3-methylphenyl]piperidin-1-yl}sulfonyl)-2,2-dimethyltetrahydro-3aH-cyclopenta[d][1,3]dioxole-5-carboxamide

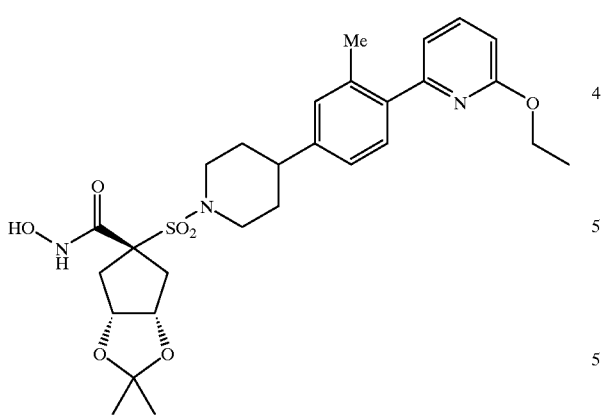

The title compound was prepared from the acid from preparation 118 in a similar procedure to that described in preparation 121. The title compound was isolated after column chromatography (using dichloromethane/methanol 99:1 as eluant) as a white solid (107 mg, 45%).

$^1$H nmr (DMSO-d$_6$, 400 MHz) δ: 1.20 (s, 3H), 1.28 (t, 3H), 1.40 (s, 3H), 1.61 (m, 2H), 1.80 (d, 2H), 2.02 (m, 2H), 2.30 (s, 3H), 2.62 (m, 1H), 2.97 (m, 4H), 3.70 (d, 2H), 4.28 (q, 2H), 4.45 (m, 2H), 6.68 (d, 1H), 7.01 (d, 1H), 7.15 (m, 2H), 7.32 (d, 1H), 7.72 (t, 1H), 9.00 (s, 1H), 10.39 (s, 1H). LRMS: m/z 560 (M+1)$^+$.

Preparation 124

(3aα,5α,6aα)-N-hydroxy-5-{4-[4-(3-methoxyphenyl)-3-methylphenyl]piperidin-1-ylsulfonyl}-2,2-dimethyltetrahydro-3aH-cyclopenta[d][1,3]dioxole-5-carboxamide

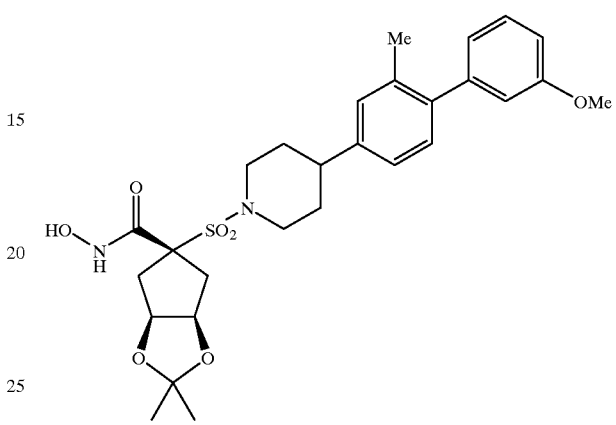

The title compound was prepared from the acid from preparation 119 in a similar procedure to that described in preparation 121, and was isolated as a white solid (110 mg, 43%).

$^1$H nmr (DMSO-d$_6$, 400 MHz) δ: 1.13 (s, 3H), 1.22 (s, 3H), 1.58 (m, 2H), 1.77 (m, 2H), 2.18 (m, 5H), 2.58 (m, 1H), 2.75 (d, 2H), 2.98 (t, 2H), 3.65 (d, 2H), 3.75 (s, 3H), 4.63 (m, 2H), 6.82 (m, 3H), 7.08 (s, 2H), 7.15 (s, 1H), 7.28 (t, 1H), 8.85 (s, 1H), 10.82 (s, 1H).

Preparation 125

(3aβ,5α,6aβ)-N-hydroxy-5-{4-[4-(3-methoxyphenyl)-3-methylphenyl]piperidin-1-ylsulfonyl}-2,2-dimethyltetrahydro-3aH-cyclopenta[d][1,3]dioxole-5-carboxamide

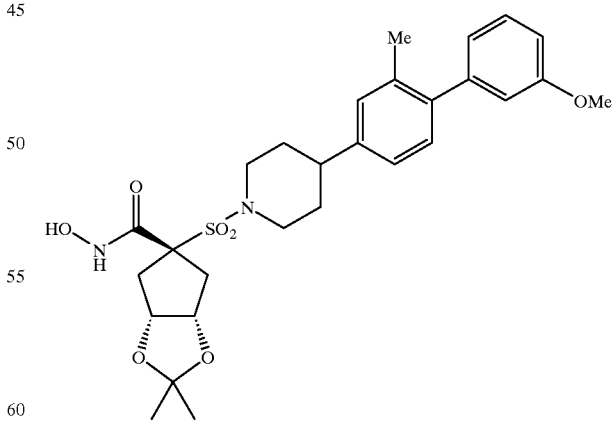

The title compound was prepared from the acid from preparation 120 in a similar procedure to that described in preparation 121. The title compound was isolated after column chromatography (using dichloromethane/methanol 98:2 as eluant) as a white solid (130 mg, 50%).

¹H nmr (DMSO-d₆, 400 MHz) δ: 1.20 (s, 3H), 1.40 (s, 3H), 1.58 (m, 2H), 1.78 (m, 2H), 2.05 (m, 2H), 2.18 (s, 3H), 2.60 (m, 1H), 2.95 (m, 4H), 3.67 (m, 2H), 3.74 (s, 3H), 4.42 (m, 2H), 6.82 (m, 3H), 7.08 (s, 2H), 7.13 (s, 1H), 7.29 (t, 1H), 9.09 (s, 1H), 10.49 (s, 1H). LRMS: m/z 543 (M−1)⁻.

Preparation 126

2-[2-(tert-butoxy)ethoxy]-6-bromopyridine

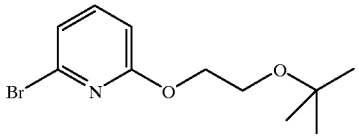

Sodium hydride (6.8 g, 60% dispersion in mineral oil, 0.169 mol) was added portionwise to an ice-cold solution of 2-(tert-butoxy)ethanol (20.0 g, 0.169 mol) in toluene (500 ml) under nitrogen, and the solution stirred for 30 minutes whilst warming to ambient temperature. 2,6-Dibromopyridine (40.0, 0.169 mol) was added, and the reaction heated under reflux for 3 hours. The mixture was allowed to cool to ambient temperature and was diluted with water (100 ml), and extracted with ethyl acetate (2×400 ml). The combined organic extracts were dried (Na₂SO₄), filtered and evaporated in vacuo to give the title compound as a yellow oil (quantitative). ¹H nmr (CDCl₃, 400 MHz) δ: 1.21 (s, 9H), 3.67 (t, 2H), 4.40 (t, 2H), 6.68 (d, 1H), 7.05 (d, 1H), 7.38 (t, 1H). LRMS: m/z 296/298 (M+23)⁺.

Preparation 127

2-[2-(tert-butoxy)ethoxy]-6-(tributylstannyl)pyridine

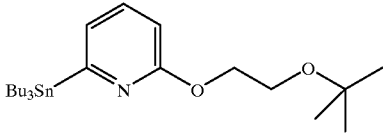

n-Butyllithium (71 ml, 2.5M solution in hexanes, 0.177 mol) was added dropwise to a cooled (−78° C.) solution of the bromide from preparation 126 (46.3 g, 0.169 mol) in anhydrous THF (1000 ml) under nitrogen, so as to maintain the internal temperature <−70° C., and the solution stirred for 10 minutes. Tri-n-butyltin chloride (48 ml, 0.177 mol) was added slowly to maintain the internal temperature <−70° C., the reaction was then allowed to warm to room temperature over 1 hour. The reaction was diluted with water (1000 ml), the mixture extracted with Et₂O (2×1000 ml), and the combined organic extracts dried (Na₂SO₄), filtered and evaporated in vacuo. The residue was purified by column chromatography on silica gel using pentane:Et₂O (110:1 to 98:2) as eluant, to afford the title compound as a colourless oil, (45.5 g, 55%).

¹H nmr (CDCl₃, 400 MHz) δ: 0.86 (t, 9H), 1.04 (m, 6H), 1.21 (s, 9H), 1.35 (m, 6H), 1.58 (m, 6H), 3.69 (t, 2H), 4.43 (t, 2H), 6.58 (d, 1H), 6.97 (m, 1H), 7.37 (m, 1H). LRMS: m/z 506/508 (M+23)⁺.

Preparation 128

2-bromo-6-ethoxypyridine

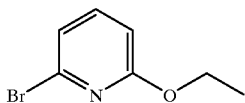

Sodium ethoxide (1.5 g, 63 mmol sodium, in ethanol (30 ml)) was added to 2,6-dibromopyridine (15 g, 63 mmol) in toluene (150 ml) at ambient temperature under nitrogen, and the reaction heated under reflux for 5 hours. The cooled mixture was diluted with water (100 ml), and extracted with ethyl acetate (2×100 ml). The combined organic extracts were dried (Na₂SO₄), filtered and evaporated in vacuo. The residue was purified by column chromatography on silica gel using pentane/ethyl acetate (100:0 to 95:5) as eluant to give the title compound as a yellow oil, (quantitative).

¹H nmr (CDCl₃, 400 MHz) δ: 1.37 (t, 3H), 4.35 (q, 2H), 6.62 (d, 1H), 7.01 (d, 1H), 7.38 (t, 1H). LRMS: m/z 202/204 (M+1)⁺.

Preparation 129

2-ethoxy-6-(tributylstannyl)pyridine

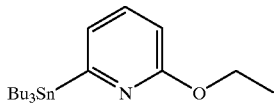

The title compound was prepared from the bromide from preparation 128 in a similar procedure to that described in preparation 127, and was isolated as a colourless oil (1.3 g, 6%).

¹H nmr (CDCl₃, 400 MHz) δ: 0.86 (t, 9H), 1.04 (m, 6H), 1.36 (m, 9H), 1.57 (m, 6H), 4.38 (q, 2H), 6.52 (d, 1H), 6.95 (m, 1H), 7.37 (m, 1H). LRMS: m/z 434/436 (M+23)⁺.

Preparation 130

Methyl 4-{[4-(4-bromo-3-methylphenyl)-4-hydroxy-1-piperidin-1-yl]sulfonyl}tetrahydro-2H-pyran-4-carboxylate

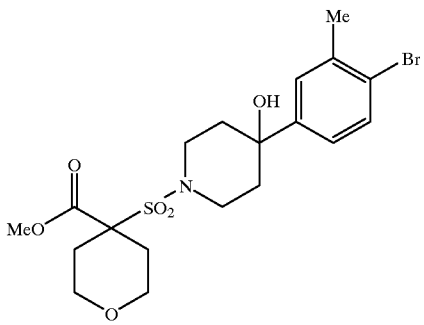

Iso-propylbromide (20 ml, 0.21 mol) was added dropwise over 1 h to a stirred mixture of magnesium (4.7 g, 0.19 mol) in THF (50 ml) and toluene (50 ml), under nitrogen. The mixture was stirred at room temperature for 1 hour and then cooled to 0° C. A solution of 2-bromo-5-iodotoluene (57 g, 0.19 mol) in toluene (50 ml) was added dropwise over 30 min, between 0 and 5° C., and the mixture was stirred at 0° C. for 30 min. The mixture was then added dropwise over 45 min to a stirred suspension the ketone from preparation 16 (50 g, 0.16 mol) in toluene (250 ml), between 0 and 5° C., under nitrogen. The resulting mixture was stirred at 0° C. for 1 hour and then citric acid solution (10%, 400 ml) and ethyl acetate (200 ml) were added. The organic phase was separated and the aqueous phase was re-extracted with ethyl acetate (2×200 ml). The combined organic phases were washed with water (200 ml) and concentrated in vacuo to a solid which was purified by re-crystallisation from toluene (500 ml) to give the title compound as a colourless solid (66 g, 84%).

$^1$H nmr (CDCl$_3$, 300 MHz) δ: 1.70–1.77 (m, 2H), 2.02–2.26 (m, 4H), 2.38–2.42 (m, 5H), 3.30 (t, 2H), 3.45 (t, 2H), 3.67–3.75 (m, 2H), 3.88 (s, 3H), 3.99 (dd, 2H), 7.14 (dd, 1H), 7.31 (d, 1H),7.50 (d, 1H).

Preparation 131

Methyl 4-{[4-(4-{6-[2-(tert-butoxy)ethoxy]pyridin-2-yl}-3-methylphenyl)piperidin-1-yl]sulfonyl}tetrahydro-2H-pyran-4-carboxylate

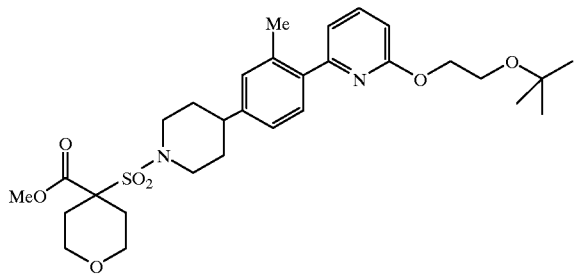

A solution of n-butyllithium in hexanes (2.5M, 3.1 ml, 7.7 mmol) was added dropwise over 5 min to a solution of the bromopyridine from preparation 126 (2.0 g, 7.3 mmol) in THF (20 ml) at −78° C., under nitrogen. The mixture was stirred at −78° C. for 10 min and then tri-iso-propylborate (1.9 ml, 8.0 mmol) was added dropwise over 10 min. The mixture was stirred at −78° C. for 10 min and then allowed to warm to room temperature over 1 hour. The aryl bromide from preparation 27 (2.7 g, 5.8 mmol), palladium acetate (82 mg, 0.36 mmol), triphenylphosphine (191 mg, 0.73 mmol), ethanol (20 ml) and aqueous sodium carbonate (2M, 20 ml) were added and the mixture was heated to reflux for 4 hours, under nitrogen, and then cooled. Ethyl acetate (50 ml) and demineralised water (50 ml) were added and the organic phase was separated. The aqueous phase was re-extracted with ethyl acetate (2×30 ml) and the combined organic phases were washed with demineralised water (50 ml) and then concentrated in vacuo to a solid. Purification by re-crystallisation from methanol (30 ml) gave the title compound as a colourless solid (2.0 g, 60%).

$^1$H nmr (CD$_3$OD, 300 MHz) δ: 1.12 (s, 9H), 1.50–1.69 (m, 2H), 1.72–1.88 (m, 2H), 1.91–2.05, (m, 2H), 2.24–2.30 (m, 2H), 2.34 (m, 3H), 2.65–2.78 (m, 1H), 3.00–3.23 (m, 4H), 3.61 (t, 2H), 3.70–3.78 (m, 2H), 3.80 (s,3H), 3.87–3.95 (m, 2H), 4.30 (t, 2H), 6.74 (d, 1H), 7.05 (d, 1H), 7.10–7.17 (m, 2H), 7.33 (d, 1H), 7.73 (t, 1H). LRMS : m/z 575 (M+H)$^+$.

Preparation 132

4-{[4-(4-{6-[2-tert-butoxyethoxy]pyridin-2-yl}-3-methylphenyl)piperidin-1-yl]sulfonyl}-tetrahydro-2H-pyran-4-carboxylic acid

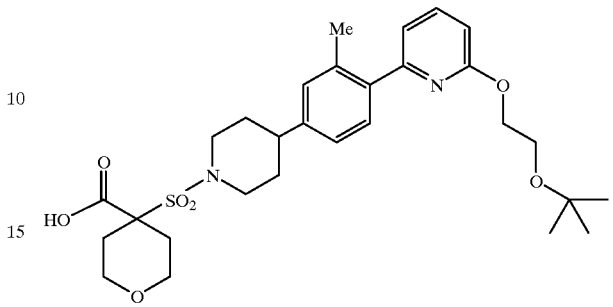

A mixture of the methyl ester from preparation 131 (9.1 g, 16.0 mmol) and aqueous sodium hydroxide (80 ml, 1N, 80.0 mmol) in dioxan (250 ml) were heated under reflux for 2 hours. Methanol (100 ml) and aqueous sodium hydroxide (40 ml, 1N, 40.0 mmol) were added and the mixture refluxed for a further 2 hours, then allowed to cool to ambient temperature. The reaction was concentrated in vacuo, the residue dissolved in water (200 ml), and the solution acidified to pH 4 with glacial acetic acid. The aqueous layer was extracted with ethyl acetate (2×200 ml) and the combined organic extracts were washed with brine 30 (200 ml), then water (2×200 ml), dried (Na$_2$SO$_4$), filtered and concentrated in vacuo. The resulting oily solid was azeotroped with toluene then triturated with cold di-isopropyl ether to afford the title compound as a pale yellow solid (7.66 g, 85%).

$^1$H nmr (DMSO-d$_6$, 400 MHz) δ: 1.13 (s, 9H), 1.61 (m, 2H), 1.79 (m, 2H), 1.95 (m, 2H), 2.22 (d, 2H), 2.32 (s, 3H), 2.66 (m, 1H), 3.05 (t, 2H), 3.20 (t, 2H), 3.60 (t, 2H), 3.76 (d, 2H), 3.88 (m, 2H), 4.28 (t, 2H), 6.73 (d, 1H), 7.03 (d, 1H), 7.12 (m, 2H), 7.31 (d, 1H), 7.75 (t, 1H), 13.77 (s, 1H). LRMS: m/z 583 (M+23)$^+$.

Preparation 133

N-Hydroxy-4-[(4-{4-[6-(2-tert-butoxyethoxy)pyridin-2-yl]-3-methylphenyl}piperidin-1-yl)sulfonyl]tetrahydro-2H-pyran-4-carboxamide

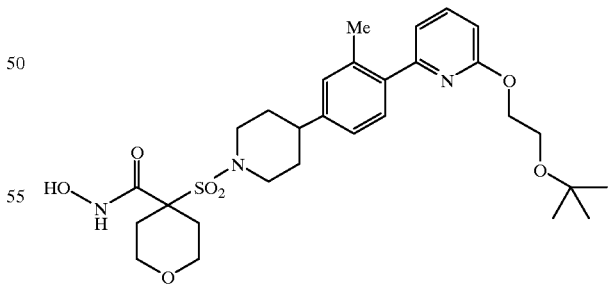

1-(3-Dimethylaminopropyl)-3-ethylcarbodiimide hydrochloride (3.15 g, 16.0 mmol) and 1-hydroxy-7-azabenzotriazole (2.05 g, 15.0 mmol) were added to a solution of the acid from preparation 132 (7.66 g, 14 mmol) in anhydrous dichloromethane (80 ml) and pyridine (80 ml) and the reaction was stirred under nitrogen for 1 hour. Hydroxylamine hydrochloride (2.85 g, 41.0 mmol) was then added, and the reaction stirred at room temperature overnight. The reaction was diluted with dichloromethane (200 ml) and washed with pH 7 phosphate buffer solution (200 ml). The aqueous layer was extracted with dichloromethane (2×200 ml) and the combined organic extracts were washed with dilute aqueous acetic acid (150 ml), brine (150 ml), then water (150 ml), dried (Na$_2$SO$_4$), filtered and concentrated in vacuo. The resulting solid was azeotroped with toluene and then recrystallised from ethyl acetate and di-isopropyl ether to afford the title compound as a white solid (6.3 g, 75%).

$^1$H nmr (DMSO-d$_6$, 400 MHz) δ: 1.13 (s, 9H), 1.61 (m, 2H), 1.78 (m, 2H), 1.91 (m, 2H), 2.37 (m, 5H), 2.62 (m, 1H), 3.05 (t, 2H), 3.20 (t, 2H), 3.60 (t, 2H), 3.73 (d, 2H), 3.83 (m, 2H), 4.28 (t, 2H), 6.73 (d, 1H), 7.03 (d, 1H), 7.12 (m, 2H), 7.31 (d, 1H), 7.72 (t, 1H), 9.05 (s, 1H), 10.90 (s, 1H). LRMS: m/z 598 (M+23)$^+$.

What is claimed is:

1. A compound which is N-Hydroxy 4-{[4-(4-{6-[2-hydroxyethoxy]pyridin-2-yl}-3-methylphenyl)piperidin-1-yl]sulphonyl}tetrahydro-2H-pyran-4-carboxamide or a pharmaceutically acceptable salt thereof, or a solvate thereof.

2. A compound selected from:
N-hydroxy 2-[(4-{4-[6-(2-hydroxyethoxy)pyridin-2-yl]-3-methylphenyl}piperidin-1-yl)sulphonyl]-2-methylpropanamide;
N-hydroxy 2-{[4-(4-{6-[2-(methoxy)ethoxy]pyridin-2-yl}-3-methylphenyl)piperidin-1-yl]sulphonyl}-2-methylpropanamide;
N-hydroxy 4-{[4-(4-{6-[2-hydroxyethoxy]pyridin-2-yl}-3-methylphenyl)piperidin-1-yl]sulphonyl}tetrahydro-2H-pyran-4-carboxamide;
N-hydroxy 4-{[4-(4-{6-[(2S)-2,3-dihydroxy-1-propoxy]pyridin-2-yl}-3-methylphenyl)piperidin-1-yl]sulphonyl}tetrahydro-2H-pyran-4-carboxamide;
N-hydroxy 4-{[4-(4-{6-[(2R)-2,3-dihydroxy-1-propoxy]pyridin-2-yl}-3-methylphenyl)piperidin-1-yl]sulphonyl}tetrahydro-2H-pyran-4-carboxamide;
N-hydroxy 4-{[4-(4-{6-[2-hydroxyethoxy]pyridin-2-yl}-3-methylphenyl)piperidin-1-yl]sulphonyl}-piperidine-4-carboxamide dihydrochloride;
N-hydroxy 4-{[4-(4-{6-[2-hydroxyethoxy]pyridin-2-yl}-3-methylphenyl)piperidin-1-yl]sulphonyl}-1-methyl-piperidine-4-carboxamide;
N-hydroxy 2-[4-(4-{3-[(2S)-2,3-dihydroxy-1-propoxy]phenyl}-3-methylphenyl)-piperidin-1-ylsulphonyl]-2-methylpropanamide;
N-hydroxy 4-{4-[4-(3-[(2R)-2,3-dihydroxy-1-propoxy]phenyl)-3-methylphenyl]-piperidin-1-ylsulphonyl}-tetrahydro-(2H)-pyran-4-carboxamide;
N-hydroxy 4-{4-[4-(3-{(2S)-2-hydroxy-2-hydroxymethyl}ethoxyphenyl)-3-methylphenyl]-piperdin-1-ylsulphonyl}-tetrahydro-2H-pyran-4-carboxamide;
N-hydroxy 4-{4-[4-(3-{1,3-dihydroxy-2-propoxyphenyl)-3-methylphenyl]-piperidin-1-ylsulphonyl}-tetrahydro-2H-pyran-4-carboxamide;
N-hydroxy 2-{[4-(4-{3-[2-(methylamino)ethoxy]phenyl}-3-methylphenyl)-piperidin-1-yl]sulphonyl}-2-methylpropanamide hydrochloride;
N-hydroxy 2-[4-(4-{3-(2-aminoethoxy)phenyl}-3-methylphenyl)-piperidin-1-ylsulphonyl]-2-methylpropanamide hydrochloride;
N-Hydroxy 4-{[4-(-4-{3-[2-aminoethoxy]phenyl}-3-methylphenyl)piperidin-1-yl]sulphonyl}tetrahydro-2H-pyran-4-carboxamide hydrochloride;
N-hydroxy 2-[4-(4-{3-(2-N,N-dimethylaminoethoxy)phenyl}-3-methylphenyl)-piperidin-1-ylsulphonyl]-2-methylpropanamide;
N-Hydroxy 4-{[4-(4-{3-(N-methylaminomethyl)phenyl}-3-methylphenyl)piperidin-1-yl]sulphonyl}tetrahydro-2H-pyran-4-carboxamide hydrochloride;
N-hydroxy 4-{[4-(3-methyl-4-{3-[4-morpholinylmethyl]}phenyl)piperidin-1-yl]sulphonyl}tetrahydro-2H-pyran-4-carboxamide;
N-hydroxy 2-({4-[4-(3-methoxy-1H-pyrazol-1-yl)-3-methylphenyl]piperidin-1-yl}sulphonyl)-2-methylpropanamide;
N-hydroxy 2-[(4-{4-[3-(2-hydroxyethoxy)-1H-pyrazol-1-yl]-3-methylphenyl}piperidin-1-yl)sulphonyl]-2-methylpropanamide;
N-hydroxy 2-methyl-2-({4-[3-methyl-4-(1,3-thiazol-2-yl)phenyl]piperidin-1-yl}sulphonyl)propanamide;
(1α,3α,4α)-N,3,4-trihydroxy-1-[(4-{4-[6-(2-hydroxyethoxy)pyridin-2-yl]-3-methylphenyl}piperidin-1-yl)sulfonyl]cyclopentanecarboxamide;
(1α,3α,4α)-1-({4-[4-(6-ethoxypyridin-2-yl)-3-methylphenyl]piperidin-1-yl}sulfonyl)-N,3,4-trihydroxycyclopentanecarboxamide;
(1α,3β,4β)-1-({4-[4-(6-ethoxypyridin-2-yl)-3-methylphenyl]piperidin-1-yl}sulfonyl)-N,3,4-trihydroxycyclopentanecarboxamide;
(1α,3α,4α)-N,3,4-trihydroxy-1-{4-[4-(3-methoxyphenyl)-3-methylphenyl]piperidin-1-ylsulfonyl}cyclopentanecarboxamide; and
(1α,3β,4β)-N,3,4-trihydroxy-1-{4-[4-(3-methoxyphenyl)-3-methylphenyl]piperidin-1-ylsulfonyl}cyclopentanecarboxamide,
and the pharmaceutically acceptable salts thereof, and solvates thereof.

3. A compound which is N-Hydroxy 4-{[4-(4-{6-[2-hydroxyethoxy]pyridin-2-yl}-3-methylphenyl)piperidin-1-yl]sulphonyl}-piperidine-4-carboxamide or a pharmaceutically acceptable salt thereof, or a solvate thereof.

4. A compound which is N-Hydroxy 4-{[4-(4-{6-[2-aminoethoxy]pyridin-2-yl}-3-methylphenyl)piperidin-1-yl]sulphonyl}tetrahydro-2H-pyran-4-carboxamide or a pharmaceutically acceptable salt thereof, or a solvate thereof.

5. A compound of formula (I):

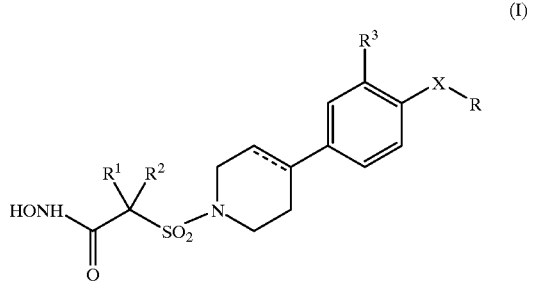

(I)

or a pharmaceutically-acceptable salt thereof, or a solvate thereof, wherein the dotted line represents an optional bond;

X is a monocyclic aromatic linker moiety selected from pyrazolylene, thiazolylene, pyrazinylene, pyridazinylene, pyrrolylene, oxazolylene, isoxazolylene, oxadiazolylene, thiadiazolylene, imidazolylene, triazolylene, or tetrazolylene;

R is H, C$_{1-4}$ alkyl optionally substituted by C$_{1-4}$ alkoxy or NR$^4$R$^5$ or OH, or C$_{1-4}$ alkoxy optionally substituted by 1 or 2 substituents selected from (C$_{1-4}$ alkyl optionally substituted by OH), C$_{1-4}$ alkoxy, OH and NR$^4$R$^5$;

R$^1$ and R$^2$ are each independently H, C$_{1-6}$ alkyl optionally substituted by OH or C$_{1-4}$ alkoxy, or C$_{2-6}$ alkenyl;

or R$^1$ and R$^2$ are taken, together with the C atom to which they are attached, to form a 3- to 7-membered ring optionally incorporating a hetero-moiety selected from O, S, SO, SO$_2$ and NR$^6$, and which 3- to 7-membered ring is optionally substituted by one or more OH;

R$^3$ is H, halo, methyl, or methoxy;

R$^4$ and R$^5$ are each independently H or C$_1$ to C$_6$ alkyl optionally substituted by OH, C$_1$ to C$_4$ alkoxy or aryl, or R$^4$ and R$^5$ can be taken together with the N atom to which they are attached, to form a 3- to 7-membered ring, optionally incorporating a further hetero-moiety selected from O, S, SO$_2$ and NR$^7$; and R$^6$ and R$^7$ are each independently H or C$_1$ to C$_4$ alkyl.

6. A compound of formula (I):

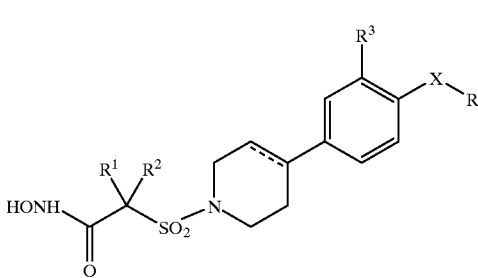

(I)

or a pharmaceutically-acceptable salt thereof, or a solvate thereof, wherein the dotted line represents an optional bond;

X is a monocyclic aromatic linker moiety selected from phenylene, pyridinylene, pyrazolylene, thiazolylene, thienylene, furylene, pyrimidinylene, pyrazinylene, pyridazinylene, pyrrolylene, oxazolylene, isoxazolylene, oxadiazolylene, thiadiazolylene, imidazolylene, triazolylene, or tetrazolylene;

R is C$_{1-4}$ alkyl substituted by NR$^4$R$^5$, C$_{1-4}$ alkoxy substituted by NR$^4$R$^5$, or C$_{1-4}$ alkoxy substituted by 2 substituents selected from (C$_{1-4}$ alkyl optionally substituted by OH), C$_{1-4}$ alkoxy, OH and NR$^4$R$^5$;

R$^1$ and R$^2$ are each independently H, C$_{1-6}$ alkyl optionally substituted by OH or C$_{1-4}$ alkoxy, or C$_{2-6}$ alkenyl;

or R$^1$ and R$^2$ are taken together, with the C atom to which they are attached, to form a 3- to 7-membered ring optionally incorporating a hetero-moiety selected from O, S, SO, SO$_2$ and NR$^6$, and which 3- to 7-membered ring is optionally substituted by one or more OH;

R$^3$ is H, halo, methyl, or methoxy;

R$^4$ and R$^5$ are each independently H or C$_1$ to C$_6$ alkyl optionally substituted by OH, C$_1$ to C$_4$ alkoxy or aryl, or R$^4$ and R$^5$ can be taken together with the N atom to which they are attached, to form a 3- to 7-membered ring, optionally incorporating a further hetero-moiety selected from O, S, SO$_2$ and NR$^7$, and R$^6$ and R$^7$ are each independently H or C$_1$ to C$_4$ alkyl.

7. A compound of formula (I):

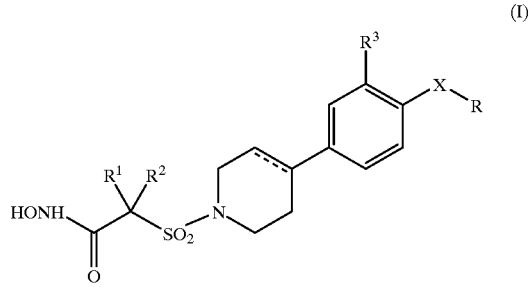

(I)

or a pharmaceutically-acceptable salt thereof, or a solvate thereof, wherein the dotted line represents an optional bond, X is a monocyclic aromatic linker moiety selected from phenylene, pyridinylene, pyrazolylene, thiazolylene, thienylene, furylene, pyrimidinylene, pyrazinylene, pyridazinylene, pyrrolylene, oxazolylene, isoxazolylene, oxadiazolylene, thiadiazolylene, imidazolylene, triazolylene, or tetrazolylene;

R is H, C$_{1-4}$ alkyl optionally substituted by C$_{1-4}$ alkoxy, NR$^4$R$^5$ or OH, or C$_{1-4}$ alkoxy optionally substituted by 1 or 2 substituents selected from (C$_{1-4}$ alkyl optionally substituted by OH), C$_{1-4}$ alkoxy, OH and NR$^4$R$^5$;

R$^1$ and R$^2$ are each independently C$_{1-6}$ alkyl substituted by OH;

or R$^1$ and R$^2$ are taken together, with the C atom to which they are attached, to form a 3- to 7-membered ring optionally incorporating a hetero-moiety selected from O, S, SO, SO$_2$ and NR$^6$, and which 3- to 7-membered ring is substituted by one or more OH;

R$^3$ is H, halo, methyl, or methoxy;

R$^4$ and R$^5$ are each independently H or C$_1$ to C$_6$ alkyl optionally substituted by OH, C$_1$ to C$_4$ alkoxy or aryl, or R$^4$ and R$^5$ can be taken together with the N atom to which they are attached, to form a 3- to 7-membered ring, optionally incorporating a further hetero-moiety selected from O, S, SO$_2$ and NR$^7$, and R$^6$ and R$^7$ are each independently H or C$_1$ to C$_4$ alkyl.

8. A compound, salt or solvate according to claim 6 or claim 7 where X is phenylene, pyridinylene, pyrazolylene or thiazolylene.

9. A compound, salt or solvate according to claim 8 wherein X is 1,3-phenylene, 2,6-pyridinylene, 1,3-pyrazolylene or 2,5-thiazolylene.

10. A compound, salt or solvate according to claim 5 wherein X is pyrazolylene or thiazolylene.

11. A compound, salt or solvate according to claim 10 wherein X is 1,3-pyrazolylene or 2,5-thiazolylene.

12. A compound, salt or solvate according to claim 5 or claim 7 wherein R is H, methoxy, O(CH$_2$)$_2$OH, O(CH$_2$)$_2$OCH$_3$, O(CH$_2$)$_2$N(CH$_3$)$_2$, O(CH$_2$)$_2$NHCH$_3$, O(CH$_2$)$_2$NH$_2$, CH$_2$NHCH$_3$, morpholinomethyl, 2-morpholinoethoxy, 2R-2,3-dihydroxy-1-propyloxy, 2S-2,3-dihydroxy-1-propyloxy or 1,3-dihydroxy-2-propyloxy.

13. A compound, salt or solvate according to claim 12 wherein R is O(CH$_2$)$_2$OH or O(CH2)2NH$_2$.

14. A compound, salt or solvate according to claim 6 wherein R is O(CH$_2$)$_2$N(CH$_3$)$_2$, O(CH2)$_2$NHCH$_3$, O(CH$_2$)$_2$NH$_2$, CH$_2$NHCH$_3$, morpholinomethyl, 2-morpholinoethoxy, 2R-2,3-dihydroxy-1-propyloxy, 2S-2,3-dihydroxy-1-propyloxy or 1,3-dihydroxy-2-propyloxy.

15. A compound, salt or solvate according to claim 14 wherein R is $O(CH_2)_2NH_2$.

16. A compound, salt or solvate according to claim 5 or claim 6 wherein $R^1$ and $R^2$ are each independently $C_{1-4}$ alkyl optionally substituted by OH, or $R^1$ and $R^2$ are taken together, with the C atom to which they are attached, to form a 3- to 7-membered ring optionally incorporating a hetero-moiety selected from O, S, SO, $SO_2$ and $NR^6$, and which 3- to 7-membered ring is optionally substituted by one or more OH.

17. A compound, salt or solvate according to claim 16 wherein $R^1$ and $R^2$ are each $CH_3$, or $R^1$ and $R^2$ are taken together, with the C atom to which they are attached, to form a tetrahydropyran-4-ylidene, piperidin-4-ylidene, 1-methylpiperidin-4-ylidene, or 3,4-dihydroxycyclopentylidene moiety.

18. A compound, salt or solvate according to claim 17 wherein $R^1$ and $R^2$ are taken together, with the C atom to which they are attached, to form a tetrahydropyran-4-ylidene, cis-3,4-dihydroxycyclopentylidene, trans-3,4-dihydroxycyclopentylidene or piperidin-4-ylidene moiety.

19. A compound, salt or solvate according to claim 18 wherein $R^1$ and $R^2$ are taken together, with the C atom to which they are attached, to form a tetrahydropyran-4-ylidene, piperidin-4-ylidene, or cis-3,4-dihydroxycyclopentylidene where the hydroxy substituents have a cis-relationship to the hydroxamate moiety.

20. A compound, salt or solvate according to claim 7 wherein $R^1$ and $R^2$ are taken together, with the C atom to which they are attached, to form a 3,4-dihydroxycyclopentylidene moiety.

21. A compound, salt or solvate according to claim 20 wherein $R^1$ and $R^2$ are taken together, with the C atom to which they are attached, to form a cis-3,4-dihydroxycyclopentylidene group where the hydroxysubstituents have a cis-relationship to the hydroxamate moiety.

22. A compound, salt or solvate according to any one of claims 5, 6, or 7 wherein $R^3$ is methyl and the optional double bond depicted as a dotted line in formula (I) is absent.

23. A pharmaceutical composition comprising a substance according to any one of claims 1, 2, 5, 6 or 7 and a pharmaceutically acceptable diluent, adjuvant or carrier.

24. A method of treatment of a MMP-mediated disease or condition in a mammal, comprising administering an effective amount of a compound according to any one of claim 1, 2, 5, 6 or 7 to the mammal.

25. A compound selected from:
methyl 4-(4-oxo-piperidin-1-ylsulphonyl)tetrahydro-2H-pyran-4-carboxylate;
methyl 4-{[4-(4-bromo-3-methylphenyl)-4-hydroxy-1-piperidin-1-yl]sulfonyl}tetrahydro-2H-pyran-4-carboxylate;
methyl 4-{[4-(4-{6-[2-(tert-butoxy)ethoxy]pyridin-2-yl}-3-methylphenyl)piperidin-1-yl]sulfonyl}tetrahydro-2H-pyran-4-carboxylate;
4-{[4-(4-{6-[2-tert-butoxyethoxy]pyridin-2-yl}-3-methylphenyl)piperidin-1-yl]sulfonyl}-tetrahydro-2H-pyran-4-carboxylic acid; and
N-hydroxy-4-[(4-{4-[6-(2-tert-butoxyethoxy)pyridin-2-yl]-3-methylphenyl}piperidin-1-yl)sulfonyl]tetrahydro-2H-pyran-4-carboxamide.

26. A compound selected from:
N-hydroxy 1-(tert-butoxycarbonyl)-4-{[4-(4-{6-[2-hydroxyethoxy]pyridin-2-yl}-3-methylphenyl)piperidin-1-yl]sulphonyl}-piperidine-4-carboxamide;
1-(tert-butoxycarbonyl)-4-[4-(4-{6-[2-hydroxyethoxy]pyridin-2-yl}-3-methylphenyl)piperidin-1-ylsulphonyl]-piperidine-4-carboxylic acid;
methyl 1-(tert-butoxycarbonyl)-4-{[4-(4-{6-[2-hydroxyethoxy]pyridin-2-yl}-3-methylphenyl)piperidin)-1-yl]sulphonyl}-4-piperidinecarboxylate;
methyl 4-{[4-(4-{6-[2-hydroxyethoxy]pyridin-2-yl}-3-methylphenyl)piperidin-1-yl]sulphonyl}-piperidine-4-carboxylate;
methyl 1-benzyl-4-{[4-(4-{6-[2-benzyloxyethoxy]pyridin-2-yl}-3-methylphenyl)piperidin-1-yl]sulphonyl}-piperidine-4-carboxylate;
methyl 1-benzyl-4-[4-(4-bromo-3-methylphenyl)piperidin-1-ylsulphonyl]-4-piperidinecarboxylate; and
methyl 2-[4-(4-bromo-3-methylphenyl)piperidin-1-ylsulphonyl]acetate.

27. A compound selected from:
N-hydroxy 4-[4-(4-{3-(2-[(N-tert-butoxycarbonyl)amino]ethoxy)phenyl}-3-methylphenyl)-piperidin-1-ylsulphonyl]-tetrahydro-2H-pyran-4-carboxamide;
N-hydroxy 4-[4-(4-{3-(2-[(tert-butoxycarbonyl)amino]ethoxy)phenyl}-3-methylphenyl)-piperidin-1-ylsulphonyl]-tetrahydro-2H-pyran-4-carboxylate;
methyl 4-[4-(4-{3-(2-[(tert-butoxycarbonyl)amino]ethoxy)phenyl}-3-methylphenyl)-piperidin-1-ylsulphonyl]-tetrahydro-2H-pyran-4-carboxylate;
methyl 4-[4-(4-{3-(2-aminoethoxy)phenyl}-3-methylphenyl)-piperidin-1-ylsulphonyl]-1-tetrahydro-2H-pyran-4-carboxylate;
methyl 4-[4-(4-{3-(2-[N-benzylamino]ethoxy)phenyl}-3-methylphenyl)-piperidin-1-ylsulphonyl]-tetrahydro-2H-pyran-4-carboxylate;
methyl 4-[4-(4-{3-(2-oxoethoxy)phenyl}-3-methylphenyl)-piperidin-1-ylsulphonyl]-tetrahydro-2H-pyran-4-carboxylate; and
methyl 4-[4-(4-{3-(2,2-diethoxyethoxy)phenyl}-3-methylphenyl)-piperidin-1-ylsulphonyl]-tetrahydro-2H-pyran-4-carboxylate.

28. A compound selected from:
4-[4-(4-{6-[2-hydroxyethoxy]pyridin-2-yl}-3-methylphenyl)piperidin-1-ylsulphonyl]tetrahydro-2H-pyran-4-carboxylic acid;
methyl 4-{[4-(4-{6-[2-hydroxyethoxy]pyridin-2-yl}-3-methylphenyl)piperidin-1-yl]sulphonyl}tetrahydro-2H-pyran-4-carboxylate;
methyl 4-[4-(4-{6-[2-benzyloxy]ethoxypyridin-2-yl}-3-methylphenyl)-1,2,3,6-tetrahydropyridin-1-ylsulphonyl]tetrahydro-2H-pyran-4-carboxylate; and
methyl 4-[4-(4-bromo-3-methylphenyl)-1,2,3,6-tetrahydropyridin-1-ylsulphonyl]tetrahydro-2H-pyran-4-carboxylate.

29. A compound of formula (VI):

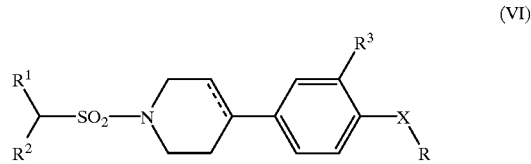

(VI)

wherein the substituents $R^1$, $R^2$, $R^3$, X and R are as defined above in relation to any one of claims 5, 6 or 7.

30. A compound of formula (VII):

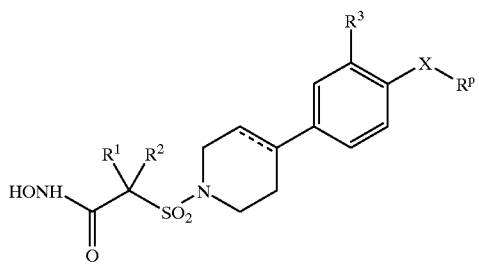

(VII)

wherein $R^1$, $R^2$, $R^3$ and X are as defined in any one of claims 5, 6 or 7, and where $R^p$ is a NH- and/or OH-protected version of the corresponding compound of formula (I) as defined in any one of claims 5, 6 or 7, and where the corresponding compound of formula (I) as defined in any one of claims 5, 6 or 7 contains a free NH, $NH_2$ or OH group.

31. A process for making a compound of formula (I) as defined in any one of claims 5, 6 or 7 where R contains a free NH, $NH_2$ or OH group, which comprises deprotecting a corresponding compound of formula (VII)

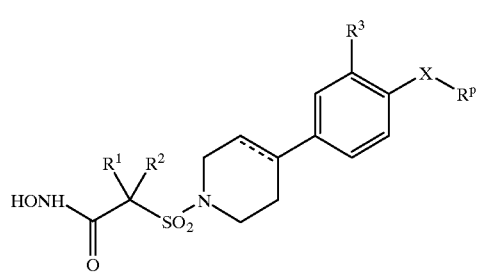

(VII)

wherein $R^1$, $R^2$, $R^3$ and X are as defined therein, and where $R^p$ is a NH- and/or OH-protected version of the corresponding compound of formula (I) as defined therein.

32. A compound of formula (VIII) or (IX):

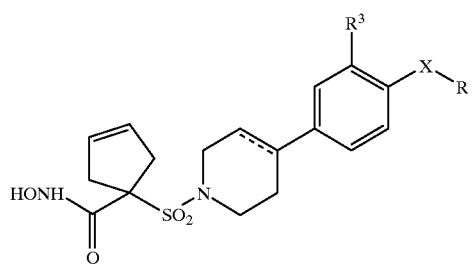

(VIII)

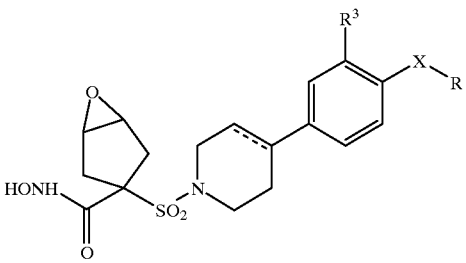

(IX)

where $R^3$, X and R are as defined in any one of claims 5, 6 or 7.

33. A compound of formula (X) or (XI):

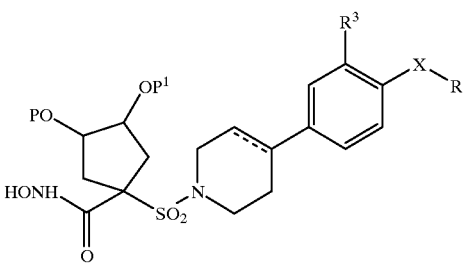

(X)

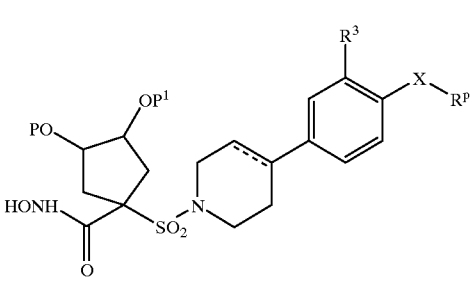

(XI)

wherein $R^3$, X and R are as defined in any one of claims 5, 6 or 7, $R^p$ is a NH- and/or OH-protected version of the corresponding compound of formula (X), and P and $P^1$ are OH-protecting groups which may be taken independently or together.

34. A compound of formula (XII)

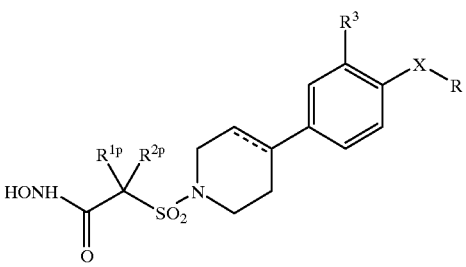

(XII)

wherein $R^3$, X and R are as defined in any one of claims 5, 6 or 7 and $R^{1p}$ and/or $R^{2p}$ is a N- and/or O-protected version of a corresponding compound of formula (I) which, on deprotection would give a corresponding compound of formula (I) as defined therein.

35. A process for making a compound of formula (I) as defined in any one of claims 5, 6 or 7 where $R^1$ and/or $R^2$ contains a free NH, $NH_2$ or OH group, which comprises deprotecting a corresponding compound of formula (XII)

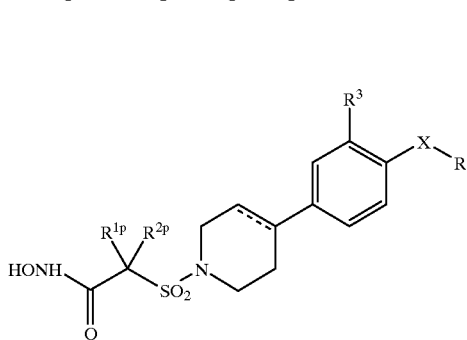

(XII)

wherein $R^3$, X and R are as defined therein and $R^{1p}$ and/or $R^{2p}$ is a N- and/or O-protected version of a corresponding compound of formula (I) as defined therein.

36. A compound of formula (II)

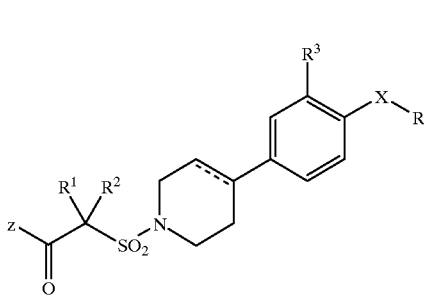

(II)

where $R^1$, $R^2$, $R^3$, X and R are as defined in any one of claims 5, 6 or 7, and where Z is chloro, bromo, iodo, $C_{1-3}$ alkyloxy or HO.

37. A process for making a compound of formula (I) as defined in any one of claims 5, 6 or 7, which comprises reacting a compound of formula (II)

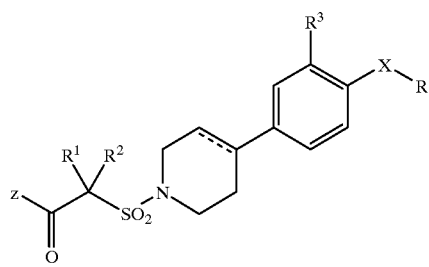

(II)

where $R^1$, $R^2$, $R^3$, X and R are as defined therein, and where Z is chloro, bromo, iodo, $C_{1-3}$ alkyloxy or HO, with hydroxylamine.

38. A compound of formula (XIII):

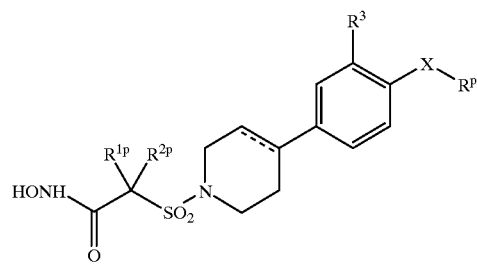

(XIII)

wherein $R^3$, X and R are as defined in any one of claims 5, 6 or 7 and $R^{1p}$, $R^{2p}$ and $R^p$ are independently a N- and/or O-protected precursor which, on deprotection would give a corresponding compound of formula (I) as defined in the corresponding claims 5, 6 or 7 where $R^1$, $R^2$ and R contain a free NH, $NH_2$ and/or OH group.

* * * * *